(12) United States Patent
Plesch et al.

(10) Patent No.: US 7,589,256 B2
(45) Date of Patent: Sep. 15, 2009

(54) PREPARATION OF ORGANISMS WITH FASTER GROWTH AND/OR HIGHER YIELD

(75) Inventors: Gunnar Plesch, Potsdam (DE); Agnes Chardonnens, Enkhuizen (NL); Oliver Schmitz, Dallgow-Doberitz (DE); Piotr Puzio, Berlin (DE); Marcus Ebneth, Berlin (DE); Xi-Qing Wang, Chapel Hill, NC (US)

(73) Assignee: Metanomics GmbH, Berlin (DE)

( * ) Notice: Subject to any disclaimer, the term of this patent is extended or adjusted under 35 U.S.C. 154(b) by 0 days.

(21) Appl. No.: 10/544,661

(22) PCT Filed: Feb. 13, 2004

(86) PCT No.: PCT/US2004/004422

§ 371 (c)(1), (2), (4) Date: Apr. 20, 2006

(87) PCT Pub. No.: WO2004/074440

PCT Pub. Date: Sep. 2, 2004

(65) Prior Publication Data

US 2006/0218659 A1 Sep. 28, 2006

(30) Foreign Application Priority Data

Feb. 17, 2003 (DE) .................. 103 06 734
Apr. 9, 2003 (DE) .................. 103 16 464
Dec. 18, 2003 (DE) .................. 103 59 613

(51) Int. Cl.
*A01H 5/00* (2006.01)
*C12N 15/82* (2006.01)
*C12N 5/14* (2006.01)

(52) U.S. Cl. .................. 800/295; 800/298; 800/278; 435/419; 435/468

(58) Field of Classification Search .................. None
See application file for complete search history.

(56) References Cited

U.S. PATENT DOCUMENTS

2002/0023281 A1 2/2002 Gorlach et al.
2002/0160378 A1* 10/2002 Harper et al. .................. 435/6

FOREIGN PATENT DOCUMENTS

| CA | 2 263 067 A1 | 8/2000 |
| WO | WO-00/37645 A2 | 6/2000 |
| WO | WO-00/47614 | 8/2000 |
| WO | WO-00/52169 | 9/2000 |
| WO | WO-00/56905 A2 | 9/2000 |
| WO | WO-01/31041 A2 | 5/2001 |
| WO | WO-03/000905 | 1/2003 |

OTHER PUBLICATIONS

Kaenko et al. (NCBI, GenBank Accession No. AB020746, pp. 1-30, Published Dec. 27, 2000).*
Antonenkov et al. (Biochimica et Biophysica Acta, 1763:1697-1706, 2006).*
Keskin et al. (Protein Science, 13:1043-1055, 2004).*
Thornton et al. (Nature structural Biology, structural genomics supplement, Nov. 2000).*
Wells, Biochemistry 29:8509-8517, 1990).*
Wang et al. (Plant Cell Physiol., 40:725-732, 1999).*
Smidansky et al. (PNAS, 99:1724-1729, 2002).*
Maniatis et al. (Molecular Cloning: A Laboratory Manual, Cold Spring Harbor Laboratory (1982).*
Ngo et al., (The Protein Folding Problem and Tertiary Structure Prediction, K. Merz., and S. Le Grand (eds.) pp. 492-495, 1994).*
Nakamura, Y. et al., "Structural analysis of Arabidopsis thaliana chromosome 3. II. Sequence features of the regions of 4,251,695 bp covered by ninety P1, TAC and BAC clines," EMBL-EBI Database Accession No. AB020746, Feb. 14, 2004.
Adams, M.D. et al., "The genome sequence of Drosophila melanogaster," NCBI Accession No. AE003492, GI:22832174, Sep. 13, 2002.
Johnson, D., "Hypothetical protein YLR245C-yeast," Protein Information Resource (PIR) Accession No. S59391, Jul. 9, 2004, and BLAST search results of this accession no. in PIR, Jan. 12, 2005.
Tugal, H.B. et al., "Arabidopsis 22-Kilodalton Peroxisomal Membrane Protein. Nucleotide Sequence Analysis and Biochemical Characterization", Plant Physiology 120 (1999) pp. 309-320.
Zwacka, R. M. et al., "The Glomerulosclerosis Gene *Mpv17* Encodes A Peroxisomal Protein Producing Reactive Oxygen Species", The EMBO Journal 13 (21) (1994), pp. 5129-5134.
Iida, R. et al., "Cloning, Mapping, Genomic Organization, And Expression Of Mouse M-LP, A New Member Of The Peroxisomal Membrane Protein Mpv17 Domain Family", Biochemical and Biophysical Research Communications 283 (2001), pp. 292-296.
Schenkel, J. et al., "Functional Rescue Of The Glomerulosclerosis Phenotype In Mpv17 Mice By Transgenesis With The Human Mpv17 Homologue", Kidney International 48 (1995), pp. 80-84.

* cited by examiner

*Primary Examiner*—Phuong T Bui
*Assistant Examiner*—Vinod Kumar
(74) *Attorney, Agent, or Firm*—Connolly Bove Lodge & Hutz, LLP

(57) ABSTRACT

A method for preparing a nonhuman organism with faster growth and/or increased yield in comparison with a reference organism, which method comprises increasing the activity of L450 in said organism or in one or parts thereof in comparison with a reference organism.

8 Claims, 9 Drawing Sheets

Figure 3:

Reference:
Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs", Nucleic Acids Res. 25:3389-3402.

Database: geneseq_DNA
           2,295,236 sequences; 1,182,512,401 total letters Sequences producing significant alignments:                          (bits)
Value ABN98933 US2002023281;Arabidopsis thaliana expressed polynucleot...   1211   0.0
ABN80328 WO200200927;Human chemically modified disease associate...     38   2.6
ABQ74506 WO200261135;Mouse Fyn nucleotide sequence SEQ ID NO:24.        38   2.6
ABL96716 WO200155317;Human testicular antigen encoding cDNA SEQ ...     38   2.6
AAK78465 WO200157182;Human immune/haematopoietic antigen genomic...     38   2.6
AAK66421 WO200157182;Human immune/haematopoietic antigen genomic...     38   2.6
AAL01257 WO200155320;Human reproductive system related antigen c...     38   2.6

Error: authentication parameters is not specified
Usage: admin_find [-help]
                  [-u User] [-p Password] [-g] [-a] [-save]
                  [-edtcw] [-e] [-d] [-t] [-c] [-w]
                  [-f DataElementList] [-l LibraryList] [-iv IndexName]
                  [-lv] [-lvf]
                  [-view ViewName] [-sf SequenceFormat] [-source SourceFormat]
        [-html]
                  [-ll EntriesNumber] [-lb EntryNumber]
                  [-ip Prefix] [-bp Prefix] [-entry_end String]
                  [-libs] [-tree] [-info LibraryName] [-stat LibraryName] [-
si]
                  [-srs] [-no_cache][-ch [EntryName]]
                  [-i FileName QueryTemplate] [-s (and|or|butnot)] [-o File-
Name]
                  QueryExpression >ABN98933 US2002023281;Arabidopsis thaliana expressed polynucleotide
         SEQ ID NO 701.
         Length = 828

Score = 1211 bits (611), Expect = 0.0
  Identities = 635/643 (98%)
  Strand = Plus / Minus Query: 66   cagttctggatttctttggggatttggcgatgtcaccgctcaatacatcactcattccac 125
            ||||||||||||||||||||||||||||||||||||||||||||||||||||||||||||
Sbjct: 817  cagttctggatttctttggggatttggcgatgtcaccgctcaatacatcactcattccac 758

Query: 126  tgcgaaacgtcgtcttcttcgtctcaccgaaacaaataaagatgctgacgcagatgcaga 185
            |||||||||||||||||||||||||||||||||| ||||||||| |||||||||||||||
Sbjct: 757  tgcgaaacgtcgtcttcttcgtctcaccgaaacgaataaagatgttgacgcagatgcaga 698

Query: 186  aattaaggtcaagtggaagcaagatgcagaattcaaagtcaactggaagcgagtagctat 245
            | |||||||||| ||||| ||||||||||||||||||||||||||||||||||||||||
Sbjct: 697  attcaaggtcaactggaagcgagatgcagaattcaaagtcaactggaagcgagtagctat 638

Query: 246  cacgagcatgtttggatttggttttgtcggacctgttggccacttctggtacgaaggctt 305
            |||||||||||||||||||||||||||||||||||||||||||||| |||||||||||||
Sbjct: 637  cacgagcatgtttggatttggttttgtcggacctgttggccacttttggtacgaaggctt 578

Figure 3 continue:

```
Query: 306 ggataaattcataaaactgaagcttcgatatgtaccaaagtcaacacgttttgtagctgc 365
           ||||||||||||||||||||||||||||||||||||||||||||||||||||||||||||
Sbjct: 577 ggataaattcataaaactgaagcttcgatatgtaccaaagtcaacacgttttgtagctgc 518

Query: 366 aaaagttgcaatggatggtcttatctttggacctgtagatctactggtgttcttcacata 425
           ||||||||||||||||||||||||||||||||||||||||||||||||||||||||||||
Sbjct: 517 aaaagttgcaatggatggtcttatctttggacctgtagatctactggtgttcttcacata 458

Query: 426 catgggattcgccacaggaaagaacacagctgaagtgaaagaaggactcaagagagattt 485
           ||||||||||||||||||||||||||||||||||||||||||||||||||||||||||||
Sbjct: 457 catgggattcgccacaggaaagaacacagctgaagtgaaagaaggactcaagagagattt 398

Query: 486 tcttccggctctagctcttgaaggcggagcatggccacttcttcagattgcaaacttcag 545
           ||||||||||||||||||||||||||||||||||||||||||||||||||||||||||||
Sbjct: 397 tcttccggctctagctcttgaaggcggagcatggccacttcttcagattgcaaacttcag 338

Query: 546 atatgttcccgtgcaataccagttgctttacgtcaacatcttttgcctagtagacagtgc 605
           ||||||||||||||||||||||||||||||||||||||||||||||||||||||||||||
Sbjct: 337 atatgttcccgtgcaataccagttgctttacgtcaacatcttttgcctagtagacagtgc 278

Query: 606 cttcctctcatgggtcgagcaacagaaggacgcagcttggaagcaatggtttacttcatc 665
           ||||||||||||||||||||||||||||||||||||||||||||||||||||||||||||
Sbjct: 277 cttcctctcatgggtcgagcaacagaaggacgcagcttggaagcaatggtttacttcatc 218

Query: 666 atttcaaccattaaaagaacgaggtggccaaggcggagtatga 708
           ||||||||||||||||||||||||| |||||||||||||||||
Sbjct: 217 atttcaaccattaaaagaacgaggaggccaaggcggagtatga 175
```

```
AT3G24570              MLKLMRWYQRCLTVHPVKTQVISSGFLWGFGDVTAQYITHSTA
51291079HYSEQCANOLA    MLKVMRWYQRCLSVHPVKTQVISSGFLWGFGDVTAQYITHSTA
POTATO2MTX             MLRLWKWYQNCLALHPVKTQVISSGLIWGLGDVSAQAVTHYTA
c48958528gm021002      MLRLWKWYQNCLAVHPVKTQVISSGLIWGAGDIAAQAVTHYTA
62820788HYSEQBARLEY    MRRLMRWYQQSLSSYPVRTQVVSSGILWALGDIGAQAVTHKSA
54861924HYSEQWHEAT     MRRLMRWYQQSLSSYPVRTQVVSSGILWALGDIGAQAVTHKSA
AP003434_15            MRRLWRWYQQCLATHPVRTQVVSSGILWGLGDIGAQAVTHYSA
HYSEQMAIZE             MRRLWRWYQQCLAAHPVRTQVVSSGILWGLGDIGAQTVTYYSA

Consensus              MlrLWRWYQxcLxxhPvKTQViSSGdlWglGDigAQavTHytA[x]35
                         r          r  v       a               s AT3G24570              RVAITSMFGFGFVGPVGHFWYEGLDKFIKLKLRYVPKSTRFVAAKVAMDGLIFGPVDLLVFFTYMGFATGKNTAEVKEGLKRDFLPALALEGGAWPLLQIANFRYVPVQYQLLYVNIFCLVDSAFLSWVEQQ
51291079HYSEQCANOLA    RVAITSMFGLGFVGPVGHFWYEGLDKFIKLKLRYVPKSTRFVAAKVAMDGLIFGPIDLLVFFTYMGYATGKNTSQVKEGLKRDFLPALALEGGAWPLLQIANFRYVPVQYQLLYVNIFCLIDSAFLSWVDQQ
POTATO2MTX             RVATTSLFGFAFVGPVGHFWYEGLDRVIRHRFQMQPKSLRFVATKVALDGIIFGPLDLLVFFTYMGYSTGKNTAQVVEGVKRDYLPALILERGIWPIVQVANFRYIPVRY---------
c48958528gm021002      RVSTTSLFGLGFVGPVGHFWYEGLDRFIRLKLMLKPNSFRFVATKVAVDGFIFGPLDLLVFFTYMGFSAGKSVPQVKEDVKRDFLPAFVLEGGIWPIVQVANFRFIPVRYQLLYNFFCLLDSCFLSWVEQQ
62820788HYSEQBARLEY    RVGITSSFGFAFVGPVGHYWYEGHYWYDYLDCLVRR--RYQPGSFKFVASKVAADGLLFGPLDLGLFFSYVGLASGRSLEQVKEDVKRDIIPALVLGGAIWPAVQIANFRFIPVRYQLLYVNLFCLLDSCFLSWIEQQ
54861924HYSEQWHEAT     RVGITSSFGFAFVGPVGHYWYEGHYWYEYLDRMVRR--RYLPGSFKFVASKVAADGLLFGPLDLGLFFSYVGLASGRSLEQVKDDVKRDIIPALVLGGAIWPAVQIANFRFIPVRYQLLYVNLFCLLDSCFLSWIEQQ
AP003434_15            RVGITSSFGFAFVGPVGHYWYEGHYWYEYLDRFILR--RYQPKTFKFVASKVAADGLLFGPVDLLLFFSYVGLASGRSVEQVKDDVKRDFIPALVLGGTIWPAVQIANFRFIPVRYQLLYVNLFCLLDSCFLSWIDQQ
HYSEQMAIZE             RVGITSSFGFAFVGPVGHYWYEGHYWYEYLDRIIRR--RFQPNTFKFVASKVAADGFLFGPLDLDLLFFSYVGLGQGRSIEQVKEDVKRDFIPALVLGGTIWPAVQIANFRFVPVRYQLLYVNLFCLLDSCFLSWIEQQ Consensus              RVgiTSsFGfaFVGPVGHfWYEgLDrfirrklryqPksfrFVAsKVaaDGllFGPlDLlvFFtYmGlaxGksteQVKedvKRDflPAlvLeGGiWPavQiANFRfiPVryQLLYVNiFCLlDScFLSWieQQ
                         y         y                k        l      l  s v       r            i              g
```

AT3G24570              unknown protein
51291079HYSEQCANOLA
POTATO2MTX
c48958528gm021002
62820788HYSEQBARLEY
54861924HYSEQWHEAT
AP003434_15            P0452F10.16 gene
HYSEQMAIZE Arabidopsis thaliana
Canola
POTATO
SOYBEAN (48958528HYSEQSOY)
BARLEY
WHEAT
Oryza sativa
MAIZE The multiple alignment has been performed with the software genomax, InforMax, Maryland, USA.

US 7,589,256 B2

SEQUENCE LISTING

<160> NUMBER OF SEQ ID NOS: 53

<210> SEQ ID NO 1
<211> LENGTH: 708
<212> TYPE: DNA
<213> ORGANISM: Arabidopsis thaliana
<220> FEATURE:
<221> NAME/KEY: CDS
<222> LOCATION: (1)..(708)

<400> SEQUENCE: 1

```
atg ttg aag ctt tgg aga tgg tac cag cga tgc ctg acg gtt cat cct      48
Met Leu Lys Leu Trp Arg Trp Tyr Gln Arg Cys Leu Thr Val His Pro
1               5                  10                  15 gtg aaa act cag gtc atc agt tct gga ttt ctt tgg gga ttt ggc gat      96
Val Lys Thr Gln Val Ile Ser Ser Gly Phe Leu Trp Gly Phe Gly Asp
            20                  25                  30 gtc acc gct caa tac atc act cat tcc act gcg aaa cgt cgt ctt ctt     144
Val Thr Ala Gln Tyr Ile Thr His Ser Thr Ala Lys Arg Arg Leu Leu
        35                  40                  45 cgt ctc acc gaa aca aat aaa gat gct gac gca gat gca gaa att aag     192
Arg Leu Thr Glu Thr Asn Lys Asp Ala Asp Ala Asp Ala Glu Ile Lys
    50                  55                  60
```

```
gtc aag tgg aag caa gat gca gaa ttc aaa gtc aac tgg aag cga gta      240
Val Lys Trp Lys Gln Asp Ala Glu Phe Lys Val Asn Trp Lys Arg Val
 65              70                  75                  80 gct atc acg agc atg ttt gga ttt ggt ttt gtc gga cct gtt ggc cac      288
Ala Ile Thr Ser Met Phe Gly Phe Gly Phe Val Gly Pro Val Gly His
                     85                  90                  95 ttc tgg tac gaa ggc ttg gat aaa ttc ata aaa ctg aag ctt cga tat      336
Phe Trp Tyr Glu Gly Leu Asp Lys Phe Ile Lys Leu Lys Leu Arg Tyr
            100                 105                 110 gta cca aag tca aca cgt ttt gta gct gca aaa gtt gca atg gat ggt      384
Val Pro Lys Ser Thr Arg Phe Val Ala Ala Lys Val Ala Met Asp Gly
        115                 120                 125 ctt atc ttt gga cct gta gat cta ctg gtg ttc ttc aca tac atg gga      432
Leu Ile Phe Gly Pro Val Asp Leu Leu Val Phe Phe Thr Tyr Met Gly
130                 135                 140 ttc gcc aca gga aag aac aca gct gaa gtg aaa gaa gga ctc aag aga      480
Phe Ala Thr Gly Lys Asn Thr Ala Glu Val Lys Glu Gly Leu Lys Arg
145                 150                 155                 160 gat ttt ctt ccg gct cta gct ctt gaa ggc gga gca tgg cca ctt ctt      528
Asp Phe Leu Pro Ala Leu Ala Leu Glu Gly Gly Ala Trp Pro Leu Leu
                165                 170                 175 cag att gca aac ttc aga tat gtt ccc gtg caa tac cag ttg ctt tac      576
Gln Ile Ala Asn Phe Arg Tyr Val Pro Val Gln Tyr Gln Leu Leu Tyr
            180                 185                 190 gtc aac atc ttt tgc cta gta gac agt gcc ttc ctc tca tgg gtc gag      624
Val Asn Ile Phe Cys Leu Val Asp Ser Ala Phe Leu Ser Trp Val Glu
        195                 200                 205 caa cag aag gac gca gct tgg aag caa tgg ttt act tca tca ttt caa      672
Gln Gln Lys Asp Ala Ala Trp Lys Gln Trp Phe Thr Ser Ser Phe Gln
210                 215                 220 cca tta aaa gaa cga ggt ggc caa ggc gga gta tga                      708
Pro Leu Lys Glu Arg Gly Gly Gln Gly Gly Val
225                 230                 235

<210> SEQ ID NO 2
<211> LENGTH: 235
<212> TYPE: PRT
<213> ORGANISM: Arabidopsis thaliana

<400> SEQUENCE: 2

Met Leu Lys Leu Trp Arg Trp Tyr Gln Arg Cys Leu Thr Val His Pro
 1               5                  10                  15

Val Lys Thr Gln Val Ile Ser Ser Gly Phe Leu Trp Gly Phe Gly Asp
                20                  25                  30

Val Thr Ala Gln Tyr Ile Thr His Ser Thr Ala Lys Arg Arg Leu Leu
            35                  40                  45

Arg Leu Thr Glu Thr Asn Lys Asp Ala Asp Ala Asp Ala Glu Ile Lys
        50                  55                  60

Val Lys Trp Lys Gln Asp Ala Glu Phe Lys Val Asn Trp Lys Arg Val
 65              70                  75                  80

Ala Ile Thr Ser Met Phe Gly Phe Gly Phe Val Gly Pro Val Gly His
                     85                  90                  95

Phe Trp Tyr Glu Gly Leu Asp Lys Phe Ile Lys Leu Lys Leu Arg Tyr
            100                 105                 110

Val Pro Lys Ser Thr Arg Phe Val Ala Ala Lys Val Ala Met Asp Gly
        115                 120                 125

Leu Ile Phe Gly Pro Val Asp Leu Leu Val Phe Phe Thr Tyr Met Gly
130                 135                 140
```

```
Phe Ala Thr Gly Lys Asn Thr Ala Glu Val Lys Gly Leu Lys Arg
145                 150                 155                 160

Asp Phe Leu Pro Ala Leu Ala Leu Glu Gly Gly Ala Trp Pro Leu Leu
                165                 170                 175

Gln Ile Ala Asn Phe Arg Tyr Val Pro Val Gln Tyr Gln Leu Leu Tyr
            180                 185                 190

Val Asn Ile Phe Cys Leu Val Asp Ser Ala Phe Leu Ser Trp Val Glu
        195                 200                 205

Gln Gln Lys Asp Ala Ala Trp Lys Gln Trp Phe Thr Ser Ser Phe Gln
    210                 215                 220

Pro Leu Lys Glu Arg Gly Gly Gln Gly Gly Val
225                 230                 235

<210> SEQ ID NO 3
<211> LENGTH: 669
<212> TYPE: DNA
<213> ORGANISM: Oryza sativa
<220> FEATURE:
<221> NAME/KEY: CDS
<222> LOCATION: (1)..(669)

<400> SEQUENCE: 3
```

| | | | | | | | | | | | | | | | | |
|---|---|---|---|---|---|---|---|---|---|---|---|---|---|---|---|---|
| atg | cgg | cgg | cta | tgg | cgg | tgg | tac | cag | cag | tgc | ctg | gcc | acc | cac | ccc | 48 |
| Met | Arg | Arg | Leu | Trp | Arg | Trp | Tyr | Gln | Gln | Cys | Leu | Ala | Thr | His | Pro | |
| 1 | | | | 5 | | | | | 10 | | | | | 15 | | |
| gtg | cgc | acg | cag | gtg | gtc | agc | tcc | ggc | atc | ctc | tgg | ggc | ctc | ggc | gac | 96 |
| Val | Arg | Thr | Gln | Val | Val | Ser | Ser | Gly | Ile | Leu | Trp | Gly | Leu | Gly | Asp | |
| | | | 20 | | | | | 25 | | | | | 30 | | | |
| atc | ggc | gcc | cag | gcc | gtc | acc | cac | tac | tcc | gcc | ccc | gga | cgc | ccc | cgc | 144 |
| Ile | Gly | Ala | Gln | Ala | Val | Thr | His | Tyr | Ser | Ala | Pro | Gly | Arg | Pro | Arg | |
| | | 35 | | | | | 40 | | | | | 45 | | | | |
| cac | cag | cac | cac | gcc | aag | aat | cct | ccc | gag | gat | aaa | gat | aaa | gag | | 192 |
| His | Gln | His | His | Ala | Lys | Asn | Pro | Pro | Glu | Asp | Lys | Asp | Lys | Glu | | |
| | 50 | | | | | 55 | | | | | 60 | | | | | |
| ttc | aaa | att | gat | tgg | aag | agg | gtg | ggc | atc | aca | agc | tca | ttt | gga | ttt | 240 |
| Phe | Lys | Ile | Asp | Trp | Lys | Arg | Val | Gly | Ile | Thr | Ser | Ser | Phe | Gly | Phe | |
| 65 | | | | 70 | | | | | 75 | | | | | 80 | | |
| gct | ttt | gtt | gga | cca | gtt | gga | cat | tac | tgg | tat | gaa | tac | ttg | gat | cgc | 288 |
| Ala | Phe | Val | Gly | Pro | Val | Gly | His | Tyr | Trp | Tyr | Glu | Tyr | Leu | Asp | Arg | |
| | | | | 85 | | | | | 90 | | | | | 95 | | |
| ttc | atc | ctg | agg | aga | tac | cag | cct | aag | acc | ttc | aaa | ttt | gtt | gcg | tca | 336 |
| Phe | Ile | Leu | Arg | Arg | Tyr | Gln | Pro | Lys | Thr | Phe | Lys | Phe | Val | Ala | Ser | |
| | | | 100 | | | | | 105 | | | | | 110 | | | |
| aaa | gtt | gct | gcg | gat | ggt | ctc | cta | ttt | gga | cca | gta | gat | ctt | ctc | ttg | 384 |
| Lys | Val | Ala | Ala | Asp | Gly | Leu | Leu | Phe | Gly | Pro | Val | Asp | Leu | Leu | Leu | |
| | | 115 | | | | | 120 | | | | | 125 | | | | |
| ttc | ttc | tca | tat | gtt | ggt | ctt | gca | tca | gga | agg | agt | gta | gag | cag | gtg | 432 |
| Phe | Phe | Ser | Tyr | Val | Gly | Leu | Ala | Ser | Gly | Arg | Ser | Val | Glu | Gln | Val | |
| | 130 | | | | | 135 | | | | | 140 | | | | | |
| aag | gat | gat | gtg | aag | agg | gac | ttc | att | cct | gct | cta | gtt | cta | ggg | gga | 480 |
| Lys | Asp | Asp | Val | Lys | Arg | Asp | Phe | Ile | Pro | Ala | Leu | Val | Leu | Gly | Gly | |
| 145 | | | | 150 | | | | | 155 | | | | | 160 | | |
| acc | atc | tgg | cca | gcc | gtg | caa | atc | gca | aat | ttc | cgc | ttc | att | cct | gtg | 528 |
| Thr | Ile | Trp | Pro | Ala | Val | Gln | Ile | Ala | Asn | Phe | Arg | Phe | Ile | Pro | Val | |
| | | | | 165 | | | | | 170 | | | | | 175 | | |
| cga | tat | cag | ctc | ctt | tac | gtg | aac | ctg | ttc | tgc | ctc | tta | gac | agt | tgc | 576 |
| Arg | Tyr | Gln | Leu | Leu | Tyr | Val | Asn | Leu | Phe | Cys | Leu | Leu | Asp | Ser | Cys | |
| | | | 180 | | | | | 185 | | | | | 190 | | | |
| ttc | ttg | tcg | tgg | atc | gat | caa | caa | gga | gat | gca | cct | tgg | aag | caa | tgg | 624 |
| Phe | Leu | Ser | Trp | Ile | Asp | Gln | Gln | Gly | Asp | Ala | Pro | Trp | Lys | Gln | Trp | |

```
                195             200             205
ttc aca tca ttc cag aaa atc gaa ggc cag aag ggc aag gtt tga        669
Phe Thr Ser Phe Gln Lys Ile Glu Gly Gln Lys Gly Lys Val
    210             215             220
```

<210> SEQ ID NO 4
<211> LENGTH: 222
<212> TYPE: PRT
<213> ORGANISM: Oryza sativa

<400> SEQUENCE: 4

```
Met Arg Arg Leu Trp Arg Trp Tyr Gln Gln Cys Leu Ala Thr His Pro
1               5                   10                  15

Val Arg Thr Gln Val Val Ser Ser Gly Ile Leu Trp Gly Leu Gly Asp
            20                  25                  30

Ile Gly Ala Gln Ala Val Thr His Tyr Ser Ala Pro Gly Arg Pro Arg
        35                  40                  45

His His Gln His His Ala Lys Asn Pro Pro Glu Asp Lys Asp Lys Glu
    50                  55                  60

Phe Lys Ile Asp Trp Lys Arg Val Gly Ile Thr Ser Ser Phe Gly Phe
65                  70                  75                  80

Ala Phe Val Gly Pro Val Gly His Tyr Trp Tyr Glu Tyr Leu Asp Arg
                85                  90                  95

Phe Ile Leu Arg Arg Tyr Gln Pro Lys Thr Phe Lys Phe Val Ala Ser
            100                 105                 110

Lys Val Ala Ala Asp Gly Leu Leu Phe Gly Pro Val Asp Leu Leu Leu
        115                 120                 125

Phe Phe Ser Tyr Val Gly Leu Ala Ser Gly Arg Ser Val Glu Gln Val
    130                 135                 140

Lys Asp Asp Val Lys Arg Asp Phe Ile Pro Ala Leu Val Leu Gly Gly
145                 150                 155                 160

Thr Ile Trp Pro Ala Val Gln Ile Ala Asn Phe Arg Phe Ile Pro Val
                165                 170                 175

Arg Tyr Gln Leu Leu Tyr Val Asn Leu Phe Cys Leu Leu Asp Ser Cys
            180                 185                 190

Phe Leu Ser Trp Ile Asp Gln Gln Gly Asp Ala Pro Trp Lys Gln Trp
        195                 200                 205

Phe Thr Ser Phe Gln Lys Ile Glu Gly Gln Lys Gly Lys Val
    210                 215                 220
```

<210> SEQ ID NO 5
<211> LENGTH: 717
<212> TYPE: DNA
<213> ORGANISM: Brassica napus
<220> FEATURE:
<221> NAME/KEY: CDS
<222> LOCATION: (1)..(717)

<400> SEQUENCE: 5

```
atg ttg aag gtg tgg aga tgg tac cag cga tgc ctg agc gtt cat ccg        48
Met Leu Lys Val Trp Arg Trp Tyr Gln Arg Cys Leu Ser Val His Pro
1               5                   10                  15 gtg aaa act cag gtc ata agc tcg ggc ttt ctt tgg gga ttc ggg gac        96
Val Lys Thr Gln Val Ile Ser Ser Gly Phe Leu Trp Gly Phe Gly Asp
            20                  25                  30 gtc acc gct caa tac atc act cat tca act gcg aaa cct cct ctt ctc       144
Val Thr Ala Gln Tyr Ile Thr His Ser Thr Ala Lys Pro Pro Leu Leu
        35                  40                  45
```

```
cgt ctc acc gac aca aat aaa gat gca gac gct gat tca gaa ttt aag      192
Arg Leu Thr Asp Thr Asn Lys Asp Ala Asp Ala Asp Ser Glu Phe Lys
     50                  55                  60 ctc aac tgg aag cga gta gct atc act agc atg ttt gga ctt ggt ttt      240
Leu Asn Trp Lys Arg Val Ala Ile Thr Ser Met Phe Gly Leu Gly Phe
 65                  70                  75                  80 gtc ggt cct gtt ggc cac ttc tgg tac gaa ggc ctt gat aaa ttc ata      288
Val Gly Pro Val Gly His Phe Trp Tyr Glu Gly Leu Asp Lys Phe Ile
                     85                  90                  95 aaa ctg aag ctt cga tac gta cca aag tca acg cgt ttt gta gca gcc      336
Lys Leu Lys Leu Arg Tyr Val Pro Lys Ser Thr Arg Phe Val Ala Ala
                100                 105                 110 aaa gtt gca atg gat ggt ctt atc ttc ggc ccc ata gat cta ctc gtg      384
Lys Val Ala Met Asp Gly Leu Ile Phe Gly Pro Ile Asp Leu Leu Val
            115                 120                 125 ttc ttc acg tac atg gga tac gcc acg ggc aag aac aca tct caa gtg      432
Phe Phe Thr Tyr Met Gly Tyr Ala Thr Gly Lys Asn Thr Ser Gln Val
        130                 135                 140 aaa gaa gga ctc aag aga gac ttt cta ccg gct cta gct ctt gaa gga      480
Lys Glu Gly Leu Lys Arg Asp Phe Leu Pro Ala Leu Ala Leu Glu Gly
145                 150                 155                 160 gga gca tgg ccg ctt ctt cag atc gct aac ttc aga tac gtt cct gtg      528
Gly Ala Trp Pro Leu Leu Gln Ile Ala Asn Phe Arg Tyr Val Pro Val
                165                 170                 175 cag tac cag ctg ctt tac gtc aac atc ttt tgc ctt ata gac agc gct      576
Gln Tyr Gln Leu Leu Tyr Val Asn Ile Phe Cys Leu Ile Asp Ser Ala
                180                 185                 190 ttt ctc tcg tgg gtg gat caa cag aag gat gca gct tgg aag cag tgg      624
Phe Leu Ser Trp Val Asp Gln Gln Lys Asp Ala Ala Trp Lys Gln Trp
            195                 200                 205 ttt act act ccg ttt cta acg ctt aaa gaa cga ggt gcg cac agg tgg      672
Phe Thr Thr Pro Phe Leu Thr Leu Lys Glu Arg Gly Ala His Arg Trp
        210                 215                 220 agt atg att cat ttc gtt ttt ctc aca tgt cat aaa aac ttt gaa          717
Ser Met Ile His Phe Val Phe Leu Thr Cys His Lys Asn Phe Glu
225                 230                 235

<210> SEQ ID NO 6
<211> LENGTH: 239
<212> TYPE: PRT
<213> ORGANISM: Brassica napus

<400> SEQUENCE: 6

Met Leu Lys Val Trp Arg Trp Tyr Gln Arg Cys Leu Ser Val His Pro
 1                   5                  10                  15

Val Lys Thr Gln Val Ile Ser Ser Gly Phe Leu Trp Gly Phe Gly Asp
                20                  25                  30

Val Thr Ala Gln Tyr Ile Thr His Ser Thr Ala Lys Pro Pro Leu Leu
            35                  40                  45

Arg Leu Thr Asp Thr Asn Lys Asp Ala Asp Ala Asp Ser Glu Phe Lys
     50                  55                  60

Leu Asn Trp Lys Arg Val Ala Ile Thr Ser Met Phe Gly Leu Gly Phe
 65                  70                  75                  80

Val Gly Pro Val Gly His Phe Trp Tyr Glu Gly Leu Asp Lys Phe Ile
                     85                  90                  95

Lys Leu Lys Leu Arg Tyr Val Pro Lys Ser Thr Arg Phe Val Ala Ala
                100                 105                 110

Lys Val Ala Met Asp Gly Leu Ile Phe Gly Pro Ile Asp Leu Leu Val
            115                 120                 125
```

```
Phe Phe Thr Tyr Met Gly Tyr Ala Thr Gly Lys Asn Thr Ser Gln Val
    130                 135                 140

Lys Glu Gly Leu Lys Arg Asp Phe Leu Pro Ala Leu Ala Leu Glu Gly
145                 150                 155                 160

Gly Ala Trp Pro Leu Leu Gln Ile Ala Asn Phe Arg Tyr Val Pro Val
                165                 170                 175

Gln Tyr Gln Leu Leu Tyr Val Asn Ile Phe Cys Leu Ile Asp Ser Ala
            180                 185                 190

Phe Leu Ser Trp Val Asp Gln Gln Lys Asp Ala Ala Trp Lys Gln Trp
        195                 200                 205

Phe Thr Thr Pro Phe Leu Thr Leu Lys Glu Arg Gly Ala His Arg Trp
    210                 215                 220

Ser Met Ile His Phe Val Phe Leu Thr Cys His Lys Asn Phe Glu
225                 230                 235
```

<210> SEQ ID NO 7
<211> LENGTH: 630
<212> TYPE: DNA
<213> ORGANISM: Glycine max
<220> FEATURE:
<221> NAME/KEY: CDS
<222> LOCATION: (1)..(630)

<400> SEQUENCE: 7

```
atg ctg agg ttg tgg aaa tgg tac cag aat tgc ttg gcg gtt cac cct    48
Met Leu Arg Leu Trp Lys Trp Tyr Gln Asn Cys Leu Ala Val His Pro
1               5                   10                  15 gtt aag aca cag gtc atc agc tct ggc ttg att tgg ggt gct ggt gac    96
Val Lys Thr Gln Val Ile Ser Ser Gly Leu Ile Trp Gly Ala Gly Asp
            20                  25                  30 ata gct gct cag gca gtt acc cac tac act gcc aag aaa cgt gtc act   144
Ile Ala Ala Gln Ala Val Thr His Tyr Thr Ala Lys Lys Arg Val Thr
        35                  40                  45 ttt gat gcg gat gac act aaa gaa ttc aag atc aac tgg aga cgg gtg   192
Phe Asp Ala Asp Asp Thr Lys Glu Phe Lys Ile Asn Trp Arg Arg Val
    50                  55                  60 tct acg acc agc ttg ttt ggg tta gga ttt gtt ggc cct gtt ggc cac   240
Ser Thr Thr Ser Leu Phe Gly Leu Gly Phe Val Gly Pro Val Gly His
65                  70                  75                  80 ttc tgg tac gaa ggt ttg gat cgg ttt ata aga ctg aaa ctc atg ctt   288
Phe Trp Tyr Glu Gly Leu Asp Arg Phe Ile Arg Leu Lys Leu Met Leu
                85                  90                  95 aaa ccg aat tcc ttc cgc ttt gtt gcc act aaa gtt gcc gtt gat ggg   336
Lys Pro Asn Ser Phe Arg Phe Val Ala Thr Lys Val Ala Val Asp Gly
            100                 105                 110 ttt atc ttt gga cca ttg gat tta ctt gtg ttt ttc act tat atg ggt   384
Phe Ile Phe Gly Pro Leu Asp Leu Leu Val Phe Phe Thr Tyr Met Gly
        115                 120                 125 ttt tct gct gga aag agt gtt cct caa gta aaa gaa gat gtg aag aga   432
Phe Ser Ala Gly Lys Ser Val Pro Gln Val Lys Glu Asp Val Lys Arg
    130                 135                 140 gat ttt ctc cca gcc ttt gtt tta gaa ggg ggc ata tgg cca att gtt   480
Asp Phe Leu Pro Ala Phe Val Leu Glu Gly Gly Ile Trp Pro Ile Val
145                 150                 155                 160 cag gtt gcg aac ttt cgg ttt ata cct gtg agg tat caa ctc ctt tat   528
Gln Val Ala Asn Phe Arg Phe Ile Pro Val Arg Tyr Gln Leu Leu Tyr
                165                 170                 175 gtc aac ttc ttc tgc ttg ttg gat agc tgt ttc ttg tct tgg gtt gag   576
Val Asn Phe Phe Cys Leu Leu Asp Ser Cys Phe Leu Ser Trp Val Glu
```

-continued

```
                180                 185                 190
caa caa cag gat gct cca tgg aaa caa tgg ttg aaa tca ttt cta cct    624
Gln Gln Gln Asp Ala Pro Trp Lys Gln Trp Leu Lys Ser Phe Leu Pro
        195                 200                 205 atg aag                                                            630
Met Lys
    210
```

<210> SEQ ID NO 8
<211> LENGTH: 210
<212> TYPE: PRT
<213> ORGANISM: Glycine max

<400> SEQUENCE: 8

```
Met Leu Arg Leu Trp Lys Trp Tyr Gln Asn Cys Leu Ala Val His Pro
1               5                   10                  15

Val Lys Thr Gln Val Ile Ser Ser Gly Leu Ile Trp Gly Ala Gly Asp
            20                  25                  30

Ile Ala Ala Gln Ala Val Thr His Tyr Thr Ala Lys Lys Arg Val Thr
        35                  40                  45

Phe Asp Ala Asp Asp Thr Lys Glu Phe Lys Ile Asn Trp Arg Arg Val
    50                  55                  60

Ser Thr Thr Ser Leu Phe Gly Leu Gly Phe Val Gly Pro Val Gly His
65                  70                  75                  80

Phe Trp Tyr Glu Gly Leu Asp Arg Phe Ile Arg Leu Lys Leu Met Leu
                85                  90                  95

Lys Pro Asn Ser Phe Arg Phe Val Ala Thr Lys Val Ala Val Asp Gly
            100                 105                 110

Phe Ile Phe Gly Pro Leu Asp Leu Leu Val Phe Phe Thr Tyr Met Gly
        115                 120                 125

Phe Ser Ala Gly Lys Ser Val Pro Gln Val Lys Glu Asp Val Lys Arg
    130                 135                 140

Asp Phe Leu Pro Ala Phe Val Leu Glu Gly Gly Ile Trp Pro Ile Val
145                 150                 155                 160

Gln Val Ala Asn Phe Arg Phe Ile Pro Val Arg Tyr Gln Leu Leu Tyr
                165                 170                 175

Val Asn Phe Phe Cys Leu Leu Asp Ser Cys Phe Leu Ser Trp Val Glu
            180                 185                 190

Gln Gln Gln Asp Ala Pro Trp Lys Gln Trp Leu Lys Ser Phe Leu Pro
        195                 200                 205

Met Lys
    210
```

<210> SEQ ID NO 9
<211> LENGTH: 666
<212> TYPE: DNA
<213> ORGANISM: Oryza sativa
<220> FEATURE:
<221> NAME/KEY: CDS
<222> LOCATION: (1)..(666)

<400> SEQUENCE: 9

```
atg cgg cgg cta tgg cgg tgg tac cag cag tgc ctg gcc acc cac ccc    48
Met Arg Arg Leu Trp Arg Trp Tyr Gln Gln Cys Leu Ala Thr His Pro
1               5                   10                  15 gtg cgc acg cag gtg gtc agc tcc ggc atc ctc tgg ggc ctc ggc gac    96
Val Arg Thr Gln Val Val Ser Ser Gly Ile Leu Trp Gly Leu Gly Asp
            20                  25                  30
```

```
atc ggc gcc cag gcc gtc acc cac tac tcc gcc ccc gga cgc ccc cgc       144
Ile Gly Ala Gln Ala Val Thr His Tyr Ser Ala Pro Gly Arg Pro Arg
        35                  40                  45 cac cac cag cac cac gcc aag aat cct ccc gag gat aaa gat aaa gag       192
His His Gln His His Ala Lys Asn Pro Pro Glu Asp Lys Asp Lys Glu
    50                  55                  60 ttc aaa att gat tgg aag agg gtg ggc atc aca agc tca ttt gga ttt       240
Phe Lys Ile Asp Trp Lys Arg Val Gly Ile Thr Ser Ser Phe Gly Phe
65                  70                  75                  80 gct ttt gtt gga cca gtt gga cat tac tgg tat gaa tac ttg gat cgc       288
Ala Phe Val Gly Pro Val Gly His Tyr Trp Tyr Glu Tyr Leu Asp Arg
                85                  90                  95 ttc atc ctg agg aga tac cag cct aag acc ttc aaa ttt gtt gcg tca       336
Phe Ile Leu Arg Arg Tyr Gln Pro Lys Thr Phe Lys Phe Val Ala Ser
            100                 105                 110 aaa gtt gct gcg gat ggt ctc cta ttt gga cca gta gat ctt ctc ttg       384
Lys Val Ala Ala Asp Gly Leu Leu Phe Gly Pro Val Asp Leu Leu Leu
        115                 120                 125 ttc ttc tca tat gtt ggt ctt gca tca gga agg agt gta gag cag gtg       432
Phe Phe Ser Tyr Val Gly Leu Ala Ser Gly Arg Ser Val Glu Gln Val
    130                 135                 140 aag gat gat gtg aag agg gac ttc att cct gct cta gtt cta ggg gga       480
Lys Asp Asp Val Lys Arg Asp Phe Ile Pro Ala Leu Val Leu Gly Gly
145                 150                 155                 160 acc atc tgg cca gcc gtg caa atc gca aat ttc cgc ttc att cct gtg       528
Thr Ile Trp Pro Ala Val Gln Ile Ala Asn Phe Arg Phe Ile Pro Val
                165                 170                 175 cga tat cag ctc ctt tac gtg aac ctg ttc tgc ctc tta gac agt tgc       576
Arg Tyr Gln Leu Leu Tyr Val Asn Leu Phe Cys Leu Leu Asp Ser Cys
            180                 185                 190 ttc ttg tcg tgg atc gat caa caa gga gat gca cct tgg aag caa tgg       624
Phe Leu Ser Trp Ile Asp Gln Gln Gly Asp Ala Pro Trp Lys Gln Trp
        195                 200                 205 ttc aca tca ttc cag aaa atc gaa ggc cag aag ggc aag gtt               666
Phe Thr Ser Phe Gln Lys Ile Glu Gly Gln Lys Gly Lys Val
    210                 215                 220
```

<210> SEQ ID NO 10
<211> LENGTH: 222
<212> TYPE: PRT
<213> ORGANISM: Oryza sativa

<400> SEQUENCE: 10

```
Met Arg Arg Leu Trp Arg Trp Tyr Gln Gln Cys Leu Ala Thr His Pro
1               5                   10                  15

Val Arg Thr Gln Val Val Ser Ser Gly Ile Leu Trp Gly Leu Gly Asp
            20                  25                  30

Ile Gly Ala Gln Ala Val Thr His Tyr Ser Ala Pro Gly Arg Pro Arg
        35                  40                  45

His His Gln His His Ala Lys Asn Pro Pro Glu Asp Lys Asp Lys Glu
    50                  55                  60

Phe Lys Ile Asp Trp Lys Arg Val Gly Ile Thr Ser Ser Phe Gly Phe
65                  70                  75                  80

Ala Phe Val Gly Pro Val Gly His Tyr Trp Tyr Glu Tyr Leu Asp Arg
                85                  90                  95

Phe Ile Leu Arg Arg Tyr Gln Pro Lys Thr Phe Lys Phe Val Ala Ser
            100                 105                 110

Lys Val Ala Ala Asp Gly Leu Leu Phe Gly Pro Val Asp Leu Leu Leu
        115                 120                 125
```

```
Phe Phe Ser Tyr Val Gly Leu Ala Ser Gly Arg Ser Val Glu Gln Val
        130                 135                 140

Lys Asp Asp Val Lys Arg Asp Phe Ile Pro Ala Leu Val Leu Gly Gly
145                 150                 155                 160

Thr Ile Trp Pro Ala Val Gln Ile Ala Asn Phe Arg Phe Ile Pro Val
                165                 170                 175

Arg Tyr Gln Leu Leu Tyr Val Asn Leu Phe Cys Leu Leu Asp Ser Cys
                180                 185                 190

Phe Leu Ser Trp Ile Asp Gln Gln Gly Asp Ala Pro Trp Lys Gln Trp
            195                 200                 205

Phe Thr Ser Phe Gln Lys Ile Glu Gly Gln Lys Gly Lys Val
        210                 215                 220

<210> SEQ ID NO 11
<211> LENGTH: 594
<212> TYPE: DNA
<213> ORGANISM: Saccharomyces cerevisiae
<220> FEATURE:
<221> NAME/KEY: CDS
<222> LOCATION: (1)..(594)

<400> SEQUENCE: 11 atg aag tta ttg cat tta tat gaa gcg agc ttg aag aga agg ccc aaa      48
Met Lys Leu Leu His Leu Tyr Glu Ala Ser Leu Lys Arg Arg Pro Lys
1               5                   10                  15 act acg aat gcg ata atg aca ggt gcg cta ttt gga att ggt gat gtt      96
Thr Thr Asn Ala Ile Met Thr Gly Ala Leu Phe Gly Ile Gly Asp Val
            20                  25                  30 tct gct caa ttg ttg ttt cca aca tcc aaa gta aac aag ggt tat gat    144
Ser Ala Gln Leu Leu Phe Pro Thr Ser Lys Val Asn Lys Gly Tyr Asp
        35                  40                  45 tat aaa agg aca gct agg gct gtc atc tat ggt tct tta att ttc tcc    192
Tyr Lys Arg Thr Ala Arg Ala Val Ile Tyr Gly Ser Leu Ile Phe Ser
    50                  55                  60 ttt ata ggt gac aag tgg tac aag atc ttg aac aac aag att tat atg    240
Phe Ile Gly Asp Lys Trp Tyr Lys Ile Leu Asn Asn Lys Ile Tyr Met
65                  70                  75                  80 cgt aac aga cct cag tac cac tgg tct aat atg gtt tta cgg gta gct    288
Arg Asn Arg Pro Gln Tyr His Trp Ser Asn Met Val Leu Arg Val Ala
                85                  90                  95 gtc gat caa ttg gcg ttt gcg ccg cta ggt ttg cca ttt tat ttc acc    336
Val Asp Gln Leu Ala Phe Ala Pro Leu Gly Leu Pro Phe Tyr Phe Thr
            100                 105                 110 tgt atg tcc atc atg gaa ggt aga tca ttt gac gta gct aag ttg aaa    384
Cys Met Ser Ile Met Glu Gly Arg Ser Phe Asp Val Ala Lys Leu Lys
        115                 120                 125 ata aaa gag caa tgg tgg cct aca ctt ttg act aat tgg gca gtt tgg    432
Ile Lys Glu Gln Trp Trp Pro Thr Leu Leu Thr Asn Trp Ala Val Trp
130                 135                 140 cca ctt ttc caa gcg att aac ttt tct gtt gtt cct tta caa cat agg    480
Pro Leu Phe Gln Ala Ile Asn Phe Ser Val Val Pro Leu Gln His Arg
145                 150                 155                 160 tta cta gct gtt aat gtc gtt gca ata ttt tgg aac act tac tta tct    528
Leu Leu Ala Val Asn Val Val Ala Ile Phe Trp Asn Thr Tyr Leu Ser
                165                 170                 175 tat aaa aac tca aag gtt atg gag aaa gac aag gta cct gtt cat tat    576
Tyr Lys Asn Ser Lys Val Met Glu Lys Asp Lys Val Pro Val His Tyr
            180                 185                 190 cca ccc gtg gtc gaa taa                                            594
```

Pro Pro Val Val Glu
        195

<210> SEQ ID NO 12
<211> LENGTH: 197
<212> TYPE: PRT
<213> ORGANISM: Saccharomyces cerevisiae

<400> SEQUENCE: 12

Met Lys Leu Leu His Leu Tyr Glu Ala Ser Leu Lys Arg Arg Pro Lys
1               5                   10                  15

Thr Thr Asn Ala Ile Met Thr Gly Ala Leu Phe Gly Ile Gly Asp Val
            20                  25                  30

Ser Ala Gln Leu Leu Phe Pro Thr Ser Lys Val Asn Lys Gly Tyr Asp
        35                  40                  45

Tyr Lys Arg Thr Ala Arg Ala Val Ile Tyr Gly Ser Leu Ile Phe Ser
    50                  55                  60

Phe Ile Gly Asp Lys Trp Tyr Lys Ile Leu Asn Asn Lys Ile Tyr Met
65                  70                  75                  80

Arg Asn Arg Pro Gln Tyr His Trp Ser Asn Met Val Leu Arg Val Ala
                85                  90                  95

Val Asp Gln Leu Ala Phe Ala Pro Leu Gly Leu Pro Phe Tyr Phe Thr
            100                 105                 110

Cys Met Ser Ile Met Glu Gly Arg Ser Phe Asp Val Ala Lys Leu Lys
        115                 120                 125

Ile Lys Glu Gln Trp Trp Pro Thr Leu Leu Thr Asn Trp Ala Val Trp
    130                 135                 140

Pro Leu Phe Gln Ala Ile Asn Phe Ser Val Val Pro Leu Gln His Arg
145                 150                 155                 160

Leu Leu Ala Val Asn Val Val Ala Ile Phe Trp Asn Thr Tyr Leu Ser
                165                 170                 175

Tyr Lys Asn Ser Lys Val Met Glu Lys Asp Lys Val Pro Val His Tyr
            180                 185                 190

Pro Pro Val Val Glu
        195

<210> SEQ ID NO 13
<211> LENGTH: 531
<212> TYPE: DNA
<213> ORGANISM: Human
<220> FEATURE:
<221> NAME/KEY: CDS
<222> LOCATION: (1)..(531)

<400> SEQUENCE: 13 atg gca ctc tgg cgg gca tac cag cgg gcc ctg gcc gct cac ccg tgg      48
Met Ala Leu Trp Arg Ala Tyr Gln Arg Ala Leu Ala Ala His Pro Trp
1               5                   10                  15 aaa gta cag gtc ctg aca gct ggg tcc ctg atg ggc ctg ggt gac att      96
Lys Val Gln Val Leu Thr Ala Gly Ser Leu Met Gly Leu Gly Asp Ile
            20                  25                  30 atc tca cag cag ctg gtg gag agg cgg ggt ctg cag gaa cac cag aga     144
Ile Ser Gln Gln Leu Val Glu Arg Arg Gly Leu Gln Glu His Gln Arg
        35                  40                  45 ggc cgg act ctg acc atg gtg tcc ctg ggc tgt ggc ttt gtg ggc cct     192
Gly Arg Thr Leu Thr Met Val Ser Leu Gly Cys Gly Phe Val Gly Pro
    50                  55                  60 gtg gta gga ggc tgg tac aag gtt ttg gat cgg ttc atc cct ggc acc     240
Val Val Gly Gly Trp Tyr Lys Val Leu Asp Arg Phe Ile Pro Gly Thr

```
                65                  70                  75                  80
acc aaa gtg gat gca ctg aag aag atg ttg ttg gat cag ggg ggc ttt        288
Thr Lys Val Asp Ala Leu Lys Lys Met Leu Leu Asp Gln Gly Gly Phe
                85                  90                  95 gcc ccg tgt ttt cta ggc tgc ttt ctc cca ctg gta ggg gca ctt aat        336
Ala Pro Cys Phe Leu Gly Cys Phe Leu Pro Leu Val Gly Ala Leu Asn
            100                 105                 110 gga ctg tca gcc cag gac aac tgg gcc aaa cta cag cgg gat tat cct        384
Gly Leu Ser Ala Gln Asp Asn Trp Ala Lys Leu Gln Arg Asp Tyr Pro
        115                 120                 125 gat gcc ctt atc acc aac tac tat cta tgg cct gct gtg cag tta gcc        432
Asp Ala Leu Ile Thr Asn Tyr Tyr Leu Trp Pro Ala Val Gln Leu Ala
    130                 135                 140 aac ttc tac ctg gtc ccc ctt cat tac agg ttg gcc gtt gtc caa tgt        480
Asn Phe Tyr Leu Val Pro Leu His Tyr Arg Leu Ala Val Val Gln Cys
145                 150                 155                 160 gtt gct gtt atc tgg aac tcc tac ctg tcc tgg aag gca cat cgg ctc        528
Val Ala Val Ile Trp Asn Ser Tyr Leu Ser Trp Lys Ala His Arg Leu
                165                 170                 175 taa                                                                    531
```

<210> SEQ ID NO 14
<211> LENGTH: 176
<212> TYPE: PRT
<213> ORGANISM: Human

<400> SEQUENCE: 14

```
Met Ala Leu Trp Arg Ala Tyr Gln Arg Ala Leu Ala Ala His Pro Trp
1               5                   10                  15

Lys Val Gln Val Leu Thr Ala Gly Ser Leu Met Gly Leu Gly Asp Ile
            20                  25                  30

Ile Ser Gln Gln Leu Val Glu Arg Arg Gly Leu Gln Glu His Gln Arg
        35                  40                  45

Gly Arg Thr Leu Thr Met Val Ser Leu Gly Cys Gly Phe Val Gly Pro
    50                  55                  60

Val Val Gly Gly Trp Tyr Lys Val Leu Asp Arg Phe Ile Pro Gly Thr
65                  70                  75                  80

Thr Lys Val Asp Ala Leu Lys Lys Met Leu Leu Asp Gln Gly Gly Phe
                85                  90                  95

Ala Pro Cys Phe Leu Gly Cys Phe Leu Pro Leu Val Gly Ala Leu Asn
            100                 105                 110

Gly Leu Ser Ala Gln Asp Asn Trp Ala Lys Leu Gln Arg Asp Tyr Pro
        115                 120                 125

Asp Ala Leu Ile Thr Asn Tyr Tyr Leu Trp Pro Ala Val Gln Leu Ala
    130                 135                 140

Asn Phe Tyr Leu Val Pro Leu His Tyr Arg Leu Ala Val Val Gln Cys
145                 150                 155                 160

Val Ala Val Ile Trp Asn Ser Tyr Leu Ser Trp Lys Ala His Arg Leu
                165                 170                 175
```

<210> SEQ ID NO 15
<211> LENGTH: 531
<212> TYPE: DNA
<213> ORGANISM: Mus musculus;
<220> FEATURE:
<221> NAME/KEY: CDS
<222> LOCATION: (1)..(531)

<400> SEQUENCE: 15

```
atg gca ctc tgg cga gca tac cag aga gcc ctg gca gca cat ccg tgg      48
Met Ala Leu Trp Arg Ala Tyr Gln Arg Ala Leu Ala Ala His Pro Trp
1               5                   10                  15 aaa gtc cag gtt ctg aca gct gga tca ctg atg ggc gta ggt gac atg      96
Lys Val Gln Val Leu Thr Ala Gly Ser Leu Met Gly Val Gly Asp Met
                20                  25                  30 atc tca cag cag ctg gtg gag agg cgg ggt ctc cag caa cac cag gca     144
Ile Ser Gln Gln Leu Val Glu Arg Arg Gly Leu Gln Gln His Gln Ala
            35                  40                  45 ggc cgc act ctg acc atg gta tcc ctg ggc tgt ggc ttt gtg ggc cct     192
Gly Arg Thr Leu Thr Met Val Ser Leu Gly Cys Gly Phe Val Gly Pro
        50                  55                  60 gtc gtc gga ggc tgg tac aaa gtt tta gac cac tta atc ccg ggc acc     240
Val Val Gly Gly Trp Tyr Lys Val Leu Asp His Leu Ile Pro Gly Thr
65                  70                  75                  80 acg aag gtg cat gca ctg aag aag atg ttg tta gat cag ggg ggc ttt     288
Thr Lys Val His Ala Leu Lys Lys Met Leu Leu Asp Gln Gly Gly Phe
                85                  90                  95 gcc cca tgt ttc cta ggc tgc ttt ctc cca ctg gtc ggg ata ctc aat     336
Ala Pro Cys Phe Leu Gly Cys Phe Leu Pro Leu Val Gly Ile Leu Asn
            100                 105                 110 gga atg tca gcc cag gac aat tgg gcc aaa ctg aag cgg gac tac cct     384
Gly Met Ser Ala Gln Asp Asn Trp Ala Lys Leu Lys Arg Asp Tyr Pro
        115                 120                 125 gat gcc ctc atc acc aac tac tat ctc tgg cct gct gtg cag tta gcc     432
Asp Ala Leu Ile Thr Asn Tyr Tyr Leu Trp Pro Ala Val Gln Leu Ala
    130                 135                 140 aac ttc tac ctg gtc ccc ctg cat tac agg ttg gct gtt gtc cag tgt     480
Asn Phe Tyr Leu Val Pro Leu His Tyr Arg Leu Ala Val Val Gln Cys
145                 150                 155                 160 gtt gct att gtc tgg aac tcc tac cta tcc tgg aag gca cat cag ttc     528
Val Ala Ile Val Trp Asn Ser Tyr Leu Ser Trp Lys Ala His Gln Phe
                165                 170                 175 taa                                                                  531

<210> SEQ ID NO 16
<211> LENGTH: 176
<212> TYPE: PRT
<213> ORGANISM: Mus musculus

<400> SEQUENCE: 16

Met Ala Leu Trp Arg Ala Tyr Gln Arg Ala Leu Ala Ala His Pro Trp
1               5                   10                  15

Lys Val Gln Val Leu Thr Ala Gly Ser Leu Met Gly Val Gly Asp Met
                20                  25                  30

Ile Ser Gln Gln Leu Val Glu Arg Arg Gly Leu Gln Gln His Gln Ala
            35                  40                  45

Gly Arg Thr Leu Thr Met Val Ser Leu Gly Cys Gly Phe Val Gly Pro
        50                  55                  60

Val Val Gly Gly Trp Tyr Lys Val Leu Asp His Leu Ile Pro Gly Thr
65                  70                  75                  80

Thr Lys Val His Ala Leu Lys Lys Met Leu Leu Asp Gln Gly Gly Phe
                85                  90                  95

Ala Pro Cys Phe Leu Gly Cys Phe Leu Pro Leu Val Gly Ile Leu Asn
            100                 105                 110

Gly Met Ser Ala Gln Asp Asn Trp Ala Lys Leu Lys Arg Asp Tyr Pro
        115                 120                 125
```

```
Asp Ala Leu Ile Thr Asn Tyr Tyr Leu Trp Pro Ala Val Gln Leu Ala
    130                 135                 140

Asn Phe Tyr Leu Val Pro Leu His Tyr Arg Leu Ala Val Val Gln Cys
145                 150                 155                 160

Val Ala Ile Val Trp Asn Ser Tyr Leu Ser Trp Lys Ala His Gln Phe
                165                 170                 175
```

```
<210> SEQ ID NO 17
<211> LENGTH: 46
<212> TYPE: DNA
<213> ORGANISM: Saccharomyces cerevisiae
<220> FEATURE:
<221> NAME/KEY: misc_feature
<222> LOCATION: (1)..(46)
<223> OTHER INFORMATION: PCR primer

<400> SEQUENCE: 17
ggaattccag ctgaccacca tgaagttatt gcatttatat gaagcg                46

<210> SEQ ID NO 18
<211> LENGTH: 44
<212> TYPE: DNA
<213> ORGANISM: Saccharomyces cerevisiae
<220> FEATURE:
<221> NAME/KEY: misc_feature
<222> LOCATION: (1)..(44)
<223> OTHER INFORMATION: PCR primer

<400> SEQUENCE: 18
gatccccggg aattgccatg ttattcgacc acgggtggat aatg                  44

<210> SEQ ID NO 19
<211> LENGTH: 34
<212> TYPE: DNA
<213> ORGANISM: Arabidopsis thaliana
<220> FEATURE:
<221> NAME/KEY: misc_feature
<222> LOCATION: (1)..(34)
<223> OTHER INFORMATION: PCR primer

<400> SEQUENCE: 19
atacccggga aacaatgttg aagctttgga gatg                             34

<210> SEQ ID NO 20
<211> LENGTH: 29
<212> TYPE: DNA
<213> ORGANISM: Arabidopsis thaliana
<220> FEATURE:
<221> NAME/KEY: misc_feature
<222> LOCATION: (1)..(29)
<223> OTHER INFORMATION: PCR primer

<400> SEQUENCE: 20
atagagctct catactccgc cttggccac                                   29

<210> SEQ ID NO 21
<211> LENGTH: 23
<212> TYPE: DNA
<213> ORGANISM: Arabidopsis thaliana
<220> FEATURE:
<221> NAME/KEY: misc_feature
<222> LOCATION: (1)..(23)
<223> OTHER INFORMATION: PCR primer

<400> SEQUENCE: 21
cgccttggcc acctcgttct ttt                                         23
```

```
<210> SEQ ID NO 22
<211> LENGTH: 25
<212> TYPE: DNA
<213> ORGANISM: Arabidopsis thaliana
<220> FEATURE:
<221> NAME/KEY: misc_feature
<222> LOCATION: (1)..(23)
<223> OTHER INFORMATION: PCR primer

<400> SEQUENCE: 22
gctgcaaaag ttgcaatgga tggtc                                          25

<210> SEQ ID NO 23
<211> LENGTH: 828
<212> TYPE: DNA
<213> ORGANISM: Arabidopsis thaliana

<400> SEQUENCE: 23
tttttttttt tttttttttt ttaattctaa cagacattta ttcacttgta ctgaattctc     60
gtgaaacgaa ataatatttg atcaagaatc tgtatcctag gcaactttcg ttgttgaaaa    120
tcgccaatta cactcgtttt tgttttcatt caaagtttat gacagggaaa acgatcatac    180
tccgccttgg cctcctcgtt cttttaatgg ttgaaatgat gaagtaaacc attgcttcca    240
agctgcgtcc ttctgttgct cgacccatga gaggaaggca ctgtctacta ggcaaaagat    300
gttgacgtaa agcaactggt attgcacggg aacatatctg aagtttgcaa tctgaagaag    360
tggccatgct ccgccttcaa gagctagagc cggaagaaaa tctctcttga gtccttcttt    420
cacttcagct gtgttctttc ctgtggcgaa tcccatgtat gtgaagaaca ccagtagatc    480
tacaggtcca aagataagac catccattgc aacttttgca gctacaaaac gtgttgactt    540
tggtacatat cgaagcttca gttttatgaa tttatccaag ccttcgtacc aaaagtggcc    600
aacaggtccg acaaaaccaa atccaaacat gctcgtgata gctactcgct tccagttgac    660
tttgaattct gcatctcgct tccagttgac cttgaattct gcatctgcgt caacatcttt    720
attcgtttcg gtgagacgaa gaagacgacg tttcgcagtg gaatgagtga tgtattgagc    780
ggtgacatcg ccaaatcccc aaagaaatcc agaactgcgg acgcgtgg                 828

<210> SEQ ID NO 24
<211> LENGTH: 708
<212> TYPE: DNA
<213> ORGANISM: Arabidopsis thaliana
<220> FEATURE:
<221> NAME/KEY: CDS
<222> LOCATION: (1)..(708)

<400> SEQUENCE: 24 atg ttg aag ctt tgg aga tgg tac cag cga tgc ctg acg gtt cat cct      48
Met Leu Lys Leu Trp Arg Trp Tyr Gln Arg Cys Leu Thr Val His Pro
1               5                  10                  15 gtg aaa act cag gtc atc agt tct gga ttt ctt tgg gga ttt ggc gat      96
Val Lys Thr Gln Val Ile Ser Ser Gly Phe Leu Trp Gly Phe Gly Asp
            20                  25                  30 gtc acc gct caa tac atc act cat tcc act gcg aaa cgt cgt ctt ctt     144
Val Thr Ala Gln Tyr Ile Thr His Ser Thr Ala Lys Arg Arg Leu Leu
        35                  40                  45 cgt ctc acc gaa aca aat aaa gat gct gac gca gat gca gaa att aag     192
Arg Leu Thr Glu Thr Asn Lys Asp Ala Asp Ala Asp Ala Glu Ile Lys
    50                  55                  60 gtc aag tgg aag caa gat gca gaa ttc aaa gtc aac tgg aag cga gta     240
Val Lys Trp Lys Gln Asp Ala Glu Phe Lys Val Asn Trp Lys Arg Val
```

```
                    65                  70                  75                  80
gct atc acg agc atg ttt gga ttt ggt ttt gtc gga cct gtt ggc cac                288
Ala Ile Thr Ser Met Phe Gly Phe Gly Phe Val Gly Pro Val Gly His
                    85                  90                  95 ttc tgg tac gaa ggc ttg gat aaa ttc ata aaa ctg aag cct cga tat                336
Phe Trp Tyr Glu Gly Leu Asp Lys Phe Ile Lys Leu Lys Pro Arg Tyr
                100                 105                 110 gta cca aag tca aca cgt ttt gta tct gca aaa gtt gca atg gat ggt                384
Val Pro Lys Ser Thr Arg Phe Val Ser Ala Lys Val Ala Met Asp Gly
            115                 120                 125 ctt atc ttt gga cct gta gat cta ctg gtg ttc ttc aca tac atg gga                432
Leu Ile Phe Gly Pro Val Asp Leu Leu Val Phe Phe Thr Tyr Met Gly
        130                 135                 140 ttc gcc aca gga aag aac aca gct gaa gtg aaa gaa gga ctc aag aga                480
Phe Ala Thr Gly Lys Asn Thr Ala Glu Val Lys Glu Gly Leu Lys Arg
145                 150                 155                 160 gat ttt ctt ccg gct cta gct ctt gaa ggc gga gca tgg cca ctt ctt                528
Asp Phe Leu Pro Ala Leu Ala Leu Glu Gly Gly Ala Trp Pro Leu Leu
                165                 170                 175 cag att gca aac ttc aga tat gtt ccc gtg caa tac cag ttg ctt tac                576
Gln Ile Ala Asn Phe Arg Tyr Val Pro Val Gln Tyr Gln Leu Leu Tyr
                180                 185                 190 gtc aac atc ttt tgc cta gta gac agt gcc ttc ctc tca tgg gtc gag                624
Val Asn Ile Phe Cys Leu Val Asp Ser Ala Phe Leu Ser Trp Val Glu
            195                 200                 205 caa cag aag gac gca gct tgg aag caa tgg ttt act tca tca ttt caa                672
Gln Gln Lys Asp Ala Ala Trp Lys Gln Trp Phe Thr Ser Ser Phe Gln
        210                 215                 220 cca tta aaa gaa cga ggt ggc caa ggc gga gta tga                                708
Pro Leu Lys Glu Arg Gly Gly Gln Gly Gly Val
225                 230                 235

<210> SEQ ID NO 25
<211> LENGTH: 235
<212> TYPE: PRT
<213> ORGANISM: Arabidopsis thaliana

<400> SEQUENCE: 25

Met Leu Lys Leu Trp Arg Trp Tyr Gln Arg Cys Leu Thr Val His Pro
1               5                   10                  15

Val Lys Thr Gln Val Ile Ser Ser Gly Phe Leu Trp Gly Phe Gly Asp
                20                  25                  30

Val Thr Ala Gln Tyr Ile Thr His Ser Thr Ala Lys Arg Arg Leu Leu
            35                  40                  45

Arg Leu Thr Glu Thr Asn Lys Asp Ala Asp Ala Asp Ala Glu Ile Lys
        50                  55                  60

Val Lys Trp Lys Gln Asp Ala Glu Phe Lys Val Asn Trp Lys Arg Val
65                  70                  75                  80

Ala Ile Thr Ser Met Phe Gly Phe Gly Phe Val Gly Pro Val Gly His
                85                  90                  95

Phe Trp Tyr Glu Gly Leu Asp Lys Phe Ile Lys Leu Lys Pro Arg Tyr
                100                 105                 110

Val Pro Lys Ser Thr Arg Phe Val Ser Ala Lys Val Ala Met Asp Gly
            115                 120                 125

Leu Ile Phe Gly Pro Val Asp Leu Leu Val Phe Phe Thr Tyr Met Gly
        130                 135                 140

Phe Ala Thr Gly Lys Asn Thr Ala Glu Val Lys Glu Gly Leu Lys Arg
145                 150                 155                 160
```

```
Asp Phe Leu Pro Ala Leu Ala Leu Glu Gly Gly Ala Trp Pro Leu Leu
            165                 170                 175

Gln Ile Ala Asn Phe Arg Tyr Val Pro Val Gln Tyr Gln Leu Leu Tyr
            180                 185                 190

Val Asn Ile Phe Cys Leu Val Asp Ser Ala Phe Leu Ser Trp Val Glu
            195                 200                 205

Gln Gln Lys Asp Ala Ala Trp Lys Gln Trp Phe Thr Ser Ser Phe Gln
            210                 215                 220

Pro Leu Lys Glu Arg Gly Gly Gln Gly Gly Val
225                 230                 235

<210> SEQ ID NO 26
<211> LENGTH: 708
<212> TYPE: DNA
<213> ORGANISM: Arabidopsis thaliana
<220> FEATURE:
<221> NAME/KEY: CDS
<222> LOCATION: (1)..(708)

<400> SEQUENCE: 26 atg ttg aag ctt tgg aga tgg tac cag cga tgc ctg acg gtt cat cct      48
Met Leu Lys Leu Trp Arg Trp Tyr Gln Arg Cys Leu Thr Val His Pro
1               5                   10                  15 gtg aaa act cag gtc atc agt tct gga ttt ctt tgg gga ttt ggc gat      96
Val Lys Thr Gln Val Ile Ser Ser Gly Phe Leu Trp Gly Phe Gly Asp
            20                  25                  30 gtc acc gct caa tac atc act cat tcc act gcg aaa cgt cgt ctt ctt     144
Val Thr Ala Gln Tyr Ile Thr His Ser Thr Ala Lys Arg Arg Leu Leu
        35                  40                  45 cgt ctc acc gaa acg aat aaa gat gtt gac gca gat gca gaa ttc aag     192
Arg Leu Thr Glu Thr Asn Lys Asp Val Asp Ala Asp Ala Glu Phe Lys
    50                  55                  60 gtc aac tgg aag cga gat gca gaa ttc aaa gtc aac tgg aag cga gta     240
Val Asn Trp Lys Arg Asp Ala Glu Phe Lys Val Asn Trp Lys Arg Val
65                  70                  75                  80 gct atc acg agc atg ttt gga ttt ggt ttt gtc gga cct gtt ggc cac     288
Ala Ile Thr Ser Met Phe Gly Phe Gly Phe Val Gly Pro Val Gly His
                85                  90                  95 ttt tgg tac gaa ggc ttg gat aaa ttc ata aaa ctg aag ctt cga tat     336
Phe Trp Tyr Glu Gly Leu Asp Lys Phe Ile Lys Leu Lys Leu Arg Tyr
            100                 105                 110 gta cca aag tca aca cgt ttt gta gct gcc aaa gtt gca atg gat ggt     384
Val Pro Lys Ser Thr Arg Phe Val Ala Ala Lys Val Ala Met Asp Gly
        115                 120                 125 ctt atc ttt gga cct ata gat cta ctg gtg ttc ttc aca tac atg gga     432
Leu Ile Phe Gly Pro Ile Asp Leu Leu Val Phe Phe Thr Tyr Met Gly
    130                 135                 140 ttc gcc aca gga aag aac aca gct gaa gtg aaa gaa gga ctc aag aga     480
Phe Ala Thr Gly Lys Asn Thr Ala Glu Val Lys Glu Gly Leu Lys Arg
145                 150                 155                 160 gat ttt ctt ccg gct cta gct ctt gaa ggc gga gca tgg cca ctt ctt     528
Asp Phe Leu Pro Ala Leu Ala Leu Glu Gly Gly Ala Trp Pro Leu Leu
                165                 170                 175 cag att gca aac ttc aga tat gtt ccc gtg caa tac cag ttg ctt tac     576
Gln Ile Ala Asn Phe Arg Tyr Val Pro Val Gln Tyr Gln Leu Leu Tyr
            180                 185                 190 gtc aac atc ttt tgc cta gta gac agt gcc ttc ctc tca tgg gtc gag     624
Val Asn Ile Phe Cys Leu Val Asp Ser Ala Phe Leu Ser Trp Val Glu
        195                 200                 205
```

```
caa cag aag gac gca gct tgg aag caa tgg ttt act tca tca ttt caa      672
Gln Gln Lys Asp Ala Ala Trp Lys Gln Trp Phe Thr Ser Ser Phe Gln
210                 215                 220 cca tta aaa gaa cga ggt ggc caa ggc gga gta tga                       708
Pro Leu Lys Glu Arg Gly Gly Gln Gly Gly Val
225                 230                 235

<210> SEQ ID NO 27
<211> LENGTH: 235
<212> TYPE: PRT
<213> ORGANISM: Arabidopsis thaliana

<400> SEQUENCE: 27

Met Leu Lys Leu Trp Arg Trp Tyr Gln Arg Cys Leu Thr Val His Pro
1               5                   10                  15

Val Lys Thr Gln Val Ile Ser Ser Gly Phe Leu Trp Gly Phe Gly Asp
                20                  25                  30

Val Thr Ala Gln Tyr Ile Thr His Ser Thr Ala Lys Arg Arg Leu Leu
            35                  40                  45

Arg Leu Thr Glu Thr Asn Lys Asp Val Asp Ala Asp Ala Glu Phe Lys
50                  55                  60

Val Asn Trp Lys Arg Asp Ala Glu Phe Lys Val Asn Trp Lys Arg Val
65                  70                  75                  80

Ala Ile Thr Ser Met Phe Gly Phe Gly Phe Val Gly Pro Val Gly His
                85                  90                  95

Phe Trp Tyr Glu Gly Leu Asp Lys Phe Ile Lys Leu Lys Leu Arg Tyr
            100                 105                 110

Val Pro Lys Ser Thr Arg Phe Val Ala Ala Lys Val Ala Met Asp Gly
            115                 120                 125

Leu Ile Phe Gly Pro Ile Asp Leu Leu Val Phe Phe Thr Tyr Met Gly
            130                 135                 140

Phe Ala Thr Gly Lys Asn Thr Ala Glu Val Lys Glu Gly Leu Lys Arg
145                 150                 155                 160

Asp Phe Leu Pro Ala Leu Ala Leu Glu Gly Gly Ala Trp Pro Leu Leu
                165                 170                 175

Gln Ile Ala Asn Phe Arg Tyr Val Pro Val Gln Tyr Gln Leu Leu Tyr
            180                 185                 190

Val Asn Ile Phe Cys Leu Val Asp Ser Ala Phe Leu Ser Trp Val Glu
            195                 200                 205

Gln Gln Lys Asp Ala Ala Trp Lys Gln Trp Phe Thr Ser Ser Phe Gln
210                 215                 220

Pro Leu Lys Glu Arg Gly Gly Gln Gly Gly Val
225                 230                 235

<210> SEQ ID NO 28
<211> LENGTH: 28
<212> TYPE: DNA
<213> ORGANISM: Arabidopsis thaliana

<400> SEQUENCE: 28
ccatctcata aataacgtca tgcattac                                         28

<210> SEQ ID NO 29
<211> LENGTH: 28
<212> TYPE: DNA
<213> ORGANISM: Unknown
<220> FEATURE:
<221> NAME/KEY: misc_feature
<222> LOCATION: (1)..(28)
```

```
<223> OTHER INFORMATION: Probe

<400> SEQUENCE: 29
tgataatcat cgcaagaccg gcaacagt                                        28

<210> SEQ ID NO 30
<211> LENGTH: 27
<212> TYPE: DNA
<213> ORGANISM: Arabidopsis thaliana

<400> SEQUENCE: 30
aacatttggc aataaagttt cttaaga                                         27

<210> SEQ ID NO 31
LENGTH: 20
<212> TYPE: DNA
<213> ORGANISM: Arabidopsis thaliana

<400> SEQUENCE: 31
agttcacccg aaaagcaacg                                                 20

<210> SEQ ID NO 32
<211> LENGTH: 33
<212> TYPE: DNA
<213> ORGANISM: Unknown
<220> FEATURE:
<221> NAME/KEY: misc_feature
<222> LOCATION: (1)..(33)
<223> OTHER INFORMATION: Probe

<400> SEQUENCE: 32
cccactgata atgatcgata tgtgaagaac tgc                                  33

<210> SEQ ID NO 33
<211> LENGTH: 20
<212> TYPE: DNA
<213> ORGANISM: Arabidopsis thaliana

<400> SEQUENCE: 33
tcgtcatgga accaccacct                                                 20

<210> SEQ ID NO 34
<211> LENGTH: 657
<212> TYPE: DNA
<213> ORGANISM: Hordeum vulgare
<220> FEATURE:
<221> NAME/KEY: CDS
<222> LOCATION: (1)..(657)

<400> SEQUENCE: 34
```

| | | | | | | | | | | | | | | | | |
|---|---|---|---|---|---|---|---|---|---|---|---|---|---|---|---|---|
| atg | cgg | agg | cta | tgg | cga | tgg | tac | cag | cag | tcc | ctg | tcc | tcc | tac | ccc | 48 |
| Met | Arg | Arg | Leu | Trp | Arg | Trp | Tyr | Gln | Gln | Ser | Leu | Ser | Ser | Tyr | Pro | |
| 1 | | | | 5 | | | | | 10 | | | | | 15 | | |
| gtg | cgg | acg | cag | gtc | gtc | agc | tcc | ggc | atc | ctc | tgg | gcc | ctc | ggc | gac | 96 |
| Val | Arg | Thr | Gln | Val | Val | Ser | Ser | Gly | Ile | Leu | Trp | Ala | Leu | Gly | Asp | |
| | | 20 | | | | | 25 | | | | | 30 | | | | |
| atc | ggc | gcg | cag | gcc | gtc | acc | cac | aaa | tcc | gcc | agc | tcc | cac | cac | cac | 144 |
| Ile | Gly | Ala | Gln | Ala | Val | Thr | His | Lys | Ser | Ala | Ser | Ser | His | His | His | |
| | 35 | | | | | 40 | | | | | 45 | | | | | |
| cac | gcc | aac | aac | ccc | gag | gat | aaa | gat | aaa | gag | ttc | aaa | att | gat | tgg | 192 |
| His | Ala | Asn | Asn | Pro | Glu | Asp | Lys | Asp | Lys | Glu | Phe | Lys | Ile | Asp | Trp | |
| 50 | | | | | 55 | | | | | 60 | | | | | | |
| aag | agg | gtc | ggc | atc | aca | agt | tca | ttt | gga | ttt | gct | ttt | gtt | gga | cct | 240 |
| Lys | Arg | Val | Gly | Ile | Thr | Ser | Ser | Phe | Gly | Phe | Ala | Phe | Val | Gly | Pro | |

```
gtg gga cat tac tgg tat gat tac ttg gat tgt ttg gtc cga cga aga    288
Val Gly His Tyr Trp Tyr Asp Tyr Leu Asp Cys Leu Val Arg Arg Arg
             85                  90                  95 tac cag cct ggt tcg ttc aaa ttt gta gcc tca aag gtt gca gca gat    336
Tyr Gln Pro Gly Ser Phe Lys Phe Val Ala Ser Lys Val Ala Ala Asp
            100                 105                 110 ggt ctc ctc ttc gga ccg cta gat ctg ggg ctg ttc ttc tct tat gtg    384
Gly Leu Leu Phe Gly Pro Leu Asp Leu Gly Leu Phe Phe Ser Tyr Val
            115                 120                 125 ggc ctt gct tca gga agg agt ctg gag cag gtg aag gaa gat gtg aag    432
Gly Leu Ala Ser Gly Arg Ser Leu Glu Gln Val Lys Glu Asp Val Lys
        130                 135                 140 agg gat atc att cct gct cta gtt tta ggg gga gcc atc tgg ccg gct    480
Arg Asp Ile Ile Pro Ala Leu Val Leu Gly Gly Ala Ile Trp Pro Ala
145                 150                 155                 160 gtg cag atc gca aac ttc cgc ttc att ccc gtg cga tat caa ctg ctt    528
Val Gln Ile Ala Asn Phe Arg Phe Ile Pro Val Arg Tyr Gln Leu Leu
                165                 170                 175 tac gtg aac ttg ttc tgc ctg tta gac agt tgt ttc ttg tct tgg atc    576
Tyr Val Asn Leu Phe Cys Leu Leu Asp Ser Cys Phe Leu Ser Trp Ile
            180                 185                 190 gag cag caa gga gat gcg gct tgg aag caa tgg ttc cca tcg ttc cag    624
Glu Gln Gln Gly Asp Ala Ala Trp Lys Gln Trp Phe Pro Ser Phe Gln
        195                 200                 205 aag aaa att gaa gac cag aag agc aac gcc tga                        657
Lys Lys Ile Glu Asp Gln Lys Ser Asn Ala
210                 215
```

<210> SEQ ID NO 35
<211> LENGTH: 218
<212> TYPE: PRT
<213> ORGANISM: Hordeum vulgare

<400> SEQUENCE: 35

```
Met Arg Arg Leu Trp Arg Trp Tyr Gln Gln Ser Leu Ser Ser Tyr Pro
1               5                   10                  15

Val Arg Thr Gln Val Val Ser Ser Gly Ile Leu Trp Ala Leu Gly Asp
            20                  25                  30

Ile Gly Ala Gln Ala Val Thr His Lys Ser Ala Ser Ser His His His
        35                  40                  45

His Ala Asn Asn Pro Glu Asp Lys Asp Lys Glu Phe Lys Ile Asp Trp
    50                  55                  60

Lys Arg Val Gly Ile Thr Ser Ser Phe Gly Phe Ala Phe Val Gly Pro
65                  70                  75                  80

Val Gly His Tyr Trp Tyr Asp Tyr Leu Asp Cys Leu Val Arg Arg Arg
                85                  90                  95

Tyr Gln Pro Gly Ser Phe Lys Phe Val Ala Ser Lys Val Ala Ala Asp
            100                 105                 110

Gly Leu Leu Phe Gly Pro Leu Asp Leu Gly Leu Phe Phe Ser Tyr Val
        115                 120                 125

Gly Leu Ala Ser Gly Arg Ser Leu Glu Gln Val Lys Glu Asp Val Lys
    130                 135                 140

Arg Asp Ile Ile Pro Ala Leu Val Leu Gly Gly Ala Ile Trp Pro Ala
145                 150                 155                 160

Val Gln Ile Ala Asn Phe Arg Phe Ile Pro Val Arg Tyr Gln Leu Leu
                165                 170                 175
```

```
Tyr Val Asn Leu Phe Cys Leu Leu Asp Ser Cys Phe Leu Ser Trp Ile
        180                 185                 190

Glu Gln Gln Gly Asp Ala Ala Trp Lys Gln Trp Phe Pro Ser Phe Gln
        195                 200                 205

Lys Lys Ile Glu Asp Gln Lys Ser Asn Ala
        210                 215

<210> SEQ ID NO 36
<211> LENGTH: 657
<212> TYPE: DNA
<213> ORGANISM: Triticum aestivum
<220> FEATURE:
<221> NAME/KEY: CDS
<222> LOCATION: (1)..(657)

<400> SEQUENCE: 36 atg cgg cgg cta tgg cga tgg tac cag cag tcc ctg tcc tcc tac ccc      48
Met Arg Arg Leu Trp Arg Trp Tyr Gln Gln Ser Leu Ser Ser Tyr Pro
1               5                   10                  15 gtg cgg acg cag gtc gtc agc tcc ggc atc ctc tgg gcc ctc ggc gac      96
Val Arg Thr Gln Val Val Ser Ser Gly Ile Leu Trp Ala Leu Gly Asp
            20                  25                  30 atc ggc gcc cag gcc gtc acc cac aaa tcc gcc agc tcc cac cac cac     144
Ile Gly Ala Gln Ala Val Thr His Lys Ser Ala Ser Ser His His His
        35                  40                  45 cac gcc aag aac ccc gag gat aaa gat aaa gag ttc aaa att gat tgg     192
His Ala Lys Asn Pro Glu Asp Lys Asp Lys Glu Phe Lys Ile Asp Trp
    50                  55                  60 aag agg gtc ggc atc aca agt tca ttt gga ttt gct ttt gtt gga cct     240
Lys Arg Val Gly Ile Thr Ser Ser Phe Gly Phe Ala Phe Val Gly Pro
65                  70                  75                  80 gtg gga cat tac tgg tac gaa tac ttg gat cgt atg gtc cga cga aga     288
Val Gly His Tyr Trp Tyr Glu Tyr Leu Asp Arg Met Val Arg Arg Arg
                85                  90                  95 tac ctg cct ggt tcg ttc aaa ttt gta gcc tca aag gtt gca gcg gat     336
Tyr Leu Pro Gly Ser Phe Lys Phe Val Ala Ser Lys Val Ala Ala Asp
            100                 105                 110 ggt ctc ctc ttt ggg cca cta gat ctg ggg ctg ttc ttc tct tat gtg     384
Gly Leu Leu Phe Gly Pro Leu Asp Leu Gly Leu Phe Phe Ser Tyr Val
        115                 120                 125 ggc ctt gct tca gga agg agt ctg gag cag gtg aag gat gat gtg aag     432
Gly Leu Ala Ser Gly Arg Ser Leu Glu Gln Val Lys Asp Asp Val Lys
    130                 135                 140 agg gat atc att cct gct ctg gtt tta ggg gga gcc atc tgg ccg gct     480
Arg Asp Ile Ile Pro Ala Leu Val Leu Gly Gly Ala Ile Trp Pro Ala
145                 150                 155                 160 gtg cag atc gca aac ttt cgc ttc att ccc gtg cga tat caa ctg ctg     528
Val Gln Ile Ala Asn Phe Arg Phe Ile Pro Val Arg Tyr Gln Leu Leu
                165                 170                 175 tac gtg aac ttg ttc tgc ctg tta gac agc tgt ttc ttg tct tgg atc     576
Tyr Val Asn Leu Phe Cys Leu Leu Asp Ser Cys Phe Leu Ser Trp Ile
            180                 185                 190 gag caa caa gga gac gcg gct tgg aag caa tgg ttc aca tcg ttc cag     624
Glu Gln Gln Gly Asp Ala Ala Trp Lys Gln Trp Phe Thr Ser Phe Gln
        195                 200                 205 aag aaa atc gaa gac cag aag agc aac gct tga                         657
Lys Lys Ile Glu Asp Gln Lys Ser Asn Ala
    210                 215

<210> SEQ ID NO 37
<211> LENGTH: 218
```

```
<212> TYPE: PRT
<213> ORGANISM: Triticum aestivum

<400> SEQUENCE: 37

Met Arg Arg Leu Trp Arg Trp Tyr Gln Gln Ser Leu Ser Ser Tyr Pro
1               5                   10                  15

Val Arg Thr Gln Val Val Ser Ser Gly Ile Leu Trp Ala Leu Gly Asp
            20                  25                  30

Ile Gly Ala Gln Ala Val Thr His Lys Ser Ala Ser Ser His His His
        35                  40                  45

His Ala Lys Asn Pro Glu Asp Lys Asp Lys Glu Phe Lys Ile Asp Trp
    50                  55                  60

Lys Arg Val Gly Ile Thr Ser Ser Phe Gly Phe Ala Phe Val Gly Pro
65                  70                  75                  80

Val Gly His Tyr Trp Tyr Glu Tyr Leu Asp Arg Met Val Arg Arg Arg
                85                  90                  95

Tyr Leu Pro Gly Ser Phe Lys Phe Val Ala Ser Lys Val Ala Ala Asp
            100                 105                 110

Gly Leu Leu Phe Gly Pro Leu Asp Leu Gly Leu Phe Phe Ser Tyr Val
        115                 120                 125

Gly Leu Ala Ser Gly Arg Ser Leu Glu Gln Val Lys Asp Asp Val Lys
    130                 135                 140

Arg Asp Ile Ile Pro Ala Leu Val Leu Gly Gly Ala Ile Trp Pro Ala
145                 150                 155                 160

Val Gln Ile Ala Asn Phe Arg Phe Ile Pro Val Arg Tyr Gln Leu Leu
                165                 170                 175

Tyr Val Asn Leu Phe Cys Leu Leu Asp Ser Cys Phe Leu Ser Trp Ile
            180                 185                 190

Glu Gln Gln Gly Asp Ala Ala Trp Lys Gln Trp Phe Thr Ser Phe Gln
        195                 200                 205

Lys Lys Ile Glu Asp Gln Lys Ser Asn Ala
    210                 215

<210> SEQ ID NO 38
<211> LENGTH: 678
<212> TYPE: DNA
<213> ORGANISM: Brassica napus
<220> FEATURE:
<221> NAME/KEY: CDS
<222> LOCATION: (1)..(678)

<400> SEQUENCE: 38 atg ttg aag gtg tgg aga tgg tac cag cga tgc ctg agc gtt cat ccg    48
Met Leu Lys Val Trp Arg Trp Tyr Gln Arg Cys Leu Ser Val His Pro
1               5                   10                  15 gtg aaa act cag gtc ata agc tcg ggc ttt ctt tgg gga ttc ggg gac    96
Val Lys Thr Gln Val Ile Ser Ser Gly Phe Leu Trp Gly Phe Gly Asp
            20                  25                  30 gtc acc gct caa tac atc act cat tca act gcg aaa cct cct ctt ctc   144
Val Thr Ala Gln Tyr Ile Thr His Ser Thr Ala Lys Pro Pro Leu Leu
        35                  40                  45 cgt ctc acc gac aca aat aaa gat gca gac gct gat tca gaa ttt aag   192
Arg Leu Thr Asp Thr Asn Lys Asp Ala Asp Ala Asp Ser Glu Phe Lys
    50                  55                  60 ctc aac tgg aag cga gta gct atc act agc atg ttt gga ctt ggt ttt   240
Leu Asn Trp Lys Arg Val Ala Ile Thr Ser Met Phe Gly Leu Gly Phe
65                  70                  75                  80 gtc ggt cct gtt ggc cac ttc tgg tac gaa ggc ctt gat aaa ttc ata   288
```

```
Val Gly Pro Val Gly His Phe Trp Tyr Glu Gly Leu Asp Lys Phe Ile
                85                  90                  95 aaa ctg aag ctt cga tac gta cca aag tca acg cgt ttt gtg gct gcc      336
Lys Leu Lys Leu Arg Tyr Val Pro Lys Ser Thr Arg Phe Val Ala Ala
            100                 105                 110 aaa gtt gca atg gac ggt ctt atc ttc ggc ccc att gat cta ctc gtg      384
Lys Val Ala Met Asp Gly Leu Ile Phe Gly Pro Ile Asp Leu Leu Val
        115                 120                 125 ttc ttc acg tac atg gga tac gcc aca ggc aag aac acg tct caa gtg      432
Phe Phe Thr Tyr Met Gly Tyr Ala Thr Gly Lys Asn Thr Ser Gln Val
    130                 135                 140 aaa gaa ggg ctc aag aga gac ttt ctt cca gct cta gct ctt gaa ggc      480
Lys Glu Gly Leu Lys Arg Asp Phe Leu Pro Ala Leu Ala Leu Glu Gly
145                 150                 155                 160 gga gca tgg ccg ctt ctt cag atc gca aac ttc aga tac gtc ccc gtg      528
Gly Ala Trp Pro Leu Leu Gln Ile Ala Asn Phe Arg Tyr Val Pro Val
                165                 170                 175 caa tac cag ctg ctt tac gtc aac atc ttt tgc ctt ata gac agc gct      576
Gln Tyr Gln Leu Leu Tyr Val Asn Ile Phe Cys Leu Ile Asp Ser Ala
            180                 185                 190 ttt ctc tcg tgg gtg gat caa cag aag gat gca gct tgg aag cag tgg      624
Phe Leu Ser Trp Val Asp Gln Gln Lys Asp Ala Ala Trp Lys Gln Trp
        195                 200                 205 ttt act act cca ttt tta act ctt aaa gaa cga ggt ggc aca ggt gga      672
Phe Thr Thr Pro Phe Leu Thr Leu Lys Glu Arg Gly Gly Thr Gly Gly
    210                 215                 220 gta tga                                                              678
Val
225

<210> SEQ ID NO 39
<211> LENGTH: 225
<212> TYPE: PRT
<213> ORGANISM: Brassica napus

<400> SEQUENCE: 39

Met Leu Lys Val Trp Arg Trp Tyr Gln Arg Cys Leu Ser Val His Pro
1               5                   10                  15

Val Lys Thr Gln Val Ile Ser Ser Gly Phe Leu Trp Gly Phe Gly Asp
            20                  25                  30

Val Thr Ala Gln Tyr Ile Thr His Ser Thr Ala Lys Pro Pro Leu Leu
        35                  40                  45

Arg Leu Thr Asp Thr Asn Lys Asp Ala Asp Ala Asp Ser Glu Phe Lys
    50                  55                  60

Leu Asn Trp Lys Arg Val Ala Ile Thr Ser Met Phe Gly Leu Gly Phe
65                  70                  75                  80

Val Gly Pro Val Gly His Phe Trp Tyr Glu Gly Leu Asp Lys Phe Ile
                85                  90                  95

Lys Leu Lys Leu Arg Tyr Val Pro Lys Ser Thr Arg Phe Val Ala Ala
            100                 105                 110

Lys Val Ala Met Asp Gly Leu Ile Phe Gly Pro Ile Asp Leu Leu Val
        115                 120                 125

Phe Phe Thr Tyr Met Gly Tyr Ala Thr Gly Lys Asn Thr Ser Gln Val
    130                 135                 140

Lys Glu Gly Leu Lys Arg Asp Phe Leu Pro Ala Leu Ala Leu Glu Gly
145                 150                 155                 160

Gly Ala Trp Pro Leu Leu Gln Ile Ala Asn Phe Arg Tyr Val Pro Val
                165                 170                 175
```

```
Gln Tyr Gln Leu Leu Tyr Val Asn Ile Phe Cys Leu Ile Asp Ser Ala
            180                 185                 190

Phe Leu Ser Trp Val Asp Gln Gln Lys Asp Ala Ala Trp Lys Gln Trp
            195                 200                 205

Phe Thr Thr Pro Phe Leu Thr Leu Lys Glu Arg Gly Gly Thr Gly Gly
            210                 215                 220

Val
225

<210> SEQ ID NO 40
<211> LENGTH: 516
<212> TYPE: DNA
<213> ORGANISM: Solanum tuberosum
<220> FEATURE:
<221> NAME/KEY: CDS
<222> LOCATION: (1)..(516)

<400> SEQUENCE: 40 atg ttg cgg ttg tgg aaa tgg tac caa aat tgc ttg gct tta cat ccg        48
Met Leu Arg Leu Trp Lys Trp Tyr Gln Asn Cys Leu Ala Leu His Pro
1               5                   10                  15 gtg aag act cag gtc atc agc tcc ggt ctt att tgg ggt ctc ggc gac        96
Val Lys Thr Gln Val Ile Ser Ser Gly Leu Ile Trp Gly Leu Gly Asp
            20                  25                  30 gta tct gct caa gcc gtc act cat tat act gca aag aaa cac cat cat       144
Val Ser Ala Gln Ala Val Thr His Tyr Thr Ala Lys Lys His His His
        35                  40                  45 ctt cat cct gat gaa gat aaa gaa ttt gca atc aac tgg aga cga gtt       192
Leu His Pro Asp Glu Asp Lys Glu Phe Ala Ile Asn Trp Arg Arg Val
    50                  55                  60 gcc aca acg agc ttg ttc ggc ttt gca ttt gtt gga cct gtt ggc cac       240
Ala Thr Thr Ser Leu Phe Gly Phe Ala Phe Val Gly Pro Val Gly His
65                  70                  75                  80 ttc tgg tat gaa ggg ttg gat cgc gtc ata aga cac aga ttt caa atg       288
Phe Trp Tyr Glu Gly Leu Asp Arg Val Ile Arg His Arg Phe Gln Met
                85                  90                  95 caa cct aaa tcc ctg cgg ttt gtt gct aca aaa gta gca ctt gat ggt       336
Gln Pro Lys Ser Leu Arg Phe Val Ala Thr Lys Val Ala Leu Asp Gly
            100                 105                 110 ata atc ttt ggg ccc ctg gat tta ctt gtc ttt ttc aca tat atg ggt       384
Ile Ile Phe Gly Pro Leu Asp Leu Leu Val Phe Phe Thr Tyr Met Gly
        115                 120                 125 tac tcc act ggc aaa aat act gct caa gtt gtt gaa ggt gtg aag aga       432
Tyr Ser Thr Gly Lys Asn Thr Ala Gln Val Val Glu Gly Val Lys Arg
    130                 135                 140 gac tat ctt ccg gct tta ata cta gaa cga ggt ata tgg cct att gtc       480
Asp Tyr Leu Pro Ala Leu Ile Leu Glu Arg Gly Ile Trp Pro Ile Val
145                 150                 155                 160 cag gtg gcc aac ttt cgc tat ata cca gtt agg tat                       516
Gln Val Ala Asn Phe Arg Tyr Ile Pro Val Arg Tyr
                165                 170

<210> SEQ ID NO 41
<211> LENGTH: 172
<212> TYPE: PRT
<213> ORGANISM: Solanum tuberosum

<400> SEQUENCE: 41

Met Leu Arg Leu Trp Lys Trp Tyr Gln Asn Cys Leu Ala Leu His Pro
1               5                   10                  15
```

```
Val Lys Thr Gln Val Ile Ser Ser Gly Leu Ile Trp Gly Leu Gly Asp
             20                  25                  30

Val Ser Ala Gln Ala Val Thr His Tyr Thr Ala Lys Lys His His His
         35                  40                  45

Leu His Pro Asp Glu Asp Lys Glu Phe Ala Ile Asn Trp Arg Arg Val
 50                  55                  60

Ala Thr Thr Ser Leu Phe Gly Phe Ala Phe Val Gly Pro Val Gly His
 65                  70                  75                  80

Phe Trp Tyr Glu Gly Leu Asp Arg Val Ile Arg His Arg Phe Gln Met
                 85                  90                  95

Gln Pro Lys Ser Leu Arg Phe Val Ala Thr Lys Val Ala Leu Asp Gly
            100                 105                 110

Ile Ile Phe Gly Pro Leu Asp Leu Leu Val Phe Phe Thr Tyr Met Gly
            115                 120                 125

Tyr Ser Thr Gly Lys Asn Thr Ala Gln Val Val Glu Gly Val Lys Arg
130                 135                 140

Asp Tyr Leu Pro Ala Leu Ile Leu Glu Arg Gly Ile Trp Pro Ile Val
145                 150                 155                 160

Gln Val Ala Asn Phe Arg Tyr Ile Pro Val Arg Tyr
                165                 170

<210> SEQ ID NO 42
<211> LENGTH: 573
<212> TYPE: DNA
<213> ORGANISM: Arabidopsis thaliana
<220> FEATURE:
<221> NAME/KEY: CDS
<222> LOCATION: (1)..(573)

<400> SEQUENCE: 42 atg gga tct tca cca ccg aag aag acg act ctg caa cgg tac ttg tca      48
Met Gly Ser Ser Pro Pro Lys Lys Thr Thr Leu Gln Arg Tyr Leu Ser
  1               5                  10                  15 cag ctt caa caa cat cct tta aga aca aag gca ata act gct gga gtt      96
Gln Leu Gln Gln His Pro Leu Arg Thr Lys Ala Ile Thr Ala Gly Val
             20                  25                  30 ttg tct ggt gtt agc gat gtt gta tca cag aag ctc tct ggc ata cag     144
Leu Ser Gly Val Ser Asp Val Val Ser Gln Lys Leu Ser Gly Ile Gln
         35                  40                  45 aag att cag ctg aga agg gtt ctt ctc aaa gtg ata ttt gct ggt ggg     192
Lys Ile Gln Leu Arg Arg Val Leu Leu Lys Val Ile Phe Ala Gly Gly
 50                  55                  60 ttt ctt gga cca gca ggg cat ttc ttt cat aca tat tta gat aag ttt     240
Phe Leu Gly Pro Ala Gly His Phe Phe His Thr Tyr Leu Asp Lys Phe
 65                  70                  75                  80 ttt aaa ggg aag aag gat aca cag act gtt gca aag aag gta att ctg     288
Phe Lys Gly Lys Lys Asp Thr Gln Thr Val Ala Lys Lys Val Ile Leu
                 85                  90                  95 gag caa ttg aca ttg tca cca ttg aac cat ttg ctt ttc atg atc tat     336
Glu Gln Leu Thr Leu Ser Pro Leu Asn His Leu Leu Phe Met Ile Tyr
            100                 105                 110 tat gga gta gtc ata gaa aga act ccc tgg acc ctt gtt aga gaa agg     384
Tyr Gly Val Val Ile Glu Arg Thr Pro Trp Thr Leu Val Arg Glu Arg
            115                 120                 125 atc aag aag act tat cca acg gtc cag ctt act gca tgg acg ttt ttc     432
Ile Lys Lys Thr Tyr Pro Thr Val Gln Leu Thr Ala Trp Thr Phe Phe
130                 135                 140 ccg gtg gtg gga tgg att aac tac aag tat gtg cca ctg cac ttc cgg     480
Pro Val Val Gly Trp Ile Asn Tyr Lys Tyr Val Pro Leu His Phe Arg
```

| | | | | | | | | | | | | | | | | |
|---|---|---|---|---|---|---|---|---|---|---|---|---|---|---|---|---|
| | | 145 | | | 150 | | | | 155 | | | | 160 | | | |
| gtc | atc | ttg | cac | agc | ctg | gtc | gca | ttc | ttt | tgg | gga | att | ttc | cta | acc | 528 |
| Val | Ile | Leu | His | Ser | Leu | Val | Ala | Phe | Phe | Trp | Gly | Ile | Phe | Leu | Thr | |
| | | | | 165 | | | | | 170 | | | | | 175 | | |
| ctg | cga | gcg | agg | tca | atg | aca | cta | gct | ttg | gca | aag | gct | aag | tga | | 573 |
| Leu | Arg | Ala | Arg | Ser | Met | Thr | Leu | Ala | Leu | Ala | Lys | Ala | Lys | | | |
| | | | | 180 | | | | | 185 | | | | 190 | | | |

<210> SEQ ID NO 43
<211> LENGTH: 190
<212> TYPE: PRT
<213> ORGANISM: Arabidopsis thaliana

<400> SEQUENCE: 43

Met Gly Ser Ser Pro Lys Lys Thr Thr Leu Gln Arg Tyr Leu Ser
1               5                   10                  15

Gln Leu Gln Gln His Pro Leu Arg Thr Lys Ala Ile Thr Ala Gly Val
            20                  25                  30

Leu Ser Gly Val Ser Asp Val Val Ser Gln Lys Leu Ser Gly Ile Gln
        35                  40                  45

Lys Ile Gln Leu Arg Arg Val Leu Leu Lys Val Ile Phe Ala Gly Gly
    50                  55                  60

Phe Leu Gly Pro Ala Gly His Phe Phe His Thr Tyr Leu Asp Lys Phe
65                  70                  75                  80

Phe Lys Gly Lys Lys Asp Thr Gln Thr Val Ala Lys Lys Val Ile Leu
                85                  90                  95

Glu Gln Leu Thr Leu Ser Pro Leu Asn His Leu Leu Phe Met Ile Tyr
            100                 105                 110

Tyr Gly Val Val Ile Glu Arg Thr Pro Trp Thr Leu Val Arg Glu Arg
        115                 120                 125

Ile Lys Lys Thr Tyr Pro Thr Val Gln Leu Thr Ala Trp Thr Phe Phe
    130                 135                 140

Pro Val Val Gly Trp Ile Asn Tyr Lys Tyr Val Pro Leu His Phe Arg
145                 150                 155                 160

Val Ile Leu His Ser Leu Val Ala Phe Phe Trp Gly Ile Phe Leu Thr
                165                 170                 175

Leu Arg Ala Arg Ser Met Thr Leu Ala Leu Ala Lys Ala Lys
            180                 185                 190

<210> SEQ ID NO 44
<211> LENGTH: 738
<212> TYPE: DNA
<213> ORGANISM: Drosophila melanogaster
<220> FEATURE:
<221> NAME/KEY: CDS
<222> LOCATION: (1)..(738)

<400> SEQUENCE: 44

| | | | | | | | | | | | | | | | | |
|---|---|---|---|---|---|---|---|---|---|---|---|---|---|---|---|---|
| atg | caa | tcc | ttg | cgt | ggc | tgc | ccg | gcc | cgt | ggc | cta | atc | ctg | tcc | aga | 48 |
| Met | Gln | Ser | Leu | Arg | Gly | Cys | Pro | Ala | Arg | Gly | Leu | Ile | Leu | Ser | Arg | |
| 1 | | | | 5 | | | | | 10 | | | | | 15 | | |
| gcc | att | cgc | ggc | cag | cgc | agc | ctg | cga | atg | agt | tgg | cca | cgg | aac | agc | 96 |
| Ala | Ile | Arg | Gly | Gln | Arg | Ser | Leu | Arg | Met | Ser | Trp | Pro | Arg | Asn | Ser | |
| | | | | 20 | | | | | 25 | | | | | 30 | | |
| agc | gcg | act | gga | gga | gcc | gga | gga | gct | gcg | ccc | ggt | gga | ggc | agc | agc | 144 |
| Ser | Ala | Thr | Gly | Gly | Ala | Gly | Gly | Ala | Ala | Pro | Gly | Gly | Gly | Ser | Ser | |
| | | | 35 | | | | | 40 | | | | | 45 | | | |
| acc | acc | acc | agc | acc | atc | ggc | ttt | gga | gcg | ctt | cag | aag | ctg | cgg | gaa | 192 |
| Thr | Thr | Thr | Ser | Thr | Ile | Gly | Phe | Gly | Ala | Leu | Gln | Lys | Leu | Arg | Glu | |

```
                 50                  55                  60
tgg cat gcg agt gca ttc agt agc cgc ttc ctc ctc ttc acc aac gtg       240
Trp His Ala Ser Ala Phe Ser Ser Arg Phe Leu Leu Phe Thr Asn Val
 65                  70                  75                  80 ggc atc tcg ctg acc ctg agc tgt gtg ggt gac gtc cta gaa cag cac       288
Gly Ile Ser Leu Thr Leu Ser Cys Val Gly Asp Val Leu Glu Gln His
                 85                  90                  95 ctg gaa atc tat tgc ggc gaa atc gag cgc ttc gaa tcc acg cgc act       336
Leu Glu Ile Tyr Cys Gly Glu Ile Glu Arg Phe Glu Ser Thr Arg Thr
            100                 105                 110 gcc cac atg gcc atc agt ggt gtg acg gtg ggc gtc atc tgt cac tac       384
Ala His Met Ala Ile Ser Gly Val Thr Val Gly Val Ile Cys His Tyr
        115                 120                 125 tgg tac aag atg ctg gac aaa cgg atg cct gga cgc act atg cgc gtg       432
Trp Tyr Lys Met Leu Asp Lys Arg Met Pro Gly Arg Thr Met Arg Val
    130                 135                 140 gtg gcc aag aag atc gtg ctc gat cag cta atc tgc tcg ccc atc tac       480
Val Ala Lys Lys Ile Val Leu Asp Gln Leu Ile Cys Ser Pro Ile Tyr
145                 150                 155                 160 atc agt gcc ttc ttc gtc acg ctg ggt ctg ctg gag caa aag acc aag       528
Ile Ser Ala Phe Phe Val Thr Leu Gly Leu Leu Glu Gln Lys Thr Lys
                165                 170                 175 cac gaa gtg tgg gag gag atc aag gag aag gcc tgg aag ctg tac gcc       576
His Glu Val Trp Glu Glu Ile Lys Glu Lys Ala Trp Lys Leu Tyr Ala
            180                 185                 190 gcc gag tgg act gtg tgg ccg gtg gcg cag ttc gtc aac ttc tac tgg       624
Ala Glu Trp Thr Val Trp Pro Val Ala Gln Phe Val Asn Phe Tyr Trp
        195                 200                 205 atc ccc acc cat tac cgc atc ttc tac gac aac atc atc agc ctg ggc       672
Ile Pro Thr His Tyr Arg Ile Phe Tyr Asp Asn Ile Ile Ser Leu Gly
    210                 215                 220 tac gat gtg ctg acc tcg aag gtt aag cac aaa cag tcg cat tcg cat       720
Tyr Asp Val Leu Thr Ser Lys Val Lys His Lys Gln Ser His Ser His
225                 230                 235                 240 ctg aag aag att ccc taa                                               738
Leu Lys Lys Ile Pro
                245

<210> SEQ ID NO 45
<211> LENGTH: 245
<212> TYPE: PRT
<213> ORGANISM: Drosophila melanogaster

<400> SEQUENCE: 45

Met Gln Ser Leu Arg Gly Cys Pro Ala Arg Gly Leu Ile Leu Ser Arg
1               5                   10                  15

Ala Ile Arg Gly Gln Arg Ser Leu Arg Met Ser Trp Pro Arg Asn Ser
            20                  25                  30

Ser Ala Thr Gly Gly Ala Gly Gly Ala Ala Pro Gly Gly Gly Ser Ser
        35                  40                  45

Thr Thr Thr Ser Thr Ile Gly Phe Gly Ala Leu Gln Lys Leu Arg Glu
    50                  55                  60

Trp His Ala Ser Ala Phe Ser Ser Arg Phe Leu Leu Phe Thr Asn Val
65                  70                  75                  80

Gly Ile Ser Leu Thr Leu Ser Cys Val Gly Asp Val Leu Glu Gln His
                85                  90                  95

Leu Glu Ile Tyr Cys Gly Glu Ile Glu Arg Phe Glu Ser Thr Arg Thr
            100                 105                 110
```

```
Ala His Met Ala Ile Ser Gly Val Thr Val Gly Val Ile Cys His Tyr
        115                 120                 125

Trp Tyr Lys Met Leu Asp Lys Arg Met Pro Gly Arg Thr Met Arg Val
        130                 135                 140

Val Ala Lys Lys Ile Val Leu Asp Gln Leu Ile Cys Ser Pro Ile Tyr
145                 150                 155                 160

Ile Ser Ala Phe Phe Val Thr Leu Gly Leu Leu Glu Gln Lys Thr Lys
                165                 170                 175

His Glu Val Trp Glu Glu Ile Lys Gly Lys Ala Trp Lys Leu Tyr Ala
                180                 185                 190

Ala Glu Trp Thr Val Trp Pro Val Ala Gln Phe Val Asn Phe Tyr Trp
                195                 200                 205

Ile Pro Thr His Tyr Arg Ile Phe Tyr Asp Asn Ile Ile Ser Leu Gly
        210                 215                 220

Tyr Asp Val Leu Thr Ser Lys Val Lys His Lys Gln Ser His Ser His
225                 230                 235                 240

Leu Lys Lys Ile Pro
                245

<210> SEQ ID NO 46
<211> LENGTH: 211
<212> TYPE: PRT
<213> ORGANISM: Consensus
<220> FEATURE:
<221> NAME/KEY: VARIANT
<222> LOCATION: (2)..(2)
<223> OTHER INFORMATION: no consensus amino acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: VARIANT
<222> LOCATION: (10)..(10)
<223> OTHER INFORMATION: no consensus amino acid
<220> FEATURE:
<221> NAME/KEY: VARIANT
<222> LOCATION: (14)..(14)
<223> OTHER INFORMATION: no consensus amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: VARIANT
<222> LOCATION: (26)..(26)
<223> OTHER INFORMATION: no consensus amino acid
<220> FEATURE:
<221> NAME/KEY: MISC_FEATURE
<222> LOCATION: (26)..(26)
<223> OTHER INFORMATION: Xaa is any amino acid
<220> FEATURE:
<221> NAME/KEY: VARIANT
<222> LOCATION: (34)..(34)
<223> OTHER INFORMATION: no consensus amino acid
<220> FEATURE:
<221> NAME/KEY: VARIANT
<222> LOCATION: (41)..(41)
<223> OTHER INFORMATION: no consensus amino acid
<220> FEATURE:
<221> NAME/KEY: VARIANT
<222> LOCATION: (44)..(78)
<223> OTHER INFORMATION: no consensus amino acid
<220> FEATURE:
<221> NAME/KEY: VARIANT
<222> LOCATION: (81)..(81)
```

```
<223> OTHER INFORMATION: no consensus amino acid
<220> FEATURE:
<221> NAME/KEY: VARIANT
<222> LOCATION: (97)..(97)
<223> OTHER INFORMATION: no consensus amino acid
<220> FEATURE:
<221> NAME/KEY: VARIANT
<222> LOCATION: (101)..(101)
<223> OTHER INFORMATION: no consensus amino acid
<220> FEATURE:
<221> NAME/KEY: VARIANT
<222> LOCATION: (107)..(115)
<223> OTHER INFORMATION: no consensus amino acid
<220> FEATURE:
<221> NAME/KEY: VARIANT
<222> LOCATION: (117)..(118)
<223> OTHER INFORMATION: no consensus amino acid
<220> FEATURE:
<221> NAME/KEY: VARIANT
<222> LOCATION: (122)..(122)
<223> OTHER INFORMATION: no consensus amino acid
<220> FEATURE:
<221> NAME/KEY: VARIANT
<222> LOCATION: (126)..(126)
<223> OTHER INFORMATION: no consensus amino acid
<220> FEATURE:
<221> NAME/KEY: VARIANT
<222> LOCATION: (130)..(130)
<223> OTHER INFORMATION: no consensus amino acid
<220> FEATURE:
<221> NAME/KEY: VARIANT
<222> LOCATION: (138)..(138)
<223> OTHER INFORMATION: no consensus amino acid
<220> FEATURE:
<221> NAME/KEY: VARIANT
<222> LOCATION: (141)..(141)
<223> OTHER INFORMATION: no consensus amino acid
<220> FEATURE:
<221> NAME/KEY: VARIANT
<222> LOCATION: (145)..(147)
<223> OTHER INFORMATION: no consensus amino acid
<220> FEATURE:
<221> NAME/KEY: VARIANT
<222> LOCATION: (151)..(153)
<223> OTHER INFORMATION: no consensus amino acid
<220> FEATURE:
<221> NAME/KEY: VARIANT
<222> LOCATION: (158)..(158)
<223> OTHER INFORMATION: no consensus amino acid
<220> FEATURE:
<221> NAME/KEY: VARIANT
<222> LOCATION: (163)..(163)
<223> OTHER INFORMATION: no consensus amino acid
<220> FEATURE:
<221> NAME/KEY: VARIANT
<222> LOCATION: (164)..(164)
<223> OTHER INFORMATION: no consensus amino acid
<220> FEATURE:
<221> NAME/KEY: VARIANT
<222> LOCATION: (168)..(168)
<223> OTHER INFORMATION: no consensus amino acid
<220> FEATURE:
<221> NAME/KEY: VARIANT
<222> LOCATION: (170)..(170)
<223> OTHER INFORMATION: no consensus amino acid
<220> FEATURE:
<221> NAME/KEY: VARIANT
<222> LOCATION: (172)..(172)
<223> OTHER INFORMATION: no consensus amino acid
<220> FEATURE:
<221> NAME/KEY: VARIANT
<222> LOCATION: (184)..(184)
<223> OTHER INFORMATION: no consensus amino acid
<220> FEATURE:
<221> NAME/KEY: VARIANT
<222> LOCATION: (203)..(203)
<223> OTHER INFORMATION: no consensus amino acid
<220> FEATURE:
<221> NAME/KEY: VARIANT
```

```
<222> LOCATION: (208)..(209)
<223> OTHER INFORMATION: no consensus amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (44)..(78)
<223> OTHER INFORMATION: Xaa is any amino acid
<220> FEATURE:
<221> NAME/KEY: MISC_FEATURE
<222> LOCATION: (81)..(81)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is any amino acid
<220> FEATURE:
<221> NAME/KEY: MISC_FEATURE
<222> LOCATION: (107)..(115)
<223> OTHER INFORMATION: Xaa is any amino acid
<220> FEATURE:
<221> NAME/KEY: MISC_FEATURE
<222> LOCATION: (117)..(118)
<223> OTHER INFORMATION: Xaa is any amino acid
<220> FEATURE:
<221> NAME/KEY: MISC_FEATURE
<222> LOCATION: (122)..(122)
<223> OTHER INFORMATION: Xaa is any amino acid
<220> FEATURE:
<221> NAME/KEY: MISC_FEATURE
<222> LOCATION: (126)..(126)
<223> OTHER INFORMATION: Xaa is any amino acid
<220> FEATURE:
<221> NAME/KEY: MISC_FEATURE
<222> LOCATION: (130)..(130)
<223> OTHER INFORMATION: Xaa is any amino acid
<220> FEATURE:
<221> NAME/KEY: MISC_FEATURE
<222> LOCATION: (138)..(138)
<223> OTHER INFORMATION: Xaa is any amino acid
<220> FEATURE:
<221> NAME/KEY: MISC_FEATURE
<222> LOCATION: (141)..(141)
<223> OTHER INFORMATION: Xaa is any amino acid
<220> FEATURE:
<221> NAME/KEY: MISC_FEATURE
<222> LOCATION: (145)..(147)
<223> OTHER INFORMATION: Xaa is any amino acid
<220> FEATURE:
<221> NAME/KEY: MISC_FEATURE
<222> LOCATION: (151)..(153)
<223> OTHER INFORMATION: Xaa is any amino acid
<220> FEATURE:
<221> NAME/KEY: MISC_FEATURE
<222> LOCATION: (158)..(158)
<223> OTHER INFORMATION: Xaa is any amino acid
<220> FEATURE:
<221> NAME/KEY: MISC_FEATURE
<222> LOCATION: (163)..(164)
<223> OTHER INFORMATION: Xaa is any amino acid
<220> FEATURE:
<221> NAME/KEY: MISC_FEATURE
<222> LOCATION: (168)..(168)
<223> OTHER INFORMATION: Xaa is any amino acid
<220> FEATURE:
<221> NAME/KEY: MISC_FEATURE
<222> LOCATION: (170)..(170)
<223> OTHER INFORMATION: Xaa is any amino acid
<220> FEATURE:
```

```
<221> NAME/KEY: MISC_FEATURE
<222> LOCATION: (172)..(172)
<223> OTHER INFORMATION: Xaa is any amino acid
<220> FEATURE:
<221> NAME/KEY: MISC_FEATURE
<222> LOCATION: (184)..(184)
<223> OTHER INFORMATION: Xaa is any amino acid
<220> FEATURE:
<221> NAME/KEY: MISC_FEATURE
<222> LOCATION: (203)..(203)
<223> OTHER INFORMATION: Xaa is any amino acid
<220> FEATURE:
<221> NAME/KEY: MISC_FEATURE
<222> LOCATION: (208)..(208)
<223> OTHER INFORMATION: Xaa is any amino acid
<220> FEATURE:
<221> NAME/KEY: MISC_FEATURE
<222> LOCATION: (209)..(209)
<223> OTHER INFORMATION: Xaa is any amino acid

<400> SEQUENCE: 46

Met Xaa Arg Leu Trp Arg Trp Tyr Gln Xaa Cys Leu Ala Xaa His Pro
  1               5                  10                  15

Val Lys Thr Gln Val Ile Ser Ser Gly Xaa Leu Trp Gly Leu Gly Asp
             20                  25                  30

Ile Xaa Ala Gln Ala Val Thr His Xaa Ser Ala Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Arg Val
 65                  70                  75                  80

Xaa Ile Thr Ser Ser Phe Gly Phe Gly Phe Val Gly Pro Val Gly His
                 85                  90                  95

Xaa Trp Tyr Glu Xaa Leu Asp Arg Phe Ile Xaa Xaa Xaa Xaa Xaa Xaa
            100                 105                 110

Xaa Xaa Xaa Ser Xaa Xaa Phe Val Ala Xaa Lys Val Ala Xaa Asp Gly
            115                 120                 125

Leu Xaa Phe Gly Pro Leu Asp Leu Leu Xaa Phe Phe Xaa Tyr Val Gly
            130                 135                 140

Xaa Xaa Xaa Gly Arg Ser Xaa Xaa Gln Val Lys Glu Xaa Val Lys
145                 150                 155                 160

Arg Asp Xaa Xaa Pro Ala Leu Xaa Leu Xaa Gly Xaa Ile Trp Pro Ala
                165                 170                 175

Val Gln Ile Ala Asn Phe Arg Xaa Val Pro Val Arg Tyr Gln Leu Leu
            180                 185                 190

Tyr Val Asn Leu Phe Cys Leu Leu Asp Ser Xaa Phe Leu Ser Trp Xaa
            195                 200                 205

Xaa Gln Gln
    210

<210> SEQ ID NO 47
<211> LENGTH: 29
<212> TYPE: PRT
<213> ORGANISM: Consensus
<220> FEATURE:
<221> NAME/KEY: VARIANT
<222> LOCATION: (11)..(11)
<223> OTHER INFORMATION: no consensus amino acid
<220> FEATURE:
<221> NAME/KEY: VARIANT
<222> LOCATION: (7)..(7)
<223> OTHER INFORMATION: no consensus amino acid
<220> FEATURE:
<221> NAME/KEY: VARIANT
```

<222> LOCATION: (23)..(23)
<223> OTHER INFORMATION: no consensus amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (23)..(23)
<223> OTHER INFORMATION: Xaa is any amino acid

<400> SEQUENCE: 47

Leu Trp Arg Trp Tyr Gln Xaa Cys Leu Ala Xaa His Pro Val Lys Thr
1               5                   10                  15

Gln Val Ile Ser Ser Gly Xaa Leu Trp Gly Leu Gly Asp
            20                  25

<210> SEQ ID NO 48
<211> LENGTH: 47
<212> TYPE: PRT
<213> ORGANISM: Consensus
<220> FEATURE:
<221> NAME/KEY: VARIANT
<222> LOCATION: (4)..(4)
<223> OTHER INFORMATION: no consensus amino acid
<220> FEATURE:
<221> NAME/KEY: VARIANT
<222> LOCATION: (5)..(5)
<223> OTHER INFORMATION: no consensus amino acid
<220> FEATURE:
<221> NAME/KEY: VARIANT
<222> LOCATION: (9)..(9)
<223> OTHER INFORMATION: no consensus amino acid
<220> FEATURE:
<221> NAME/KEY: VARIANT
<222> LOCATION: (11)..(11)
<223> OTHER INFORMATION: no consensus amino acid
<220> FEATURE:
<221> NAME/KEY: VARIANT
<222> LOCATION: (13)..(13)
<223> OTHER INFORMATION: no consensus amino acid
<220> FEATURE:
<221> NAME/KEY: VARIANT
<222> LOCATION: (25)..(25)
<223> OTHER INFORMATION: no consensus amino acid
<220> FEATURE:
<221> NAME/KEY: VARIANT
<222> LOCATION: (44)..(44)
<223> OTHER INFORMATION: no consensus amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (25)..(25)

```
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid

<400> SEQUENCE: 48

Lys Arg Asp Xaa Xaa Pro Ala Leu Xaa Leu Xaa Gly Xaa Ile Trp Pro
1               5                   10                  15

Ala Val Gln Ile Ala Asn Phe Arg Xaa Val Pro Val Arg Tyr Gln Leu
            20                  25                  30

Leu Tyr Val Asn Leu Phe Cys Leu Leu Asp Ser Xaa Phe Leu Ser
        35                  40                  45

<210> SEQ ID NO 49
<211> LENGTH: 210
<212> TYPE: PRT
<213> ORGANISM: Consensus
<220> FEATURE:
<221> NAME/KEY: VARIANT
<222> LOCATION: (10)..(10)
<223> OTHER INFORMATION: no consensus amino acid
<220> FEATURE:
<221> NAME/KEY: VARIANT
<222> LOCATION: (13)..(13)
<223> OTHER INFORMATION: no consensus amino acid
<220> FEATURE:
<221> NAME/KEY: VARIANT
<222> LOCATION: (14)..(14)
<223> OTHER INFORMATION: no consensus amino acid
<220> FEATURE:
<221> NAME/KEY: VARIANT
<222> LOCATION: (44)..(78)
<223> OTHER INFORMATION: no consensus amino acid
<220> FEATURE:
<221> NAME/KEY: VARIANT
<222> LOCATION: (147)..(147)
<223> OTHER INFORMATION: no consensus amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (44)..(78)
<223> OTHER INFORMATION: Xaa is any amino acid
<220> FEATURE:
<221> NAME/KEY: MISC_FEATURE
<222> LOCATION: (147)..(147)
<223> OTHER INFORMATION: Xaa is any amino acid
<220> FEATURE:
<221> NAME/KEY: MISC_FEATURE
<222> LOCATION: (2)..(2)
<223> OTHER INFORMATION: l or r
<220> FEATURE:
<221> NAME/KEY: MISC_FEATURE
<222> LOCATION: (18)..(18)
<223> OTHER INFORMATION: k or r
<220> FEATURE:
<221> NAME/KEY: MISC_FEATURE
<222> LOCATION: (22)..(22)
<223> OTHER INFORMATION: i or v
<220> FEATURE:
<221> NAME/KEY: MISC_FEATURE
<222> LOCATION: (29)..(29)
<223> OTHER INFORMATION: g or a
<220> FEATURE:
```

```
<221> NAME/KEY: MISC_FEATURE
<222> LOCATION: (42)..(42)
<223> OTHER INFORMATION: t or s
<220> FEATURE:
<221> NAME/KEY: MISC_FEATURE
<222> LOCATION: (97)..(97)
<223> OTHER INFORMATION: f or y
<220> FEATURE:
<221> NAME/KEY: MISC_FEATURE
<222> LOCATION: (101)..(101)
<223> OTHER INFORMATION: g or y
<220> FEATURE:
<221> NAME/KEY: MISC_FEATURE
<222> LOCATION: (118)..(118)
<223> OTHER INFORMATION: r or k
<220> FEATURE:
<221> NAME/KEY: MISC_FEATURE
<222> LOCATION: (130)..(130)
<223> OTHER INFORMATION: i or l
<220> FEATURE:
<221> NAME/KEY: MISC_FEATURE
<222> LOCATION: (138)..(138)
<223> OTHER INFORMATION: v or l
<220> FEATURE:
<221> NAME/KEY: MISC_FEATURE
<222> LOCATION: (141)..(141)
<223> OTHER INFORMATION: t or s
<220> FEATURE:
<221> NAME/KEY: MISC_FEATURE
<222> LOCATION: (143)..(143)
<223> OTHER INFORMATION: m or v
<220> FEATURE:
<221> NAME/KEY: MISC_FEATURE
<222> LOCATION: (149)..(149)
<223> OTHER INFORMATION: k or r
<220> FEATURE:
<221> NAME/KEY: MISC_FEATURE
<222> LOCATION: (163)..(163)
<223> OTHER INFORMATION: l or i
<220> FEATURE:
<221> NAME/KEY: MISC_FEATURE
<222> LOCATION: (169)..(169)
<223> OTHER INFORMATION: e or g

<400> SEQUENCE: 49

Met Leu Arg Leu Trp Arg Trp Tyr Gln Xaa Cys Leu Xaa Xaa His Pro
1               5                   10                  15

Val Lys Thr Gln Val Ile Ser Ser Gly Ile Leu Trp Gly Leu Gly Asp
            20                  25                  30

Ile Gly Ala Gln Ala Val Thr His Tyr Thr Ala Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Arg Val
65                  70                  75                  80

Gly Ile Thr Ser Ser Phe Gly Phe Ala Phe Val Pro Val Gly His
                85                  90                  95

Phe Trp Tyr Glu Gly Leu Asp Arg Phe Ile Arg Arg Lys Leu Arg Tyr
                100                 105                 110

Gln Pro Lys Ser Phe Arg Phe Val Ala Ser Lys Val Ala Ala Asp Gly
            115                 120                 125

Leu Ile Phe Gly Pro Leu Asp Leu Leu Val Phe Phe Thr Tyr Met Gly
    130                 135                 140

Leu Ala Xaa Gly Lys Ser Thr Glu Gln Val Lys Glu Asp Val Lys Arg
145                 150                 155                 160

Asp Phe Leu Pro Ala Leu Val Leu Glu Gly Gly Ile Trp Pro Ala Val
                165                 170                 175
```

Gln Ile Ala Asn Phe Arg Phe Ile Pro Val Arg Tyr Gln Leu Leu Tyr
            180                 185                 190

Val Asn Leu Phe Cys Leu Leu Asp Ser Cys Phe Leu Ser Trp Ile Glu
        195                 200                 205

Gln Gln
    210

<210> SEQ ID NO 50
<211> LENGTH: 29
<212> TYPE: PRT
<213> ORGANISM: Consensus
<220> FEATURE:
<221> NAME/KEY: VARIANT
<222> LOCATION: (7)..(7)
<223> OTHER INFORMATION: no consensus amino acid
<220> FEATURE:
<221> NAME/KEY: VARIANT
<222> LOCATION: (10)..(10)
<223> OTHER INFORMATION: no consensus amino acid
<220> FEATURE:
<221> NAME/KEY: VARIANT
<222> LOCATION: (11)..(11)
<223> OTHER INFORMATION: no consensus amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (15)..(15)
<223> OTHER INFORMATION: k or r
<220> FEATURE:
<221> NAME/KEY: MISC_FEATURE
<222> LOCATION: (19)..(19)
<223> OTHER INFORMATION: i or v
<220> FEATURE:
<221> NAME/KEY: MISC_FEATURE
<222> LOCATION: (26)..(26)
<223> OTHER INFORMATION: g or a

<400> SEQUENCE: 50

Leu Trp Arg Trp Tyr Gln Xaa Cys Leu Xaa Xaa His Pro Val Lys Thr
1               5                   10                  15

Gln Val Ile Ser Ser Gly Ile Leu Trp Gly Leu Gly Asp
            20                  25

<210> SEQ ID NO 51
<211> LENGTH: 48
<212> TYPE: PRT
<213> ORGANISM: Consensus
<220> FEATURE:
<221> NAME/KEY: MISC_FEATURE
<222> LOCATION: (5)..(5)
<223> OTHER INFORMATION: l or i
<220> FEATURE:
<221> NAME/KEY: MISC_FEATURE
<222> LOCATION: (11)..(11)
<223> OTHER INFORMATION: e or g

<400> SEQUENCE: 51

Lys Arg Asp Phe Leu Pro Ala Leu Val Leu Glu Gly Gly Ile Trp Pro
1               5                   10                  15

Ala Val Gln Ile Ala Asn Phe Arg Phe Ile Pro Val Arg Tyr Gln Leu

```
                    20                  25                  30
Leu Tyr Val Asn Leu Phe Cys Leu Leu Asp Ser Cys Phe Leu Ser Trp
            35                  40                  45

<210> SEQ ID NO 52
<211> LENGTH: 678
<212> TYPE: DNA
<213> ORGANISM: Zea mays
<220> FEATURE:
<221> NAME/KEY: CDS
<222> LOCATION: (1)..(678)

<400> SEQUENCE: 52 atg cgg cgg cta tgg cgg tgg tac cag cag tgc ctg gcc gcg cac ccg      48
Met Arg Arg Leu Trp Arg Trp Tyr Gln Gln Cys Leu Ala Ala His Pro
1               5                   10                  15 gtg cgc acg cag gtc gtc agc tcc ggc atc ctc tgg ggc ctc ggc gac      96
Val Arg Thr Gln Val Val Ser Ser Gly Ile Leu Trp Gly Leu Gly Asp
                20                  25                  30 atc ggc gcc cag acc gtc acc tac tac tcc gct cgc ccc gac cgt cgc     144
Ile Gly Ala Gln Thr Val Thr Tyr Tyr Ser Ala Arg Pro Asp Arg Arg
            35                  40                  45 ggc cac gac agc agc cct ccc gac ccc gag gat aaa gat aat aaa gac     192
Gly His Asp Ser Ser Pro Pro Asp Pro Glu Asp Lys Asp Asn Lys Asp
        50                  55                  60 aat aaa gag ttt aaa gtt gat tgg aag agg gtg ggc atc aca agc tcc     240
Asn Lys Glu Phe Lys Val Asp Trp Lys Arg Val Gly Ile Thr Ser Ser
65                  70                  75                  80 ttc gga ttt gct ttt gtt ggt cca gtt ggg cat tac tgg tat gaa tac     288
Phe Gly Phe Ala Phe Val Gly Pro Val Gly His Tyr Trp Tyr Glu Tyr
                85                  90                  95 ctg gat cgc atc atc cgg cgg agg ttt cag cct aac acg ttc aaa ttc     336
Leu Asp Arg Ile Ile Arg Arg Arg Phe Gln Pro Asn Thr Phe Lys Phe
            100                 105                 110 gtc gcc tca aaa gtt gcc gcg gat gga ttc ctc ttc gga cca cta gac     384
Val Ala Ser Lys Val Ala Ala Asp Gly Phe Leu Phe Gly Pro Leu Asp
        115                 120                 125 ctc ctc ctg ttc ttc tca tat gtt ggt ctg ggt caa gga agg agc ata     432
Leu Leu Leu Phe Phe Ser Tyr Val Gly Leu Gly Gln Gly Arg Ser Ile
    130                 135                 140 gag cag gtg aag gag gac gtg aag agg gac ttc att ccg gct ctg gtg     480
Glu Gln Val Lys Glu Asp Val Lys Arg Asp Phe Ile Pro Ala Leu Val
145                 150                 155                 160 tta ggc gga acc atc tgg cct gct gtg cag atc gcg aac ttc cgc ttc     528
Leu Gly Gly Thr Ile Trp Pro Ala Val Gln Ile Ala Asn Phe Arg Phe
                165                 170                 175 gtt ccc gtg cgg tac cag ctc ctg tat gtg aac ttg ttc tgc ctc ctg     576
Val Pro Val Arg Tyr Gln Leu Leu Tyr Val Asn Leu Phe Cys Leu Leu
            180                 185                 190 gac agc tgc ttc ctg tcg tgg att gag cag cag ggt gac gcc tcc tgg     624
Asp Ser Cys Phe Leu Ser Trp Ile Glu Gln Gln Gly Asp Ala Ser Trp
        195                 200                 205 aag cgg tgg ttc act tcg ttc cag aaa atc gaa gac cag aag ggt aag     672
Lys Arg Trp Phe Thr Ser Phe Gln Lys Ile Glu Asp Gln Lys Gly Lys
    210                 215                 220 gtt taa                                                              678
Val
225

<210> SEQ ID NO 53
<211> LENGTH: 225
```

```
<212> TYPE: PRT
<213> ORGANISM: Zea mays

<400> SEQUENCE: 53

Met Arg Arg Leu Trp Arg Trp Tyr Gln Gln Cys Leu Ala Ala His Pro
1               5                   10                  15

Val Arg Thr Gln Val Val Ser Ser Gly Ile Leu Trp Gly Leu Gly Asp
                20                  25                  30

Ile Gly Ala Gln Thr Val Thr Tyr Tyr Ser Ala Arg Pro Asp Arg Arg
            35                  40                  45

Gly His Asp Ser Ser Pro Pro Asp Pro Glu Asp Lys Asp Asn Lys Asp
        50                  55                  60

Asn Lys Glu Phe Lys Val Asp Trp Lys Arg Val Gly Ile Thr Ser Ser
65                  70                  75                  80

Phe Gly Phe Ala Phe Val Gly Pro Val Gly His Tyr Trp Tyr Glu Tyr
                85                  90                  95

Leu Asp Arg Ile Ile Arg Arg Arg Phe Gln Pro Asn Thr Phe Lys Phe
                100                 105                 110

Val Ala Ser Lys Val Ala Ala Asp Gly Phe Leu Phe Gly Pro Leu Asp
            115                 120                 125

Leu Leu Leu Phe Phe Ser Tyr Val Gly Leu Gly Gln Gly Arg Ser Ile
        130                 135                 140

Glu Gln Val Lys Glu Asp Val Lys Arg Asp Phe Ile Pro Ala Leu Val
145                 150                 155                 160

Leu Gly Gly Thr Ile Trp Pro Ala Val Gln Ile Ala Asn Phe Arg Phe
                165                 170                 175

Val Pro Val Arg Tyr Gln Leu Leu Tyr Val Asn Leu Phe Cys Leu Leu
            180                 185                 190

Asp Ser Cys Phe Leu Ser Trp Ile Glu Gln Gln Gly Asp Ala Ser Trp
        195                 200                 205

Lys Arg Trp Phe Thr Ser Phe Gln Lys Ile Glu Asp Gln Lys Gly Lys
        210                 215                 220

Val
225
```

PREPARATION OF ORGANISMS WITH FASTER GROWTH AND/OR HIGHER YIELD

RELATED APPLICATIONS

This application is a national stage application (under 35 U.S.C. 371) of PCT/US2004/004422 filed Feb. 13, 2004 which claims benefit to German application 103 06 734.5 filed Feb. 17, 2003, German application 103 16 464.2 filed Apr. 9, 2003, and German application 103 59 613.5 filed Dec. 18, 2003.

BACKGROUND OF THE INVENTION

Field of the Invention

The present invention relates to a method for preparing a nonhuman organism with faster growth and/or higher yield in comparison with a reference organism, which method comprises increasing in said nonhuman organism or in one or more parts thereof the activity of L450 in comparison with said reference organism, for example on the basis of increasing the amount of L450 RNA and/or L450 polypeptide, advantageously on the basis of increased expression of L450. In further embodiments, the invention relates to a method for preparing plants, microorganisms or useful animals which grow faster or give higher yields, which method comprises an increased L450 activity in said organisms, and to a plant, a microorganism and useful animal whose L450 activity is increased and to the yield or biomass thereof. Furthermore, the invention also relates to an L450 polypeptide, to a polynucleotide coding therefor and to cells, plants, microorganisms and useful animals transformed therewith and to methods for preparing fine chemicals by using said embodiments of the present invention.

Ever since useful plants were first cultivated, increasing the crop yield has, in addition to improving resistance to abiotic and biotic stress, been the most important aim when growing new plant varieties. Means as diverse as tilling, fertilizing, irrigation, cultivation or crop protection agents, to name but a few, are used for improving yields. Thus, cultivation successes in increasing the crop, for example by increasing the seed setting, and those in reducing the loss of crop, for example owing to bad weather, i.e. weather which is too dry, too wet, too hot or too cold, or due to infestation with pests such as, for example, insects, fungi or bacteria, complement one another. In view of the rapidly growing world population, a substantial increase in yield, without extending the economically arable areas, is absolutely necessary in order to provide sufficient food and, at the same time, protect other existing natural spaces.

The methods of classical genetics and cultivation for developing new varieties with better yields are increasingly supplemented by genetic methods. Thus, genes have been identified which are responsible for particular properties such as resistance to abiotic or biotic stress or growth rate control. Interesting genes or gene products thereof may be appropriately regulated in the desired useful plants, for example by mutation, (over)expression or reduction/inhibition of such genes or their products, in order to achieve the desired increased yield or higher tolerance to stress.

The same applies to microorganisms and useful animals, the breeding of which is primarily and especially concerned with likewise achieving a particular biomass or a particular weight more rapidly, in addition to higher resistance to biotic or abiotic stress.

One example of a strategy resulting in better or more rapid plant growth is to increase the photosynthetic capability of plants (U.S. Pat. No. 6,239,332 and DE 19940270). This approach, however, is promising only if the photosynthetic performance of said plants is growth-limiting. Another approach is to modulate regulation of plant growth by influencing cell cycle control (WO 0131041, CA 2263067, WO 56905, WO 37645). However, a change in the plant's architecture may be the undesired side effect of a massive intervention in the control of plant growth (WO 0131041; CA 2263067).

Despite a few very promising approaches, there is nevertheless still a great need of providing methods for preparing organisms with faster growth and higher yield, in particular plants and microorganisms, and of providing such organisms, in particular plants and microorganisms.

BRIEF SUMMARY OF THE INVENTION

It is an object of the present invention to provide a method of this kind for increasing the yield and growth of organisms, in particular of plants.

We have found that this object is achieved by the inventive method described herein and the embodiments characterized in the claims.

Consequently, the invention relates to a method for preparing a nonhuman organism with increased growth rate, i.e. with faster growth and/or increased yield in comparison with a reference organism, which method comprises increasing in said nonhuman organism or in one or more parts thereof the activity of L450 in comparison with a reference organism, for example on the basis of increasing the amount of L450 RNA and/or L450 polypeptide.

BRIEF DESCRIPTION OF THE DRAWINGS

FIG. 3 depicts the Blast comparison between the sequence depicted in SEQ ID NO: 1 (Query) and the sequence depicted in SEQ ID NO: 23 (Sbjct). SEQ ID NO: 23 was published under SEQ ID NO: 701 in US 2002/0023281.

FIG. 7 shows multiple alignment and consensus sequence of plant, microorganism and animal derived sequences and the consensus sequence of the shown sequences. The sequences are: AT3G24570 (SEQ ID NO: 2), 51291079HYSEQCANOLA (SEQ ID NO: 6), POTATO2MTX (SEQ ID NO: 41), c48958528 gm021002 (SEQ ID NO: 8), 62820788HYSEOBARLEY (SEQ ID NO: 35), 54861924HYSEQWHEAT (SEQ ID NO: 37), AP003434_15 (SEQ ID NO: 4), HYSEOMAIZE (SEQ ID NO: 53), PIR:S45343 (SEQ ID NO: 14), PIR:S29031 (SEQ ID NO: 16), AE003492_22 (SEQ ID NO: 45), PIR:S59397 (SEQ ID NO: 12), PIR:T51590 (SEQ ID NO: 43), and Consensus (SEQ ID NO: 46).

FIG. 8 shows multiple alignment and consensus sequence of the plant derived sequences without SEQ ID NO: 43, and the consensus sequence of the shown sequences. The sequences are: AT3G24570 (SEQ ID NO: 2), 51291079HYSEQCANOLA (SEQ ID NO: 6), POTATO2MTX (SEQ ID NO: 41), c48958528gm021002 (SEQ ID NO: 8), 62820788HYSEQBARLEY (SEQ ID NO: 35), 54861924HYSEQWHEAT (SEQ ID NO: 37), AP003434_15 (SEQ ID NO: 4), HYSEQMAIZE (SEQ ID NO: 53), and Consensus (SEQ ID NO:49).

DETAILED DESCRIPTION OF THE INVENTION

Figure 1:
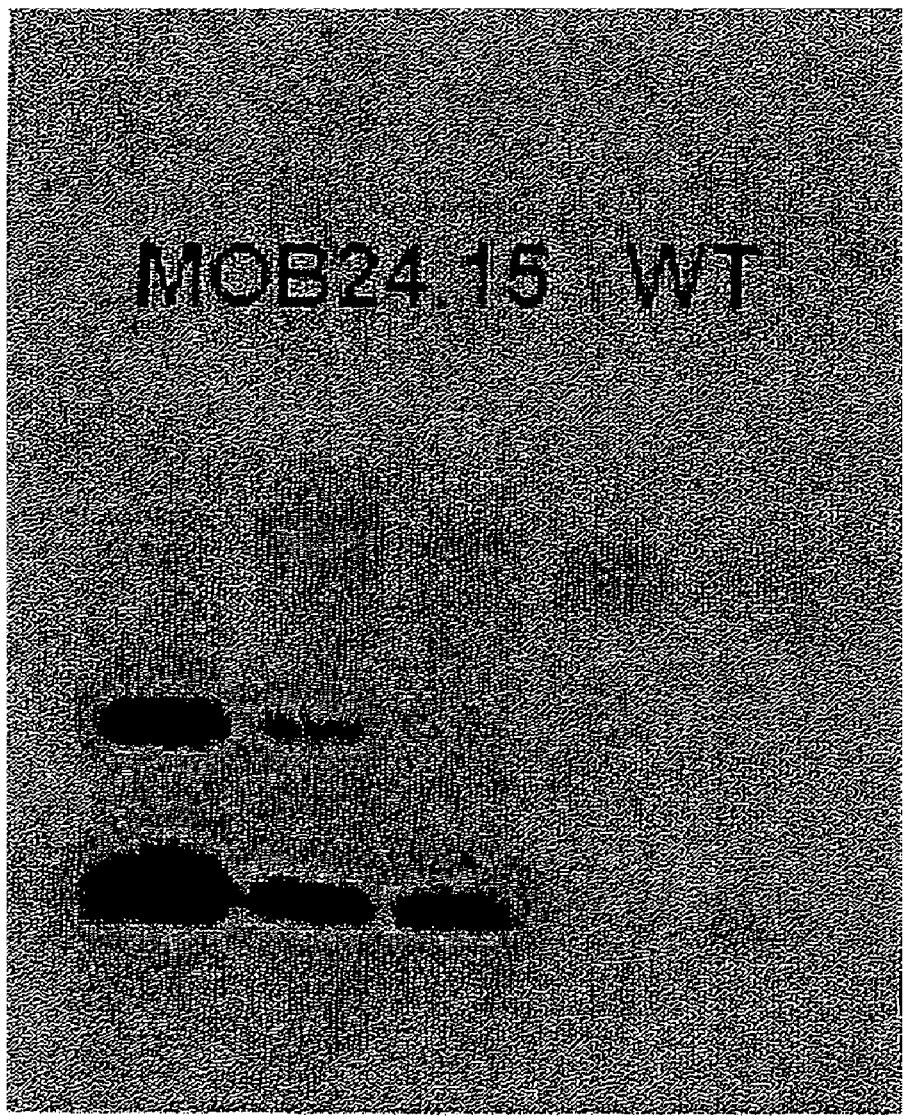
FIG. 1 depicts the Northern blot analysis of an L450-overexpressing line (450B). Three plants of this line and two wild-type plants were analyzed. The lower, strongly hybridizing band corresponds to the L450 transcript.

Increased expression of L450 in *Arabidopsis thaliana* has been found to lead to accelerated growth of the plants and to an increased final weight and an increased amount of seeds. L450 has been described as ORF MOB24.15 on BAC MOB24 (GenBank Accession No.: AB020746)and in US2002/0023281. An L450 function is mentioned neither in the annotation of the ORF nor in the description of US2002/0023281. However, a Blastp comparison of the L450 sequence of *Arabidopsis thaliana* under standard conditions revealed a significant homology to the yeast protein YLR251w (Accession PIR:S59397) and to the peroximal mouse protein MVP17 and to the human homolog thereof. Interestingly a homolog in *Drosophila* (Accession AE 003492-22) was also found.

A particular surprise was the finding that expression of the L450 homolog of the evolutionarily distant yeast *Saccharomyces cerevisiae* increases growth in *Arabidopsis thaliana*. It may also be assumed that L450 is a functionally conserved gene and that an increase in the activity of MVP17, YLR251c or of their specific homologs also leads to faster growth or increased yield in an organism in the same manner as has been observed according to the invention for L450 and YLR251c in *Arabidopsis*. Presumably, therefore, transgenic expression of other distant L450 homologs in an organism also result in the observed faster growth and higher yield.

In a preferred embodiment, the invention relates to a method for preparing an organism, a cell, a tissue, e.g. an animal, a microorganism or a plant with increased growth rate, i.e. with faster growth and/or increased yield, which method comprises increasing in said plant or in one or more parts thereof the activity of L450, for example on the basis of increasing the amount of L450 RNA and/or L450 polypeptide.

"Organism" here means any organism which is not a human being. Consequently, the term relates to prokaryotic and eukaryotic cells, microorganisms, higher and lower plants, including mosses and algae, and to nonhuman animals, or to cells. Consequently, organisms of human origin are also included, as long as said organism is not a human being. In one embodiment, the organism is unicellular or multicellular.

"Increased growth", "faster growth" or "increased growth rate" here means that the increase in weight, for example fresh weight, or in biomass per time unit is greater than that of a reference, in particular of the starting organism from which the nonhuman organism of the invention is prepared. Faster growth preferably results in a higher final weight of said nonhuman organism. Thus, for example, faster growth makes it possible to reach a particular developmental stage earlier or to prolong growth in a particular developmental stage. Preference is given to attaining a higher final weight.

The terms "wild type", "control" or "reference" are exchangeable and can be a cell or a part of organisms such as an organelle or a tissue, or an organism, in particular a microorganism or a plant, which was not modified or treated according to the herein described method according to the invention. Accordingly, the cell or a part of organisms such as an organelle or a tissue, or an organism, in particular a microorganism or a plant used as wild type, control or reference corresponds to the cell, organism or part thereof as much as possible and is in any other property but in the result of the method of the invention as identical to the subject matter of the invention as possible. Thus, the wild type, control or reference is treated identically or as identical as possible, saying that only conditions or properties might be different which do not additionally influence the quality of the tested property.

Preferably, any comparison is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant or a microorganism, which was not modified or treated according to the herein described method of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, -tissue or -organism, in particular plant or microorganism, relates to an organelle, cell, tissue or organism, in particular plant or micororganism, which is nearly genetically identical to the organelle, cell, tissue or organism, in particular microorganism or plant, of the present invention or a part thereof preferably 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is preferably a subject, e.g. an organelle, a cell, a tissue, an organism, which is genetically identical to the organism, cell organelle used according to the method of the invention except that nucleic acid molecules or the gene product encoded by them are changed according to the inventive method.

Preferably, the reference, control or wild type differs form the subject of the present invention only in the cellular activity of the polypeptide of the invention, e.g. as result of an increase in the level of the nucleic acid molecule of the present invention or an increase of the specific activity of the polypeptide of the invention, e.g. by or in the expression level or activity of an protein having an said activity and its biochemical or genetical causes.

In case, a control, reference or wild type differing from the subject of the present invention only by not being subject of the method of the invention can not be provided, a control, reference or wild type can be an organism in which the cause for the modulation of an activity conferring the increase of the yield or growth or expression of the nucleic acid molecule of the invention as described herein has been switched back or off, e.g. by knocking out the expression of the responsible gene product, e.g. by antisense inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc.

Accordingly, preferred reference subject is the starting subject of the present method of the invention. Preferably, the reference and the subject matter of the invention are compared after standardization and normalization, e.g. to the amount of total RNA, DNA, or Protein or activity or expression of reference genes, like housekeeping genes, such as ubiquitin.

A series of mechanisms exists via which a modification in the polypeptide of the invention can directly or indirectly affect the yield. For example, the molecule number or the specific activity of the polypeptide of the invention or the nucleic acid molecule of the invention may be increased. Larger amounts of the desired product can be produced if the polypeptide or the number of expression of the nucleic acid of the invention is expressed de novo if the organism lacked the enzymatic activity, which had been introduced. However, it is also possible to increase the expression of the gene which is naturally present in the organisms, for example by modifying the regulation of the gene, or by increasing the stability of the mRNA or of the gene product encoded by the nucleic acid molecule of the invention.

Accordingly, preferred reference subject is the starting subject of the present inventive method. Preferably, the reference and the inventive subject are compared after normalization, e.g. to the amount of total RNA, DNA, or protein or activity or expression of reference genes, like housekeeping genes or shown in the examples.

The inventive increase, decrease or modulation can be constitutive, e.g. due to a stable expression, or transient, e.g. due to an transient transformation or temporary addition of a modulator as a agonist or antagonist or inducible, e.g. after transformation with a inducible construct carrying the inventive sequences and adding the inducer.

The term "increase" or "decrease" of an activity in a cell, tissue, organism, e.g. plant or microorganism, means that the overall activity in said compartment is increased or decreased, e.g. as result of an increased or decreased expression of the gene product, the addition or reduction of an agonist or antagonist, the inhibition or activation of an enzyme, or a modulation of the specific activity of the gene product, for example as result of a mutation. A mutation in the catalytic centre of an inventive enzyme can modulate the turn over rate of the enzyme, e.g. a knock out of an essential amino acid can lead to a reduced or completely knock out activity of the enzyme. The specific activity of an enzyme of the present invention can be increased such that the turn over rate is increased or the binding of a co-factor is improved. Improving the stability of the encoding mRNA or the protein can also increase the activity of a gene product. The stimulation of the activity is also under the scope of the term "increased activity".

The specific activity of an inventive protein or a protein encoded by an inventive polynucleotide or expression cassette can be tested as described in the examples. In particular, the expression of said protein in a cell, e.g. a plant cell or a microorganism and the detection of an increase in fresh weight, dry weight, seed number and/or seed weight in comparison to a control is an easy test.

Accordingly, the term "increase" or "decrease" means that the specific activity as well as the amount of a compound, e.g. of the inventive protein, mRNA or DNA, can be increased or decreased.

The term "increase" also means, that a compound or an activity is introduced into a cell de novo or that the compound or the activity has not been detectable. Accordingly, in the following, the term "increasing" also comprises the term "generating" or "stimulating"

In general, an activity of a gene product in an organism, in particular in a plant cell, a plant, or a plant tissue or a part thereof can be increased by increasing the amount of the specific encoding mRNA or the corresponding protein in said organism or part thereof. "Amount of protein or mRNA" is understood as meaning the molecule number of inventive polypeptide or mRNA molecules in an organism, a tissue, a cell or a cell compartment. "Increase" in the amount of the inventive protein means the quantitative increase of the molecule number of said protein in an organism, a tissue, a cell or a cell compartment or part thereof—for example by one of the methods described herein below—in comparison to a wild type, control or reference.

The increase in molecule number amounts preferably to at least 1%, preferably to more than 10%, more preferably to 30% or more, especially preferably to 50%, 100% or more, very especially preferably to 500%, most preferably to 1000% or more. However, a de novo expression is also regarded as subject of the present invention.

A modification, i.e. an increase or decrease, can be caused by endogenous or exogenous factors. For example, an increase in activity in an organism or a part thereof can be caused by adding a gene product or a precursor or an activator or an agonist to the media or nutrition or can be caused by introducing said subjects into an organism, transient or stable.

Accordingly, in one embodiment, the method of the present invention comprises one or more of the following steps a) stabilizing the inventive protein;
b) stabilizing the inventive protein encoding mRNA;
c) increasing the specific activity of the inventive protein;
d) expressing or increasing the expression of a homologous or artificial transcription factor for inventive protein expression;
e) stimulating the inventive protein activity through exogenous inducing factors;
f) expressing a transgenic inventive protein encoding gene; and/or
g) increasing the copy number of the inventive protein encoding gene.

In general, the amount of mRNA or polypeptide in a cell or a compartment of an organism correlates with the activity of the encoded protein or enzyme in said volume. Said correlation is not always linear, the activity in the volume is dependent on the stability of the molecules or the presence of activating or inhibiting co-factors. Further, product and educt inhibitions of enzymes are well known. However, in one embodiment, the activity of the inventive polypeptide is increased via increasing the expression of the encoding gene, in particular of a nucleic acid molecule comprising the sequence of the inventive polynucleotide, leading regularly to an increase in amount of inventive polypeptide.

In one embodiment the increase fresh weight, dry weight, seed weight and/or seed amount is by increasing the endogenous level of the inventive protein. The endogenous level of the inventive protein can for example be increased by modifying the transcriptional or translational regulation of the polypeptide. Regulatory sequences are operatively linked to the coding region of an endogenous protein and control its transcription and translation or the stability or decay of the encoding mRNA or the expressed protein. In order to modify and control the expression, promoter, UTRs, splicing sites, processing signals, polyadenylation sites, terminators, enhancers, post transcriptional or posttranslational modification sites can be changed or amended. For example, the expression level of the endogenous protein can be modulated by replacing the endogenous promoter with a stronger transgenic promoter or by replacing the endogenous 3'UTR with a 3'UTR which provides more stability without amending the coding region. Further, the transcriptional regulation can be modulated by introduction of a artificial transcription factor as described in the examples. Alternative promoters, terminators and UTR are described below.

In one advantageous embodiment, in the method of the present invention the activity of a polypeptide is increased comprising or consisting of the following consensus sequence:

group. Presently, the capital letters indicate that in less than 10% of all aligned sequences the amino acids in this position are not identical with the shown consensus residue. The lower letters indicate that in 10% to 60% of all aligned sequences the amino acids in this position are not identical with the shown consensus residue. Anyhow, x indicates any given amino acid. Core consensus sequences are underlined and represent the essential part of the consensus sequence:

lwrwYqxcLaxhPvktqvissGxlwglGD (Seq ID No.: 47)

whereby 10 or less, preferably 7, preferred 4 or 3, more preferred 2, even more preferred 1, most preferred 0 of the amino acids positions indicated by a capital or lower letter can

```
Mxrlwrwyqxclaxhpvktqvissgxlwglgdixaqavthxsa[x]35Rvxitssfgfgfvgpv     (Seq ID No.: 46)

ghxWYexLDrfixxxxxxxxxxxxsxxfvaxKvaxDglxfgPldllxFfxyvGxxxgrsxxxqvkex vKrdxxpalxlxgxiWPavQiaNFrxvPvryqllyvnlfclldsxfLSwxxqq
``` whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter can be replaced by an x.

In one embodiment not more than 5, preferably 4, even more preferred 3 or 2, most preferred one or non amino acid position indicated by a capital letter are/is replaced by an x.

In one embodiment 20 or less, preferably 15 or 10, preferably 9, 8, 7, or 6, more preferred 5 or 4, even more preferred 3., even more preferred 2, even more preferred 1, most preferred 0 amino acids are inserted into the consensus sequence.

Figure 7:
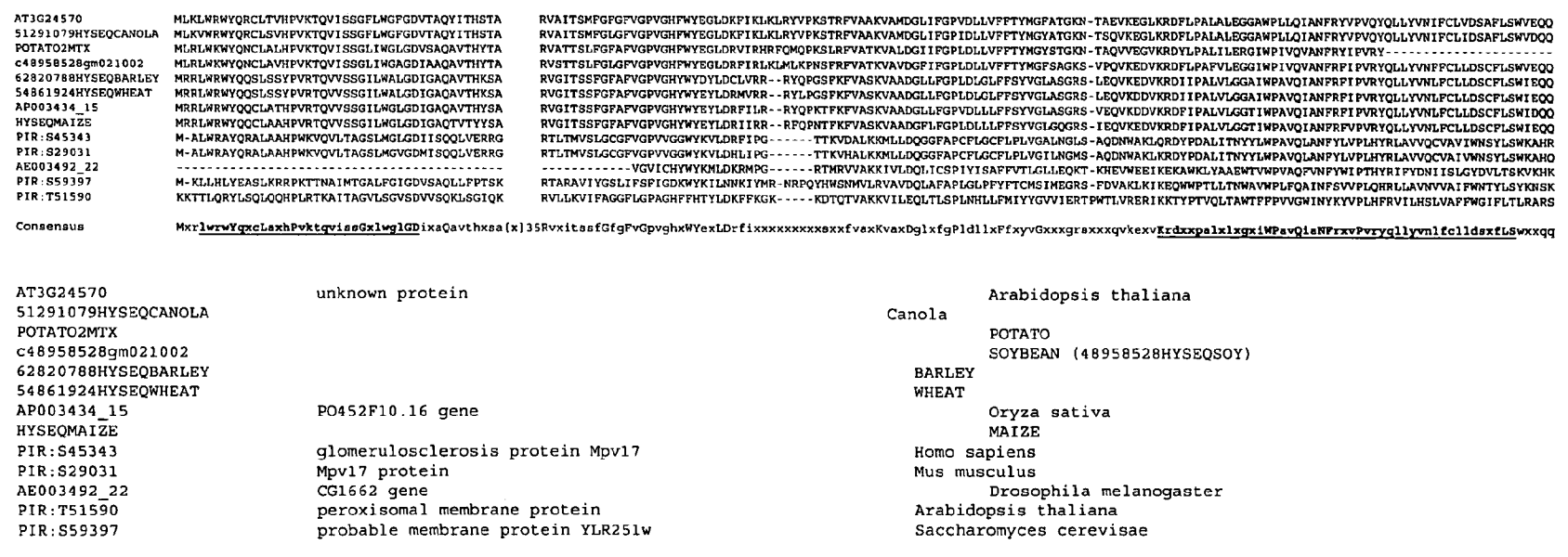

In one embodiment, the consensus sequence consists of only the capital letters of above shown sequence or shown in FIG. 7. In one embodiment, the consensus sequence consists of only the capital letters and lower letters of above shown sequence or shown in FIG. 7.

In one embodiment, the activity of a polypeptide is increased comprising or consisting of one of said consensus sequences, e.g. comprising or consisting of a consensus sequence characterized by the capital letters of above consensus sequence. In one embodiment, the activity of a polypeptide is increased comprising or consisting of a consensus sequence characterized by the capital and lower letters of above consensus sequence (or FIG. 7).

The consensus sequence was derived from a multiple alignment of the sequences of *Arabidopsis thaliana*, Canola, potato, soybean, barley, wheat, rice, corn, human, mice, *Drosophila melanogaster* and *Saccharomyces cerevisae* as shown in FIG. 7. The capital letters indicate that the amino acids are conserved in all or near all aligned proteins, and the small letters indicate that the amino acids are conserved in some of the aligned proteins, forming some kind of a subbe replaced by an x. Preferably, not more than one amino acid position indicated by a capital letter is replaced by an x. and KrdxxpalxlxgxiwPavQiaNFrxvPvryqllyvnlfclldsxfLS (Seq ID No.: 48)

whereby 10 or less, preferably 7, preferred 4 or 3, more preferred 2, even more preferred 1, most preferred 0 of the amino acids positions indicated by a capital or lower letter can be replaced by an x. Preferably, not more than one amino acid position indicated by a capital letter is replaced by an x.

Accordingly, in one embodiment, in the method of the present invention the activity of a polypeptide comprising one or both said core consensus sequence is increased whereby 10 or less, preferably 7, preferred 4 or 3, more preferred 2, even more preferred 1, most preferred 0 of the amino acids positions indicated by a capital or lower letter can be replaced by an x. Preferably, not more than one amino acid position indicated by a capital letter is replaced by an x.

The multiple alignment was performed with the Software GenoMax Version 3.4, InforMax™, Invitrogen™ life science software, U.S. Main Office, 7305 Executive Way, Frederick, Md. 21704, USA with the following settings:

Gap opening penalty: 10.0; Gap extension penalty: 0.05; Gap separation penalty range: 8; % identity for alignment delay: 40; Residue substitution matrix: blosum; Hydrophilic residues: G P S N D Q E K R; Transition weighting: 0.5; Consensus calculation options: Residue fraction for consensus: 0.5.

In one advantageous embodiment, the method of the present invention comprises the increasing of a polypeptide comprising or consisting of the following plant consensus sequence:

```
MlrLWRWYQxcLxxhPVkTQViSSGilWglGDigAQavTHytA[x]35              (Seq ID No.: 49)
  r          r    v    a           s RVgiTSsFGfaFVGPVGHfWYEgLDrfirrklryqPksfrFVAsKVAaDGliFGPlDLlvFF
         y y                   k          l         l tYmGlaxGksteQVKedvKRDflPAlvLeGGiWPavQiANFRfiPVrYQLLYVNlFCLlD
s v      r                i         g ScFLSWieQQ
``` whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter can be replaced by an x.

In one embodiment not more than 5, preferably 4, even more preferred 3 or 2, most preferred one or non amino acid position indicated by a capital letter are/is replaced by an x.

In one embodiment 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence.

In one embodiment, the consensus sequence consists of only the capital letters of above shown sequence or shown in FIG. 8.

In one embodiment, the consensus sequence consists of the capital letters and lower letters of above shown sequence or shown in FIG. 8.

In one embodiment, the activity of a polypeptide is increased comprising or consisting of one of said consensus sequences, e.g. comprising or consisting of a consensus sequence characterized by the capital letters of above consensus sequence. In one embodiment, the activity of a polypeptide is increased comprising or consisting of a consensus sequence characterized by the capital and lower letters of above consensus sequence.

The consensus sequence was derived from a multiple alignment of the plant sequences, i.e. of *Arabidopsis thaliana*, Canola, potato, soybean, barley, wheat, rice and corn as shown in FIG. 8. The capital letters indicate that the amino acids are conserved in all or near all aligned proteins, and the small letters indicate that the amino acids are conserved in some of the aligned proteins, forming some kind of a subgroup. The indication of a further amino acid residue represents that at this position two amino acid residues are prominent. Said amino acids are conserved in subgroup of the sequences aligned. Anyhow, x indicates any given amino acid. Core consensus sequences are underlined and represent the essential part of the consensus sequence.

```
    LWRWYQxcLxxhPVkTQViSSGilWglGD    (Seq ID No.: 50)
           r       v       a
``` whereby 10 or less, preferably 7, preferred 4 or 3, more preferred 2, even more preferred 1, most preferred 0 of the amino acids positions indicated by a capital or lower letter can be replaced by a x. Preferably, not more than one amino acid position indicated by a capital letter is replaced by an x.

In one embodiment, the positions indicated with two preferred amino residues are replaced with an x. Preferred is, however, a consensus sequence, in which the indicated amino acids are met. and

```
                                    (Seq ID No.: 51)
KRDflPAlvLeGGiWPavQiANFRfiPVrYQLLYVNlFCLlDScFLSW
   i    g
``` whereby 10 or less, preferably 7, preferred 4 or 3, more preferred 2, even more preferred 1, most preferred 0 of the amino acids positions indicated by a capital or lower letter can be replaced by a x. Preferably, not more than one amino acid position indicated by a capital letter is replaced by an x.

Accordingly, in one embodiment, in the method of the present invention the activity of a polypeptide comprising one or both said core consensus sequence is increased, whereby 10 or less, preferably 7, preferred 4 or 3, more preferred 2, even more preferred 1, most preferred 0 of the amino acids positions indicated by a capital or lower letter can be replaced by a x. Preferably, not more than one amino acid position indicated by a capital letter is replaced by an x.

In the following, under term "consensus sequence" the above consensus sequences, core sequences, plant consensus sequence, plant core consensus sequence in all described variations will be understood.

The multiple alignment was performed with the Software GenoMax Version 3.4, InforMax™, Invitrogen™ life science software, U.S. Main Office, 7305 Executive Way, Frederick, Md. 21704, USA with the following settings:

Gap opening penalty: 10.0; Gap extension penalty: 0.05; Gap separation penalty range: 8; % identity for alignment delay: 40; Residue substitution matrix: blosum; Hydrophilic residues: G P S N D Q E K R; Transition weighting: 0.5; Consensus calculation options: Residue fraction for consensus: 0.5.

Reference organism preferably means the starting organism (wild type) prior to carrying out the method of the invention or a control organism.

If the organism is a plant and a line of origin cannot be determined as reference, the variety which has been approved by the European or German plant variety office at the time of application and which has the highest genetic homology to the plant to be studied may be accepted as reference for determining an increased L450 activity. Consequently, a plant variety which has already been approved at the time of application is then likewise a suitable reference or source for a reference organelle, a reference cell, a reference tissue or a reference organ. The genetic homology may be determined via methods which are well known to the skilled worker, for example via finger-print analyses, for example as described in Roldan-Ruiz, Theor. Appl. Genet., 2001, 1138-1150. A plant or a variety which has increased L450 activity and increased yield or faster growth, compared to the, if possible, genetically identical plant, as described herein, may consequently be regarded as plant of the invention. Where appropriate, the specific L450 activity may be replaced by the amount of L450 mRNA or L450 protein, as described herein. Similar methods for determining the genetic relationship of animals and microorganisms are sufficiently known to the skilled worker, in particular to sytematists. Where appropriate, the organisms and, in particular, the strains mentioned in the examples serve as reference organisms. In particular, the plant strains mentioned there serve as reference organisms for the particular plant species in the rare cases, a reference described above can not be provided.

The line of origin, which has been used for carrying out the method of the invention is a preferred reference.

Various strains or varieties of a species may have different amounts or activities of L450. The amounts or activities of L450 in a cell compartment, cell organelle, cell, tissue, in organs or in the whole plant may be found to differ between different strains or varieties. However, owing to the observation on which the invention is based, it may be assumed that the increase, in particular in a total extract of the organism, preferably of the plant, in comparison with the respective starting strain or the respective starting variety or with the abovementioned reference, results in faster growth and/or higher yield. However, it is also conceivable that even the increased activity, for example due to overexpression, in specific organs may cause the desired effect, i.e. faster growth and higher yield.

In the following, the term "increasing" comprises the generating as well as the stimulating of a property.

In order to determine the "increase in amount", "increase in expression", "increase in activity", or "increase in mass", this property is compared to that of a reference or starting organism, but normalized to a defined size. For example, expression between the transgenic nonhuman organism and the reference (wild type) is compared, normalizing, for example, to the amount of total RNA, total DNA or protein or to the activity or amount of mRNA of a particular gene (or gene product), for example of a housekeeping gene. Increasing the mass or yield likewise involves comparison of the modified and starting organisms, but with normalization to the individual plant or to the yield per hectare, etc.

The L450 activity is preferably at least 5%, more preferably 10%, even more preferably 20%, 30%, 50% or 100%, higher than that of the reference organism. Most preferably, the activity is 200%, 500% or 1 000% or more, higher than in the reference organism.

Owing to the higher L450 activity, in particular owing to a from 5% to 1 000% increase in L450 activity, preferably owing to a from 10% to 100% increase, growth is preferably 5%, preferably 10%, 20% or 30%, faster. More preferably, growth is faster by 50%, 100%, 200% or 500% or more, in comparison with a reference organism. Preference is also given to increasing the L450 activity by 10%, 20%, 30% or from 50% to 100% and to a faster growth of 10%, 20%, 30% or 50%.

Owing to the higher L450 activity, in particular owing to a from 5% to 1 000% increase in L450 activity, preferably owing to a from 10% to 100% increase, yield is preferably 5%, preferably 10%, 20% or 30%, higher. More preferably, yield is higher by 50%, 100%, 200% or 500% or more, in comparison with a reference organism. Preference is also given to increasing the L450 activity by 10%, 20%, 30% or from 50% to 100% and to a higher yield of 10%, 20%, 30% or 50%.

"Accelerated growth", "faster growth" or "increased growth rate" in plants means faster "plant growth", i.e. that the increase in fresh weight in the vegetative phase is greater than that of a reference plant, in particular of the starting plant from which the plant of the invention has been prepared. Preferably, the final weight of said plant is also higher than that of the reference plant.

For microorganisms or cells, faster growth refers to higher production of biomass.

"Final weight" means a weight typically reached at the end of a particular phase or the produced biomass of an organism. For plants, "increased final weight" preferably means the higher fresh weight reached at the end of vegetative phase, in comparison with the fresh weight of a reference organism. More specifically, the higher final weight may be due to a higher yield, as discussed below. For microorganisms or cells, "increased final weight" means the amount of biomass produced by said microorganisms or cells in the exponential phase.

The term "yield" means according to the invention that the biomass or biomaterial suitable for further processing has increased. The term "further processing" refers both to industrial processing and to instant usage for feeding. If the method refers to a plant, this includes plant cells and tissue, organs and parts of plants in all of their physical forms such as seeds, leaves, fibers, roots, stems, embryos, calli, harvest material, wood, or plant tissue, reproductive tissue and cell cultures which are derived from the actual plant and/or may be used for producing a plant of the invention. Preference is given to any parts or organs of plants, such as leaf, stalk, shoot, flower, root, tubers, fruits, bark, seed, wood, etc. or the whole plant. Seeds comprise any seed parts such as seed covers, epidermal and seed cells or embryonic tissue. Particular preference is given to the agricultural or harvested products, in particular fruits, seeds, tubers, fruits, roots, bark or leaves or parts thereof.

Thus, *Arabidopsis* plants having increased L450 expression not only reach a defined weight significantly earlier than the reference plants but also attained a higher maximum fresh weight, dry weight, seed weight and/or higher yield. Thus, for example, the fresh weight of *Arabidopsis thaliana* having increased L450 expression increased by from 17% to 31%, and the number of leaves was increased by from 11 to 26%, compared to the wild type. A difference in the average fresh weight of 346 mg in the plant line of the invention, compared to 245 mg in the wild-type plant grown under identical conditions, was found as early as during the production experiment P1. Further comparisons are illustrated in the examples.

Furthermore, a significantly higher seed yield is found in *Arabidopsis* plants with increased L450 activity. Thus, *Arabidopsis* plants with increased L450 activity yielded on average 97 mg of seeds under greenhouse conditions, while an average of only 78 mg of seeds was obtained from unmodified control plants. Thus a 24% increase in yield is achieved. If the method relates to a useful animal, "yield" means the amount of biomass or biomaterial of a useful animal, which is suitable for further processing, in particular meat, fat, bones, organs, skin, fur, eggs or milk.

If the method of the invention relates to a microorganism, the term "yield" means both the biomass produced by said microorganism, for example the fermentation broth, and the cells themselves. If said microorganism produces a particular product suitable for further processing or for direct application, for example the fine chemicals described below, the method of the invention preferably increases production of said product per microorganism or per unit time.

"Increasing the amount", "increasing expression", "increasing the activity" or "increasing the mass" means in each case increasing the particular property compared to the wild type or to a reference, taking into account the same growth conditions. The wild type or reference may be a cell compartment, a cell organelle, a cell, a tissue, an organ or a nonhuman organism, preferably a plant, which has not been subjected to the method of the invention but which is otherwise incubated under as identical conditions as possible and which is then compared to a product prepared according to the invention, with respect to the features mentioned herein.

An "increase" may also refer to a cell compartment, a cell organelle, a cell, a tissue, an organ or a nonhuman organism, preferably a plant, as reference which has been modified, altered and/or manipulated in such a way that it is possible to measure in it an increased absolute L450 activity (product of the amount of L450 and the relative activity thereof) or amount of L450 (amount per compartment, organelle, cell, tissue, organ and/or nonhuman organism).

The increase may also be effected by endogenous or exogenous factors, for example by adding L450 or a precursor or an activator thereof to nutrients or animal feed. The increase may also be carried out by increasing endogenous or transgenic expression of a gene coding for L450 or for a precursor or activator or by increasing the stability of the abovementioned factors. The phenotypic action of a factor, in particular its L450 activity, may be determined, for example in *Arabidopsis*, by constitutive expression, as described in the examples. L450 activity here means an activity as described below.

Preference is given to increasing the L450 activity in a cell, and more preference is given to the activity having increased in one or more tissues or one or more organs. Normally, the increase in a nonhuman organism entails an increase in one or more tissues or one or more organs, and this in turn often entails the increase in a cell, unless a protein is secreted. A higher L450 activity in a cell may be caused, for example, by a higher activity in one of the cellular compartments as listed below.

"Increasing the amount", "increasing expression", "increasing the activity" or "increasing the mass" means in each case increasing in a constitutive or inducible, stable or transient manner. For example, the increase may also be increased in a cell or a tissue only at a particular time, in comparison with the reference, for example only in a particular developmental stage or only in a particular phase of the cell cycle. The term "increase" also refers to an increase due to different amounts, which may be caused by the response to different inducing reagents such as, for example, hormones or biotic or abiotic signals. However, the activity may also be increased by L450 interacting with exogenous or endogenous modulators which act either in an inhibiting or activating manner.

"L450 activity" of a polypeptide here preferably means that increased expression or activity of said polypeptide results in higher fresh weight, dry weight, seed weight and/or yield, and this particularly preferably results in a plurality of said features, even more preferably in all of said features. Most preferably, "L450 activity" of a polypeptide here means that said polypeptide comprises the polypeptide consensus or consensus core sequence defined above, e.g. preferably shown in anyone of SEQ ID No.: 46, 47, 48, 49, 50 and/or 51, whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter in FIG. 7 or 8 can be replaced by an x and/or not more than 5, preferably 4, even more preferred 3 or 2, most preferred one or non amino acid position indicated by a capital letter in FIG. 7 or 8 are/is replaced by an x and/or 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence or is encoded by a nucleic acid molecule comprising a nucleic acid molecule selected from the group consisting of:

(a) nucleic acid molecule encoding an L450 polypeptide or encoding, preferably at least the mature form of the, polypeptide which is depicted in Seq. ID No.: 2, 4, 6, 8, 10, 12, 14, 16, 25 27, 35, 37, 39, 41, 43, 45, 46, 47, 48, 49, 50, 51 or 5341, 43, 45, 46, 47, 48, 49, 50, 51 or 53;

(b) nucleic acid molecule comprising, preferably at least the mature, polynucleotide of the coding sequence according to Seq. ID No: 1, 3, 5, 7, 9, 11, 13, 15, 24 26, 34, 36, 38, 40, 42, 44 or 52;

(c) nucleic acid molecule whose sequence is derivable from a polypeptide sequence encoded by a nucleic acid molecule according to (a) or (b), due to the degeneracy of the genetic code;

(d) nucleic acid molecule encoding an L450 polypeptide whose sequence is at least 20%, preferably 35%, more preferably 45%, even more preferably 60%, even more preferably 70%, 80%, 90%, 95%, 97%, 98% and 99%, identical to the amino acid sequence of the polypeptide encoded by the nucleic acid molecule according to (a) to (c);

(e) nucleic acid molecule encoding an L450 polypeptide that is derived from an L450 polypeptide encoded by a nucleic acid molecule according to (a) to (d) by substitution, deletion and/or addition of one or more amino acids of the amino acid sequence of the polypeptide encoded by the nucleic acid molecules (a) to (d);

(f) nucleic acid molecule encoding a fragment or an epitope of the L450 polypeptide encoded by any of the nucleic acid molecules according to (a) to (e);

(g) nucleic acid molecule comprising a polynucleotide which comprises the sequence of a nucleic acid molecule obtained by amplification of a preferably microbial or plant cDNA bank using the primers in Seq. ID No.: 19 and 20 and/or 28 and 30 or a combination thereof or of a preferably microbial or plant genomic bank using the primers in Seq. ID No.: 21 and 22;

(h) nucleic acid molecule encoding an L450 polypeptide which has been isolated with the aid of monoclonal antibodies against a polypeptide encoded by any of the nucleic acid molecules according to (a) to (g); and (i) nucleic acid molecule which is obtainable by screening an appropriate library under stringent conditions using a probe comprising any of the sequences according to (a) to (h) or a fragment of at least 15 nt, preferably 20 nt, 30 nt, 50 nt, 100 nt, 200 nt or 500 nt, of the nucleic acid shown in (a) to (h) and which encodes an L450 polypeptide;

(j) nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

and that its increased activity in a nonhuman organism, in comparison with a reference organism, preferably in a plant, results in faster growth and/or increased yield in comparison with a reference organism, as described above. The polynucleotide is preferably of plant origin or originates from a prokaryotic or eukaryotic microorganism, for example *Saccheromyces* sp. The plant or the microorganism preferably grows faster or stronger and/or has a higher yield, as defined below.

Increased expression of L450 preferably also changes the oxidative state in the nonhuman organism, in particular in the cell having higher L450 activity or in a microorganism of this kind. For example, L450 activity may increase the amount of reactive oxygen species in the cells and cause accelerated growth. The oxidative state of a cell may be measured using methods known to the skilled worker, for example via the state of oxidation of the SH groups present in the cell, via measuring the hydrogen peroxide level in the cell or via other known assay systems. Particularly preferably, the change in the oxidative state results in increased tolerance to biotic or abiotic stress. Consequently, one embodiment of the invention also relates to a nonhuman organism with increased tolerance to abiotic or biotic stress in comparison with a reference organism of increased tolerance, wherein the L450 activity, where appropriate the amount of L450 RNA or protein, has increased or the activity of the polypeptide of the invention or of the polypeptide encoded by the polynucleotide of the invention has increased.

In another embodiment, the invention also relates to a method for preparing a nonhuman organism with increased tolerance to stress in comparison with a reference organism, which method comprises increasing the L450 activity in said organism or in one or more parts thereof in comparison with a reference organism.

In another embodiment, the invention consequently also relates to a nonhuman organism with a modulated, preferably increased, production or amount of reactive oxygen species in the cells.

"Increasing the L450 activity" in a cell compartment, a cell organelle, a cell, a tissue, an organ or a nonhuman organism, preferably a plant, preferably means "increasing the absolute L450 activity", i.e. independently of whether this is due to more protein or more active protein in a cell compartment, a cell organelle, a cell, a tissue, an organ or a nonhuman organism in a cell compartment, a cell organelle, a cell, a tissue, an organ or a nonhuman organism.

The specific activity may be increased, for example, by mutating the polypeptide, the consequence of which is higher turnover or better binding of cofactors, for example. Increasing the stability of the polypeptide increases, for example, the activity per unit, for example per volume or per cell, i.e. a loss of activity with time, due to degradation of said polypeptide, is prevented. An in-vitro assay for determining the specific activity of L450 is not yet known to the skilled worker.

The specific activity of a polypeptide may be determined as described in the examples below. For example, it is possible to express a potential L450 gene in a model organism and to compare the growth curve with that of a reference under identical conditions. Preferably, an increase in growth can already be detected at the cellular level, but it may be necessary to observe a full vegetative period. Preference may be given here to using a plant expression and assay system for this purpose. Thus it was surprisingly found that constitutive expression of the yeast protein YLR251w in plants also results in faster growth.

If L450 influences the oxidative state of the cell, it is possible, for example, to (over)express a candidate protein in a cell and to assay the oxidative state of this cell in comparison with a reference.

The term "increasing" means both that a substance or an activity, here L450 RNA or L450 DNA or L450 protein or L450 activity, for example, is introduced to a particular environment for the first time or has previously not been detectable in said environment, for example by expressing a transgenic L450 gene in an L450-deficient nonhuman organism, and that the activity or the amount of substance in a particular environment is increased in comparison with the original state, for example by coexpression of a transgenic L450 gene in an L450-expressing organism or by uptake of L450 from the environment. The term "increasing" thus also comprises de-novo expression.

According to the knowledge of the skilled worker, the amount of RNA or polypeptide in a cell, a compartment, etc. regularly correlates to the activity of a protein in a volume. This correlation is not always linear, for example the activity also depends on the stability of the molecules or on the presence of activating or inhibiting cofactors. Likewise, product and reactant inhibitions are known. The invention on which the present application is based shows a dependence between the amount of L450 RNA and the increase in the amount of biomaterial, in particular fresh weight, number of leaves and yield. Normally, increased expression of a gene results in an increase of the amount of the mRNA of said gene and of encoded polypeptide, as is also shown here in the examples.

Consequently, an increased activity within an organelle, a cell, a tissue, an organ or a plant can be expected when the amount of L450 is increased there. The same may also be expected when the amount of L450 is increased in a different way.

In one embodiment the amount of L450 mRNA or L450 protein in the nonhuman organism or in the parts mentioned, for example organ, cell, tissue or organelle, is therefore increased. The amount may also be increased by, for example, de-novo or enhanced expression in the cells of the nonhuman organisms, by increased stability, reduced degradation or (increased) uptake from the outside.

In one embodiment, the method of the invention relates to faster growth and/or higher yield of a plant. Consequently, in a preferred embodiment, the method of the invention comprises increasing the activity of an L450 polypeptide encoded by a polynucleotide which comprises any of the abovementioned nucleic acid molecules (a) to (i) in a plant. More preferably, the polynucleotide encompasses any of the abovementioned nucleic acids molecules (a) to (c). Even more preference is given to increasing the activity of a polypeptide encoded by a polynucleotide which comprises any of the sequences depicted in Seq. ID No. 1, 3, 5, 7, 9, 11, 13, 15, 24 26, 34, 36, 38, 40, 42, 44 or 52 or which comprises a nucleic acid coding for a polypeptide depicted in Seq. ID. No. 2, 4, 6, 8, 10, 12, 14, 16, 25 27, 35, 37, 39, 41, 43, 45, 46, 47, 48, 49, 50, 51 or 53 or for a homolog thereof.

Surprisingly, expression of the L450 homolog of yeast YLR251w (PIR:S59397), which is depicted in Seq. ID No. 11 and 12, also leads to faster growth in *Arabidopsis* and may lead to a higher yield. Consequently, said polynucleotide comprises in one embodiment Seq. ID No. 11 or a polynucleic acid coding for the polypeptide according to Seq. ID No. 12 or for a homolog thereof. Most preference is given to increasing the activity of a plant homolog of L450 in a plant according to the method of the invention. Plant homologs are depicted in Seq. ID No.: 1, 3, 5, 7, 9, 24, 26, 34, 36, 38, 40, 42 or 52 and Seq. ID No. 2, 4, 6, 8, 10, 25 27, 35, 37, 39, 41, 43 or 53. Preference is given to increasing the activity of an L450 encoded by a polynucleotide which comprises or encodes any of these sequences or a homolog thereof according to features (b) to (g). Preferred homologs are described below. Thus, a particularly preferred homolog at the amino acid level is at least 20%, preferably 40%, more preferably 50%, even more preferably 60%, even more preferably 70%, even more preferably 80, even more preferably 90%, and most preferably 95%, 96%, 97%, 98% or 99%, identical to a polypeptide encoded according to Seq. ID No.: 1, 3, 5, 7, 9, 11, 13, 15, 24 26, 34, 36, 38, 40, 42, 44 or 52 or depicted in Seq. ID No.: 2, 4, 6, 8, 10, 12, 14, 16, 25 27, 35, 37, 39, 41, 43, 45, 46, 47, 48, 49, 50, 51 or 53, with. preference again being given to a homolog of an amino acid sequence encoded according to Seq. ID No.: 1, 3, 5, 7, 9, 11, 24 26, 34, 36, 38, 40, 42, 44 or 52 or an amino acid sequence depicted in Seq. ID No.: 2, 4, 6, 8, 10, 12, 25 27, 35, 37, 39, 41, 43, 45, 46, 47, 48, 49, 50, 51 or 53. Even more preference, however, is given to a homolog of a protein sequence encoded by Seq. ID No.: 1, 3, 5, 7, 9, 24 26, 34, 36, 38, 40, 42, 44 or 5238, 40, 42, 44 or 52 or a sequence depicted according to Seq. ID No.: 2, 4, 6, 8, 10, 25 27, 35, 37, 39, 41, 43, 45, 46, 47, 48, 49, 50, 51 or 53.

Interestingly an additional L450 variant has been identified in *Arabidopsis*.

L450 from *Arabidopsis thaliana* has already been published as MOB24.15 on BAC MOB24 (BAC Accession NO.: AB020746 in GenBank) and in US 2002/0023281 (Seq. ID No. 1 and 2, respectively). As mentioned above, a function of the polypeptide of the invention in plants has not yet been described. The annotations of the ORF in GenBank and US 2002/0023281 do not mention any function. A Blastp comparison under standard conditions reveals significant homologies of L450, inter alia to various peroxisomal membrane proteins from different organisms. A homologue of said gene in *Arabidposis thaliana* was identified and is shown in Seq ID No.: 42 and 43.

A very high homology is found with a rice protein of likewise unknown function (P0452F10.16 from *Oryza sativa* nipponbare(GA3)) and oz1116c1058 (Seq. ID No.: 9 and 10 and, respectively, 3 and 4). The *Arabidopsis* protein and the rice proteins are 54% identical. In particular, the N-terminal, central and C-terminal regions are very highly identical and homologous. The *Arabidopsis* protein likewise exhibits very high homology to a protein from Glycine max (soybean) (Seq. ID No.: 7 and 8; 60% identical to Seq. ID No.: 8 at the amino acid level). The *Arabidopsis* protein is furthermore highly homologous to a protein from *Hordeum vulgare* (barley) and *Triticum aestivum* (wheat) (Seq. ID No.: 34 and 35 and also 36 and 37.). The highest homology was found with a protein from Canola (*Brassicus napus*) (Seq. ID No.: 5 and 6 and also 38 and 39: said protein is 83% identical at the amino acid level to Seq. ID No.: 5. (see also table 7). Further plant homologs were identified in potato (*S. tubrosum*) and corn (Maize) (*Zea mays*) and are shown in Seq. ID No. 40 and 41 or 52 and 53, resp.

FIG. 7 shows a multiple alignment of all sequences mentioned herein, and the derived consensus sequence as well as the concerned core sequences. FIG. 8 shows a multiple alignment of all plant Sequences mentioned herein and the derived consensus and core consensus sequences.

If the present invention relates to a plant or to a method for increasing growth or yield in a plant, the L450 activity in the plant is increased compared to the reference organism by 5% or more, more preferably by 10%, even more preferably by 20%, 30%, 50% or 100%. Most preferably, the activity is increased compared to the reference organism by 200%, 500% or 1 000% or more.

Owing to the higher L450 activity, in particular owing to a from 5% to 1 000% increase in L450 activity, preferably owing to a from 10% to 100% increase, growth of the plant is preferably 5%, preferably 10%, 20% or 30%, faster. More preferably, growth is faster by 50%, 100%, 200% or 500% or more, in comparison with a reference organism. Preference is also given to increasing the L450 activity by 10%, 20%, 30% or from 50% to 1 000% and to a faster growth of 10%, 20%, 30% or from 50% to 200%.

Owing to the higher L450 activity, in particular owing to a from 5% to 1 000% increase in L450 activity, preferably owing to a from 10% to 100% increase, yield of the plant is preferably 5%, preferably 10%, 20% or 30%, higher. More preferably, yield is higher by 50%, 100%, 200% or 500% or more, in comparison with a reference organism. Preference is also given to increasing the L450 activity by 10%, 20%, 30% or from 50% to 100% and to a higher yield of 10%, 20%, 30% or 50%.

In another embodiment, the method of the invention relates to faster growth and/or higher yield or a higher biomass in microorganisms. Surprisingly, expression of the L450 homolog YLR251w of the yeast *Saccharomyces cerevisiae*, which is depicted in Seq. ID No. 11 and 12, also leads to faster growth in *Arabidopsis* and may lead to a higher yield. Owing to the highly conserved nature of L450, the increased activity of L450 in microorganisms or animals can likewise be expected to result in faster growth, i.e. in a higher rate of division or higher growth rate or due to larger cells. Consequently, in a preferred embodiment, the method of the invention comprises increasing in a microorganism, an animal or a cell the activity of an L450 polypeptide encoded by a polynucleotide which comprises any of the abovementioned nucleic acids (a) to (i). More preferably, the polynucleotide comprises any of the abovementioned nucleic acids (a) to (c). Even more preference is given to increasing the activity of a polypeptide encoded by a polynucleotide which comprises the sequence depicted in Seq. ID No. 11 or a polynucleic acid which codes for a polypeptide depicted in Seq. ID No.: 12 or for any of said homologs thereof. Preferred homologs are described below. For example, a particularly preferred homolog is at least 30%, preferably 40%, more preferably 50%, even more preferably 60%, even more preferably 70%, even more preferably 80, even more preferably 90%, and most preferably 95%, 96%, 97%, 98%, or 99%, identical at the amino acid level to a polypeptide encoded according to Seq. ID No.: 1, 3, 5, 7, 9, 11, 13, 15, 24 26, 34, 36, 38, 40, 42, 44 or 5238, 40, 42, 44 or 52 or depicted in Seq. ID No.: 2, 4, 6, 8, 10, 12, 14, 16, 25 27, 35, 37, 39, 41, 43, 45, 46, 47, 48, 49, 50, 51 or 53, with preference in turn being given to a homolog of an amino acid sequence encoded according to Seq. ID No.: 11 or an amino acid sequence depicted in Seq. ID No.: 12.

In one embodiment, the nucleic acid molecule encodes a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

In one embodiment, the nucleic acid molecule encodes a polypeptide comprising or consisting of a polypeptide comprising the consensus or consensus core sequence defined above, e.g. as shown FIG. 7 or 8 or in SEQ ID No.: 46, 47, 48, 49, 50 and/or 51, whereby 20 or less, preferably 15 or 10, , preferably 9, 8, 7, or 6, more preferred 5 or 4, even more preferred 3, even more preferred 2, even more preferred 1, most preferred 0 of the amino acids positions indicated by a capital or lower letter in FIG. 7 or 8 can be replaced by an x and/or not more than 5, preferably 4, even more preferred 3 or 2, most preferred one or non amino acid position indicated by a capital letter in FIG. 7 or 8 are/is replaced by an x and/or 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence In one embodiment, the nucleic acid molecule encodes a polypeptide comprising or consisting of a polypeptide shown in any one of SEQ. ID No.: 46, 47, 48, 49, 50 or 51.

If the present invention relates to a microorganism or to a method for increasing growth or yield in microorganisms, the L450 activity is preferably al least 5%, more preferably 10%, even more preferably 20%, 30%, 50% or 100%, higher than that of the reference organism. Most preferably, the activity is 200%, 500% or 1 000% or more, higher than in the reference organism.

Owing to the higher L450 activity, in particular owing to a from 5% to 1 000% increase in L450 activity, preferably owing to a from 10% to 100% increase, growth of the microorganism is preferably 5%, preferably 10%, 20% or 30%, faster. More preferably, growth is faster by 50%, 100%, 200% or 500% or more, in comparison with a reference organism. Preference is also given to increasing the L450 activity by 10%, 20%, 30% or from 50% to 100% and to a faster growth of 10%, 20%, 30% or 50%.

Owing to the higher L450 activity, in particular owing to a from 5% to 1 000% increase in L450 activity, preferably owing to a from 10% to 100% increase, yield, in particular the biomass, of the microorganism is preferably 5%, preferably 10%, 20% or 30%, higher. More preferably, yield is higher by 50%, 100%, 200% or 500% or more, in comparison with a reference organism. Preference is also given to increasing the L450 activity by 10%, 20%, 30% or from 50% to 100% and to a higher yield of 10%, 20%, 30% or 50%.

In a further embodiment, the method of the invention relates to faster growth and/or higher yield of a useful animal. Consequently, in a preferred embodiment, the method of the invention comprises increasing in a useful animal the activity of an L450 polypeptide encoded by a polynucleotide which comprises any of the abovementioned nucleic acids. More preferably, the polynucleotide comprises any of the abovementioned nucleic acids (a) to (c). Even more preference is given to increasing the activity of a polypeptide encoded by a polynucleotide which comprises either of the sequences depicted in Seq. ID No. 13 or 15 or a polynucleic acid encoding a polypeptide depicted in Seq. ID No. 14 or 16 or of a homolog thereof. Surprisingly, expression of the L450 homolog YLR251w of the yeast Saccharomyces cerevisiae, which is depicted in Seq. ID No. 11 and 12, also leads to faster growth in *Arabidopsis* and may lead to a higher yield. From this, a highly conserved nature of the L450 activity may be assumed. Consequently, in one embodiment, the polynucleotide comprises Seq. ID No. 11 or a nucleic acid which comprises a protein encoded in Seq. ID No.: 12 or a homolog thereof. As the polypeptide of the invention seems to be quite conserved the expression of insect homologs may be advantageous. Thus in one embodiment an insect homolog might be expressed in the organism, e.g. a *Drosophila* homolog as shown in SEQ. ID No.: 44 and 45. More preference is given, however, to increasing the activity of an animal homolog of L450 in a useful animal according to the method of the invention. Animal homologs, in this case human and murine homologs, are depicted in Seq. ID No.: 13 and 15 and, respectively, Seq. ID No.: 14 and 16. Preference is given to increasing the activity of an L450 encoded by a polynucleotide which comprises any of these sequences or a homolog thereof according to features (b) to (g).

Preferred homologs are described below. For example, a particularly preferred homolog is at least 30%, preferably 40%, more preferably 50%, even more preferably 60%, even more preferably 70%, even more preferably 80, even more preferably 90%, most preferably 95%, 96%, 97%, 98% or 99%, identical at the amino acid level to a polypeptide encoded according to Seq. ID No.: 1, 3, 5, 7, 9, 11, 13, 15, 24 26, 34, 36, 38, 40, 42, 44 or 5238, 40, 42, 44 or 52 or depicted in Seq. ID No.: 2, 4, 6, 8, 10, 12, 14, 16, 25 27, 35, 37, 39, 41, 43, 45, 46, 47, 48, 49, 50, 51 or 53, with preference in turn being given to a homolog of an amino acid sequence encoded according to Seq. ID No.: 13 or 15 or an amino acid sequence depicted in Seq. ID No.: 14 or 16.

The L450 protein of *Arabidopsis thaliana* is 31% identical and 43% homologous to the murine protein MPV17, with PMP20 of *Arabidopsis thaliana* being 26% identical and 44% homologous. In principle, it may be assumed that MVP17 and PMP20 can be combined into a group, with L450 being slightly more identical to MVP17 than PMP20, but homology to PMP20 being higher. Conspicuously, the mentioned ORF from rice is distinctly more homologous to the ORF L450 found in *Arabidopsis* than to PMP20. Presumably, L450 thus forms together with P0452F10.16" from *Oryza sativa* (japonica cultivar-group) and further homologs which are described in the examples a separate subgroup.

The literature on MVP17 defective mice describes the protein as a peroxisomal protein involved in the metabolism of reactive oxygen species. MPV17 (−/−) cells were found to contain increased (mRNA- and enzyme-level) activity of gamma-glutamyl transpeptidase and reduced activity of plasma glutathione peroxidase and superoxide dismutase. An increased production of superoxide anions was detected. A pathological change in MVP17 KO mice was remedied by treatment with antioxidants, thereby establishing a causal link between increased ROS production (ROS is "reactive oxygen species") and the pathology. In contrast to this, another source (Zwacka, EMBO J. 13, 1994, 5129-34) reports that the loss of MPV17 protein does not impair peroxisome biogenesis but results in a reduced ability to produce reactive oxygen species (ROS). Correspondingly, overproduction of MPV17 in transfected cells causes a dramatically increasing level of intracellular ROS, indicating direct involvement of MPV17 in ROS production. Thus, a peroxisomal location of the protein may be suspected, possibly as a function within the ROS-producing or the protective system of a cell. ROS production may be involved in establishing the defenses against pathogens by programmed cell death in plants and mammalian cells. On the other hand, excessive ROS production leads to cell damage, to the formation of necroses and to retarded growth.

If the present invention relates to a useful animal or to a method for increasing growth or yield of a useful animal in comparison with a reference animal, the L450 activity is preferably at least 5%, more preferably 10%, even more preferably 20%, 30%, 50% or 100%, higher than that of the reference organism. Most preferably, the activity is 200%, 500% or 1 000% or more, higher than in the reference organism.

Owing to the higher L450 activity, in particular owing to a from 5% to 1 000% increase in L450 activity, preferably owing to a from 10% to 100% increase, growth of the useful animal is preferably 5%, preferably 10%, 20% or 30%, faster, by comparison. More preferably, growth is faster by 50%, 100%, 200% or 500% or more, in comparison with a reference organism. Preference is also given to increasing the L450 activity by 10%, 20%, 30% or from 50% to 100% and to a faster growth of 10%, 20%, 30% or 50%.

Owing to the higher L450 activity, in particular owing to a from 5% to 1 000% increase in L450 activity, preferably owing to a from 10% to 100% increase, yield of the useful animal is preferably 5%, preferably 10%, 20% or 30%, higher. More preferably, yield is higher by 50%, 100%, 200% or 500% or more, in comparison with a reference organism. Preference is also given to increasing the L450 activity by 10%, 20%, 30% or from 50% to 100% and to a higher yield of 10%, 20%, 30% or 50%.

Consequently, the nucleic acid sequences and polypeptides used in the method of the invention are nucleic acid sequences coding for polypeptides whose activity is not exactly known yet. Owing to the homology of said proteins to the murine MPV17 protein, however, it may be assumed that it is a peroxisomal membrane protein which is directly or indirectly involved in the metabolism of reactive oxygen species. Thus it would be possible to determine increased activity of the L450 protein in a cell, an organelle, a compartment, a tissue, an organ or a nonhuman organism, in particular a plant, by measuring said reactive oxygen species. The reactive oxygen species may be measured as described, for example, in O'Kane, D., Planta, 1996, 198(3), 371-377.

Apart from that, the L450 activity may be determined indirectly via measuring the amount of L450 DNA, L450 RNA or L450 protein. Thus, a quantitative Northern blot or quantitative PCR of the inventive polynucleotides described herein may determine the amount of mRNA, for example in a cell or in a total extract, and a Western blot may be used to compare the amount of the protein, for example in a cell or a total extract, to that in a reference. Methods of this kind are known to the skilled worker and have been extensively described, for example also in Sambrook, Molecular Cloning: A Laboratory Manual, Cold Spring Harbor Laboratory, Cold Spring Harbor Laboratory Press, Cold Spring Harbor, N.Y., 1989 or in Current Protocols, 1989 and updates, John Wiley & Sons, N.Y., or in other sources cited below.

A suitable nonhuman organism (host organism) for preparation in the method of the invention is in principle any nonhuman organism for which faster growth is useful and desirable, such as, for example, microorganisms such as yeasts, fungi or bacteria, monocotyledonous or dicotyledonous plants, mosses, algae, and also useful animals, as listed below. The term nonhuman organism, host organism or useful animal also includes an organism of human origin, for example human cell lines, but does not include a human organism.

The term "plants", as used herein, may include higher plants, lower plants, mosses and algae; however, in a preferred embodiment of the method of the invention, the term "plants" relates to higher plants.

Advantageously, the method of the invention uses plants which belong to the useful plants, as listed below. Apart from production of animal feed or food, the plants prepared according to the invention may in particular also be used for the preparation of fine chemicals.

In one embodiment of the present invention, the L450 protein comprises the consensus sequence described above, e.g. shown in SEQ ID No. 46, 47, 48, 49, 50 or 51, whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter in FIG. 7 or 8 can be replaced by an x and/or not more than 5, preferably 4, even more preferred 3 or 2, most preferred one or non amino acid position indicated by a capital letter in FIG. 7 or 8 are/is replaced by an x and/or 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence but not consisting of one of the public known sequences mentioned herein. In one embodiment, the present invention relates to an nucleic acid molecule encoding a protein having the consensus sequence described above, e.g. as shown in SEQ ID No. 46, 47, 48, 49, 50 or 51, whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter in FIG. 7 or 8 can be replaced by an x and/or not more than 5, preferably 4, even more preferred 3 or 2, most preferred one or non amino acid position indicated by a capital letter in FIG. 7 or 8 are/is replaced by an x and/or 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence and which does not encode an polypeptide of the public known sequences published herein and/or which does not consist of the nucleic acid molecules known to the public as mentioned herein.

In one embodiment, the method of the invention comprises increasing the activity of the L450 polypeptide by increasing the activity of at least one polypeptide in said organism or in one or more parts thereof, which is encoded by a nucleic acid molecule comprising a nucleic acid molecule selected from the group consisting of:

(aa) nucleic acid molecule encoding an L450 polypeptide or encoding, preferably at least the mature, form of the polypeptide which is depicted in Seq. ID No.: 2, 4, 6, 8, 10, 12, 14, 16, 25 27, 35, 37, 39, 41, 43, 45, 46, 47, 48, 49, 50, 51 or 53;

(bb) nucleic acid molecule comprising, preferably at least the mature, polynucleotide of the coding sequence according to Seq. ID No: 1, 3, 5, 7, 9, 11, 13, 15, 24 26, 34, 36, 38, 40, 42, 44 or 5238, 40, 42, 44 or 52;

(cc) nucleic acid molecule whose sequence is derivable from a polypeptide sequence encoded by a nucleic acid molecule according to (aa) or (bb), due to the degeneracy of the genetic code;

(dd) nucleic acid molecule encoding a polypeptide whose sequence is at least 20%, preferably 35%, more preferably 45%, even more preferably 60%, even more preferably 70%, 80%, 90%, 95%, 97%, 98% and 99%, identical to the amino acid sequence of the polypeptide encoded by the nucleic acid molecule according to (aa) to (cc);

(ee) nucleic acid molecule encoding a polypeptide which is derived from an L450 polypeptide encoded by a nucleic acid molecule according to (aa) to (dd,) preferably (aa) to (cc), by substitution, deletion and/or addition of one or more amino acids of the amino acid sequence of the polypeptide encoded by the nucleic acid molecules (aa) to (dd), preferably (aa) to (cc);

(ff) nucleic acid molecule encoding a fragment or an epitope of the L450 polypeptide encoded by any of the nucleic acid molecules according to (aa) to (ee), preferably (aa) to (cc);

(gg) nucleic acid molecule comprising a polynucleotide which comprises the sequence of a nucleic acid molecule obtained by amplification of a preferably microbial or plant cDNA bank using the primers in Seq. ID No.: 19 and 20 and/or 28 and 30 or a combination thereof or of a preferably microbial or plant genomic bank using the primers in Seq. ID No.: 21 and 22;

(hh) nucleic acid molecule encoding an L450 polypeptide which is isolated with the aid of monoclonal antibodies against a polypeptide encoded by any of the nucleic acid molecules according to (aa) to (gg), preferably (aa) to (cc) and (ii) nucleic acid molecule which is obtainable by screening an appropriate library under stringent conditions using a probe comprising any of the sequences according to (aa) to (hh), preferably (aa) to (cc), or a fragment of at least 15 nt, preferably 20 nt, 30 nt, 50 nt, 100 nt, 200 nt or 500 nt, of the nucleic acid characterized in (aa) to (hh), preferably (aa) to (cc), and which encodes an L450 polypeptide; or (jj) nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

or which comprises a complementary sequence thereof

In one embodiment, the activity of the L450 protein is increased by (a) increasing the expression of a L450 polypeptide;

(b) increasing the stability of L450 RNA or of the L450 protein, preferably of a polypeptide or polynucleotide as described in (a);

(c) increasing the specific activity of the L450 protein, preferably of a polypeptide as described in (a) or encoded by a polynucleotide described in (a);

(d) expressing a homologous or artificial transcription factor capable of increasing expression of an endogenous L450 gene function, preferably comprising the sequence of a polynucleotide described in (a); or (e) adding an exogenous factor which increases or induces L450 activity or L450 expression to the food or the medium, preferably of a polynucleotide or polynucleotide described in (a).

In one embodiment, the method of the invention comprises increasing the activity of L450 polypeptide by introducing a polynucleotide into the organism, preferably into a plant, or into one or more parts thereof, which polynucleotide codes for an L450 polypeptide encoded by a nucleic acid molecule comprising a nucleic acid molecule selected from the group consisting of:

(a) nucleic acid molecule encoding an L450 polypeptide or encoding, preferably at least the mature form of, the polypeptide that is depicted in Seq. ID No.: 2, 4, 6, 8, 10, 12, 14, 16, 25 27, 35, 37, 39, 41, 43, 45, 46, 47, 48, 49, 50, 51 or 53;

(b) nucleic acid molecule comprising, preferably at least the mature, polynucleotide of the coding sequence according to Seq. ID No: 1, 3, 5, 7, 9, 11, 13, 15, 24 26, 34, 36, 38, 40, 42, 44 or 52;

(c) nucleic acid molecule whose sequence is derivable from a polypeptide sequence encoded by a nucleic acid molecule according to (a) or (b), due to the degeneracy of the genetic code;

(d) nucleic acid molecule encoding a polypeptide whose sequence is at least 20%, preferably 35%, more preferably 45%, even more preferably 60%, even more preferably 70%, 80%, 90%, 95%, 97%, 98% and 99%, identical to the amino acid sequence of the polypeptide encoded by the nucleic acid molecule according to (a) to (c);

(e) nucleic acid molecule encoding a polypeptide that is derived from an L450 polypeptide encoded by a nucleic acid molecule according to (a) to (d) preferably (a) to (c) by substitution, deletion and/or addition of one or more amino acids of the amino acid sequence of the polypeptide encoded by the nucleic acid molecules (a) to (d), preferably (a) to (c);

(f) nucleic acid molecule encoding a fragment or an epitope of the L450 polypeptide encoded by any of the nucleic acid molecules according to (a) to (e), preferably (a) to (c);

(g) nucleic acid molecule comprising a polynucleotide which comprises the sequence of a nucleic acid molecule obtained by amplification of preferably microbial or a plant cDNA bank using the primers in Seq. ID No.: 19 and 20 and/or 28 and 30 or a combination thereof or of a preferably microbial or plant genomic bank using the primers in Seq. ID No.: 21 and 22;

(h) nucleic acid molecule encoding an L450 polypeptide which is isolated with the aid of monoclonal antibodies against a polypeptide encoded by any of the nucleic acid molecules according to (a) to (g), preferably (a) to (c); and (i) nucleic acid molecule which is obtainable by screening an appropriate library under stringent conditions using a probe comprising any of the sequences according to (a) to (h) preferably (a) to (c) or a fragment of at least 15 nt, preferably 20 nt, 30 nt, 50 nt, 100 nt, 200 nt or 500 nt, of the nucleic acid characterized in (a) to (h), preferably (a) to (c) and which encodes an L450 polypeptide;

(j) nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

or which comprises a complementary sequence thereof.

The organism is preferably a microorganism or, more preferably a plant.

The term "coding" sequence or "to code" means according to the invention both the codogenic sequence and the complementary sequence or a reference to these, i.e. both DNA and RNA sequences are regarded as coding. For example, a structural gene encodes an mRNA via transcription and a protein via translation, and a coding mRNA is translated into a protein. Both molecules contain the information leading to the sequence of the coded polypeptide, i.e. they encode the latter. Posttranscriptional and posttranslational modifications of RNA and polypeptide are sufficiently known to the skilled worker and are likewise included.

According to the invention, "organism or one or more parts thereof" means a cell, a cell compartment, an organelle, a tissue or an organ of an organism or a nonhuman organism.

According to the invention, "plant or one or more parts thereof" means a cell, a cell compartment, an organelle, a tissue, an organ or a plant.

The terms "nucleic acid", "nucleic acid molecule" and "polynucleotide" and also "polypeptide" and "protein" are used herein synonymously.

In the method of the invention, "nucleic acids" or "polynucleotides" mean DNA or RNA sequences which may be single- or double-stranded or may have, where appropriate, synthetic, non-natural or modified nucleotide bases which can be incorporated into DNA or RNA.

Consequently, the present invention also relates to a polynucleotide, which comprises a nucleic acid molecule selected from the group consisting of:

(a) nucleic acid molecule encoding, preferably at least the mature form of, the polypeptide as depicted in Seq. ID No. 2, 4, 6, 8, 10, 12, 14, 16, 25 27, 35, 37, 39, 41, 43, 45, 46, 47, 48, 49, 50, 51 or 53 or comprising, at least the mature form of, the polynucleotide depicted in Seq. ID No. 1, 3, 5, 7, 9, 11, 13, 15, 24 26, 34, 36, 38, 40, 42, 44 or 52;

(b) nucleic acid molecule whose sequence is derivable from a polypeptide sequence encoded by a nucleic acid molecule according to (a) due to the degeneracy of the genetic code;

(c) nucleic acid molecule encoding an L450 polypeptide whose sequence is at least 30%, preferably 35%, more preferably 45%, even more preferably 60%, even more preferably 70%, 80%, 90%, 95%, 97%, 98% and 99%, identical to the amino acid sequence of the polypeptide encoded by the sequence depicted in Seq. ID No.: 4, 6, 8, 10, 12, 14, 16, 25 27, 35, 37, 39, 41, 43, 45, 46, 47, 48, 49, 50, 51 or 53 or comprising the sequence depicted in Seq. ID No. 3, 5, 7, 9, 11, 13, 15, 24 26, 34, 36, 38, 40, 42, 44 or 52;

(d) nucleic acid molecule encoding a polypeptide that is derived from an L450 polypeptide encoded by a polynucleotide according to (a) to (c) by substitution, deletion and/or addition of one or more amino acids of the amino acid sequence of the polypeptide encoded by the nucleic acid molecules (a) to (c) and encoding L450;

(e) nucleic acid molecule encoding a fragment or an epitope of the L450 polypeptide encoded by any of the nucleic acid molecules according to (a) to (d), preferably (a) to (c) and encoding L450;

(f) nucleic acid molecule comprising a polynucleotide which comprises the sequence of a nucleic acid molecule obtained by amplification of a plant cDNA bank using the primers in Seq. ID No.: 19 and 20 and/or 28 and 30 or a combination thereof or of a preferably microbial or plant genomic bank using the primers in Seq. ID No.: 21 and 22;

(g) nucleic acid molecule encoding an L450 polypeptide which has been isolated with the aid of monoclonal antibodies against a polypeptide encoded by any of the nucleic acid molecules according to (a) to (f), preferably (a) to (c) and encoding L450;

(h) nucleic acid molecule which is obtainable by screening an appropriate library under stringent conditions using a probe comprising any of the sequences according to (a) to (g) or a fragment of at least 15 nt, preferably 20 nt, 30 nt, 50 nt, 100 nt, 200 nt or 500 nt, of the nucleic acid characterized in (a) to (g), preferably (a) to (c) and which encodes an L450 polypeptide, (i) nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

or the complementary strand thereof, said polynucleotide or said nucleic acid molecule according to (a) to (i) not comprising the sequence depicted in Seq. ID No.: 1, 3, 9, 11, 13, 15, 23, 42 or 44or the sequence complementary thereto, where appropriate the one depicted in Seq. ID No. 24. In one embodiment, a polypeptide is also not encoded which comprises the sequence depicted in Seq. 2, 4, 10, 12, 14, 16, 43 or 45, where appropriate also Seq. ID No. 25, or which is encoded by the sequence depicted in Seq. ID No. 23 or the sequence complementary thereto.

Preferably, the polynucleotide of the present invention differs from the herein shown previously published polypeptides by at least one nucleotide, e.g. from SEQ ID No.: 1, 3, 9, 11, 13, 15, 23, 42 or 44. Preferably, the polypeptide encoded differs from the previously published polypeptides by at least one amino acid, e.g. from SEQ ID No.: 2, 4, 10, 12, 14, 16, 43 or 45.

Seq. ID No.: 1 and 2 describe the L450 polypeptide (Seq. ID No.: 2) and the sequence it is based on (Seq. ID No.: 1) of *Arabidopsis thaliana*, as disclosed under Accession AU 237476.

Seq. ID No.: 3 and 4 describe the L450 polypeptide (Seq. ID No.: 4) and the sequence it is based on (Seq. ID No.: 3) of *Oryza sativa*, as disclosed under Accession Q8WOA7.

Seq. ID No.: 5 and 6 describe the L450 polypeptide (Seq. ID No.: 6) and the sequence it is based on (Seq. ID No.: 5) of *Brassica napus*.

Seq. ID No.: 7 and 8 describe the L450 polypeptide (Seq. ID No.: 8) and the sequence it is based on (Seq. ID No.: 7) of *Glycine max*.

Seq. ID No.: 9 and 10 describe the L450 polypeptide (Seq. ID No.: 10) and the sequence it is based on (Seq. ID No.: 9), of *Oryza sativa*.

Seq. ID No.: 11 and 12 describe the L450 polypeptide (Seq. ID No.: 12) and the sequence it is based on (Seq. ID No.: 11), of *Saccharomyces cerevisiae*, as disclosed under Accession PIR:S59397.

Seq. ID No.: 13 and 14 describe human MVP17 (Seq. ID No.: 14) and the sequence it is based on (Seq. ID No.: 13), as disclosed under Accession PIR:S45343.

Seq. ID No.: 15 and 16 describe murine MVP17 (Seq. ID No.: 16) and the sequence it is based on (Seq. ID No.: 15), as disclosed under Accession PIR:S29031.

Seq. ID No.: 23 corresponds to the sequence (ID No. 701) published in US 2002/0023281. US 2002/0023281 describes 999 different sequences without indicating the function. The sequence Seq. ID No. 701 is not depicted completely and does not display a start codon. Moreover, the sequence Seq. ID No. 701 is depicted in antisense orientation. The sequence depicted in Seq. ID No. 701 is, over a sequence from nucleotide 66 to nucleotide 708 of the 828 nt in total, 98% identical to the sequence depicted in Seq. ID No. 1 of the present application. FIG. 3 depicts the Blast comparison between the sequence depicted in US 2002/0023281 and the sequence depicted in Seq. ID No. 1.

Seq. ID No. 26, 24, 25 and 27 depict various L450 homologs of ecotype C24 (Nottingham *Arabidopsis* Stock Centre, UK; NASC Stock N906).

Seq. ID No.: 34 and 35 describe the L450 polypeptide (Seq. ID No.: 35) and the sequence it is based on (Seq. ID No.: 34) of *Hordeum vulgare*.

Seq. ID No.: 36 and 37 describe the L450 polypeptide (Seq. ID No.: 37) and the sequence it is based on (Seq. ID No.: 36) of *Triticum aestivum*.

Seq. ID No.: 38 and 39 describe the L450 polypeptide (Seq. ID No.: 39) and the sequence it is based on (Seq. ID No.: 38) of *Brassica napus*. This was a sequencing check of the sequences depicted in Seq. ID No. 5 (2+1 sequencing). The comparison of sequences 5 and 38 revealed the following alterations at the nucleotide (Nt) level:

| Nt | Seq. ID No.: 5 | Seq. ID No.: 38 |
| --- | --- | --- |
| 330 | A | G |
| 333 | A | T |
| 351 | T | C |
| 372 | A | T |
| 411 | G | A |
| 423 | A | G |
| 441 | A | G |
| 459 | A | T |
| 462 | G | A |
| 480 | A | C |
| 507 | T | A |
| 522 | T | C |
| 525 | T | C |
| 531 | G | A |
| 636 | G | A |
| 640 | C | T |
| 645 | G | T |
| 662 | C | — |

This resulted in the following changes when the sequences of Seq. ID No.: 6 and 39 (protein) were compared:

| AA | Seq. ID No.: 6 | Seq. ID No.: 39 |
| --- | --- | --- |
| 221 | A | G |
| 222 | H | T |
| 223 | R | G |
| 224 | W | G |
| 225 | S | V |
| 226 | M | Stop |

SEQ ID No.: 40 and 41 describe the L450 polypeptide (SEQ ID No.: 41) and the encoding polynucleotide sequence (SEQ ID No.: 40) of potato (*S. tuberosum*).

SEQ ID No.: 42 and 43 describe the L450 polypeptide (SEQ ID No.: 43) and the encoding polynucleotide sequence (SEQ ID No.: 42) of a further gene identified in *Arabidposis thaliana*, suggesting a gene family.

SEQ ID No.: 44 and 45 describe the L450 polypeptide (SEQ ID No.: 45) and the encoding polynucleotide sequence (SEQ ID No.: 44) of *Drosophila*.

The SEQ ID No.: 52 and 53 describe the L450 polypeptide (SEQ ID No.: 53) and the encoding polynucleotide (Seq ID No.: 52 and 53) of corn (*Zea mays*).

In one embodiment, the invention furthermore relates to a polynucleotide encoding an L450 polypeptide, e.g. derived from plants, which comprises a nucleic acid molecule encoding a polypeptide comprising any one of SEQ ID No.: 46, 47, 48, 49, 50 or 51 or selected from the group consisting of:

(a) nucleic acid molecule encoding preferably at least the mature, form of the polypeptide as depicted in Seq. ID No. 2, 4, 6, 8, 25, 27, 35, 37, 39, 41, 43, 46, 47, 48, 49, 50, 51 or 53 or comprising, preferably at least the mature form of the polynucleotide depicted in Seq. ID No. 1, 3, 5, 7, 24, 26, 34, 36 38, 40, 42 or 52;

(b) nucleic acid molecule whose sequence is derivable from a polypeptide sequence encoded by a nucleic acid molecule according to (a) due to the degeneracy of the genetic code;

(c) nucleic acid molecule encoding a polypeptide whose sequence is at least 55%, preferably 60%, more preferably 70%, even more preferably 80%, even more preferably 90%, most preferably 95%, 96%, 97%, 98% or 99% identical to the amino acid sequence of the polypeptide encoded by the sequence depicted in Seq. ID No.: 2 or 4 or comprising the sequence depicted in Seq. ID No. 1 or 3;

(d) nucleic acid molecule encoding a polypeptide whose sequence is at least 90%, preferably 95%, 96%, 97%, 98% or 99%, identical to the amino acid sequence of the polypeptide encoded by the sequence depicted in Seq. ID No.: 6 or comprising the sequence depicted in Seq. ID No. 5;

(e) nucleic acid molecule encoding a polypeptide whose sequence is at least 65%, more preferably 70%, even more preferably 80%, even more preferably 90%, most preferably 95%, 96%, 97%, 98% or 99%, identical to the amino acid sequence of the polypeptide encoded by the sequence depicted in Seq. ID No.: 8 or comprising the sequence depicted in Seq. ID No. 7;

(f) nucleic acid molecule encoding a polypeptide whose sequence is at least 55%, more preferably 70%, even more preferably 80%, even more preferably 90%, most preferably 95%, 96%, 97%, 98% or 99%, identical to the amino acid sequence of the polypeptide encoded by the sequence depicted in Seq. ID No.: 10 or comprising the sequence depicted in Seq. ID No. 9;

(g) nucleic acid molecule encoding a polypeptide whose sequence is at least 35%, more preferably 50%, 60% or 70%, even more preferably 80%, even more preferably 90%, most preferably 95%, 96%, 97%, 98% or 99%, identical to the amino acid sequence of the polypeptide encoded by the sequence depicted in Seq. ID No.: 12 or comprising the sequence depicted in Seq. ID No. 11;

(h) nucleic acid molecule encoding a polypeptide whose sequence is at least 35%, more preferably 50%, 60% or 70%, even more preferably 80%, even more preferably 90%, most preferably 95%, 96%, 97%, 98% or 99%, identical to the amino acid sequence of the polypeptide encoded by the sequence depicted in Seq. ID No.: 14 or 45 or comprising the sequence depicted in Seq. ID No. 13 or 44;

(i) nucleic acid molecule encoding a polypeptide whose sequence is at least 35%, more preferably 50%, 60% or 70%, even more preferably 80%, even more preferably 90%, most preferably 95%, 96%, 97%, 98% or 99%, identical to the amino acid sequence of the polypeptide encoded by the sequence depicted in Seq. ID No.: 16 or comprising the sequence depicted in Seq. ID No. 15;

(j) nucleic acid molecule encoding a polypeptide whose sequence is at least 55%, preferably 60%, more preferably 70%, even more preferably 80%, even more preferably 90%, most preferably 95%, 96%, 97%, 98% or 99% identical to the amino acid sequence of the polypeptide encoded by the sequence depicted in Seq. ID No.: 35 or 41 or comprising the sequence depicted in Seq. ID No. 34 or 42;

(k) nucleic acid molecule encoding a polypeptide whose sequence is at least 55%, preferably 60%, more preferably 70%, even more preferably 80%, even more preferably 90%, most preferably 95%, 96%, 97%, 98% or 99% identical to the amino acid sequence of the polypeptide encoded by the sequence depicted in Seq. ID No.: 37 or comprising the sequence depicted in Seq. ID No. 36;

(l) nucleic acid molecule encoding a polypeptide whose sequence is at least 90%, preferably 95%, 96%, 97%, 98% or 99%, identical to the amino acid sequence of the polypeptide encoded by the sequence depicted in Seq. ID No.: 39 or comprising the sequence depicted in Seq. ID No. 38;

(m) nucleic acid molecule encoding a polypeptide that is derived from an L450 polypeptide encoded by a polynucleotide according to (a) to (l) by substitution, deletion and/or addition of one or more amino acids of the amino acid sequence of the polypeptide encoded by the nucleic acid molecules (a) to (l);

(n) nucleic acid molecule encoding a fragment or an epitope of the L450 polypeptide encoded by any of the nucleic acid molecules according to (a) to (m);

(o) nucleic acid molecule comprising a polynucleotide which comprises the sequence of a nucleic acid molecule obtained by amplification of a preferably microbial or plant cDNA bank using the primers in Seq. ID No.: 19 and 20 and/or 28 and 30 or a combination thereof or of a preferably microbial or plant genomic bank using the primers in Seq. ID No.: 21 and 22;

(p) nucleic acid molecule encoding an L450 polypeptide which has been isolated with the aid of monoclonal antibodies against a polypeptide encoded by any of the nucleic acid molecules according to. (a) to (o);

(q) nucleic acid molecule which is obtainable by screening an appropriate library under stringent conditions using a probe comprising any of the sequences according to (a) to (p) or a fragment of at least 15 nt, preferably 20 nt, 30 nt, 50 nt, 100 nt, 200 nt or 500 nt, of the nucleic acid characterized in (a) to (p) and which encodes an L450 polypeptide, (r) nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence;

or the complementary strand thereof, preferably said polynucleotide or said nucleic acid molecule according to (a) to (r) not comprising the sequence depicted in Seq. ID No.: 1, 3, 9, 11, 13, 15, 23, 42 or 44 or the sequence complementary thereto, where appropriate the one depicted in Seq. ID No. 24. In one embodiment, a polypeptide be also not encoded which consists of, preferably comprises the sequence depicted in Seq. 2, 4, 10, 12, 14, 16, 43 or 45, where appropriate also Seq. ID No. 25, or which is encoded by the sequence depicted in Seq. ID No. 23 or the sequence complementary thereto.

According to the invention, the polynucleotide may be DNA or RNA.

In principle, any nucleic acids coding for polypeptides with L450 activity may be used in the method of the invention. Advantageously, said nucleic acids are from plants such as algae, mosses or higher plants.

In the method of the invention, a nucleic acid sequence is advantageously selected from the group consisting of the sequence depicted in table 7 or the above-described derivatives or homologs thereof coding for polypeptides which still have an L450 biological activity. These sequences are cloned individually or in combination, including with other genes, into expression constructs.

Nucleic acid sequences of a particular donor organism, which code for polypeptides with L450 activity, are usually generally accessible. Particular mention must be made here of general gene databases such as the EMBL database (Stoesser G. et al., Nucleic Acids Res. 2001, Vol. 29, 17-21), the GenBank database (Benson D. A. et al., Nucleic Acids Res. 2000, Vol. 28, 15-18), or the PIR database (Barker W. C. et al., Nucleic Acids Res. 1999, Vol. 27, 39-43). It is furthermore possible to use organism-specific gene databases such as, for example, advantageously the SGD database (Cherry J. M. et al., Nucleic Acids Res. 1998, Vol. 26, 73-80) or the MIPS database (Mewes H. W. et al., Nucleic Acids Res. 1999, Vol. 27, 44-48) for yeast, the GenProtEC database (http://web.bham.ac.uk/bcm4ght6/res.html) for *E. coli*, and the TAIR database (Huala, E. et al., Nucleic Acids Res. 2001 Vol. 29(1), 102-5) or the MIPS database for *Arabidopsis*.

Advantageously, L450 used in the method of the invention and the nonhuman organism employed are from the same origin or from an origin which is genetically as close as possible, for example from the same or a very closely related type or species. However, a synthetic L450 may also be used in a nonhuman organism.

The term "gene" means in accordance with the invention a nucleic acid sequence which comprises a codogenic gene section and regulatory elements. "Codogenic gene sections" mean in accordance with the invention a continuous nucleic acid sequence ("open reading frame, abbreviated ORF). Said ORF may contain no, one or more introns which are linked via suitable splice sites to the exons present in the ORF. An ORF and its regulatory elements encode, for example, structural genes which are translated into enzymes, transporters, ion channels, etc., for example, or non-structural genes such as regulatory genes such as the Rho or Sigma protein, for example. However, genes may also be encoded which are not translated into proteins. For expression in a nonhuman organism, a codogenic gene section is expressed together with particular regulatory elements such as promoter, terminator, UTR, etc., for example. The regulatory elements may be of homologous or heterologous origin. Gene, codogenic gene section (ORFs), regulatory sequence are covered by the terms nucleic acid and polynucleotide hereinbelow.

The term "expression" means transcription and/or translation of a codogenic gene section or gene. The resulting product is usually an mRNA or a protein. However, expressed products also include RNAs such as, for example, regulatory RNAs or ribozymes. Expression may be systemic or local, for example restricted to particular cell types, tissues or organs. Expression includes processes in the area of transcription which relate especially to transcription of rRNA, tRNA and mRNA, to RNA transport and to processing of the transcript. In the area of protein biosynthesis, especially ribosome biogenesis, translation, translational control and aminoacyl-tRNA synthetases are included. Functions in the area of protein processing relate especially to folding and stabilizing, to targeting, sorting and translocation and to protein modification, assembly of protein complexes and proteolytic degradation of proteins.

The expression products of the codogenic gene sections (ORFs) and of their regulatory elements can be characterized by their function. Examples of these functions are those in the areas metabolism, energy, transcription, protein synthesis, protein processing, cellular transport and transport mechanisms, cellular communication and signal transduction, cell rescue, cellular defense and cell virulence, regulation of the cellular environment and interaction of the cell with its environment, cell fate, transposable elements, viral proteins and plasmid proteins, control of cellular organization, subcellular location, regulation of protein activity, proteins with binding function or cofactor requirement and facilitated transport. Genes with identical functions are grouped together in "functional gene families". According to the invention, expression of L450 results in an increased growth rate. A polynucleotide usually includes an untranslated sequence, located at the 3' and 5' ends of the coding gene region, for expression: for example, from 500 to 100 nucleotides of the sequence upstream of the 5' end of the coding region and/or, for example, from 200 to 20 nucleotides of the sequence downstream of the 3' end of the coding gene region. An "isolated" nucleic acid molecule is removed from other nucleic acid molecules present in the natural source of the nucleic acid. An "isolated" nucleic acid preferably has no sequences which naturally flank the nucleic acid in the genomic DNA of the organism from which said nucleic acid originates (e.g. sequences located at the 5' and 3' ends of said nucleic acid). In various embodiments, the isolated L450 nucleic acid molecule may contain, for example, 5 kb, 4 kb, 3 kb, 2 kb, 1 kb, 0.5 kb, 0.1 kb or 0 kb of nucleotide sequences which naturally flank the nucleic acid molecule in the genomic DNA of the cell from which the nucleic acid originates.

The nucleic acid molecules used in the present method, for example a nucleic acid molecule having a nucleotide sequence of the nucleic acid molecules used in the method of the invention or of a part thereof, may be isolated using molecular-biological standard techniques and the sequence information provided herein. It is also possible to identify, for example, a homologous sequence or homologous, conserved sequence regions at the DNA or amino acid level with the aid of comparative algorithms. These sequence regions may be used as hybridization probes by means of standard hybridization techniques, as described, for example, in Sambrook, Molecular Cloning: A Laboratory Manual, Cold Spring Harbor Laboratory, Cold Spring Harbor Laboratory Press, Cold Spring Harbor, N.Y., 1989, to isolate further nucleic acid sequences useful in the method. In addition, a nucleic acid molecule comprising a complete sequence of SEQ. ID NO: 1, 3, 5, 7, 9, 11, 13, 15, 24 26, 34, 36, 38, 40, 42, 44 or 52 or of the other nucleic acid molecules used in the method of the invention or a part thereof can be isolated by polymerase chain reaction (PCR) and prepared according to known methods. It is possible to amplify a nucleic acid of the invention according to standard PCR amplification techniques using cDNA prepared by means of reverse transcription or, alternatively, genomic DNA as template and suitable oligonucleotide primers. The nucleic acid amplified in this way may be cloned into a suitable vector and characterized by means of DNA sequence analysis.

Examples of homologs of the nucleic acid molecules used in the method of the invention are allelic variants which are at least 30%, preferably 40%, more preferably 50%, 60%, 70%, 80% or 90% and even more preferably 95%, 96%, 97%, 98%, 99% or more, identical to any of the nucleotide sequences depicted in SEQ. ID NO: 1, 3, 5, 7, 9, 11, 13, 15, 24, 26, 34, 36, 38, 40, 42, 44 or 52. Allelic variants include in particular functional variants which can be obtained by deletion, insertion or substitution of nucleotides from/into/in the sequence depicted in SEQ. ID NO: 1, 3, 5, 7, 9, 11, 13, 15, 24 26, 34, 36, 38, 40, 42, 44 or 52, but with the idea of retaining or increasing the L450 activity of the synthetized proteins derived therefrom. Proteins which still possess the biological or enzymic activity of L450 also include those whose activity is essentially not reduced, i.e. proteins having 5%, preferably 20%, particularly preferably 30%, very particularly preferably 40% or more of the original biological activity, compared to the protein encoded by SEQ. ID NO: 1, 3, 5, 7, 9, 11, 13, 15, 24, 26, 34, 36, 38, 40, 42, 44 or 52. Preferably, however, the homologous activity is increased compared to heterologous expression of L450 in the particular nonhuman organism.

Homologs of SEQ. ID NO: 1, 3, 5, 7, 9, 11, 13, 15, 24, 26, 34, 36, 38, 40, 42, 44 or 52 of the nucleic acid molecules used in the method of the invention also mean, for example, prokaryotic or eukaryotic, i.e. for example bacterial, animal, fungal and plant homologs, truncated sequences, single-stranded DNA or RNA of the coding and noncoding DNA sequence.

Homologs of SEQ. ID NO: 1, 3, 5, 7, 9, 11, 13, 15, 24, 26, 34, 36, 38, 40, 42, 44 or 52 of the nucleic acid molecules used in the method of the invention also include derivatives such as, for example, variants of the coding sequence or of the regulatory sequences, such as, for example, promoter, UTR, enhancer, splice signals, processing signals, polyadenylation signals, etc. The derivatives of the nucleotide sequences indicated may be modified by one or more nucleotide substitutions, by insertion(s) and/or deletion(s), without disturbing functionality or activity, however. It is furthermore possible that the activity of the derivatives is increased by modification of their sequence or that said derivatives are completely replaced with more active elements, even those from heterologous organisms.

In order to determine the percentage homology (=identity) of two amino acid sequences (e.g. any of the sequences of SEQ. ID NO: 2, 4, 6, 8, 10, 12, 14, 16, 25, 27, 35, 37, 39, 41, 43, 45, 46, 47, 48, 49, 50, 51 or 53 or of two nucleic acids (e.g. any of the sequences of SEQ. ID NO: 1, 3, 5, 7, 9, 11, 13, 15, 24 26, 34, 36, 38, 40, 42, 44 or 52), the sequences are compared to one another, for example by aligning said sequences or by analyzing both sequences with the aid of computer programs. Gaps may be introduced in the sequence of one protein or one nucleic acid to produce optimal alignment with the other protein or the other nucleic acid. The amino acid residues or nucleotides at the corresponding amino acid positions or nucleotide positions are then compared. When a position in one sequence is occupied by the same amino acid residue or the same nucleotide as the corresponding position in the other sequence, then the molecules are identical at this position (i.e. amino acid or nucleic acid "homology", is used herein, is equivalent to amino acid or nucleic acid "identity"). The percentage homology between the two sequences is a function of the number of identical positions shared by the sequences (i.e. % homology=number of identical positions/total number of positions×100). The terms homology and identity are thus used synonymously herein.

"Identity" between two proteins or nucleic acid sequences means identity over the entire length, in particular the identity carried out as described in the examples.

The NCBI standard settings were used for the blastp comparison of the amino acid sequences, i.e. using the following parameters: "composition based statics" and "low complexity filter, "Expect":10, "Word Size":3, "Matrix": Blosum62 and "Gap cost": Existence :11 Extension: 1.

The identity of various amino acid sequences to the amino acid sequence of *Arabidopsis thaliana* Accession AB020746 is indicated below by way of example.

However, for the determination of the percentage homology (=identity) of two or more amino acids or of two or more nucleotide sequences several other computer software programs have been developed. The homology of two or more sequences can be calculated with for example the software fasta, which presently has been used in the version fasta 3 (W. R. Pearson and D. J. Lipman (1988), Improved Tools for Biological Sequence Comparison. PNAS 85:2444-2448; W. R. Pearson (1990) Rapid and Sensitive Sequence Comparison with FASTP and FASTA, Methods in Enzymology 183:63 -98; W. R. Pearson and D. J. Lipman (1988) Improved Tools for Biological Sequence Comparison. PNAS 85:2444-2448; W. R. Pearson (1990); Rapid and Sensitive Sequence Comparison with FASTP and FASTAMethods in Enzymology 183:63 -98). Another useful program for the calculation of homologies of different sequences is the standard blast program, which is included in the Biomax pedant software (Biomax, Munich, Federal Republic of Germany). This leads unfortunately sometimes to suboptimal results since blast does not always include complete sequences of the subject and the querry. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=-3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast[nx] only) [Integer]; default=1;

-a Number of processors to use [Integer]; default=1; -O SeqAlign file [File Out] Optional; -J Believe the query define [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -l Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351-360, 1987, Higgins et al., CABIOS, 5 1989: 151-153) or preferably with the programs Gap and BestFit, which are respectively based on the algorithms of Needleman and Wunsch [J. Mol. Biol. 48; 443-453 (1970)] and Smith and Waterman [Adv. Appl. Math. 2; 482-489 (1981)]. Both programs are part of the GCG software-package [Genetics Computer Group, 575 Science Drive, Madison, Wis., USA 53711 (1991); Altschul et al. (1997) Nucleic Acids Res. 25:3389 et seq.]. Therefore preferably the calculations to determine the perentages of sequence homology are done with the program Gap over the whole range of the sequences. The following standard adjustments for the comparison of nucleic acid sequences can be used: gap weight: 50, length weight: 3, average match: 10.000, average mismatch: 0.000.

Nucleic acid molecules advantageous to the method of the invention may be isolated on the basis of their homology to the nucleic acids disclosed herein and used in the method of the invention by using the sequences or a part thereof as hybridization probe according to standard hybridization techniques under stringent hybridization conditions, as described also, for example, in US 2002/0023281, which is hereby expressly incorporated by reference. It is possible here to use, for example, isolated nucleic acid molecules which are at least 10, preferably at least 15, nucleotides in length and hybridize under stringent conditions with the nucleic acid molecules which comprise a nucleotide sequence of SEQ. ID NO: 1, 3, 5, 7, 9, 11, 13, 15, 24 26, 34, 36, 38, 40, 42, 44 or 52. The term "hybridizes under preferably stringent conditions", as used herein, is intended to describe hybridization and washing conditions under which nucleotide sequences, which are at least 20% identical to one another hybridize with one another. The term "hybridizes under stringed conditions", as used herein, is intended to describe hybridization and washing conditions under which nucleotide sequences which are 30%, but preferably 50% or more, identical to one another hybridize with one another. Preferably, the conditions are such that sequences which are 60%, more preferably 75% and even more preferably at least approximately 85% or more, identical to one another usually remain hybridized to one another. The identity of two polynucleic acids or amino acids may be determined as described herein. These stringent conditions are known to the skilled worker and can be found in Current Protocols in Molecular Biology, John Wiley & Sons, N.Y. (1989), 6.3.1-6.3.6., or in Sambrook, Molecular Cloning: A Laboratory Manual, Cold Spring Harbor Laboratory, Cold Spring Harbor Laboratory Press, Cold Spring Harbor, N.Y., 1989. A preferred, nonlimiting example of stringent hybridization conditions is hybridizations in 6× sodium chloride/sodium citrate (SSC) at about 45° C., followed by one or more washing steps in 0.2×SSC, 0.1% SDS at from 50 to 65° C. It is known to the skilled worker that these hybridization conditions differ depending on the type of nucleic acids, in particular according to the AT or GC content, or on the presence of organic solvents, with respect to temperature, duration of washing and salt concentration of the hybridization solutions and the washing solution. Under "standard hybridization conditions", for example, the temperature differs between 42° C. and 58° C. in aqueous buffer with a concentration of from 0.1 to 5×SSC (pH 7.2), depending on the type of nucleic acid. If an organic solvent is present in the abovementioned buffer, for example 50% formamide, the temperature under standard conditions is about 42° C. The hybridization conditions for DNA:DNA hybrids, for example, are 0.1×SSC and 20° C. to 45° C., preferably between 30° C. and 45° C. The hybridization conditions for DNA:RNA hybrids, for example, are preferably 0.1×SSC and from 30° C. to 55° C., preferably between 45° C. and 55° C. The hybridization temperatures mentioned above are determined, for example, for a nucleic acid of about 100 bp (=base pairs) in length and with a G+C content of 50% in the absence of formamide. The skilled worker knows how to determine the required hybridization conditions on the basis of textbooks such as the one mentioned above or the following textbooks: Sambrook, "Molecular Cloning", Cold Spring Harbor Laboratory, 1989; Hames and Higgins (eds.) 1985, "Nucleic Acids Hybridization: A Practical Approach", IRL Press at Oxford University Press, Oxford; Brown (eds.) 1991, "Essential Molecular Biology: A Practical Approach", IRL Press at Oxford University Press, Oxford or "Current Protocols in Molecular Biology", John Wiley & Sons, N.Y. (1989).

Some examples of conditions for DNA hybridization (Southern blot assays) and wash step are shown hereinbelow:
(1) Hybridization conditions can be selected, for example, from the following conditions:
a) 4×SSC at 65° C.,
b) 6×SSC at 45° C.,
c) 6×SSC, 100 mg/ml denatured fragmented fish sperm DNA at 68° C.,
d) 6×SSC, 0.5% SDS, 100 mg/ml denatured salmon sperm DNA at 68° C.,
e) 6×SSC, 0.5% SDS, 100 mg/ml denatured fragmented salmon sperm DNA, 50% formamide at 42° C.,
f) 50% formamide, 4×SSC at 42° C.,
g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
h) 2× or 4×SSC at 50° C. (low-stringency condition), or
i) 30 to 40% formamide, 2× or 4×SSC at 42° C. (low-stringency condition).

(2) Wash steps can be selected, for example, from the following conditions:
a) 0.015 M NaCl/0.0015 M sodium citrate/0.1% SDS at 50° C.
b) 0.1×SSC at 65° C.
c) 0.1×SSC, 0.5% SDS at 68° C.
d) 0.1×SSC, 0.5% SDS, 50% formamide at 42° C.
e) 0.2×SSC, 0.1% SDS at 42° C.
f) 2×SSC at 65° C. (low-stringency condition).

Furthermore, it is possible to identify, by comparing protein sequences of L450 genes or proteins of various organisms, conserved regions from which then in turn degenerated primers can be derived. These degenerated primers may then be used further by means of PCR for amplification of fragments of new L450 genes from other organisms. These fragments may then be used as hybridization probes for isolating the complete gene sequence. Alternatively, the missing 5' and 3' sequences may be isolated by means of RACE-PCR. In this respect, reference is expressly made to the disclosures in US 2002/0023281 and to the abovementioned literature on molecular-biological methods, in particular Sambrook, "Molecular Cloning" and "Current Protocols in Molecular Biology", John Wiley & Sons.

An isolated nucleic acid molecule coding for a protein used in the method of the invention, in particular L450, which protein is homologous in particular to a protein sequence of SEQ. ID NO: 2, 4, 6, 8, 10, 12, 14, 16, 25, 27, 35, 37, 39, 41, 43, 45, 46, 47, 48, 49, 50, 51 or 53, may be generated, for example, by introducing one or more nucleotide substitutions, additions or deletions into a nucleotide sequence of SEQ. ID NO: 1, 3, 5, 7, 9, 11, 13, 15, 24, 26, 34, 36, 38, 40, 42, 44 or 52 so that one or more amino acid substitutions, additions or deletions are introduced into the encoded protein. Mutations may be introduced in any of the sequences of the nucleic acid molecules used in the method of the invention by means of standard techniques such as site-specific mutagenesis and PCR-mediated mutagenesis.

Preference is given to generating conservative amino acid substitutions on one or more of the predicted nonessential amino acid residues. In a "conservative amino acid substitution", the amino acid residue is replaced by an amino acid residue having a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue is thus preferably replaced by another amino acid residue from the same side chain family. Preference is given to carrying out "conservative" substitutions in which the replaced amino acid has a property similar to that of the original amino acid, for example a substitution of Asp for Glu, Asn for Gln, Ile for Val, Ile for Leu, Thr for Ser.

In another embodiment, the mutations may alternatively be introduced randomly across all or part of the coding sequence, for example by saturation mutagenesis, and the resulting mutants may be screened for the L450 activity described herein in order to identify mutants which lead, for example, to plants with an increased growth rate, preferably faster growth and/or higher yield. After mutagenesis, the encoded protein may be recombinantly expressed, and the activity of said protein may be determined using the assays described herein, for example.

The nucleic acid molecules used in the method of the invention code for proteins or parts thereof. Said proteins or the individual protein or parts thereof preferably comprises one of the consensus sequences or core consensus sequences shown above, e.g. an amino acid sequence as shown in FIG. 7 or 8 SEQ ID No.: 46, 47, 48, 49, 50 or 51, whereby 20 or less, preferably 15 or 10, preferably 9, 8, 7, or 6, more preferred 5 or 4, even more preferred 3, even more preferred 2, even more preferred 1, most preferred 0 of the amino acids positions indicated by a capital or lower letter in FIG. 7 or 8 can be replaced by an x and/or not more than 5, preferably 4, even more preferred 3 or 2, most preferred one or non amino acid position indicated by a capital letter in FIG. 7 or 8 are/is replaced by an x and/or 20 or less, preferably 15 or 10, preferably 9, 8, 7, or 6, more preferred 5 or 4, even more preferred 3, even more preferred 2, even more preferred 1, most preferred 0 amino acids are inserted into the consensus sequence or, which is sufficiently homologous to an amino acid sequence of the sequence SEQ. ID NO: 2, 4, 6, 8, 10, 12, 14, 16, 25, 27, 35, 37, 39, 41, 43, 45, 46, 47, 48, 49, 50, 51 or 53, so that said protein or said part thereof retains L450 activity. In one embodiment, the said said proteins or the individual protein or parts thereof preferably are encoded by a nucleic acid molecule encoding a L450 polypeptide comprising the sequence shown in Seq. ID No: 46 or 49, whereby 20 or less, preferably 15 or 10, of the amino acid positions indicated can be replaced by an X and/or whereby 20 or less, preferably 15 or 10, of the amino acid are inserted into the shown sequence or shown in Seq ID N.: 47, 48, 50 or 51, whereby 10 or less, preferably 7, of the amino acid positions indicated can be replaced by an X and/or whereby 10 or less, preferably 7, of the amino acid are inserted into the shown sequence. Preferably, the nucleic acid molecule-encoded protein or part thereof has its essential biological activity which causes, inter alia, the target organism, preferably the target plant, to exhibit a higher growth rate or faster growth and thus higher biomass production and an increased yield. Conserved regions of a protein may be determined by sequence comparisons of various homologs or derivatives of a protein or of various members of a protein family. Moreover, computer programs which predict the structure of a protein, owing to its sequence and other properties, are known to the skilled worker. Antibody binding studies and studies on the sensitivity or hypersensitivity of protein domains with regard to protease digestion may likewise be used to study the structure of a polypeptide or its location in a particular environment, for example in a cell. Further methods of this kind for characterizing L450 are known to the skilled worker and are disclosed in the literature described herein, for example also in US 2002/0023281.

Preferably, the used part of a protein or a domain is highly conserved among the sequences described herein, for example among the plant sequences, or animal sequences, preferably among all sequences.

Advantageously, the protein encoded by the nucleic acid molecules is at least 20%, preferably 40% and more preferably 50%, 60%, 70%, 80% or 90% and most preferably 95%, 96%, 97%, 98%, 99% or more, homologous to an amino acid sequence of the sequence SEQ. ID NO: 2, 4, 6, 8, 10, 12, 14, 16, 25 27, 35, 37, 39, 41, 43, 45, 46, 47, 48, 49, 50, 51 or 53. Said protein is preferably a full-length protein which is essentially in parts homologous to a total amino acid sequence of SEQ. ID NO: 2, 4, 6, 8, 10, 12, 14, 16, 25 27, 35, 37, 39, 41, 43, 45, 46, 47, 48, 49, 50, 51 or 53 and which is preferably derived from the open reading frame depicted in SEQ. ID NO:

1, 3, 5, 7, 9, 11, 13, 15, 24 26, 34, 36, 38, 40, 42, 44 or 52. However, preferably, the core consensus sequences or the consensus sequences as described above, e.g. as shown in FIGS. 7 and 8 or depicted in SEQ ID No.: 46, 47, 48, 49, 50 or 51 are maintained.

"Essential biological activity" of the proteins or polypeptides used means, as discussed above, that said proteins or polypeptides possess the biological activity of L450. The "biological activity of L450" means that expression of the polypeptide in a nonhuman organism results in accelerated growth or in an increase of the yield by 5% or more, compared to a nonhuman organism which does not express said polypeptide, or expresses it to a lesser extent. More preference is given to an acceleration by 10%, even more preference to 20%, most preference to 50%, 100% or 200% or more. A test system for determining the biological activity of a putative L450, which may be studied, is the phenotype of expression in *Arabidopsis thaliana* or, where appropriate, also (over)expression in the organism from which the putative L450 is derived.

The cellular activity or function of L450 and its homologs is, as described above, not yet known and, consequently, an in-vitro assay system is likewise not available yet. Presumably, however, it is possible for the skilled worker to measure a specific L450 activity of a protein or polypeptide by (over) expressing said protein or polypeptide in a cell, preferably in a deficient cell, and comparing it with the phenotype of a deficient cell. Advantageously, the tolerance of the cell to abiotic or biotic stress increases. It is possible, for example, to measure the oxidative state of the cell. Advantageously, the concentration of reactive oxygen species in particular cells is modulated. If (over)expression of a putative L450 causes a change in the oxidative state of the cell, which is similar to that of a cell, is (over)expressed into one of the sequences according to Seq. ID No.: 2, 4, 6, 8, 10, 12, 14, 16, 25 27, 35, 37, 39, 41, 43, 45, 46, 47, 48, 49, 50, 51 or 53, then the corresponding polypeptide has a similar activity, i.e. an L450 activity according to the invention.

Proteins which may be used advantageously in the method are derived from plant organisms such as algae or mosses or, especially, from higher plants.

Advantageously, the increased activity of the protein characterized in the method of the invention in a cell, an organ, a tissue or a nonhuman organism, in particular in a microorganism, particularly advantageously in a plant, also results in increased tolerance to abiotic and biotic stress. The aforementioned nucleic acids and protein molecules with L450 activity which are possibly involved in the metabolism of reactive oxygen species are used for increasing the growth, the yield or the amount produced of biomass, but preferably also for increasing the tolerance of an organ, a tissue or a nonhuman organism, in particular of a microorganism, particularly advantageously in a plant, to abiotic or biotic stress.

Consequently, one embodiment of the method of the invention comprises introducing a polynucleotide into a nonhuman organism, in particular a plant, a useful animal or a microorganism, or one or more parts thereof, which polynucleotide codes for an L450 polypeptide. The polynucleotide preferably comprises a polynucleotide characterized herein, in particular a polynucleotide encoding a protein with the sequence according to Seq. ID No.: 2, 4, 6, 8, 10, 12, 14, 16, 25 27, 35, 37, 39, 41, 43, 45, 46, 47, 48, 49, 50, 51 or 53 or encoding a polypeptide encoded by a nucleic acid molecule characterized herein, in particular according to SEQ. ID NO: 1, 3, 5, 7, 9, 11, 13, 15, 24 26, 34, 36, 38, 40, 42, 44 or 52 or comprising any of these sequences so that a transgenic plant with faster growth, higher yield and/or higher tolerance to stress is obtained. Preference is given to a plant expressing any of the plant sequences mentioned herein or their plant homologs, to animals expressing the animal sequences mentioned herein or their animal homologs and to microorganisms expressing the microbial sequences mentioned herein or their microbial homologs. As mentioned, however, yeast L450 also exhibits L450 activity in plants.

In one embodiment, the present invention relates to a polypeptide encoded by the nucleic acid molecule according to the present invention, preferably conferring above-mentioned activity.

The present invention also relates to a method for the production of a polypeptide according to the present invention, the polypeptide being expressed in a host cell according to the invention, preferably in a transgenic microorganism or a transgenic plant cell.

In one embodiment, the nucleic acid molecule used in the method for the production of the polypeptide is derived from a microorganism, with an eukaryotic organism as host cell. In one embodiment the polypeptide is produced in a plant cell or plant with a nucleic acid molecule derived from a prokaryote or a fungus or an alga or an other microorganismus but not from plant.

The skilled worker knows that protein and DNA expressed in different organisms differ in many respects and properties, e.g. methylation, degradation and post-translational modification as for example glucosylation, phosphorylation, acetylation, myristoylation, ADP-ribosylation, farnesylation, carboxylation, sulfation, ubiquination, etc. though having the same coding sequence. Preferably, the cellular expression control of the corresponding protein differs accordingly in the control mechanisms controlling the activity and expression of an endogenous protein or another eukaryotic protein The polypeptide of the present invention is preferably produced by recombinant DNA techniques. For example, a nucleic acid molecule encoding the protein is cloned into an vector (as described above), the vector is introduced into a host cell (as described above) and said polypeptide is expressed in the host cell. Said polypeptide can then be isolated from the cells by an appropriate purification scheme using standard protein purification techniques. Alternative to recombinant expression, the polypeptide or peptide of the present invention can be synthesized chemically using standard peptide synthesis techniques. Moreover, native polypeptide can be isolated from cells (e.g., endothelial cells), for example using the antibody of the present invention as described, which can be produced by standard techniques utilizing the polypeptid of the present invention or fragment thereof, i.e., the polypeptide of this invention.

In one embodiment, the present invention relates to a L450 protein. In one embodiment, the present invention relates to a polypeptide comprising or consisting of a polypeptide sequence shown in SEQ ID No: 2, 4, 6, 8, 10, 12, 14, 16, 25, 27, 35, 39, 41, 43, 45, 46, 47, 48, 49, 50, 51 or 53, or a homolog thereof of 50%, 70%, 80%, 85%, 90%, 95%, 97%, 99% or 99,5% or more but not being, preferably not consisting of the sequence shown in SEQ ID No.: 2, 4, 10, 12, 14, 16, 43 or 46.

In one embodiment, the protein of the present invention does not comprise the sequence shown in Seq ID NO.: 2, 4, 10, 12, 14, 16, 43 or 46.

In one embodiment, the present invention relates to a polypeptide having the amino acid sequence encoded by a nucleic acid molecule of the invention or obtainable by a method of the invention. Said polypeptide confers preferably the aforementioned activity, in particular, the polypeptide confers the increase of the yield or growth as described herein in a cell or an organism or a part thereof after increasing the cellular activity, e.g. by increasing the expression or the specific activity of the polypeptide. In one embodiment, said polypeptide distinguishes over the sequence depicted in SEQ ID No: 2, 4, 10, 12, 14, 16, 43 or 45 by one or more amino acids. In an other embodiment, said polypeptide of the invention does not consist of the sequence shown in SEQ ID NO: 2, 4, 10, 12, 14, 16, 43 or 45. In one embodiment, said polypeptide does not consist of the sequence encoded by the nucleic acid molecules shown in SEQ ID NO: 1, 3, 9, 11, 13, 15, 29, 42 or 44. In one embodiment, the polypeptide of the invention orginates from an non-plant cell, in particular from a microorganism, and was expressed in a plant cell The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

Preferably, the polypeptide is isolated. An "isolated" or "purified" protein or polynucleotide or biologically active portion thereof is substantially free of cellular material when produced by recombinant DNA techniques or chemical precursors or other chemicals when chemically synthesized.

The language "substantially free of cellular material" includes preparations of the polypeptide of the invention in which the protein is separated from cellular components of the cells in which it is naturally or recombinantly produced. In one embodiment, the language "substantially free of cellular material" includes preparations having less than about 30% (by dry weight) of "contaminating protein", more preferably less than about 20% of "contaminating protein", still more preferably less than about 10% of "contaminating protein", and most preferably less than about 5% "contaminating protein". The term "Contaminating protein" relates to polypeptides, which are not polypeptides of the present invention. When the polypeptide of the present invention or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations in which the polypeptide or of the present invention is separated from chemical precursors or other chemicals which are involved in the synthesis of the protein.

A polypeptide of the invention can participate in the method of the present invention.

Further, the polypeptide can have an amino acid sequence which is encoded by a nucleotide sequence which hybridizes, preferably hybridizes under stringent conditions as described above, to a nucleotide sequence of the polynucleotide of the present invention. Accordingly, the polypeptide has an amino acid sequence which is encoded by a nucleotide sequence that is at least about 35%, 50%, or 60% preferably at least about 70%, more preferably at least about 80%, 90%, 95%, and even more preferably at least about 96%, 97%, 98%, 99% or more homologous to one of the amino acid sequences of the polypeptide of the invention and shown herein. The preferred polypeptide of the present invention preferably possesses at least one of the activities according to the invention and described herein. A preferred polypeptide of the present invention includes an amino acid sequence encoded by a nucleotide sequence which hybridizes, preferably hybridizes under stringent conditions, as defined above.

The invention also provides chimeric or fusion proteins.

As used herein, an "chimeric protein" or "fusion protein" comprises an polypeptide operatively linked to a polypeptide which does not confer above-mentioned activity Within the fusion protein, the term "operatively linked" is intended to indicate that the polypeptide of the invention and a non-invention polypeptide are fused to each other so that both sequences fulfill the proposed function addicted to the sequence used. The non-invention polypeptide can be fused to the N-terminus or C-terminus of the polypeptide of the invention. For example, in one embodiment the fusion protein is a GST-LMRP fusion protein in which the sequences of the polypeptide of the invention are fused to the C-terminus of the GST sequences. Such fusion proteins can facilitate the purification of recombinant polypeptides of the invention.

In another embodiment, the fusion protein is a polypeptide of the invention containing a heterologous signal sequence at its N-terminus. In certain host cells (e.g., mammalian host cells), expression and/or secretion can be increased through use of a heterologous signal sequence. Targeting sequences, are required for targeting the gene product into specific cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, elaioplasts, peroxisomes, glycosomes, and other compartments of cells or extracellular. Sequences, which must be mentioned in this context are, in particular, the signal-peptide- or transit-peptide-encoding sequences which are known per se. For example, plastid-transit-peptide-encoding sequences enable the targeting of the expression product into the plastids of a plant cellTargeting sequences are also known for eukaryotic and to a lower extent for prokaryotic organisms and can advantageously be operable linked with the nucleic acid molecule of the present invention to achieve an expression in one of said compartments or extracellular.

Preferably, an chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). The polynucleotide of the invention can be cloned into such an expression vector such that the fusion moiety is linked in-frame to the encoded protein.

Furthermore, folding simulations and computer redesign of structural motifs of the protein of the invention can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). The appropriate programs can be used for the identification of interactive sites the polypeptide of the invention and its substrates or binding factors or other interacting proteins by computer assistant searches for complementary peptide sequences (Fassina, Immunomethods (1994), 114-120). Further appropriate computer systems for the design of protein and peptides are described in the prior art, for example in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used for, e.g., the preparation of peptidomimetics of the protein of the invention or fragments thereof. Such pseudopeptide analogues of the, natural amino acid sequence of the protein may very efficiently mimic the parent protein (Benkirane, J. Biol. Chem. 271 (1996), 33218-33224). For example, incorporation of easily available achiral Q-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769-777).

Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Rutenber, Bioorg. Med. Chem. 4 (1996),1545-1558).

Furthermore, a three-dimensional and/or crystallographic structure of the protein of the invention and the identification of interactive sites the polypeptide of the invention and its substrates or binding factors can be used for design of mutants with modulated binding or turn over activities. For example, the active center of the polypeptide of the present invention can be modelled and amino acid residues participating in the catalytic reaction can be modulated to increase or decrease the binding of the substrate to inactivate the polypeptide. The identification of the active center and the amino acids involved in the catalytic reaction facilitates the screening for mutants having an increased activity. In particular, the information about the conservative amino acids in the consensus sequences can help to modulate the activity.

Where appropriate, however, expression of a polynucleotide of a distant nonhuman organism, which encodes an L450, may, according to the knowledge of the skilled worker, result in a particularly strong effect of the invention, i.e. in a particularly large increase in growth and/or yield, since the encoded polypeptide is possibly not accessible to endogenous regulatory influences.

"Transgenic" or "recombinant" means in accordance with the invention, for example with regard to a nucleic acid sequence, to an expression cassette (=gene construct) or to a vector comprising the nucleic acid sequence of the invention or to a nonhuman organism transformed with the nucleic acid molecule sequences, expression cassette or vector of the invention, all those constructions produced by genetic methods, in which a) the nucleic acid sequence used in the method of the invention or
b) a genetic control or regulatory sequence functionally linked to a nucleic acid sequence used in the method of the invention, for example a promotor, or
c) (a) and (b)

are not present in their natural, genetic environment or have been modified by genetic methods, said modification possibly being, by way of example, a substitution, addition, deletion, inversion or insertion of one or more nucleotide residues. Natural genetic environment means the natural genomic or chromosomal locus in the source organism or the presence in a genomic library. In the case of a genomic library, the natural, genetic environment of the nucleic acid sequence is preferably at least partially still retained. The environment flanks the nucleic acid sequence at least on one side and its sequence is from 0 or more bp, preferably 50 bp, more preferably from 100 to 500 bp, particularly preferably 1 000 bp or more, in length, although sequences of 5 000 bp or more have also been described. A naturally occurring expression cassette, for example the naturally occurring combination of the natural promoter of the L450 nucleic acid sequence, becomes a transgenic expression cassette when altered by nonnatural, synthetic ("artificial") methods such as, for example, mutagenesis. Corresponding methods are described, for example, in U.S. Pat. No. 5,565,350 or WO 00/15815.

The regulatory functions of a natural as well as artificial expression cassette may was altered indirectly or in trans by changing factors which regulate said expression cassette. This includes, in particular, homologous, heterologous and artificial transcription factors influencing regulation.

Cloning vectors as described in detail in the prior art and also herein may be used for transformation. Vectors and methods suitable for transformation of plants have been published or cited in, for example: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, eds: Kung and R. Wu, Academic Press, 1993, 15-38; B. Jenes et al., Techniques for Gene Transfer, in: Transgenic Plants, vol. 1, Engineering and Utilization, eds: Kung and R. Wu, Academic Press (1993), 128-143; Potrykus, Annu. Rev. Plant Physiol. Plant Molec. Biol. 42 (1991), 205-225)).

The transformation of microorganisms and higher eukaryotes is described in numerous textbooks, for example in Sambrook, Molecular Cloning, 1989, Cold Spring Harbor Laboratory and in "Current Protocols in Molecular Biology", John Wiley & Sons, N.Y. (1989).

It is possible to express homologous or heterologous nucleic acids, i.e. the acceptor and donor organisms belong to the same species, where appropriate to the same variety, or to different species, where appropriate varieties. However, transgenic also means that the nucleic acids of the invention are located at their natural location in the genome of an organism but that the sequence has been altered compared to the natural sequence and/or the regulatory sequences of the natural sequences have been altered. Transgenic preferably means expression of the nucleic acids of the invention at a nonnatural site in the genome, i.e. homologous or, preferably, heterologous expression of said nucleic acids occurs.

The term "regulatory sequences" also includes those sequences which control constitutive expression of a nucleotide sequence in many host cell species and those which control direct expression of the nucleotide sequence only in particular host cells under particular conditions. The skilled worker appreciates that the design of the expression vector may depend on factors such as selection of the host cell to be transformed, degree of expression of the desired protein, etc. Transcription may be increased, for example, by using strong transcription signals such as promoter and/or enhancer or mRNA stabilizers, for example by particular 5' and/or 3'UTRs. Thus, for example, signals leading to a higher rate of transcription or to a more stable mRNA may be substituted for endogenous signals. In addition, however, it is also possible to enhance translation by improving, for example, ribosome binding or mRNA stability. In principle, those promoters may be used which are able to stimulate transcription of genes in organisms such as micro-organisms, plants or animals. Suitable promoters which are functional in said organisms are well known. They may be constitutive or inducible promoters. Suitable promoters may enable development- and/or tissue-specific expression in multi-cellular eukaryotes, and it is thus possible to use advantageously leaf-, root-, flower-, seed-, guard cell- or fruit-specific promoters in plants. Further regulatory sequences are described above and below.

The term "transgenic", used according to the invention, also refers to the progeny of a transgenic nonhuman organism, for example a plant, for example the $T_1$, $T_2$, $T_3$ and subsequent plant generations or the $BC_1$, $BC_2$, $BC_3$ and subsequent plant generations. Thus, the transgenic plants of the invention may be grown and crossed with themselves or with other individuals in order to obtain further transgenic plants of the invention. It is also possible to obtain transgenic plants by vegetative propagation of transgenic plant cells.

In a preferred embodiment, faster growth and/or a higher yield are achieved by increasing endogenous L450 expression. Thus it is possible to increase the amount of L450 in the method of the invention by functionally linking an endogenous, L450-encoding polynucleotide to regulatory sequences which lead to an increased amount of said L450 polypeptide.

The amount of expression of a gene is regulated at the transcriptional or translational level or with respect to the stability and degradation of a gene product.

Regulatory sequences are usually arranged upstream (5'), within and/or downstream (3') with respect to a particular nucleic acid or a particular codogenic gene section. They control in particular transcription and/or translation and also transcript stability of the codogenic gene section, where appropriate in cooperation with further functional systems intrinsic to the cell, such as the protein biosynthesis apparatus of the cell. Thus it is possible to influence promoter, UTR, splice sites, polyadenylation signals, terminators, enhancers, processing signals, posttranscriptional and/or posttranslational modifications, etc. according to the knowledge of the skilled worker in order to increase expression of an endogenous protein without influencing the sequence of said protein itself. Consequently, the amount of L450 may also be increased according to the invention when manipulating the L450 regions flanking the coding sequence. Thus, for example, an exogenous promoter mediating higher or more specific expression may replace the endogenous L450 promoter and thus result in higher expression of the protein. It is also possible, for example, to increase the stability of the mRNA product by replacing the endogenous 5' UTR or 3' UTR, without influencing the endogenous sequence of the protein. Other methods of this kind for increasing expression of a protein in an organism are known to the skilled worker. Thus it is also possible, for example, to increase the stability of L450 by deleting degradation-controlling elements in the protein, thereby increasing the amount and consequently the activity in the cell. Further functional or regulatory sequences which are replaced with those making possible a larger amount or, where appropriate, higher activity are described herein. The L450 activity may possibly also be regulated via the redox equilibrium in the environment of the polypeptide. Redox modulation is described, for example, for AGPase in Tiessen, Plant Cell, 2002, 14, 2191-2213. It is possible, for example, to modulate, the concentration of reactive oxygen species in particular cells, resulting in accelerated growth. Furthermore, transcriptional regulation may be specifically altered by introducing an artificial transcription factor, as described below and in the examples.

Regulatory sequences are disclosed, for example, in Goeddel: Gene Expression Technology: Methods in Enzymology 185, Academic Press, San Diego, Calif. (1990), or in Gruber; Methods in Plant Molecular Biology and Biotechnolgy, CRC Press, Boca Raton, Fla., eds.: Glick and Thompson, chapter 7, 89-108, including the references therein.

It is also possible to identify positive and negative regulators which have an inhibiting or activating influence on expression or activity (allosteric effects) of L450 and which are then switched off or enhanced. Such mechanisms are sufficiently known to the skilled worker in a multiplicity of metabolic pathways. It is possible, for example, for abiotic or biotic stress effects to play a substantial regulative part in the regulation of expression or activity of L450 in a nonhuman organism. Thus, increased or reduced oxidative stress of the cells might control expression or activity of L450 as protein which is presumably involved in ROS regulation. Infestation with parasites leads in many cases also to alterations in the oxidative environment of a cell or of a nonhuman organism. These observations may be utilized for increasing the L450 activity and may, for example, be artificially mimicked, for example by activating or inhibiting particular regulators.

In one embodiment of the method of the invention, expression of the L450 protein is increased by an increase in the amount of a transcription factor increasing L450 transcription in the nonhuman organism or in one or more parts thereof. Thus it is possible, for example by means of promoter analyses, to identify endogenous transcription factors involved in transcriptional regulation of an endogenous L450 gene. Increased activity of positive regulators or else reduced activity of negative regulators may increase transcription of an endogenous L450 gene.

Furthermore, methods for altering expression of genes by means of artificial transcription factors are known to the skilled worker.

Thus, for example, an alteration in expressing a gene, in particular a gene expressing L450, may be achieved by modifying or synthesizing particular specific DNA-binding factors such as, for example, zinc-finger transcription factors. These factors bind to particular genomic regions of an endogenous target gene, preferably to the regulatory sequences, and may cause activation or repression of said gene. The use of such a method make it possible to activate or reduce expression of the endogenous gene, avoiding a recombinant manipulation of the sequence of said gene. Corresponding methods are described, for example, in Dreier B [(2001) J. Biol. Chem. 276(31): 29466-78 and (2000) J. Mol. Biol. 303(4): 489-502], Beerli R R (1998) Proc. Natl. Acad. Sci. USA 95(25): 14628-14633; (2000) Proc. Natl. Acad. Sci. USA 97(4): 1495-1500 and (2000) J. Biol. Chem. 275(42): 32617-32627), Segal D J and Barbas C F (2000) Curr. Opin. Chem. Biol. 4(1): 34-39, Kang J S and Kim J S (2000) J. Biol. Chem. 275(12): 8742-8748, Kim J S, (1997) Proc. Natl. Acad. Sci. USA 94(8): 3616-3620, Klug A (1999) J. Mol. Biol. 293(2): 215-218, Tsai S Y, (1998) Adv. Drug Deliv. Rev. 30(1-3): 23-31], Mapp A K (2000) Proc. Natl. Acad. Sci. USA 97(8): 3930-3935, Sharrocks A D (1997) Int. J. Biochem. Cell Biol. 29(12): 1371-1387 and Zhang L (2000) J. Biol. Chem. 275(43): 33850-33860.

Examples of applying the method for modification of gene expression in plants are described, for example, in WO 01/52620, Ordiz M I, (2002) Proc. Natl. Acad. Sci. USA, 99(20):13290-13295) or Guan (2002) Proc. Natl. Acad. Sci. USA, 99(20): 13296-13301) and in the examples mentioned below.

In one embodiment, the method of the invention comprises increasing the gene copy number of the polynucleotide used in the method of the invention and characterized herein in the plant.

Advantageously, the method described herein increases the number and size of leaves, the number of fruits and/or the size of fruits of a plant whose L450 activity is increased, fruit meaning any harvested products of a plant, such as, for example, seeds, tubers, leaves, flowers, bark, fruits and roots.

The plant prepared in the method of the invention preferably has a fresh weight which is increased by 5%, more preferably by 10%, even more preferably by more than 15%, 20%, or 30%. Even more preference is given to an increase in yield by 50% or more, for example by 75%, 100% or 200% or more.

The yield of the plant prepared in the method of the invention is preferably increased by at least 5%, more preferably by more than 10%, even more preferably by more than 15%, 20%, or 30%. Even more preference is given to an increase in yield by more than 50% or more, for example by 75%, 100% or 200% or more.

In a further embodiment, the plant prepared in the method of the invention is more tolerant to abiotic or biotic stress.

In a preferred embodiment, the invention also relates to a method for preparing fine chemicals. The method comprises providing a cell, a tissue or an organism having increased L450 activity and culturing said cell, said tissue or said organism under conditions which allow production of the desired fine chemicals in said cell, said tissue or said organism. Preference is given to providing in the method a plant of the invention, a microorganism of the invention or a useful animal of the invention.

As described above, increasing the activity of L450 in a nonhuman organism, in particular in plants, results in an increase in the yield and in faster growth. By now, however, many organisms are used for producing fine chemicals. The production of fine chemicals nowadays is unimaginable without microorganisms which produce inexpensive and specific, even complex molecules whose chemical synthesis comprises many process stages and purification steps. Thus, fine chemicals such as vitamins and amino acids are industrially produced on a large scale in the same way as complex pharmaceutical active compounds such as, for example, growth factors, antibodies, etc., and the term fine chemicals is intended to also include these active compounds hereinbelow. Plants are likewise already used for producing various fine chemicals such as, for example, polymers, e.g. polyhydroxyalkanoids, vitamins, amino acids, sugars, fatty acids, in particular polyunsaturated fatty acids, etc. Even useful animals are already used for producing fine chemicals. Thus, production of antibodies and other pharmaceutical active compounds in the milk of goats or cows has already been described.

In a particularly preferred embodiment, the method of the invention consequently relates to a method in which the L450 activity in a nonhuman organism, preferably a plant or a microorganism, is increased and one or more metabolic pathways are modulated in such a way that the yield and/or efficiency of production of one or more fine chemicals is increased.

The terms production or productivity are known to the skilled worker and comprise increasing the concentration of desired products (e.g. fatty acids, carotenoids, (poly)saccharides, vitamins, isoprenoids, lipids, fatty acid (esters), and/or polymers such as polyhydroxyalkanoids and/or their metabolic products or other desired fine chemicals as described herein) within a particular time and a particular volume (e.g. kilogram/hour/liter).

The term "fine chemical" is known in the art and includes molecules which are produced by a nonhuman organism and are used in various branches of industry such as, for example, but not restricted to, the pharmaceutical industry, the agricultural industry and the cosmetics industry. These compounds comprise organic acids such as tartaric acid, itaconic acid and diaminopimelic acid, polymers or macromolecules such as, for example, polypeptides, e.g. enzymes, antibodies, growth factors or fragments thereof, nucleic acids, including polynucleic acids, both proteinogenic and nonproteinogenic amino acids, purine and pyrimidine bases, nucleosides and nucleotides (as described, for example, in Kuninaka, A. (1996) Nucleotides and related compounds, pp. 561-612, in Biotechnology vol. 6, Rehm et al., eds VCH: Weinheim and the references therein), lipids, saturated and unsaturated fatty acids (e.g. arachidonic acid), diols (e.g. propanediol and butanediol), carbohydrates (e.g. pentoses, hexoses, hyaluronic acid and trehalose), aromatic compounds (e.g. aromatic amine, vanillin and indigo), isoprenoids, prostagladins, triacylglycerol, cholesterol, polyhydroxyalkanoids, vitamins and cofactors (as described in Ullmann's Encyclopedia of Industrial Chemistry, vol. A27, "Vitamins", pp. 443-613 (1996) VCH: Weinheim and the references therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The term "fine chemicals", as used herein, thus also includes pharmaceutical compounds which can be produced in organisms, for example antibodies, growth factors, etc. or fragments thereof.

The term "amino acid" is known in the art. Amino acids comprise the fundamental structural units of all proteins and are thus essential for normal cell functions. Proteinogenic amino acids, of which there are 20 types, serve as structural units for proteins in which they are linked together by peptide bonds, whereas the nonproteinogenic amino acids (hundreds of which are known) usually do not occur in proteins (see Ullmann's Encyclopedia of Industrial Chemistry, vol. A2, pp. 57-97 VCH: Weinheim (1985)). Amino acids can exist in the D or L configuration, although L-amino acids are usually the only type found in naturally occurring proteins. Biosynthetic and degradation pathways of each of the 20 proteinogenic amino acids are well characterized both in prokaryotic and eukaryotic cells (see, for example, Stryer, L. Biochemistry, 3rd edition, pp. 578-590 (1988)). Apart from their function in protein biosynthesis, these amino acids are interesting chemicals as such, and it has been found that many have various applications in the human food, animal feed, chemical, cosmetic, agricultural and pharmaceutical industries. Lysine is an important amino acid not only for human nutrition but also for monogastric animals such as poultry and pigs. Glutamate is most frequently used as a flavor additive (monosodium glutamate, MSG) and elsewhere in the food industry, as are aspartate, phenylalanine, glycine and cysteine. Glycine, L-methionine and tryptophan are all used in the pharmaceutical industry. Glutamine, valine, leucine, isoleucine, histidine, arginine, proline, serine and alanine are used in the pharmaceutical industry and the cosmetics industry.

Threonine, tryptophan and D-/L-methionine are widely used animal feed additives (Leuchtenberger, W. (1996) Amino acids—technical production and use, pp. 466-502 in Rehm et al., (eds) Biotechnology vol. 6, chapter 14a, VCH: Weinheim). It has been found that these amino acids are moreover suitable as precursors for synthesizing synthetic amino acids and proteins, such as N-acetylcysteine, S-carboxymethyl-L-cysteine, (S)-5-hydroxytryptophan and other substances described in Ullmann's Encyclopedia of Industrial Chemistry, vol. A2, pp. 57-97, VCH, Weinheim, 1985.

The term "vitamin" is known in the art and comprises nutrients which are required for normal functioning of an organism but cannot be synthesized by this organism itself. The group of vitamins may include cofactors and nutraceutical compounds.

The term "cofactor" comprises nonproteinaceous compounds necessary for the appearance of a normal enzymic activity. These compounds may be organic or inorganic; the cofactor molecules of the invention are preferably organic.

The term "nutraceutical" comprises food additives which are health-promoting in plants and animals, especially humans. Examples of such molecules are vitamins, antioxidants and likewise certain lipids (e.g. polyunsaturated fatty acids).

Vitamins, cofactors and nutraceuticals consequently comprise a group of molecules which cannot be synthesized by higher animals which therefore have to take them in, although they are readily synthesized by other organisms such as bacteria. These molecules are either bioactive molecules per se or precursors of bioactive substances which serve as electron carriers or intermediate products in a number of metabolic pathways. Besides their nutritional value, these compounds also have a substantial industrial value as colorants, antioxidants and catalysts or other processing auxiliaries. For an overview of the structure, activity and industrial applications of these compounds, see, for example, Ullmann's Encyclopedia of Industrial Chemistry, "Vitamins", vol. A27, pp. 443-613, VCH: Weinheim, 1996. Polyunsaturated fatty acids are described in particular in: Simopoulos 1999, Am. J. Clin. Nutr., 70 (3 Suppl):560-569, Takahata et al., Biosc. Biotechnol. Biochem, 1998, 62 (11):2079-2085, Willich and Winther, 1995, Deutsche Medizinische Wochenschrift, 120 (7): 229 ff and the references therein.

The term "purine" or "pyrimidine" comprises nitrogen-containing bases which form part of nucleic acids, coenzymes and nucleotides. The term "nucleotide" comprises the fundamental structural units of nucleic acid molecules, which comprise a nitrogen-containing base, a pentose sugar (the sugar is ribose in the case of RNA and D-deoxyribose in the case of DNA) and phosphoric acid. The term "nucleoside" comprises molecules which serve as precursors of nucleotides but have, in contrast to the nucleotides, no phosphoric acid unit. It is possible to inhibit RNA and DNA synthesis by inhibiting the biosynthesis of these molecules or their mobilization to form nucleic acid molecules; targeted inhibition of this activity in cancer cells allows the ability of tumor cells to divide and replicate to be inhibited. Moreover, there are nucleotides which do not form nucleic acid molecules but serve as energy stores (i.e. AMP) or as coenzymes (i.e. FAD and NAD). However, purine and pyrimidine bases, nucleosides and nucleotides also have other possible uses: as intermediate products in the biosynthesis of various fine chemicals (e.g. thiamine, S-adenosylmethionine, folates or riboflavin), as energy carriers for the cell (e.g. ATP or GTP) and for chemicals themselves; they are ordinarily used as flavor enhancers (e.g. IMP or GMP) or for many medical applications (see, for example, Kuninaka, A., (1996) "Nucleotides and Related Compounds in Biotechnology" vol. 6, Rehm et al., eds. VCH: Weinheim, pp. 561-612). Enzymes involved in purine, pyrimidine, nucleoside or nucleotide metabolism are also increasingly serving as targets against which chemicals are being developed for crop protection, including fungicides, herbicides and insecticides.

A cell contains different carbon sources which are also included in the term "fine chemicals", for example sugars such as glucose, fructose, mannose, galactose, ribose, sorbose, ribulose, lactose, maltose, sucrose or raffinose, starch or cellulose, alcohols (e.g. methanol or ethanol), alkanes, fatty acids, in particular polyunsaturated fatty acids and organic acids such as acetic acid or lactic acid. Sugars may be transported by a multiplicity of mechanisms via the cell membrane into the cell. The ability of cells to grow and to divide rapidly in culture depends to a high degree on the extent of the ability of said cells to absorb and utilize energy-rich molecules such as glucose and other sugars. Trehalose consists of two glucose molecules linked together by an $\alpha,\alpha$-1,1-linkage.

It is ordinarily used in the food industry as sweetener, as additive for dried or frozen foods and in beverages. However, it is also used in the pharmaceutical industry, the cosmetics industry and the biotechnology industry (see, for example, Nishimoto et al., (1998) U.S. Pat. No. 5,759,610; Singer, M. A. and Lindquist, S. Trends Biotech. 16 (1998) 460-467; Paiva, C. L. A. and Panek, A. D. Biotech Ann. Rev. 2 (1996) 293-314; and Shiosaka, M. J. Japan 172 (1997) 97-102). Trehalose is used by enzymes of many microorganisms and is naturally released into the surrounding medium from which it can be isolated by methods known in the art.

The biosynthesis of said molecules in organisms has been comprehensively characterized, for example in Ullmann's Encyclopedia of Industrial Chemistry, VCH: Weinheim, 1996, e.g. chapter "Vitamins", vol. A27, pp. 443-613, Michal, G. (1999) Biochemical Pathways: An Atlas of Biochemistry and Molecular Biology, John Wiley & Sons; Ong, A. S., Niki, E. and Packer, L. (1995) "Nutrition, Lipids, Health and Disease" Proceedings of the UNESCO/Confederation of Scientific and Technological Associations in Malaysia and the Society for free Radical Research—Asia, held on Sep. 1-3, 1994 in Penang, Malaysia, AOCS Press, Champaign, Ill. X, 374 S).

Consequently, one embodiment of the present invention relates to a method for increasing oil production of a plant.

Plants may be used advantageously, for example, for the production of fatty acids. For example, storage lipids in the seeds of higher plants are synthesized from fatty acids which mainly have from 16 to 18 carbons. Said fatty acids are located in the seed oils of various plant species. An increase in L450 activity in *Arabidopsis* has already shown that seed production is increased by approx. 30%. The production of said oils in plants may be increased, for example, by expressing polynucleotides characterized herein. Vegetable oils may then be used, for example, as fuel or as material for various products such as, for example, plastics, drugs, etc. Polyunsaturated fatty acids may be used particularly advantageously in nutrition and feeding.

In one embodiment, said method of the invention comprises preparing fine chemicals by transforming the nonhuman organism with one or more further polynucleotides whose gene products are part of one of the abovementioned metabolic pathways or whose gene products are involved in the regulation of one of these metabolic pathways so that the nonhuman organism produces the desired fine chemicals or the production of a desired fine chemical is increased. Advantageously, coexpression of the genes used in the method together with the increase in L450 activity advantageously achieves an increase in production of said fine chemicals. Genes which serve the production of said fine chemicals are known to the skilled worker and have been described in the literature in many different ways.

The biosynthesis of said fine chemicals, for example of fatty acids, carotenoids, (poly)saccharides, vitamins, isoprenoids, lipids, fatty esters or polyhydroxyalkanoids and the abovementioned metabolic products, in plants often takes place in special metabolic pathways of particular cell organelles. Consequently, polynucleotides whose gene products play a part in these biosynthetic pathways and which are consequently located in said special organelles include sequences which code for corresponding signal peptides.

Further polynucleotides may be introduced into the host cell, preferably into a plant cell, with the gene constructs, expression cassettes, vectors, etc. described herein. Expression cassettes, gene constructs, vectors, etc. of this kind may be introduced by simultaneous transformation of a plurality of individual expression cassettes, gene constructs, vectors, etc. or, preferably, by combining a plurality of genes, ORFs or expression cassettes in one construct. It is also possible to use a plurality of vectors with in each case a plurality of expression cassettes for transformation and introduce them into the host cell.

Consequently, the gene constructs, expression cassettes, vectors, etc. described above for the method of the invention may mediate according to the invention also the increase or reduction in further genes, in addition to the increase in L450 expression.

It is therefore advantageous to introduce into the host organisms and express therein regulator genes such as genes for inducers, repressors or enzymes which, due to their activity, intervene in the regulation of one or more genes of a biosynthetic pathway. These genes may be of heterologous or homologous origin. Furthermore, it is possible additionally to introduce biosynthesis genes for producing fine chemicals so that the production of said fine chemicals is particularly effective due to the accelerated growth.

For this purpose, the aforementioned nucleic acids may be used for transformation of plants, for example with the aid of Agrobacterium, after they have been cloned into expression cassettes of the invention, for example in combination with nucleic acid molecules encoding other polypeptides. The genes encoding "other polypeptides" or "regulators" may also be introduced into the desired nonhuman organisms in independent transformations. This may take place before or after increasing the L450 activity in said nonhuman organism. Cotransformation with a second expression construct or vector and subsequent selection for the appropriate marker is also possible.

In one embodiment, the invention relates to a gene construct, an expression cassette or a vector which comprises one or more of the nucleic acid molecules or polynucleotides described herein. Cassettes, constructs or vectors are preferably suitable for use in the method of the invention and comprise, for example, the abovementioned L450-encoding polynucleotides, preferably functionally linked to one or more regulatory signals for mediating or increasing gene expression in plants. Said homologs, derivatives or analogs which are functionally linked to one or more regulatory signals or regulatory sequences, advantageously for increasing gene expression, are included.

The regulatory sequences are intended to make possible targeted expression of the genes and synthesis of the encoded proteins. The term "regulatory sequence" is defined above and includes, for example, include the described terminator, processing signals, posttranscriptional, posttranslational modifications, promoter, enhancer, UTR, splice sites, polyadenylation signals and other expression control elements known to the skilled worker and mentioned herein.

Depending on the host organism, for example, this may mean that the gene is expressed and/or overexpressed only after induction or that it is expressed and/or overexpressed immediately. Examples of these regulatory sequences are sequences to which inducers or repressors bind and thus regulate expression of the nucleic acid. In addition to these new regulatory sequences or instead of these sequences, the natural regulation of said sequences may still be present upstream of the actual structural genes and, where appropriate, may have been genetically modified so that natural regulation has been switched off and expression of the genes has been increased. However, the expression cassette (=expression construct=gene construct) may also have a simpler structure, i.e. no additional regulatory signals are inserted upstream of the nucleic acid sequence or derivatives thereof and the natural promoter with its regulation is not deleted. Instead, the natural regulatory sequence is mutated so that regulation no longer takes place and/or gene expression is increased. These modified promoters may also be put in the form of partial sequences (=promoter with parts of the nucleic acid sequences of the invention) alone upstream of the natural gene to increase the activity. Moreover, the gene construct may advantageously also comprise one or more "enhancer" sequences functionally linked to the promoter, which make increased expression of the nucleic acid sequence possible. Additional advantageous sequences such as further regulatory elements or terminators may also be inserted at the 3' end of the DNA sequences. The nucleic acid sequence(s) of the invention coding preferably for an L450 activity may be present in one or more copies in the expression cassette (=gene construct). One or more copies of the genes may be present in the expression cassette. This gene construct or the gene constructs may be expressed together in the host organism. It is possible for the gene construct or gene constructs to be inserted in one or more vectors and be present in free form in the cell or else be inserted in the genome. In the case of plants, integration into the plastid genome or into the cell genome may have taken place. Cloning vectors as are comprehensively described in the prior art and here may be used for transformation.

Preference is given to introducing the nucleic acid sequences used in the method into an expression cassette which enables the nucleic acids to be expressed in a nonhuman organism, preferably in a plant.

The expression cassettes may in principle be used directly for introduction into the plant or else be introduced into a vector.

In another embodiment, the invention also relates to the complementary sequences of said polynucleotide of the invention and to an antisense polynucleic acid.

An antisense nucleic acid molecule comprises, for example, a nucleotide sequence which is complementary to the "sense" nucleic acid molecule encoding a protein, for example complementary to the coding strand of a double-stranded cDNA molecule or complementary to an mRNA sequence. Consequently, an antisense nucleic acid molecule is capable of forming hydrogen bonds with a sense nucleic acid molecule. The antisense nucleic acid molecule may be complementary to any of the coding strands depicted here or only to a part thereof. An antisense oligonucleotide may, for example, be 5, 10, 15, 20, 25, 30, 35, 40, 45 or 50, nucleotides in length. An antisense nucleic acid molecule may be prepared by chemical synthesis and enzymic ligation according to methods known to the skilled worker. An antisense nucleic acid molecule may be chemically synthesized using naturally occurring nucleotides or nucleotides modified in various ways so as to increase the biological stability of the molecules or to enhance the physical stability of the duplex forming between the antisense nucleic acid and the sense nucleic acid; it is possible to use, for example, phosphorothioate derivatives and acridine-substituted nucleotides. Alternatively, it is possible to prepare antisense nucleic acid molecules biologically by using expression vectors into which polynucleotides have been cloned whose orientation is antisense. The antisense nucleic acid molecule may also be an "α-anomeric" nucleic acid molecule. An "α-anomeric" nucleic acid molecule forms specific double-stranded hybrids with complementary RNAs, in which the strands run parallel to one another, in contrast to ordinary β-units. The antisense nucleic acid molecule may comprise 2-0-methylribonucleotides or chimeric RNA-DNA analogs. The antisense nucleic acid molecule may also be a ribozyme. Ribozymes are catalytic RNA molecules having a ribonuclease activity and are capable of cleaving single-stranded nucleic acids to which they have a complementary region, such as mRNA, for example.

In another preferred embodiment, the invention relates to the polypeptide encoded by the polynucleotide of the invention and to a polyclonal or monoclonal antibody, preferably a monoclonal antibody, directed against said polypeptide.

"Antibodies" mean, for example, polyclonal, monoclonal, human or humanized or recombinant antibodies or fragments thereof, single-chain antibodies or else synthetic antibodies. Antibodies of the invention or fragments thereof mean in principle all the immunoglobulin classes such as IgM, IgG, IgD, IgE, IgA or their subclasses such as the IgG subclasses, or mixtures thereof. Preference is given to IgG and its subclasses such as, for example, IgG1, IgG2, IgG2a, IgG2b, IgG3 and IgGM. Particular preference is given to the IgG subtypes IgG1 and IgG2b. Fragments which may be mentioned are any truncated or modified antibody fragments having one or two binding sites complementary to the antigen, such as antibody moieties having a binding site which corresponds to the antibody and is composed of a light chain and a heavy chain, such as Fv, Fab or F(ab')2 fragments or single-strand fragments. Preference is given to truncated double-strand fragments such as Fv, Fab or F(ab')2. These fragments may be obtained, for example, either enzymatically, by cleaving off the Fc moiety of the antibodies using enzymes such as papain or pepsin, by means of chemical oxidation or by means of genetic manipulation of the antibody genes. Genetically manipulated nontruncated fragments may also be advantageously used. The antibodies or fragments may be used alone or in mixtures. Antibodies may also be part of a fusion protein.

In other embodiments, the present invention relates to a method for preparing a vector, which comprises inserting the polynucleotide of the invention or the expression cassette into a vector, and to a vector comprising the polynucleotide of the invention or prepared according to the invention. In a preferred embodiment, the polynucleotide is functionally linked to regulatory sequences which allow expression in a prokaryotic or eukaryotic host.

The term "vector", as used herein, refers to a nucleic acid molecule capable of transporting another nucleic acid to which it is bound. An example of a type of vector is a "plasmid", i.e. a circular double-stranded DNA loop. Another type of vector is a viral vector, it being possible here to ligate additional DNA segments into the viral genome. Particular vectors such as, for example, vectors having an origin of replication may replicate autonomously in a host cell into which they have been introduced. Other preferred vectors are advantageously integrated into the genome of a host cell into which they have been introduced and thereby are replicated together with the host genome. Moreover, particular vectors can control expression of genes to which they are functionally linked. These vectors are referred to herein as "expression vectors". As mentioned above, they may replicate autonomously or be integrated into the host genome. Expression vectors suitable for DNA recombination techniques are usually in the form of plasmids. "Plasmid" and "vector" may be used synonymously in the present description. Consequently, the invention also comprises phages, viruses, for example SV40, CMV or TMV, transposons, IS elements, phasmids, phagemids, cosmids, linear or circular DNA and other expression vectors known to the skilled worker.

The recombinant expression vectors used advantageously in the method comprise the nucleic acids of the invention or the gene construct of the invention in a form suitable for expression of the nucleic acids used in a host cell, meaning that the recombinant expression vectors comprise one or more regulatory sequences which are selected on the basis of the host cells to be used for expression and which is functionally linked to the nucleic acid sequence to be expressed.

In a recombinant expression vector, "functionally linked" means that the nucleotide sequence of interest is bound to the regulatory sequence(s) in such a way that expression of said nucleotide sequence is possible and that they are bound to one another so that both sequences fulfill the predicted function attributed to the sequence (e.g. in an in-vitro transcription/translation system or in a host cell when introducing the vector into said host cell).

The recombinant expression vectors used may be designed especially for expression in prokaryotic and/or eukaryotic cells, preferably in plants. For example, L450 genes may be expressed in bacterial cells, insect cells, e.g. by using baculovirus expression vectors, yeast cells and other fungal cells [e.g. according to Romanos, (1992), Yeast 8:423-488; van den Hondel, C. A. M. J. J., (1991), in J. W. Bennet & L. L. Lasure, eds, pp. 396-428: Academic Press: San Diego; and van den Hondel, C. A. M. J. J., (1991) in: Applied Molecular Genetics of Fungi, Peberdy, J. F, ed., pp. 1-28, Cambridge University Press: Cambridge, in algae, e.g. according to Falciatore, 1999, Marine Biotechnology.1, 3:239-251, in ciliates, e.g. in *Holotrichia, Peritrichia, Spirotrichia, Suctoria, Tetrahymena, Paramecium, Colpidium, Glaucoma, Platyophrya, Potomacus, Desatuaseudocohnilembus, Euplotes, Engelmaniella, Stylonychia*, or in the genus *Stylonychia lemnae*, using vectors according to a transformation method as described in WO 98/01572, and preferably in cells of multicellular plants [see Schmidt, R., (1988) Plant Cell Rep.: 583-586; Plant Molecular Biology and Biotechnology, C Press, Boca Raton, Fla., chapter 6/7, pp. 71-119 (1993); F. F. White, B. Jenes, Transgenic Plants, vol. 1, Engineering and Utilization, eds: Kung and R. Wu, Academic Press (1993), 128-43; Potrykus, Annu. Rev. Plant Physiol. Plant Molec. Biol. 42 (1991), 205-225, and the references in the documents mentioned here. Suitable host cells are also discussed in Goeddel, Gene Expression Technology: Methods in Enzymology 185, Academic Press, San Diego, Calif. (1990). Alternatively, the recombinant expression vector may be transcribed and translated in vitro using, for example, T7-promoter regulatory sequences and T7 polymerase.

A plant expression cassette or a corresponding vector preferably comprises regulatory sequences which are capable of controlling gene expression in plant cells and are functionally linked to the ORF so that each sequence its function.

The expression cassette is preferably linked to a suitable promoter which carries out gene expression at the right time and in a cell- or tissue-specific manner.

Consequently, advantageous regulatory sequences for the novel method are present in the plant promoters CaMV/35S [Franck, Cell 21 (1980) 285-294, U.S. Pat. No. 5,352,605], PRP1 [Ward, Plant. Mol. Biol. 22 (1993)], SSU, PGEL1, OCS [Leisner, (1988) Proc Natl Acad Sci USA 85:2553], lib4, usp, mas [Comai (1990) Plant Mol Biol 15:373], STLS1, ScBV [Schenk(1999) Plant Mol Biol 39:1221, B33, SAD1 and SAD2 (flax promoter, [Jain, (1999) Crop Science, 39:1696) and nos [Shaw (1984) Nucleic Acids Res. 12:7831]. The various ubiquitin promoters of *Arabidopsis* [Callis (1990) J Biol Chem 265:12486; Holtorf (1995) Plant Mol Biol 29:637], *Pinus*, maize [(Ubi1 and Ubi2), U.S. Pat. No. 5,510,474; U.S. Pat. No. 6,020,190 and U.S. Pat. No. 6,054,574] or parsley [Kawalleck (1993) Plant Molecular Biology, 21:673] or phaseolin promoters may be used advantageously. Inducible promoters such as the promoters described in EP-A-0 388 186 (benzylsulfonamide-inducible), Gatz, (1992) Plant J. 2:397 (tetracycline-inducible), EP-A-0 335 528 (abscisic acid-inducible) or WO 93/21334 (ethanol- or cyclohexanol-inducible) are likewise advantageous in this connection. Further suitable plant promoters are the promoter of cytosolic FBPase or the potato ST-LSI promoter (Stockhaus, 1989, EMBO J. 8, 2445), the Glycine max phosphoribosyl-pyrophosphate amidotransferase promoter (GenBank accession No. U87999) or the node-specific promoter described in EP-A-0 249 676. Promoters which make expression possible in specific tissues or show a preferential expression in certain tissues may also be suitable. Also advantageous are seed-specific promoters such as the USP promoter but also other promoters such as the LeB4, DC3, SAD1, phaseolin or napin promoter. Leaf-specific promoters as described in DE-A 19644478 or light-regulated promoters such as, for example, the petE promoter are also available for expression of genes in plants. Further advantageous promoters are seed-specific promoters which may be used for monocotyledonous or dicotyledonous plants and are described in U.S. Pat. No. 5,608,152 (oil seed rape napin promoter), WO 98/45461 (*Arabidopsis* oleosin promoter), U.S. Pat. No. 5,504,200 (*Phaseolus vulgaris* phaseolin promoter), WO 91/13980 (Brassica Bce4 promoter) and von Baeumlein, 1992, Plant J., 2:233 (Legume LeB4 promoter), these promoters being suitable for dicotyledons. Examples of promoters suitable for monocotyledons are the following: barley lpt-2- or lpt-1 promoter (WO 95/15389 and WO 95/23230), barley hordein promoter, the corn ubiquitin promoter and other suitable promoters described in WO 99/16890.

In order to express heterologous sequences strongly in as many tissues as possible, in particular also in leaves, preference is given to using, in addition to various of the abovementioned and promoters, plant promoters of actin or ubiquitin genes, such as, for example, the rice actin1 promoter. Another example of constitutive plant promoters are the sugar beet V-ATPase promoters (WO 01/14572).

It is possible in principle to use all natural promoters with their regulatory sequences, such as those mentioned above, for the novel method. It is likewise possible and advantageous to use synthetic promoters additionally or alone, particularly if they mediate constitutive expression. Examples of synthetic constitutive promoters are the Super promoter (WO 95/14098) and promoters derived from G boxes (WO 94/12015).

Plant genes can also be expressed via a chemically inducible promoter. (see a review in Gatz 1997, Annu. Rev. Plant Physiol. Plant Mol. Biol., 48:89-108). Chemically inducible promoters are particularly suitable when it is desired to express genes in a time-specific manner. Examples of such promoters are a salicylic acid-inducible promoter (WO 95/19443), a tetracycline-inducible promoter (Gatz et al. (1992) Plant J. 2, 397-404), an ethanol-inducible promoter and EP-A 388186, EP-A 335528, WO 97/06268. Expression specifically in gymnosperms or angiosperms are also possible in principle.

Promoters responding to biotic or abiotic stress conditions are also suitable promoters, for example in plants the pathogen-induced PRP1 gene promoter (Ward, Plant. Mol. Biol. 22 (1993) 361), the tomato heat-inducible hsp80 promoter (U.S. Pat. No. 5,187,267), the potato cold-inducible alpha-amylase promoter (WO 96/12814) or the wound-inducible pinII promoter (EP-A-0 375 091).

Preferred polyadenylation signals are sufficiently known to the skilled worker, for example for plants those derived from Agrobacterium tumefaciens t-DNA, such as gene 3, known as octopine synthase (ocs gene) of the Ti plasmid pTiACH5 (Gielen, EMBO J. 3 (1984) 835), the nos gene or functional equivalents thereof. Other known terminators which are functionally active in plants are also suitable.

Further regulatory sequences which are expedient where appropriate also include sequences which control transport and/or location of the expression products (targeting). In this connection, mention should be made particularly of the signal peptide- or transit peptide-encoding sequences known per se. For example, it is possible with the aid of plastid transit peptide-encoding sequences to guide the expression product into the plastids of a plant cell. Consequently, preference is given to using for functional linkage in plant gene expression cassettes in particular targeting sequences which are required for guiding the gene product to its appropriate cell compartment (see a review in Kermode, Crit. Rev. Plant Sci. 15, 4 (1996) 285 and references therein), for example into the vacuole, the nucleus, any kind of plastids such as amyloplasts, chloroplasts, chromoplasts, the extracellular space, the mitochondria, the endoplasmic reticulum, oil bodies, peroxisomes and other compartments of plant cells. Thus, in particular peroxisome-targeting signals have been described, for example in Olsen L J, Plant Mol Biol 1998, 38:163-189).

According to the invention, the gene construct, the vector, the expression cassette, etc. are advantageously constructed in such a way that a promoter is followed by a suitable cleavage site for insertion of the nucleic acid to be expressed, for example in a polylinker, and a terminator is then located, where appropriate, downstream of the polylinker or the insert. This sequence may be repeated several times, for example three, four or five times, so that multiple genes are combined in one construct and can be introduced in this way into the transgenic plant for expression. Advantageously, each nucleic acid sequence has its own promoter and, where appropriate, its own terminator. In the case of microorganisms capable of processing a polycistronic RNA, it is also possible to insert a plurality of nucleic acid sequences downstream of a promoter and, where appropriate, upstream of a terminator. It is advantageously possible to use in the expression cassette different promoters. A different terminator sequence may be used advantageously for each gene.

The plant expression cassette preferably contains further functionally linked sequences such as translation enhancers, for example the overdrive sequence comprising the 5'-untranslated leader sequence of tobacco mosaic virus, which increases the protein/RNA ratio (Gallie, 1987, Nucl. Acids Research 15:8693).

The vectors, cassettes, nucleic acid molecules, etc. to be introduced can be introduced into prokaryotic or eukaryotic cells via conventional transformation or transfection techniques.

The terms "transformation" and "transfection", conjugation and transduction, as used herein, are intended to include a multiplicity of methods known in the prior art for introducing foreign nucleic acid (e.g. DNA) into a host cell, including calcium phosphate or calcium chloride coprecipitation, DEAE-dextran-mediated transfection, lipofection, natural competence, chemically mediated transfer, electroporation or particle bombardment. Methods suitable for transforming or transfecting host cells, including plant cells, can be found in Sambrook et al. (Molecular Cloning: A Laboratory Manual., 2nd edition, Cold Spring Harbor Laboratory, Cold Spring Harbor Laboratory Press, Cold Spring Harbor, N.Y., 1989) and other laboratory manuals such as Methods in Molecular Biology, 1995, vol. 44, *Agrobacterium* protocols, eds: Gartland and Davey, Humana Press, Totowa, N.J.

Thus it is possible for the nucleic acids, gene constructs, expression cassettes, vectors, etc. used in the method to be integrated either in the plastid genome or preferably in the genome of the host cell, after introduction into a plant cell or plant. Integration into the genome may be random or may be carried out via recombination in such a way that the introduced copy replaces the native gene, thereby modulating production of the desired compound by the cell, or by using a gene in trans so that said gene is functionally linked to a functional expression unit which comprises at least one sequence guaranteeing expression of a gene and at least one sequence guaranteeing polyadenylation of a functionally transcribed gene. Where appropriate, the nucleic acids are transferred into the plants via multiexpression cassettes or constructs for multiparallel expression of genes. In another embodiment, the nucleic acid sequence is introduced into the plant without further, different nucleic acid sequences.

As described above, the transfer of foreign genes into the genome of a plant is referred to as transformation. In this case, the methods described for transformation and regeneration of plants from plant tissues or plant cells are utilized for transient or stable transformation. Suitable methods are protoplast transformation by polyethylene glycol-induced DNA uptake, the biolistic method using the gene gun—the "particle bombardment" method, electroporation, incubation of dry embryos in DNA-containing solution, microinjection and *Agrobacterium*-mediated gene transfer. Said methods are described, for example, in B. Jenes, Techniques for Gene Transfer, in: Transgenic Plants, Vol. 1, Engineering and Utilization, edited by S. D. Kung and R. Wu, Academic Press (1993) 128-143 and in Potrykus Annu. Rev. Plant Physiol. Plant Molec. Biol. 42 (1991) 205-225).

The construct to be expressed is preferably cloned into a vector which is suitable for transforming *Agrobacterium tumefaciens*, for example as described herein, for example pBin19 (Bevan, Nucl. Acids Res. 12 (1984) 8711). Agrobacteria transformed with such a vector may then be used in the known manner for transforming plants, in particular crop plants, such as, for example, tobacco plants, by, for example, bathing wounded leaves or pieces of leaf in a solution of agrobacteria and then cultivating said leaves or pieces of leaf in suitable media. The transformation of plants with *Agrobacterium tumefaciens* is described, for example, by Hbfgen, Nucl. Acid Res. (1988) 16, 9877 or is disclosed, inter alia, in F. F. White, Vectors for Gene Transfer in Higher Plants; in Transgenic Plants, Vol. 1, Engineering and Utilization, edited by S. D. Kung and R. Wu, Academic Press, 1993, pp. 15-38.

The nucleic acids, gene constructs, expression cassettes, vectors, etc. used in the method are checked, where appropriate, and then used for transforming the plants. For this purpose, it may be required first to obtain the constructs, plasmids, vectors, etc. from an intermediate host. For example, the constructs can be isolated as plasmids from bacterial hosts, following a conventional plasmid isolation. Numerous methods for transforming plants are known. Since stable integration of heterologous DNA into the genome of plants is advantageous according to the invention, T-DNA-mediated transformation, in particular, has proved to be expedient and may be carried out in a manner known per se. For example, the plasmid construct generated according to what has been said above may be transformed into competent agrobacteria by means of electroporation or heat shock. In principle, the distinction to be made here is between the formation of cointegrated vectors on the one hand and the transformation with binary vectors. In the first alternative, the vector constructs comprising the codogenic gene section do not contain any T-DNA sequences, rather the cointegrated vectors are formed in the agrobacteria by homologous recombination of the vector construct with T-DNA. T-DNA is present in agrobacteria in the form of Ti or Ri plasmids in which the oncogenes have conveniently been replaced by exogenous DNA. When using binary vectors, these may be transferred by means of bacterial conjugation or direct transfer to agrobacteria. Said agrobacteria conveniently already comprise the vector carrying the vir genes (frequently referred to as helper Ti(Ri) plasmid). Expediently, one or more markers may be used, on the basis of which the selection of transformed agrobacteria and transformed plant cells is possible. A multiplicity of markers is known to the skilled worker.

It is known about stable or transient integration of nucleic acids that, depending on the expression vector used and transfection technique used, only a small proportion of the cells takes up the foreign DNA and, if desired, integrates it in their genome. For identification and selection of these integrants, usually a gene which encodes a selectable marker (e.g. antibiotic resistance) is introduced together with the gene of interest into the host cells.

Marker genes are advantageously used for selection for successful introduction of the nucleic acids of the invention into a host organism, in particular into a plant. These marker genes make it possible to identify successful introduction of the nucleic acids of the invention by a number of different principles, for example by visual recognition with the aid of fluorescence, luminescence or in the wavelength range of light which is visible to humans, via a herbicide or antibiotic resistance, via "nutritional" (auxotrophic) markers or anti-nutritional markers, by enzyme assays or via phytohormones. Examples of such markers which may be mentioned here are GFP (=Green fluorescent Protein); the luciferin/luciferase system; β-galactosidase with its colored substrates, e.g. X-Gal; herbicide resistances to, for example, imidazolinone, glyphosate, phosphothricin or sulfonylurea; antibiotic resistances to, for example, bleomycin, hygromycin, streptomycin, kanamycin, tetracycline, chloramphenicol, ampicillin, gentamycin, geneticin (G418), spectinomycin or blasticidin, to mention only a few; nutritional markers such as utilization of mannose or xylose or antinutritional markers such as 2-deoxyglucose resistance. This list represents a small section of possible markers. Markers of this kind are well known to the skilled worker.

Different markers are preferred, depending on organism and selection method. Preferred selectable markers include in plants those which confer resistance to a herbicide such as glyphosate or glufosinate. Further suitable markers are, for example, markers which encode genes which are involved in biosynthetic pathways of, for example, sugars or amino acids, such as β-galactosidase, ura3 or ilv2. Markers encoding genes such as luciferase, gfp or other fluorescence genes are likewise suitable. These markers can be used in mutants in which said genes are not functional because, for example, they have been deleted by means of conventional methods. Furthermore, markers may be introduced into a host cell on the same vector as that coding for L450 or another of the inventive nucleic acid molecules described herein, or they may be introduced on a separate vector.

Since the marker genes, especially the antibiotic and herbicide resistance gene, are normally no longer required or are unwanted in the transgenic host cell after successful introduction of the nucleic acids, techniques making it possible to delete these marker genes are advantageously used in the method of the invention for introducing the nucleic acids. One such method is "cotransformation". Cotransformation involves using simultaneously two vectors for transformation, one vector harboring the nucleic acids of the invention and the second one harboring the marker gene(s). A large proportion of the transformants acquires or contains both vectors in the case of plants (up to 40% of the transformants and more). It is then possible to remove the marker genes from the transformed plant by crossing. A further method uses marker genes integrated into a transposon for the transformation together with the desired nucleic acids ("Ac/Ds technology). In some cases (approx. 10%), after successful transformation, the transposon jumps out of the genome of the host cell and is lost. In a further number of cases, the transposon jumps into another site. In these cases, it is necessary to outcross the marker gene again. Microbiological techniques enabling or facilitating detection of such events have been developed. A further advantageous method uses "recombination systems" which have the advantage that it is possible to dispense with outcrossing. The best-known system of this kind is the "Cre/lox" system. Cre1 is a recombinase which deletes the sequences located between the loxP sequence. If the marker gene is integrated between the loxP sequence, it is deleted by means of Cre1 recombinase after successful transformation. Further recombinase systems are the HIN/HIX, FLP/FRT and the REP/STB system (Tribble et al., J. Biol. Chem., 275, 2000: 22255-22267; Velmurugan et al., J. Cell Biol., 149, 2000: 553-566). Targeted integration of the nucleic acid sequences of the invention into the plant genome is also possible in principle, but less preferred up until now because of the large amount of work involved. These methods are, of course, also applicable to microorganisms such as yeasts, fungi or bacteria.

Agrobacteria transformed with an expression vector of the invention may likewise be used in a known manner for transforming plants such as test plants such as Arabidopsis or crop plants such as, for example, cereals, corn, oats, rye, barley, wheat, soybean, rice, cotton, sugar beet, canola, sunflower, flax, hemp, potato, tobacco, tomato, carrot, paprika, oilseed rape, tapioca, cassava, arrowroot, tagetes, alfalfa, lettuce and the various tree, nut and grape species, oil-containing crop plants such as soybean, peanut, castor oil plant, sunflower, corn, cotton, flax, oilseed rape, coconut, oil palm, safflower (Carthamus tinctorius) or cocoa bean or the other plants mentioned below, for example by bathing wounded leaves or pieces of leaf in a solution of agrobacteria and then cultivating said leaves or pieces of leaf in suitable media.

The genetically modified plant cells may be regenerated by any methods known to the skilled worker. Appropriate methods can be found in the abovementioned publications by S. D. Kung and R. Wu, Potrykus or Höfgen and Willmitzer.

If desired, the plasmid constructs may be checked again with regard to identity and/or integrity by means of PCR or Southern blot analysis, prior to their transformation into agrobacteria. It is normally desired that the codogenic gene sections with the linked regulatory sequences in the plasmid constructs are flanked on one or both sides by T-DNA. This is particularly useful when bacteria of the species Agrobacterium tumefaciens or Agrobacterium rhizogenes are used for transformation. The transformed agrobacteria may be cultured in a manner known per se and are thus available for convenient transformation of the plants. The plants or parts of plants to be transformed are grown and provided in a conventional manner. The agrobacteria may act on the plants or parts of plants in different ways. Thus it is possible, for example, to use a culture of morphogenic plant cells or tissues. Following T-DNA transfer, the bacteria are usually eliminated by antibiotics and regeneration of plant tissue is induced. For this purpose, particular use is made of suitable plant hormones in order to promote the formation of shoots, after initial callus formation. According to the invention, preference is given to carrying out in planta transformation. For this purpose, it is possible to expose plant seeds, for example, to the agrobacteria or to inoculate plant meristems with agrobacteria. It has proved particularly expedient according to the invention to expose the whole plant or at least the flower primordia to a suspension of transformed agrobacteria. The former is then grown further until seeds of the treated plant are obtained (Clough and Bent, Plant J. (1998) 16, 735). To select transformed plants, the plant material obtained from the transformation is usually subjected to selective conditions so that transformed plants can be distinguished from untransformed plants. For example, the seeds obtained in the manner described above can be sown anew and, after growing, subjected to a suitable spray selection. Another possibility is to grow the seeds, if necessary after sterilization, on agar plates, using a suitable selecting agent, in such a way that only the transformed seeds are able to grow to plants.

The invention furthermore relates to a host cell which has been stably or transiently transformed or transfected with the vector of the invention or with the polynucleotide of the invention. Consequently, the invention relates in one embodiment also to microorganisms whose L450 activity is increased, for example due to (over)expression of the polynucleic acids characterized herein.

In one embodiment, the host cell or microorganism is a bacterial cell or a eukaryotic cell, preferably a unicellular microorganism or a plant cell.

In another embodiment, the invention also relates to an animal cell or plant cell which contains the polynucleotide of the invention or the vector of the invention. In a preferred embodiment, the invention relates in particular to a plant tissue or to a plant having an increased amount of L450 and/or containing the plant cell of the invention. In one embodiment, the invention also relates to a plant compartment, a plant organelle, a plant cell, a plant tissue or a plant having an increased L450 activity or an increased amount of P450.

Host cells which are suitable in principle for taking up the nucleic acid of the invention, the gene product of the invention or the vector of the invention are cells of any prokaryotic or eukaryotic organisms. Organisms or host organisms suitable for the nucleic acid of the invention, the expression cassette or the vector are in principle any organisms for which faster growth and higher yield are desirable, with preference being given, as mentioned, to crop plants.

A further aspect of the invention therefore relates to transgenic organisms transformed with at least one nucleic acid sequence, expression cassette or vector of the invention and to cells, cell cultures, tissues, parts or propagation material derived from such organisms.

The terms "host organism", "host cell", "recombinant (host) organism", "recombinant (host) cell", "transgenic (host) organism" and "transgenic (host) cell" are used interchangeably herein. These terms relate, of course, not only to the particular host organism or to the particular target cell but also to the progeny or potential progeny of said organisms or cells. Since certain modifications may occur in subsequent generations, owing to mutation or environmental effects, these progeny are not necessarily identical to the parental cell but are still included within the scope of the term as used herein.

Examples which should be mentioned here are microorganisms such as fungi, for example the genus *Mortierella*, *Saprolegnia* or *Pythium*, bacteria such as, for example, the genus *Escherichia*, yeasts such as, for example, the genus *Saccharomyces*, cyanobacteria, ciliates, algae or protozoa such as, for example, dinoflagellates such as *Crypthecodinium*.

The increased growth rate of the microorganisms is particularly advantageous in combination with the synthesis of products of value, for example in the method of the invention for preparing fine chemicals. An advantageous embodiment is thus, for example, microorganisms which (naturally) synthesize relatively large amounts of vitamins, sugars, polymers, oils, etc. Examples which may be mentioned here are fungi such as, for example, *Mortierella alpina*, *Pythium insidiosum*, yeasts such as, for example, *Saccharomyces cerevisiae* and the microorganisms of the genus *Saccharomyces*, cyanobacteria, ciliates, algae or protozoa such as, for example, dinoflagellates such as *Crypthecodinium*.

Utilizable host cells are furthermore mentioned in: Goeddel, *Gene Expression Technology: Methods in Enzymology* 185, Academic Press, San Diego, Calif. (1990). Usable expression strains, for example those having relatively low protease activity, are described in: Gottesman, S., *Gene Expression Technology: Methods in Enzymology* 185, Academic Press, San Diego, Calif. (1990) 119-128.

Proteins are usually expressed in prokaryotes by using vectors which contain constitutive or inducible promoters controlling expression of fusion or nonfusion proteins. Typical fusion expression vectors are, inter alia, pGEX (Pharmacia Biotech Inc; Smith, D. B., and Johnson, K. S. (1988) Gene 67:31-40), PMAL (New England Biolabs, Beverly, Mass.) and pRIT5 (Pharmacia, Piscataway, N.J.). Examples of suitable inducible nonfusion *E. coli* expression vectors are inter alia, pTrc (Amann et al. (1988) Gene 69:301-315) and pET 11d [Studier, Gene Expression Technology: Methods in Enzymology 185, Academic Press, San Diego, Calif. (1990) 60].

Other vectors suitable in prokaryotic organisms are known to the skilled worker and are, for example, in *E. coli* pLG338, pACYC184, the pBR series such as pBR322, the pUC series such as pUC18 or pUC19, the M113mp series, PKC30, pRep4, pHS1, pHS2, pPLc236, pMBL24, pLG200, pUR290, pIN-III[113]-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

However, preference is given to eukaryotic expression systems. In a further embodiment, the expression vector is a yeast expression vector. Examples of vectors for expression in the yeast *S. cerevisiae* include pYeDesaturasecl (Baldari (1987) Embo J. 6:229), pMFa (Kurjan (1982) Cell 30:933), pJRY88 (Schultz (1987) Gene 54:113), 2∞M, pAG-1, YEp6, YEp13, pEMBLYe23 and pYES2 (Invitrogen Corporation, San Diego, Calif.). Vectors and methods for constructing vectors suitable for use in other fungi such as filamentous fungi include those described in detail in: van den Hondel, C. A. M. J. J. (1991) in: Applied Molecular Genetics of fungi, J. F. Peberdy, ed., pp. 1-28, Cambridge University Press: Cambridge; or in: J. W. Bennet, ed., p. 396: Academic Press: San Diego]. Examples of vectors in fungi are pALS1, pIL2 or pBB116 or in plants pLGV23, pGHlac', pBIN19, pAK2004 or pDH51.

Alternatively, a product of value, for example the fine chemicals mentioned, may be expressed in insect cells using baculovirus expression vectors. Baculovirus vectors available for expression of proteins in cultured insect cells (e.g. Sf9 cells) include the pAc series (Smith (1983) Mol. Cell Biol. 3:2156) and the pVL series (Lucklow (1989) Virology 170:31).

The abovementioned vectors offer only a small overview over possible suitable vectors. Further plasmids are known to the skilled worker and are described, for example, in: Cloning Vectors (eds Pouwels, P. H., et al., Elsevier, Amsterdam-New York-Oxford, 1985, ISBN 0 444 904018). For further expression systems suitable for prokaryotic and eukaryotic cells, see in chapters 16 and 17 of Sambrook, Molecular Cloning: A Laboratory Manual, 2nd edition, Cold Spring Harbor Laboratory Press, Cold Spring Harbor, N.Y., 1989 or Current Protocols in Molecular Biology, John Wiley & Sons, N.Y. (1989).

The microorganism has preferably been transiently or stably transformed with a polynucleotide which comprises a nucleic acid molecule described above which is suitable for the method of the invention.

In another advantageous embodiment of the invention, it is possible to express, for example, a product of value or the fine chemicals also in unicellular plant cells (such as algae), see Falciatore, 1999, Marine Biotechnology 1 (3):239 and references therein, and in plant cells of higher plants (e.g. spermatophytes such as crops) so that said plants have higher L450 activity and, consequently, a higher growth rate. Examples of plant expression vectors include those described in detail above or those from Becker, (1992), Plant Mol. Biol. 20:1195 and Bevan, (1984), Nucl. Acids Res. 12:8711; Vectors for Gene Transfer in Higher Plants; in: Transgenic Plants, vol. 1, Engineering and Utilization, eds: Kung and R. Wu, Academic Press, 1993, p. 15. A relatively recent review of *Agrobacterium* binary vectors can be found in Hellens, 2000, Trends in Plant Science, Vol. 5, 446.

Host organisms which are advantageously used are bacteria, fungi, yeasts or plants, preferably crop plants or parts thereof. Preference is given to using fungi, yeasts or plants, particularly preferably plants, and special mention may be made of agricultural useful plants such as cereals and grasses, e.g. *Triticum* spp., *Zea mais*, *Hordeum vulgare*, oats, *Secale cereale*, *Oryza sativa*, *Pennisetum glaucum*, *Sorghum* bicolor, Triticale, Agrostis spp., Cenchrus ciliaris, Dactylis glomerata, Festuca arundinacea, Lolium spp., Medicago spp., Alfalfa and Saccharum spp., legumes and oil seed crops, e.g. Brassica juncea, Brassica napus, Brassica nigra, Sinapes alba, Glycine max, Arachis hypogaea, canola, castor oil plant, coconut, oil palm, cocoa bean, date palm, Gossypium hirsutum, Cicer arietinum, Helianthus annuus, Lens culinaris, Linum usitatissimum, Sinapis alba, Trifolium repens, Carthamus tinctorius and Vicia narbonensis, hemp, vegetables, lettuce and fruits, e.g. bananas, grapes, Lycopersicon esculentum, asparagus, cabbage, watermelons, kiwis, Solanum tuberosum, Solanum lypersicum, carrots, paprika, tapioca, manioc, Beta vulgaris, cassava and chicory, arrowroot, nut and grape species, trees, e.g. Coffea species, Citrus spp., Eucalyptus spp., Picea spp., Pinus spp. and Populus spp., tobacco, medicinal plants and trees and flowers, e.g. Tagetes.

If plants are selected as danor organism, said plant may in principle have any phylogenetic relationship to the receptor plant. Thus danor plant and receptor plant may belong to the same family, genus, species, variety or line, which results in increasing homology between the nucleic acids to be integrated and corresponding parts of the genome of the receptor plant.

According to a particular embodiment of the present invention, the donor organism is a higher plant, preferably of the genus Arabidapsis thaliana particularly preferred, are crop plants as are mentioned herein.

Preferred receptor plants are particularly plants which can be appropriately transformed. These include mono- and dicotyledonous plants. In particular mention should be made of the agricultural useful plants such as cereals and grasses, e.g. Triticum spp., Zea mais, Hordeum vulgare, oats, Secale cereale, Oryza sativa, Pennisetum glaucum, Sorghum bicolor, Triticale, Agrostis spp., Cenchrus ciliaris, Dactylis glomerata, Festuca arundinacea, Lolium spp., Medicago spp. and Saccharum spp., legumes and oil seed crops, e.g. Brassica juncea, Brassica napus, Glycine max, Arachis hypogaea, Gossypium hirsutum, Cicer arietinum, Helianthus annuus, Lens culinaris, Linum usitatissimum, Sinapis alba, Trifolium repens und Vicia narbonensis, vegetables and fruits, e.g. bananas, grapes, Lycopersicon esculentum, asparagus, cabbage, watermelons, kiwis, Solanum tuberosum, Beta vulgaris, cassava and chicory, trees, e.g. Coffea species, Citrus spp., Eucalyptus spp., Picea spp., Pinus spp. and Populus spp., medicinal plants and trees, and flowers. According to a particular embodiment, the present invention relates to transgenic plants of the genus Arabidopsis, e.g. Arabidopsis thaliana and of the genus Oryza.

After transformation, plants are first regenerated as described above and then cultivated and grown as usual.

The plant compartments, plant organelles, plant cells, plant tissues or plants of the invention is preferably produced according to the method of the invention or contains the gene construct described herein or the described vector.

In one embodiment, the invention relates to the yield or the propagation material of a plant of the invention or of a useful animal of the invention or to the biomass of a microorganism, i.e. the biomaterial of a nonhuman organism prepared according to the method of the invention.

The present invention also relates to transgenic plant material derivable from an inventive population of transgenic plants. Said material includes plant cells and certain tissues, organs and parts of plants in any phenotypic forms thereof, such as seeds, leaves, anthers, fibers, roots, root hairs, stalks, embryos, kalli, cotyledons, petioles, harvested material, plant tissue, reproductive tissue and cell cultures, which has been derived from the actual transgenic plant and/or may be used for producing the transgenic plant.

Preference is given to any plant parts or plant organs such as leaf, stem, shoot, flower, root, tubers, fruits, bark, wood, seeds, etc. or the entire plant. Seeds include in this connection all seed parts such as seed covers, epidermal and seed cells, endosperm or embryonic tissue. Particular preference is given to harvested products, in particular fruits, seeds, tubers, fruits, roots, bark or leaves or parts thereof.

In the method of the invention, transgenic plants also mean plant cells, plant tissues or plant organs to be regarded as agricultural product.

The biomaterial produced in the method, in particular of plants which have been modified by the method of the invention, may be marketed directly.

The invention likewise relates in one embodiment to propagation material of a plant prepared according to the method of the invention. Propagation material means any material which may serve for seeding or growing plants, even if it may have, for example, another function, e.g. as food.

"Growth" also means, for example, culturing the transgenic plant cells, plant tissues or plant organs on a nutrient medium or the whole plant on or in a substrate, for example in hydroculture or on a field.

Use of the polynucleotide used in the method of the invention and characterized herein, of the gene construct, of the vector, of the plant cell or of the plant or of the plant tissue or of the plant material for preparing a plant with increased yield.

Suitable host organisms are in principle, in addition to the aforementioned transgenic organisms, also transgenic nonhuman useful animals, for example pigs, cattle, sheep, goats, chickens, geese, ducks, turkeys, horses, donkeys, etc., which have preferably been transiently or stably transformed with a polynucleotide which comprises a nucleic acid molecule encoding an L450 polypeptide or a nucleic acid molecule characterized herein as suitable for the method of the invention.

In another preferred embodiment, the invention relates in particular to a useful animal or animal organ having an increased amount of L450 and/or containing the useful animal cell of the invention.

The useful animals comprise an increased amount of L450, in particular an increase in expression or activity, and consequently an increased growth rate, i.e. faster growth and increased weight or increased production of agricultural products as listed above.

Preference is given to the useful animals being cattle, pigs, sheep or goats.

In one embodiment, the invention relates to the use of an L450 polypeptide or of the polynucleotide or polypeptide of the invention for increasing the yield and/or increasing growth of a nonhuman organism compared to a starting organism.

A further embodiment of the invention is the use of the products obtained by means of said methods, for example biomaterial, in particular plant materials as mentioned, in food products, animal feed products, nutrients, cosmetics or pharmaceuticals. It is also possible to isolate commercially utilizable substances such as fine chemicals from the plants or parts of plants obtained by means of the method of the invention.

The examples and figures below which should not be regarded as limiting further illustrate the present invention.

In a further embodiment, the present invention relates to a method for the generation of a microorganism, comprising the introduction, into the microorganism or parts thereof, of the expression construct of the invention, or the vector of the invention or the polynucleotide of the invention.

In another embodiment, the present invention relates also to a transgenic microorganism comprising the polynucleotide of the invention, the expression construct of the invention or the vector as of the invention. Appropriate microorganisms have been described herein before, preferred are in particular aforementioned strains suitable for the production of fine chemicals.

The fine chemicals obtained in the method are suitable as starting material for the synthesis of further products of value. For example, they can be used in combination with each other or alone for the production of pharmaceuticals, foodstuffs, animal feeds or cosmetics. Accordingly, the present invention relates a method for the production of a pharmaceuticals, food stuff, animal feeds, nutrients or cosmetics comprising the steps of the method according to the invention, including the isolation of the fine chemicals, in particular amino acid composition produced e.g. methionine produced if desired and formulating the product with a pharmaceutical acceptable carrier or formulating the product in a form acceptable for an application in agriculture. A further embodiment according to the invention is the use of the fine chemicals produced in the method or of the transgenic organisms in animal feeds, foodstuffs, medicines, food supplements, cosmetics or pharmaceuticals.

It is advantageous to use in the method of the invention transgenic microorganisms such as fungi such as the genus Claviceps or Aspergillus or Gram-positive bacteria such as the genera *Bacillus, Corynebacterium, Micrococcus, Brevibacterium, Rhodococcus, Nocardia, Caseobacter* or *Arthrobacter* or Gram-negative bacteria such as the genera *Escherichia, Flavobacterium* or *Salmonella* or yeasts such as the genera *Rhodotorula, Hansenula* or *Candida*. Particularly advantageous organisms are selected from the group of genera *Corynebacterium, Brevibacterium, Escherichia, Bacillus, Rhodotorula, Hansenula, Candida, Claviceps* or *Flavobacterium*. It is very particularly advantageous to use in the method of the invention microorganisms selected from the group of genera and species consisting of *Hansenula anomala, Candida utilis, Claviceps purpurea, Bacillus circulans, Bacillus subtilis, Bacillus sp., Brevibacterium albidum, Brevibacterium album, Brevibacterium cerinum, Brevibacterium flavum, Brevibacterium glutamigenes, Brevibacterium iodinum, Brevibacterium ketoglutamicum, Brevibacterium lactofermentum, Brevibacterium linens, Brevibacterium roseum, Brevibacterium saccharolyticum, Brevibacterium sp., Corynebacterium acetoacidophilum, Corynebacterium acetoglutamicum, Corynebacterium ammoniagenes, Corynebacterium glutamicum* (=*Micrococcus glutamicum*), *Corynebacterium melassecola, Corynebacterium sp.* or *Escherichia coli*, specifically *Escherichia coli* K12 and its described strains.

The method of the invention is, when the host organisms are microorganisms, advantageously carried out at a temperature between 0° C. and 95° C., preferably between 10° C. and 85° C., particularly preferably between 15° C. and 75° C., very particularly preferably between 15° C. and 45° C. The pH is advantageously kept at between pH 4 and 12, preferably between pH 6 and 9, particularly preferably between pH 7 and 8, during this. The method of the invention can be operated batchwise, semibatchwise or continuously. A summary of known cultivation methods is to be found in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)). The culture medium to be used must meet the requirements of the respective strains in a suitable manner. Descriptions of culture media for various microorganisms are present in the handbook "Manual of Methods for General Bacteriology" of the American Society for Bacteriology (Washington D.C., USA, 1981). These media, which can be employed according to the invention include, as described above, usually one or more carbon sources, nitrogen sources, inorganic salts, vitamins and/or trace elements. Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses, or other byproducts of sugar refining. It may also be advantageous to add mixtures of various carbon sources. Other possible carbon sources are oils and fats such as, for example, soybean oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol and/or organic acids such as, for example, acetic acid and/or lactic acid. Nitrogen sources are usually organic or inorganic nitrogen compounds or materials, which contain these compounds. Examples of nitrogen sources include ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as corn steep liquor, soybean meal, soybean protein, yeast extract, meat extract and others. The nitrogen sources may be used singly or as a mixture. Inorganic salt compounds, which may be present in the media include the chloride, phosphorus or sulfate salts of calcium, magnesium, sodium, cobalt, molybdenum, potassium, manganese, zinc, copper and iron. For preparing sulfur-containing fine chemicals, in particular amino acids, e.g. methionine, it is possible to use as sulfur source inorganic sulfur-containing compounds such as, for example, sulfates, sulfites, dithionites, tetrathionates, thiosulfates, sulfides or else organic sulfur compounds such as mercaptans and thiols. It is possible to use as phosphorus source phosphoric acid, potassium dihydrogenphosphate or dipotassium hydrogenphosphate or the corresponding sodium-containing salts. Chelating agents can be added to the medium in order to keep the metal ions in solution. Particularly suitable chelating agents include dihydroxyphenols such as catechol or protocatechuate, or organic acids such as citric acid. The fermentation media employed according to the invention for cultivating microorganisms normally also contain other growth factors such as vitamins or growth promoters, which include, for example, biotin, riboflavin, thiamine, folic acid, nicotinic acid, pantothenate and pyridoxine. Growth factors and salts are often derived from complex media components such as yeast extract, molasses, corn steep liquor and the like.

Suitable precursors can moreover be added to the culture medium. The exact composition of the media compounds depends greatly on the particular experiment and is chosen individually for each specific case. Information about media optimization is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers such as Standard 1 (Merck) or BHI (Brain heart infusion, DIFCO) and the like. All media components are sterilized either by heat (1.5 bar and 121° C. for 20 min) or by sterilizing filtration. The components can be sterilized either together or, if necessary, separately. All media components can be present at the start of the cultivation or optionally be added continuously or batchwise. The temperature of the culture is normally between 15° C. and 45° C., preferably at 25° C. to 40° C., and can be kept constant or changed during the experiment. The pH of the medium should be in the range from 5 to 8.5, preferably around 7. The pH for the cultivation can be controlled during the cultivation by adding basic compounds such as sodium hydroxide, potassium hydroxide, ammonia or aqueous ammonia or acidic compounds such as phosphoric acid or sulfuric acid. Foaming can be controlled by employing antifoams such as, for example, fatty acid polyglycol esters. The stability of plasmids can be maintained by adding to the medium suitable substances having a selective effect, for example antibiotics. Aerobic conditions are maintained by introducing oxygen or oxygen-containing gas mixtures such as, for example, ambient air into the culture. The temperature of the culture is normally from 20° C. to 45° C. and preferably from 25° C. to 40° C. The culture is continued until formation of the desired product is at a maximum. This aim is normally achieved within 10 hours to 160 hours. The fermentation broths obtained in this way, containing in particular fine chemicals, normally have a dry matter content of from 7.5 to 25% by weight. Sugar-limited fermentation is additionally advantageous, at least at the end, but especially over at least 30% of the fermentation time. This means that the concentration of utilizable sugar in the fermentation medium is kept at, or reduced to, $\geqq 0$ to 3 g/l during this time. The fermentation broth is then processed further. Depending on requirements, the biomass can be removed entirely or partly by separation methods, such as, for example, centrifugation, filtration, decantation or a combination of these methods, from the fermentation broth or left completely in it. The fermentation broth can then be thickened or concentrated by known methods, such as, for example, with the aid of a rotary evaporator, thin-film evaporator, falling film evaporator, by reverse osmosis or by nanofiltration. This concentrated fermentation broth can then be worked up by freeze-drying, spray drying, spray granulation or by other methods.

However, it is also possible to purify the fine chemicals produced further. For this purpose, the product-containing composition is subjected to a chromatography on a suitable resin, in which case the desired product or the impurities are retained wholly or partly on the chromatography resin. These chromatography steps can be repeated if necessary, using the same or different chromatography resins. The skilled worker is familiar with the choice of suitable chromatography resins and their most effective use. The purified product can be concentrated by filtration or ultrafiltration and stored at a temperature at which the stability of the product is a maximum.

The identity and purity of the isolated compound(s) can be determined by prior art techniques. These include high performance liquid chromatography (HPLC), spectroscopic methods, mass spectrometry (MS), staining methods, thin-layer chromatography, NIRS, enzyme assay or microbiological assays. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ulmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

In yet another aspect, the invention also relates to harvestable parts and to propagation material of the transgenic plants according to the invention which either contain transgenic plant cells expressing a nucleic acid molecule according to the invention or which contains cells which show an increased cellular activity of the polypeptide of the invention, e.g. an increased expression level or higher activity of the described protein.

Harvestable parts can be in principle any useful parts of a plant, for example, flowers, pollen, seedlings, tubers, leaves, stems, fruit, seeds, roots etc. Propagation material includes, for example, seeds, fruits, cuttings, seedlings, tubers, rootstocks etc.

The invention furthermore relates to the use of the transgenic organisms according to the invention and of the cells, cell cultures, parts—such as, for example, roots, leaves and the like as mentioned above in the case of transgenic plant organisms—derived from them, and to transgenic propagation material such as seeds or fruits and the like as mentioned above, for the production of foodstuffs or feeding stuffs, pharmaceuticals or fine chemicals.

Accordingly in another embodiment, the present invention relates to the use of the polynucleotide, the organism, e.g. the microorganism, the plant, plant cell or plant tissue, the vector, or the polypeptide of the present invention for making fatty acids, carotenoids, isoprenoids, vitamins, lipids, wax esters, (poly)saccharides and/or polyhydroxyalkanoates, and/or its metabolism products, in particular, steroid hormones, cholesterol, prostaglandin, triacylglycerols, bile acids and/or ketone bodies producing cells, tissues and/or plants. There are a number of mechanisms by which the yield, production, and/or efficiency of production of fatty acids, carotenoids, isoprenoids, vitamins, wax esters, lipids, (poly)saccharides and/or polyhydroxyalkanoates, and/or its metabolism products, in particular, steroid hormones, cholesterol, triacylglycerols, prostaglandin, bile acids and/or ketone bodies or further of above defined fine chemicals incorporating such an altered protein can be affected. In the case of plants, by e.g. increasing the expression of acetyl-CoA which is the basis for many products, e.g., fatty acids, carotenoids, isoprenoids, vitamins, lipids, (poly)saccharides, wax esters, and/or polyhydroxyalkanoates, and/or its metabolism products, in particular, prostaglandin, steroid hormones, cholesterol, triacylglycerols, bile acids and/or ketone bodies in a cell, it may be possible to increase the amount of the produced said compounds thus permitting greater ease of harvesting and purification or in case of plants more efficient partitioning. Further, one or more of said metabolism products, increased amounts of the cofactors, precursor molecules, and intermediate compounds for the appropriate biosynthetic pathways maybe required. Therefore, by increasing the number and/or activity of transporter proteins involved in the import of nutrients, such as carbon sources (i.e., sugars), nitrogen sources (i.e., amino acids, ammonium salts), phosphate, and sulfur, it may be possible to improve the production of acetyl CoA and its metabolism products as mentioned above, due to the removal of any nutrient supply limitations on the biosynthetic process. In particular, it may be possible to increase the yield, production, and/or efficiency of production of said compounds, e.g. fatty acids, carotenoids, isoprenoids, vitamins, was esters, lipids, (poly)saccharides, and/or polyhydroxyalkanoates, and/or its metabolism products, in particular, steroid hormones, cholesterol, prostaglandin, triacylglycerols, bile acids and/or ketone bodies molecules etc. in plants. Furthermore preferred is a method for the recombinant production of pharmaceuticals or fine chemicals in host organisms, wherein a host organism is transformed with one of the above-described expression constructs comprising one or more structural genes which encode the desired fine chemical or catalyze the biosynthesis of the desired fine chemical, the transformed host organism is cultured, and the desired fine chemical is isolated from the culture medium. This method can be applied widely to fine chemicals such as enzymes, vitamins, amino acids, sugars, fatty acids, and natural and synthetic flavorings, aroma substances and colorants or compositions comprising these. Especially preferred is the additional production of amino acids, tocopherols and tocotrienols and carotenoids or compositions comprising said compounds. The transformed host organisms are cultured and the products are recovered from the host organisms or the culture medium by methods known to the skilled worker or the organism itself servers as food or feed supplement. The production of pharmaceuticals such as, for example, antibodies or vaccines, is described by Hood E E, Jilka J M. Curr Opin Biotechnol. 1999 August; 10(4):382-6; Ma J K, Vine N D. Curr Top Microbiol Immunol. 1999; 236:275-92.

In one embodiment, the present invention relates to a method for the identification of a gene product conferring an increase in growth or yield in an organism, comprising the following steps:
 a) contacting e.g. hybridising, the nucleic acid molecules of a sample, e.g. cells, tissues, plants or microorganisms or a nucleic acid library, which can contain a candidate gene encoding a gene product conferring an in yield or growth as described above after expression, with the polynucleotide of the present invention;
 b) identifying the nucleic acid molecules, which hybridize under relaxed stringent conditions with the polynucleotide of the present invention and, optionally, isolating the full length cDNA clone or complete genomic clone;
 c) introducing the candidate nucleic acid molecules in host cells, preferably in a plant cell or a microorganism;
 d) expressing the identified nucleic acid molecules in the host cells;
 e) deriving, a transgenic organism and assaying the growth rate or yield in the host cells; and
 f) identifying the nucleic acid molecule and its gene product which expression confers an increase after expression compared to the wild type.

Relaxed hybridisation conditions are: After standard hybridisation procedures washing steps can be performed at low to medium stringency conditions usually with washing conditions of 40°-55° C. and salt conditions between 2×SSC and 0.2×SSC with 0.1% SDS in comparison to stringent washing conditions as e.g. 60°-68° C. with 0.1×SSC and 0.1% SDS. Further examples can be found in the references listed above for the stringend hybridization conditions. Usually washing steps are repeated with increasing stringency and length until a useful signal to noise ratio is detected and depend on many factors as the target, e.g. its purity, GC-content, size etc, the probe, e.g. its length, is it a RNA or a DNA probe, salt conditions, washing or hybridisation temperature, washing or hybridisation time etc.

In an other embodiment, the present invention relates to a method for the identification of a gene product conferring an increase in yield or growth in an organism, comprising the following steps:
 a) identifiying nucleic acid molecules of an organism; which can contain a candidate gene encoding a gene product conferring an increase in growth rate and/or yield after expression, which are at least 20%, preferably 25%, more preferably 30%, even more preferred are 35%. 40% or 50%, even more preferred are 60%, 70% or 80%, most preferred are 90% or 95% or more homology to the nucleic acid molecule of the present invention, for example via homology search in a data bank;
 b) introducing the candidate nucleic acid molecules in host cells, preferably in a plant cells or microorganisms, appropriate for producing feed or food stuff or fine chemicals;
 c) expressing the identified nucleic acid molecules in the host cells;
 d) deriving the organism and assaying the yield or growth of the organism;
 e) and identifying the nucleic acid molecule and its gene product which expression confers an increase in the yield or growth of the host cell after expression compared to the wild type.

The nucleic acid molecules identified can then be used in the same way as the polynucleotide of the present invention.

Furthermore, in one embodiment, the present invention relates to a method for the identification of a compound stimulating growth or yield to said plant comprising:
 a) contacting cells which express the polypeptide of the present invention or its mRNA with a candidate compound under cell cultivation conditions;
 b) assaying an increase in expression of said polypeptide or said mRNA;
 c) comparing the expression level to a standard response made in the absence of said candidate compound; whereby, an increased expression over the standard indicates that the compound is stimulating yield or growth.

Furthermore, in one embodiment, the present invention relates to a method for the screening for agonists of the activity of the polypeptide of the present invention:
 a) contacting cells, tissues, plants or microorganisms which express the polypeptide according to the invention with a candidate compound or a sample comprising a plurality of compounds under conditions which permit the expression the polypeptide of the present invention;
 b) assaying the growth, yield or the polypeptide expression level in the cell, tissue, plant or microorganism or the media the cell, tissue, plant or microorganisms is cultured or maintained in; and
 c) identifying an agonist or antagonist by comparing the measured growth or yield or polypeptide expression level with a standard growth, yield or polypeptide expression level measured in the absence of said candidate compound or a sample comprising said plurality of compounds, whereby an increased level over the standard indicates that the compound or the sample comprising said plurality of compounds is an agonist and a decreased level over the standard indicates that the compound or the sample comprising said plurality of compounds is an antagonist.

Furthermore, in one embodiment, the present invention relates to process for the identification of a compound conferring increased growth and/or yield production in a plant or microorganism, comprising the steps:
 a) culturing a cell or tissue or microorganism or maintaining a plant expressing the polypeptide according to the invention or a nucleic acid molecule encoding said polypeptide and a readout system capable of interacting with the polypeptide under suitable conditions which permit the interaction of the polypeptide with said readout system in the presence of a compound or a sample comprising a plurality of compounds and capable of providing a detectable signal in response to the binding of a compound to said polypeptide under conditions which permit the expression of said readout system and the polypeptide of the present invention; and b) identifying if the compound is an effective agonist by detecting the presence or absence or increase of a signal produced by said readout system.

Said compound may be chemically synthesized or microbiologically produced and/or comprised in, for example, samples, e.g., cell extracts from, e.g., plants, animals or microorganisms, e.g. pathogens. Furthermore, said compound(s) may be known in the art but hitherto not known to be capable of suppressing or activating the polypeptide of the present invention. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994), in particular Chapter 17. The compounds may be, e.g., added to the reaction mixture, culture medium, injected into the cell or sprayed onto the plant.

If a sample containing a compound is identified in the method of the invention, then it is either possible to isolate the compound from the original sample identified as containing the compound capable of activating or increasing, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above described method or its derivative is further formulated in a form suitable for the application in plant breeding or plant cell and tissue culture.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can be tested for their effects according to methods known in the art. Furthermore, peptidomimetics and/or computer aided design of appropriate derivatives and analogues can be used, for example, according to the methods described above. The cell or tissue that may be employed in the method of the invention preferably is a host cell, plant cell or plant tissue of the invention described in the embodiments hereinbefore.

Thus, in a further embodiment the invention relates to a compound obtained or identified according to the method for identifiying an agonist of the invention said compound being an agonist of the polypeptide of the present invention.

Accordingly, in one embodiment, the present invention further relates to a compound identified by the method for identifying a compound of the present invention.

Said compound is, for example, a homologous of the polypeptide of the present invention. Homologues of the polypeptid of the present invention can be generated by mutagenesis, e.g., discrete point mutation or truncation of the polypeptide of the present invention. As used herein, the term "homologue" refers to a variant form of the protein, which acts as an agonist of the activity of the polypeptide of the present invention. An agonist of said protein can retain substantially the same, or a subset, of the biological activities of the polypeptide of the present invention. In particular, said agonist confers the increase of the expression level of the polypeptide of the present invention and/or the expression of said agonist in an organisms or part thereof confers the increase in growth and/or yield.

In one embodiment, the invention relates to an antibody specifically recognizing the compound or agonist of the present invention.

The invention also relates to a diagnostic composition comprising at least one of the aforementioned polynucleotide, nucleic acid molecules, vectors, proteins, antibodies or compounds of the invention and optionally suitable means for detection.

The diagnostic composition of the present invention is suitable for the isolation of mRNA from a cell and contacting the mRNA so obtained with a probe comprising a nucleic acid probe as described above under hybridizing conditions, detecting the presence of mRNA hybridized to the probe, and thereby detecting the expression of the protein in the cell. Further methods of detecting the presence of a protein according to the present invention comprise immunotechniques well known in the art, for example enzyme linked immunosorbent assay.

Furthermore, it is useful to use the nucleic acid molecules according to the invention as molecular markers or primer in association mapping or plant breeding expecially marker assisted breeding. Suitable means for detection are well known to a person skilled in the arm, e.g. buffers and solutions for hydridization assays, e.g. the aforementioned solutions and buffers, further and means for Southern-, Western-, Northern- etc. -blots, as e.g. described in Sambrook et al. are known.

In another embodiment, the present invention relates to a kit comprising the nucleic acid molecule, the vector, the host cell, the polypeptide, the antisense nucleic acid, the antibody, plant cell, the plant or plant tissue, the harvestable part, the propagation material and/or the compound or agonist identified according to the method of the invention.

The compounds of the kit of the present invention may be packaged in containers such as vials, optionally with/in buffers and/or solution. If appropriate, one or more of said components might be packaged in one and the same container. Additionally or alternatively, one or more of said components might be adsorbed to a solid support as, e.g. a nitrocellulose filter, a glas plate, a chip, or a nylon membrane or to the well of a micro titerplate. The kit can be used for any of the herein described methods and embodiments, e.g. for the production of the host cells, transgenic plants, pharmaceutical compositions, detection of homologous sequences, identification of antagonists or agonists, as food or feed or as a supplement thereof, as supplement for the treating of plants, etc.

Further, the kit can comprise instructions for the use of the kit for any of said embodiments, in particular for the use for producing organisms or part thereof.

In one embodiment said kit comprises further a nucleic acid molecule encoding one or more of the aforementioned protein, and/or an antibody, a vector, a host cell, an antisense nucleic acid, a plant cell or plant tissue or a plant.

In a further embodiment, the present invention relates to a method for the production of a agricultural composition providing the nucleic acid molecule, the vector or the polypeptide of the invention or comprising the steps of the method according to the invention for the identification of said compound, agonist or antagonist; and formulating the nucleic acid molecule, the vector or the polypeptide of the invention or the agonist, or compound identified according to the methods or processes of the present invention or with use of the subject matters of the present invention in a form applicable as plant agricultural composition.

In another embodiment, the present invention relates to a method for the production of an agricultural composition conferring increased growth or yield of a plant comprising the steps of the method for of the present invention; and formulating the compound identified in a form acceptable as agricultural composition.

Under "acceptable as agricultural composition" is understood, that such a composition is in agreement with the laws regulating the content of fungicides, plant nutrients, herbizides, etc. Preferably such a composition is without any harm for the protected plants and the animals (humans included) fed therewith.

The present invention also pertains to several embodiments relating to further uses and methods. The polynucleotide, polypeptide, protein homologues, fusion proteins, primers, vectors, host cells, described herein can be used in one or more of the following methods: identification of plants useful pro amino acid production as mentioned and related organisms; mapping of genomes; identification and localization of sequences of interest; evolutionary studies; determination of regions required for function; modulation of an activity.

Advantageoudly, inhibitor of the polypeptide of the present invention, identified in an analogous way to the identification of agonist, can be used as herbicides. The inhibition of the polypeptide of the present invention can reduce the growth of plants. For example, the application of the inhibitor on a field is inhibiting the growth of plants not desired if useful plants which are over-expressing the polypeptide of the invention can survive.

Accordingly, the polynucleotide of the present invention have a variety of uses. First, they may be used to identify an organism or a close relative thereof. Also, they may be used to identify the presence thereof or a relative thereof in a mixed population of microorganisms or plants. By probing the extracted genomic DNA of a culture of a unique or mixed population of plants under stringent conditions with a probe spanning a region of the gene of the present invention which is unique to this, one can ascertain whether the present Further, the polynucleotide of the invention may be sufficiently homologous to the sequences of related species such that these nucleic acid molecules may serve as markers for the construction of a genomic map in related organism.

The polynucleotide of the invention are also useful for evolutionary and protein structural studies. By comparing the sequences of to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Further, the polynucleotide of the invention, the polypeptide of the invention, the nucleic acid construct of the invention, the organisms, the host cell, the microorgansims, the plant, plant tissue, plant cell, or the part thereof of the invention, the vector of the invention, the antagonist or the agonist identified with the method of the invention, the antibody of the presen invention, the antisense molecule of the present invention or the nucleic acid molecule identified with the method of the present invention, can be used for the preparation of an agricultural composition.

Furthermore, the polynucleotide of the invention, the polypeptide of the invention, the nucleic acid construct of the invention, the organisms, the host cell, the microorgansims, the plant, plant tissue, plant cell, or the part thereof of the invention, the vector of the invention, antagonist or the agonist identified with the method of the invention, the antibody of the present invention, the antisense molecule of the present invention or the nucleic acid molecule identified with the method of the present invention, can be used for the identification and production of compounds capable of conferring a modulation of yield or growth levels in an organism or parts thereof, preferably to identify and produce compounds conferring an increase of growth and yield levels or rates in an organism or parts thereof, if said identified compound is applied to the organism or part thereof, i.e. as part of its food, or in the growing or culture media.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "medline" may be utilized which is available on the Internet, for example under hftp://www.ncbi.nlm.nih.gov/PubMed/medline.html. Further data-bases and addresses, such as hftp://www.ncbi.nlm.nih.gov/, hftp://www.infobiogen.fr/, http://www.fmi.ch/biology/research-tools.html, hftp://www.tigr.org/, are known to the person skilled in the art and can also be obtained using, e.g., hftp://www.lycos.com. An overview of patent information in biotechnology and a survey of relevant sources of patent information useful for retrospective searching and for current awareness is given in Berks, TIBTECH 12 (1994), 352-364.

FIG. 1 depicts the Northern blot analysis of an L450-overexpressing line (450B). Three plants of this line and two wild-type plants were analyzed. The lower, strongly hybridizing band corresponds to the L450 transcript.

Figure 2:
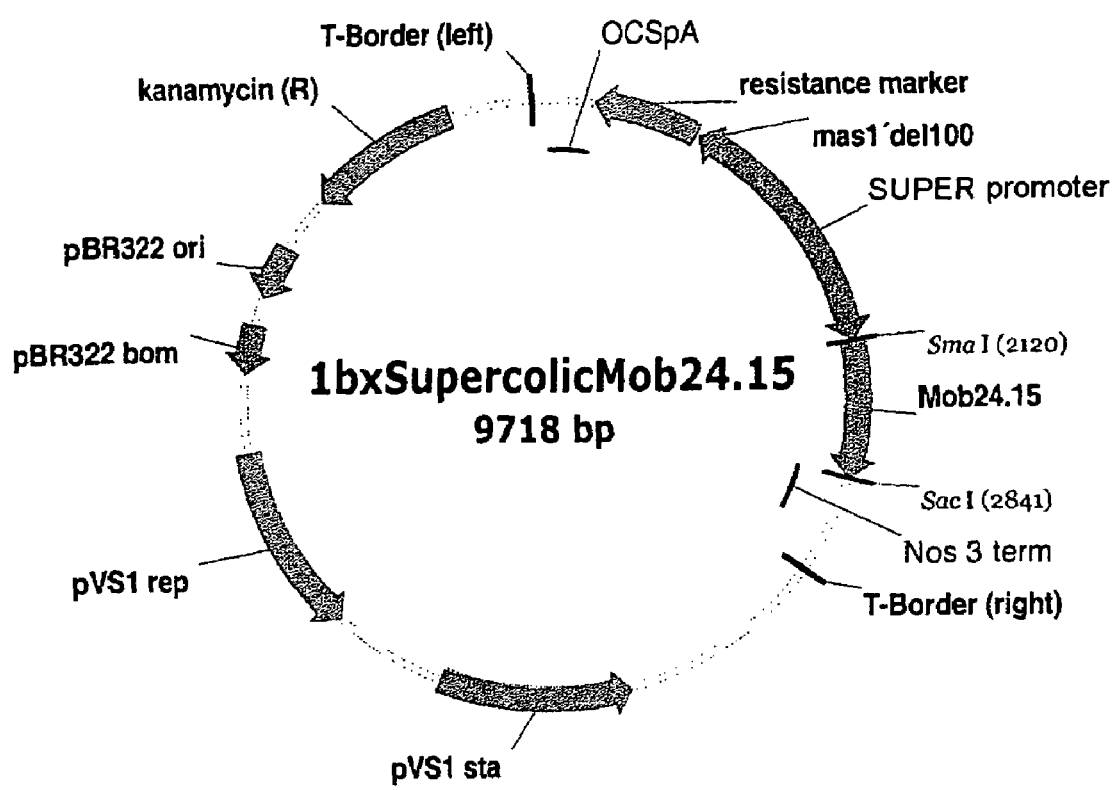
FIG. 2 depicts the construct 1 bx SuperColicMOB24.15.

FIG. 2 depicts the construct 1bx SuperColicMOB24.15.

FIG. 3 depicts the Blast comparison between the sequence depicted in Seq. ID No. 1 and the sequence published under Seq. ID No. 701 in US 2002/0023281 (Seq. ID No. 23).

Figure 4:
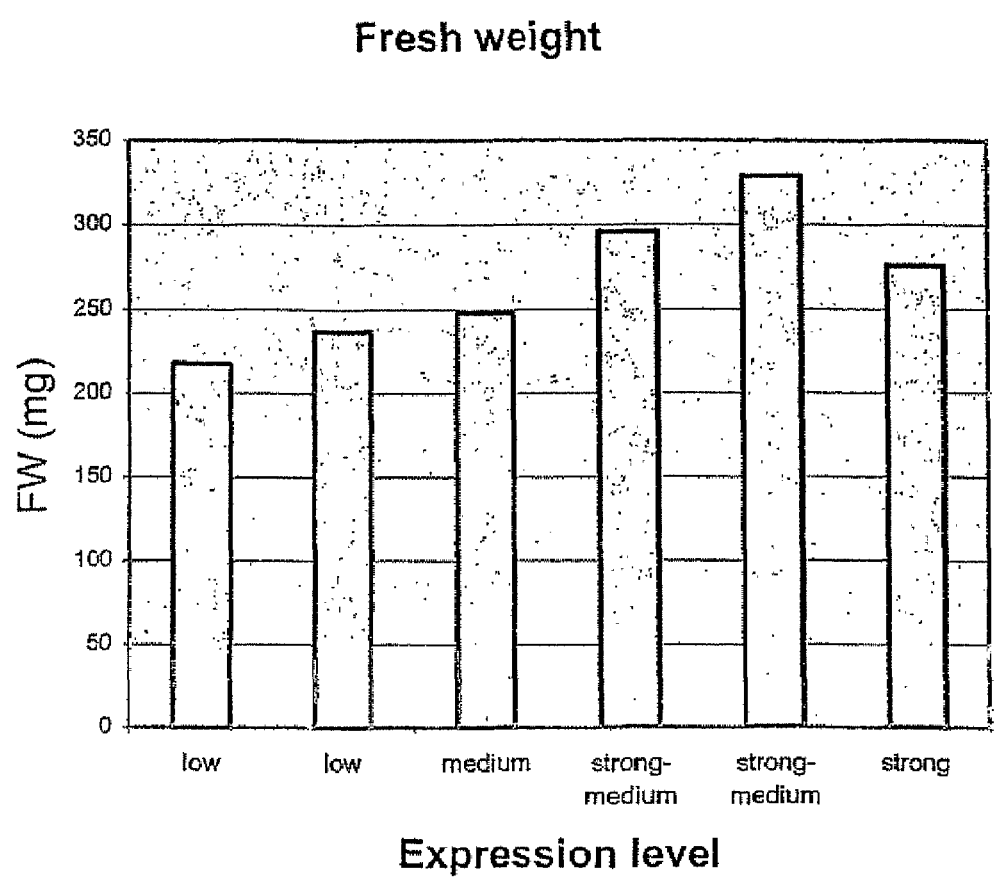
FIG. 4 depicts the observed correlation of the expression level of the transgenic At3g24570 gene as a function of the increase in fresh weight.

FIG. 4 depicts the observed correlation of the expression level of the transgenic At3g24570 gene as a function of the increase in fresh weight.

Figure 5:
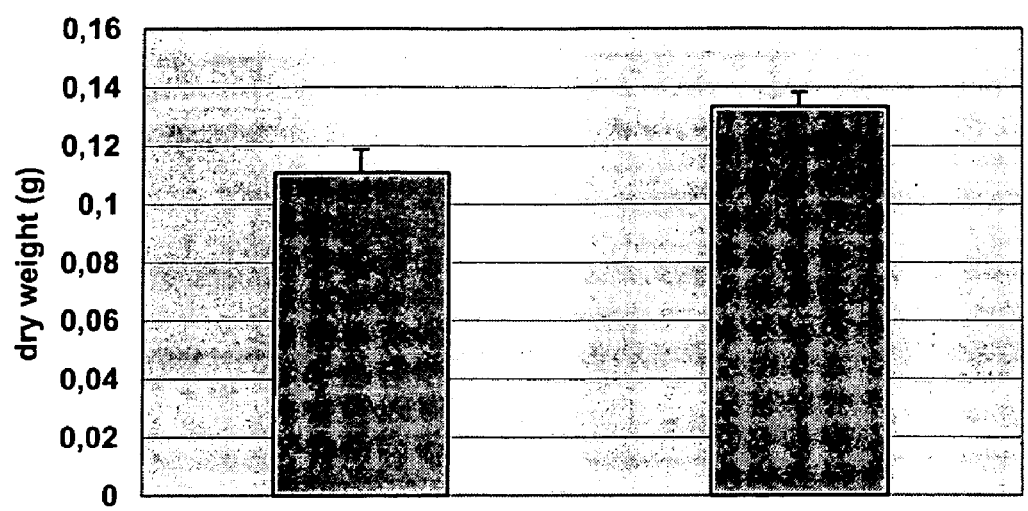
FIG. 5 shows the increased biomass of Arabidopsis plants after over expression of L450 (MOB 24.15) compared to wildtype.

FIG. 5 shows the increased biomass of *Arabidopsis* plants after over expression of L450 (MOB 24.15) compared to wildtype.

Figure 6:
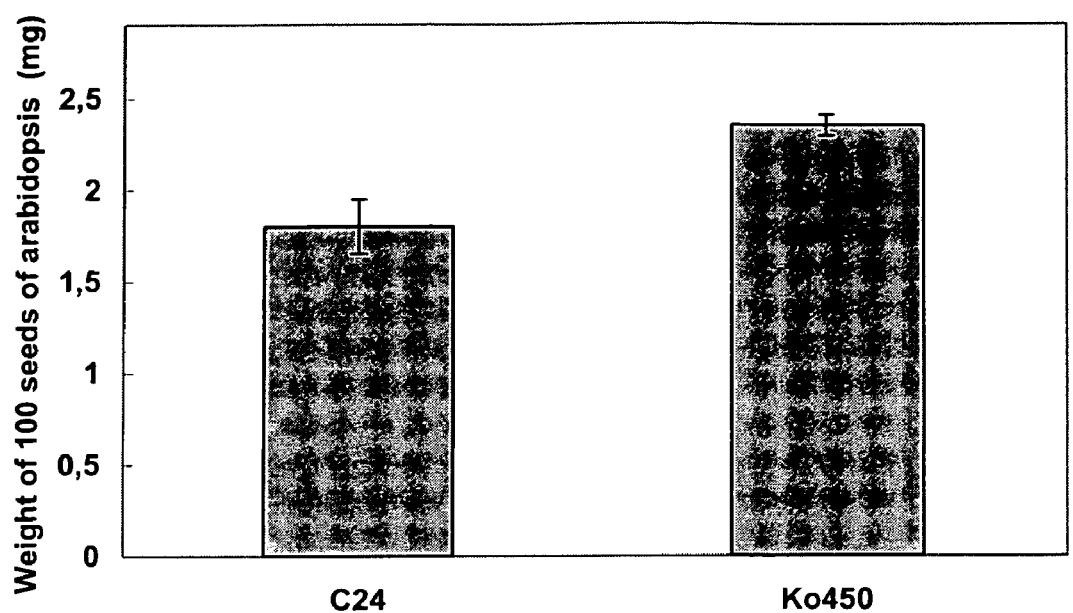
FIG. 6 shows that the 100-seeds weight of lines over expressing L450 (KO450 lines) is increased compared to the wildtype C24.

FIG. 6 shows, that the 100-seeds weight of lines, over expressing L450 (KO450 lines) is increased compared to the wildtype C24.

FIG. 7 shows multiple aligment and consensus sequence of plant, microorganism and animal derived sequences and the consensus sequence of the shown sequences.

FIG. 8 shows multiple aligment and consensus sequence of the plant derived sequences without Seq ID No. 43, and the consensus sequence of the shown sequences.

FIGS. 7 and 8: Multiple aligment and consensus sequence, consisting of capitel and small letters. The capital letters indicate that the amino acids are conserved in all or near all aligned proteins, and the small letters indicate that amino acids are conserved in some of the aligned proteins. Anyhow, x indicates any given amino acid. Core Consensus Sequence (in bold) represents the essential part of the Consensus Sequence.

The multiple alignment was performed with the Software GenoMax Version 3.4, InforMax™, Invitrogen™ life science software, U.S. Main Office, 7305 Executive Way, Frederick, Md. 21704, USA with the following settings:

Gap opening penalty: 10.0; Gap extension penalty: 0.05; Gap separation penalty range: 8; % identity for alignment delay: 40; Residue substitution matrix: blosum; Hydrophilic residues: G P S N D Q E K R; Transition weighting: 0.5; Consensus calculation options: Residue fraction for consensus: 0.5.

The contents of all references, patent applications, patents and published patent applications cited in the present patent application are hereby incorporated by reference.

EXAMPLES

Example 1

Amplification and Cloning of L450

Unless stated otherwise, standard methods according to Sambrook et al., Molecular Cloning: A laboratory manual, Cold Spring Harbor 1989, Cold Spring Harbor Laboratory Press, are used in all examples. Leaf material of 3 week old *Arabidopsis* plants of the C24 ecotype (Nottingham *Arabidopsis* Stock Centre, UK; NASC Stock N906) was harvested and total RNA extracted using the Nucleospin RNA Plant Kit (Macherey and Nagel) according to the manufacturer's instructions. Said total RNA was photometrically quantified and 1.5 µg of said RNA were used for cDNA synthesis. First-strand cDNA was prepared by means of oligo-dT starter molecules and the SuperScript First-Strand Synthesis System (Invitrogen) according to the manufacturer's instructions. Oligonucleotides were derived from the sequence of the annotated open reading frame MOB24.15 (Accession: AB020746)also annotated as ORF At3g24570. The oligos were derived from the sequence of base pairs 1-20 and 689-708. Recognition sequences of restriction enzymes were attached to said oligonucleotides for cloning and, in addition, a Kozak sequence was inserted upstream of the start codon of the gene (Joshi, (1997) Plant Molecular Biology, 35(6):993). The sequences of said oligos were as follows MOB24155Sma:

```
                                  (Seq. ID NO.: 19)
ATACCCGGGAAACAATGTTGAAGCTTTGGAGATG
and MOB24153Sac:

(Seq. ID NO.: 20)
ATAGAGCTCTCATACTCCGCCTTGGCCAC
```

The oligos were adjusted to a concentration of 20 µM and used in a PCR. The PCR mixture contained:
15 µl of Ex Taq polymerase buffer (TAKARA)
12 µl of dNTPs (2.5 mM each) (TAKARA)
0.8 µl of primer MOB24155Sma
0.8 µl of primer MOB24153Sac
0.75 µl of Ex Taq polymerase (TAKARA)
3.0 µl of cDNA
117 µl of water The PCR program (MJ-Cycler Tetrad, BioZym) was as follows: 3 min 94° C., 1 min 94° C., 1 min 52° C., 1 min 72° C. and 10 min 72° C. The middle cycle was repeated 30 times. To clone the PCR fragment, the PCR mixture was purified using the Qiagen PCR purification kit according to the manufacturer's instructions and then cloned into the PCR vector, using the TA-Cloning Kit (Invitrogen) according to the manufacturer's instructions, followed by a maxi preparation from a correct clone (Machery und Nagel). The correct sequence of the insert was checked by sequencing. Compared to the published sequence of MOB24.15 (Seq. ID No. 1), a substitution was found in two positions: base pair 329 T to C and base pair 361 G to T (Seq. ID No.: 24). This results in an amino acid substitution of Pro for Leu in position 110 and of Ser for Ala in position 121 of Seq. ID No.: 2, in comparison with Seq. ID No.: 25. In another independent clone (Seq. ID No.: 26), nucleotide substitutions were identified in positions 159 (G for A), 170 (T for C), 187 (T for A), 189 (C for T), 198 (C for G), 206 (G for A), 291 (T for C), 366 (C for A) and 400 (A for G), compared to the published sequence of MOB24.15 (Seq. ID No.: 1). These nucleotide substitutions result in the amino acid sequence (Seq. ID No.: 27) which contains five amino acid substitutions (AA57: AV, AA63: IF, AA66: KN, AA69: QR, 134: VI), compared to the published amino acid sequence. Since this sequence, Seq. ID No.: 26, and therefore the amino acid sequence Seq. ID No.: 27 were independently confirmed several times, work for the following clonings was continued using said sequence. This construct was cleaved with restriction enzymes SmaI and SacI. The L450 fragment obtained in the process was eluted from an agarose gel by means of the Gel Extraction Kit (Qiagen) according to the manufacturer's instructions. The isolated fragment was cloned into a binary vector for plant transformation, which had previously been cleaved likewise with restriction enzymes SmaI and SacI. Apart from the resistance cassette for selection in plants, said vector contained the superpromotor ((ocs$_3$mas, Ni, et al., The Plant Journal 1995, 7, 661-676) and the nos terminator sequence for expression of the transgene. The construct 1bx SuperColicMOB24.15 was produced.

Example 2

Amplification and Cloning of the Yeast ORF YLR251w

Unless stated otherwise, standard methods according to Sambrook et al., Molecular Cloning: A laboratory manual, Cold Spring Harbor 1989, Cold Spring Harbor Laboratory Press, are used. PCR amplification of YLR251w was carried out according to the protocol of Pfu Turbo DNA polymerase (Stratagene). The composition was as follows: 1× PCR buffer [20 mM Tris-HCl (pH 8.8), 2 mM MgSO4, 10 mM KCl, 10 mM (NH4)SO4, 0.1 Triton X-100, 0.1 mg/ml BSA)], 0.2 mM d-thio-dNTP and dNTP (1:125), 100 ng of genomic DNA of *Saccharomyces cerevisiae* (strain S288C; Research Genetics, Inc., now Invitrogen), 50 pmol of forward primer, 50 pmol of reverse primer, 2.5 u of Pfu Turbo DNA polymerase. The amplification cycles were as follows: 1 cycle of 3 min at 95° C., followed by 36 cycles of in each case 1 min at 95° C., 45 s at 50° C. and 210 s at 72° C., followed by 1 cycle of 8 min at 72° C., then 4° C.

The following primer sequences were chosen for amplification of the Saccharomyces cerevisiae gene according to SEQ. ID: NO 11:

```
forward primer for YLR251w:     (SEQ. ID NO.: 17)
5'-GGAATTCCAGCTGACCACCATGAAGTTATTGCATTTATATGAAGCG-
3' reverse primer for YLR251w:     (SEQ. ID NO.: 18)
5'-GATCCCCGGGAATTGCCATGTTATTCGACCACGGGTGGATAATG-3'
```

The amplicon was subsequently purified via QIAquick columns according to a standard protocol (Qiagen).

Restriction of the vector DNA (30 ng) was carried out with EcoRI and SmaI according to the standard protocol, the EcoRI cleavage site was filled in according to the standard protocol (MBI-Fermentas) and the reaction was stopped by adding high-salt buffer. The cleaved vector fragments were purified via Nucleobond columns according to standard protocol (Machery-Nagel). A binary vector was used which contained a selection cassette (promoter, selection marker, terminator) and an expression cassette comprising a constitutive promoter such as the superpromoter ((ocs3mas)), Ni, et al., The Plant Journal 1995, 7, 661-676), a cloning cassette and a terminator sequence between the T-DNA border sequences. Other than in the cloning cassette, the binary vector had no EcoRI and SmaI cleavage sites. Binary vectors which may be used are known to the skilled worker, and a review on binary vectors and their use can be found in Hellens, R., Mullineaux, P. and Klee H., (2000) "A guide to Agrobacterium binary vectors", Trends in Plant Science, Vol. 5 No. 10, 446-451. Depending on the vector used, cloning may advantageously also be carried out using other restriction enzymes. Corresponding advantageous cleavage sites may be attached to the ORF by using corresponding primers for PCR amplification.

Approx. 30 ng of prepared vector and a defined amount of prepared amplicon were mixed and ligated by adding ligase. The ligated vectors were transformed in the same reaction vessel by adding competent *E. coli* cells (DH5alpha strain) and incubating at 1° C. for 20 min, followed by a heat shock at 42° C. for 90 s and cooling to 4° C. This was followed by addition of complete medium (SOC) and incubation at 37° C. for 45 min. The entire mixture was then plated out on an agar plate containing antibiotics (selected depending on the binary vector used) and incubated at 37° C. overnight.

Successful cloning was checked by amplification with the aid of primers which bind upstream and downstream of the restriction cleavage site and thus make amplification of the insertion possible. The amplification was carried out according to the Taq DNA polymerase protocol (Gibco-BRL). The composition was as follows: 1× PCR buffer [20 mM Tris-HCL (pH 8.4), 1.5 mM MgCl2, 50 mM KCl, 0.2 mM DNTP, 5 pmol of forward primer, 5 pmol of reverse primer, 0.625 u of Taq DNA polymerase.

The amplification cycles were as follows: 1 cycle of 5 min at 94° C., followed by 35 cycles of in each case 15 s at 94° C., 15 s at 66° C. and 5 min at 72° C., followed by 1 cycle of 10 min at 72° C., then 4° C.

Several colonies were checked, and only one colony for which a PCR product of the expected size had been detected was used further.

One aliquot of this positive colony was transferred to a reaction vessel filled with complete medium (LB) and incubated at 37° C. overnight. The LB medium contained an antibiotic for selection of the clone, which was selected according to the binary vector used and the resistance gene contained therein. Plasmid preparation was carried out according to the guidelines of the Qiaprep standard protocol (Qiagen).

Example 3

General Plant Transformation

Plant transformation via transfections with *Agrobacterium* and regeneration of the plants may be carried out according to standard methods, for example as described herein or in Gelvin, Stanton B.; Schilperoort, Robert A, "Plant Molecular Biology Manual", 2nd Ed.—Dordrecht: Kluwer Academic Publ., 1995.—in Sect., Ringbuc Zentrale Signatur: BT11-P ISBN 0-7923-2731-4; Glick, Bernard R.; Thompson, John E., "Methods in Plant Molecular Biology and Biotechnology", Boca Raton: CRC Press, 1993.-360 S., ISBN 0-8493-5164-2.

Oil seed rape may be transformed by means of cotyledon transformation, for example according to Moloney et al., Plant cell Report 8 (1989), 238-242; De Block et al., Plant Physiol. 91 (1989, 694-701).

Soybeans may be transformed, for example, according to the methods described in EP 0424 047, U.S. Pat. No. 322,783 or in EP 0397 687, U.S. Pat. Nos. 5,376,543, 5,169,770.

Alternatively, DNA uptake may be achieved and a plant may be transformed also by particle bombardment, polyethylene glycol mediation or via the "silicon carbide fiber" technique, rather than by *Agrobacterium*-mediated plant transformation, see, for example, Freeling and Walbot "The maize handbook" (1993) ISBN 3-540-97826-7, Springer Verlag New York).

Example 4

Preparation of Plants Overexpressing L450 or ORF YLR251w

The respective plasmid constructs were transformed by means of electroporation into the agrobacterial strain pGV3101 containing the pMP90 plasmid, and the colonies were plated out on TB medium (QBiogen, Germany) containing the selection markers kanamycin, gentamycin and rifampicin and incubated at 28° C. for 2 days. The antibiotics or selection agents are to be selected according to the plasmid used and to the compatible agrobacterial strain. A review on binary plasmids and agrobacteria strains can be found in Hellens, R., Mullineaux, P. and Klee H., (2000) "A guide to *Agrobacterium* binary vectors", Trends in Plant Science, Vol 5 No. 10, 446-451.

A colony was picked from the agar plate with the aid of a toothpick and taken up in 3 ml of TB medium containing the abovementioned antibiotics.

The preculture grew in a shaker incubator at 28° C. and 120 rpm for 48 h. 400 ml of LB medium containing the appropriate antibiotics were used for the main culture. The preculture was transferred into the main culture which grew at 28° C. and 120 rpm for 18 h. After centrifugation at 4000 rpm, the pellet was resuspended in infiltration medium (M & S medium with 10% sucrose). Dishes (Piki Saat 80, green, provided with a screen bottom, 30×20×4.5 cm, from Wiesauplast, Kunststofftechnik, Germany) were half-filled with a GS 90 substrate (standard soil, Werkverband E. V., Germany). The dishes were watered overnight with 0.05% Previcur solution (Previcur N, Aventis CropScience). Transformation of *Arabidopsis* was carried out following Bechtold N. and Pelletier G. (1998) In planta *Agrobacterium*-mediated transformation of adult *Arabidopsis thaliana* plants by vacuum infiltration. Methods in Molecular Biology. 82:259-66 and Clough and Bent Clough, J C and Bent, A F. 1998 Floral dip: a simplified method for *Agrobacterium*-mediated transformation of *Arabidopsis thaliana*, Plant J. 16:735-743). *Arabidopsis thaliana*, C24 seeds (Nottingham *Arabidopsis* Stock Centre, UK; NASC Stock N906) were scattered over the dish, approx. 1000 seeds per dish. The dishes were covered with a hood and placed in the stratification facility (8 h 110 µE, 5° C.; 16 h dark 6° C.). After 5 days, the dishes were placed into the short-day phytotron (8 h 130 µE, 22° C.; 16 H dark 20° C.), where they remained for 10 days, until the first true leaves had formed. The seedlings are transferred into pots containing the same substrate (Teku pots, 10 cm φ, LC series, manufactured by Pöppelmann GmbH&Co, Germany). Nine plants were pricked out into each pot. The pots were then returned into the short-day phytotron for the plants to continue growing.

After 10 days, the plants were transferred into a greenhouse cabinet, 16 h 340 µE 22° C. and 8 h dark 20° C., where they grew for a further 10 days.

Seven-week-old *Arabidopsis* plants which had just started flowering were immersed for 10 sec into the above-described agrobacterial suspension which had previously been treated with 10 µl of Silwett L77 (Crompton S. A., Osi Specialties, Switzerland). The method is described in Bechtold N. and Pelletier G. (1998). The plants were subsequently placed into a humid chamber for 18 h and the pots were subsequently returned to the greenhouse for the plants to continue growing. The plants remained there for another 10 weeks until the seeds were harvested.

Depending on the resistance marker used for selecting the transformed plants, the harvested seeds were sown in a greenhouse and subjected to spray selection or else, after sterilization, cultivated on agar plates with the appropriate selecting agent. After approx. 10-14 days, the transformed resistant plants differed distinctly from the dead wild-type seedlings and could be pricked out into 6-cm pots.

Example 5a

Analysis of Lines Overexpressing Endogenous L450: Determination of Fresh Weight, Number of Leaves and Weight of Seeds A line overexpressing MOB24.15 RNA was selected. For this purpose, total RNA was extracted from three-week-old Arabidopsis plants transgenic for MOB24.15. For hybridization, 20 μg of RNA were electrophoretically fractionated, blotted to Hybond N membrane (Amersham Biosciences Europe GmbH, Freiburg, Germany) according to the manufacturer's instructions and hybridized with an MOB24.15-specific probe. Rothi-Hybri-Quick buffer (Roth, Karlsruhe, Germany) was used for hybridization and the probe was labeled using the Rediprime II DNA Labeling System (Amersham Biosciences Europe GmbH Freiburg, Germany) according to the manufacturer's instructions. The DNA fragment for this probe was prepared by means of a standard PCR of Arabidopsis genomic DNA and the primers MOB24.15fw:

```
                                    (SEQ. ID NO.: 21)
5'-CGCCTTGGCCACCTCGTTCTTTT-3'
and MOB24.15revno:

(SEQ. ID NO.: 22)
5'-GCTGCAAAAGTTGCAATGGATGGTC-3'.
```

FIG. 1 depicts the Northern blot analysis of a line overexpressing the L450 sequence (450B). Three plants of this line and two wild-type plants were analyzed. The lower, strongly hybridizing band corresponds to the L450 transcript.

For analysis, the plants were cultivated in a phytotron from Swalöf Weibull (Sweden) under the following conditions. After stratification, the test plants were cultured in a 16 h light/8 h dark rhythm at 20° C., a humidity of 60% and a $CO_2$ concentration of 400 ppm for 22-23 days. The light sources used were Powerstar HQI-T 250 W/D Daylight lamps from Osram, which generate light of a color spectrum similar to that of the sun with a light intensity of 220 $\mu E/m^2/s^{-1}$.

On days 21, 24 and 28 after sowing, which days correspond to approximately days 14, 17 and 21, respectively, after germination, in each case 14 to 15 randomly selected individual plants of both the wild type (WT) and the L450-overexpressing line (450B) were studied. The number of leaves was determined, not counting the cotyledons. Subsequently, the shoot (the green part of the plants) was cut off directly above the substrate. The fresh weight was determined immediately thereafter, using a precision balance. The differences between the results for the wild-type plants and the plants of the transgenic line were tested for significance by means of a T test for each harvest day.

The result is depicted in tables 1 and 2.

TABLE 1

Number of leaves and fresh shoot weight (mg) of line 450b and wild-type plants. Average and standard deviation of 14-15 replicons. Significant differences ($p < 0.05$) between line 450b and WT on the particular day of harvest were be found, in the case of the number of leaves, on all days of harvest and, in the case of fresh weight, for the harvest after 17 and 24 days. The significant differences are indicated by the different letters. The significant differences in number of leaves and fresh weight between the wild type and the transgenic lines were also reproduced in comparable experiments under greenhouse conditions.

| | Days after sowing | | | | | |
|---|---|---|---|---|---|---|
| | 14 | | 17 | | 21 | |
| Population | 450B | WT C24 | 450B | WT C24 | 450B | WT C24 |
| Number of leaves | $14.5 \pm 2.2^a$ | $12.9 \pm 1.0^b$ | $19.3 \pm 2.6^a$ | $17.3 \pm 1.8^b$ | $41.2 \pm 7.3^a$ | $32.7 \pm 6.4^b$ |
| Fresh weight (mg) | $185 \pm 56^a$ | $159 \pm 33^a$ | $352 \pm 55^a$ | $274 \pm 66^b$ | $954 \pm 249^a$ | $724 \pm 162^b$ |

Furthermore, plants of the transgenic line 450B and wild-type control plants were cultivated in parallel in a greenhouse under identical conditions and the total weight of the seeds obtained was analyzed. It was found that line 450B produces more seeds than the wild type in a statistically significant manner.

TABLE 2

Seed production of wild-type MC24 Arabidopsis plants and of plants of the transgenic line 450B, which overexpresses L450, is shown. The data indicate the average for 50 and 51 plants, respectively, and the corresponding standard deviation. The statistically significant difference between the values is indicated by the different letters.

| | C24 wild type | Transgenic line 450B |
|---|---|---|
| Seed production (mg/plant) | $77.9 \pm 17.8^a$ | $97.5 \pm 15.2^b$ |

The achieved increase in yield and biomass is further shown in FIG. 5.

Example 5b

Analysis of *Arabidopsis thaliana* Plants Transformed with the 1bxSuperColicMOB24.15 Construct Transformation with the 1bxSuperColicMOB24.15 construct produced 7 independent lines.

6 of these lines were first studied for the level of transgene expression by means of qPCR using an ABI Prism7700 instrument. Total RNA was extracted from leaves of 3-week-old, BASTA-selected T1 plants by means of the Invisorb plant kit (Invitek, according to the manufacturer's instructions).

The reagents for cDNA synthesis and Q-PCR reaction were from Eurogentec and were used according to the manufacturer's instructions. The analysis was carried out by quantitative PCR using TaqMan probes and the ABIPrism7000 (PE Applied Biosystems) (Gibson et al., 1996; Lie and Petropulos 1998).

The following probe system was used for detecting At3g24570 mRNA:

```
Seq. ID No.: 28:
Oligo1: 5' ccatctcataaataacgtcatgcattac 3'

Seq. ID No.: 29:
probe: 5' tgataatcatcgcaagaccggcaacagt 3'

Seq. ID No.: 30:
Oligo2: 5' aacatttggcaataaagtttcttaaga 3'
```

The probe was labeled with FAM, the quencher was TAMRA.

The amount of total RNA used was normalized by using a probe system which detects mRNA of ubiquitin conjugating enzyme 18 (Ubi18):

```
Seq. ID No.: 31:
Oligo1: 5' agttcacccgaaaagcaacg 3'

Seq. ID No.: 32:
probe: 5' cccactgataatgatcgatatgtgaagaactgc 3'

Seq. ID No.: 33:
Oligo2: 5' tcgtcatggaaccaccacct 3'
```

The probe was VIC-labeled, the quencher was TAMRA.

The Ct value for Ubi18 mRNA was determined for each plant and subtracted from the Ct value for the transgenic At3g24570 mRNA which had been determined from the same reaction mixture. The delta Ct value calculated therefrom is a relative value and a measure for the amount of transgenic At3g24570 mRNA contained in a particular amount of mRNA (table 3). The Q-PCR is monitored over 40 cycles. Samples indicating a Ct value of 40 are negative, since they have not developed any fluorescence above the background, even in the 40th cycle.

TABLE 3 delta Ct value of the At3g24570 gene in 6 independent lines

| Sample Name | FAM | VIC | delta Ct |
|---|---|---|---|
| No. 12 - 1bxSuperColicMOB24.15 | 26.67 | 28.94 | −2.27 |
| No. 13 - 1bxSuperColicMOB24.15 | 29.03 | 29.85 | −0.82 |
| No. 14 - 1bxSuperColicMOB24.15 | 28.02 | 29.59 | −1.57 |
| No. 15 - 1bxSuperColicMOB24.15 | 27.08 | 29.89 | −2.82 |
| No. 16 - 1bxSuperColicMOB24.15 | 28.03 | 29.92 | −1.89 |
| No. 17 - 1bxSuperColicMOB24.15 | 28.11 | 30.20 | −2.09 |

In a further transgenic line (No. 1), expression of the transgene was not studied.

Determination of the fresh weight of *Arabidopsis thaliana* plants transformed with the 1bxSuperColicMOB24.15 construct.

Between 93 and 100 siblings were cultivated of 7 independent lines overexpressing the At3g24570 gene. 100 siblings were cultivated as wild-type control from a transformant cultivated containing an empty vector. The plants were sprayed with BASTA in order to exclude nontransgenic plants. 3 weeks after sowing, the fresh weight of the above-ground parts of the plants was determined. As table 4 shows, the fresh weight of all lines is increased in a statistically significant manner in comparison with that of the transformant not overexpressing the At3g24570 gene.

TABLE 4

Fresh weight of *Arabidopsis thaliana* plants transformed with the 1bxSuperColicMOB24.15 construct

| Construct | Line | Fresh weight | Standard deviation | n | p (vs control) |
|---|---|---|---|---|---|
| Empty vector | 24 | 183 | 66 | 100 | |
| 1bxSupercolicMOB24.15 | 1-1 | 327 | 149 | 100 | 0 |
| | 12 | 296 | 92 | 93 | 0 |
| | 13 | 218 | 96 | 97 | 0.004 |
| | 14 | 237 | 107 | 97 | 0 |
| | 15 | 276 | 103 | 99 | 0 |
| | 16 | 248 | 134 | 98 | 0 |
| | 17 | 329 | 104 | 100 | 0 |

The increase in fresh weight can be correlated with the level of expression.

FIG. 4 depicts the observed correlation of the level of expression of the transgenic At3g24570 gene with the increase in fresh weight.

Furthermore, the dry weight of the lines was determined. Here too, an increase was found.

TABLE 5

Dry weight of *Arabidopsis thaliana* plants transformed with the 1bxSuperColicMOB24.15 construct

| Construct | Line | Dry weight | Standard deviation | n | p (vs control) |
|---|---|---|---|---|---|
| Empty vector | 24 | 34.38 | 10.3 | 99 | |
| 1bxSupercolicMOB24.15 | 1-1 | 51.11 | 20.2 | 99 | 0 |
| | 12 | 44.56 | 12.7 | 93 | 0 |
| | 13 | 39.04 | 14.9 | 97 | 0.009 |
| | 14 | 41.44 | 18.9 | 97 | 0 |
| | 15 | 45.41 | 14.9 | 99 | 0 |
| | 16 | 39.14 | 21.8 | 98 | 0.015 |
| | 17 | 53.98 | 16.3 | 100 | 0 |

Literature:

Gibson, (1996) A novel method for real time quantitative RT-PCR. Genome Res. 6, 995-1001

Lie, (1998) Advances in quantitative PCR technology: 5'nuclease assays

Example 5c

Increased 100 Seeds Weight After Over Expression of Endogenous MOB24.15(L450)

KO450 T-DNA-insertion lines, which show an increase in MOB24.15 expression (over expression), show an increased

*Arabidopsis* seed weight. 100 seeds of the wild type (C24) and of the K0450-line were collected under the same conditions and were weightened.

The seeds of the MOB24.15 (L450) over expressing lines (KO450-lines) had a weight of 2.35 mg/100 seeds, whereas the wild type only shows a weight of 1.8 mg/100 seeds. FIG. 6 shows the increased 100 seed weight of the K0450-line compared to the wild type.

Example 6

Analysis of Lines Overexpressing the Yeast ORF YLR251w

Two transgenic *Arabidopsis* lines overexpressing the yeast ORF YLR251w and corresponding wild-type C24 plants and, as control, plants of the selected lines overexpressing the *Arabidopsis* L450 ORF (450B) were cultivated in a greenhouse under standard conditions. The fresh weight was determined at the end of the vegetative phase, with the floral shoot having a length of 4.5 cm. The two transgenic lines 7 and 9 which express the yeast ORF showed a significantly increased fresh weight compared to the control plants.

The result is depicted in table 6.

TABLE 6

Fresh weight of the various transgenic lines and of the wild type at the end of the vegetative phase, with the floral shoot being 4.5 cm in length. The line 450B overexpresses the *Arabidopsis* ORF MOB24.15, actual annotated as ORF At3g24570 and the lines yeast-7 and yeast-9 overexpress the yeast ORF YLR251w. Indicated for each line are the average of the particular fresh weight and the corresponding standard deviation and also the number of plants analyzed of the particular lines. Significant differences ($p < 0.05$) were found between the transgenic lines and the WT. Said significant differences are marked by the different letters.

| Line | Average fresh weight | Standard deviation fresh weight | Number of plants analyzed | Significance of deviation compared to WT |
|---|---|---|---|---|
| WT | 925.6 | 204.4 | 25 | a |
| 450B (MOB24.15) | 1184.4 | 268.4 | 25 | b |
| Yeast-7 (YLR251w) | 1243.8 | 175 | 5 | b |
| Yeast-9 (YLR251w) | 1279.4 | 155.4 | 5 | b |

Example 7a

Overexpression of L450 in Tobacco and Canola

For transformation of canola (*Brassica napus*), cotyledonary petioles and hypocotyls of seedlings at an age of from 5 to 6 days were used as explants for the tissue culture and transformed as described, inter alia, in Babic et al. (1998, Plant Cell Rep 17: 183-188). The commercial variety Westar is the standard variety for transformation but other varieties may also be utilized. The sequence encoding the L450 activity is cloned into the expression cassette of a binary vector containing a selection cassette according to molecular standard methods. Exemplary clonings are described elsewhere in the examples and are known to the skilled worker.

The agrobacterial strain *Agrobacterium tumefaciens* LBA4404 containing, which is transformed with the binary vector, is used for transformation. A multiplicity of binary vectors for plant transformation have already been described (inter alia, An, G. in *Agrobacterium* Protocols. Methods in Molecular Biology vol. 44, pp. 47-62, Gartland K M A and Davey M R eds. Humana Press, Totowa, N.J.). Many binary vectors derive from the binary vector pBIN19 which has been described by Bevan (Nucleic Acid Research. 1984. 12:8711-8721) and which comprises an expression cassette for plants which is flanked by the left and right border of the *Agrobacterium tumefaciens* Ti plasmid. A plant expression cassette comprises at least two components, a selection marker gene and a suitable promoter capable of regulating the transcription of cDNA or genomic DNA in plant cells in the desired manner. A multiplicity of selection marker genes such as antibiotic resistance or herbicide resistance genes may be used, such as, for example, a mutated *Arabidopsis* gene which encodes a mutated herbicide-resistant AHAS enzyme (U.S. Pat. Nos. 57,673,666 and 6,225,105). Similarly, it is also possible to use different promoters for expressing the gene with L450 activity. For example, either constitutive expression as is mediated by the 34S promoter (GenBank Accession No.: M59930 and X16673) or else seed-specific expression may be desired.

Canola seeds are sterilized in 70% ethanol for two minutes and then in 30% chlorox containing a drop of Tween-20 for 10 minutes, followed by three washing steps in sterile water. The seeds are incubated in vitro on semi-concentrated MS medium without hormones, containing 1% sucrose, 0.7% phytagar at 23° C. and in a 16/8 h day/night rhythm for 5 days for germination. The cotyledonary petiole explants were separated together with the cotyledons from seedlings and inoculated with the agrobacteria by dipping the site of the cutting into the bacterial suspension. The explants were then incubated on MSBAP-3 medium containing 3 mg/l BAP, 3% sucrose and 0.7% phytagar at 23° C. and 16 h of light for two days. After two days of cocultivation with the agrobacteria, the explants are transferred to MSBAP-3 medium containing 3 mg/l BAP, cefotaxime, carbenicillin or timentin (300 mg/l) for 7 days and then to MSBAP-3 medium containing cefotaxime, carbenicillin or timentin and selecting agent until shoot regeneration. When the shoots are 5-10 mm in length, they are cut off and transferred to "shoot elongation medium" (MSBAP-0.5, containing 0.5 mg/l BAP). Shoots of approx. 2 cm in length are then transferred to root medium (MSO) for induction of roots.

Material of primary transgenic plants is studied by means of PCR in order to verify incorporation of the T-DNA into the genome. Positive results are then confirmed by means of Southern blot analysis.

Confirmed transgenic plants are then tested for faster growth and higher yield.

Sterile Culture of Tobacco Plants

Tobacco plants cultivated under aseptic conditions are propagated in vitro by placing stem pieces of approx. 1-2 cm in length and with, in each case, one internodium on sterile medium. (Murashige and Skoog medium containing 2% sucrose and 0.7% agar-agar)(Murashige, T. and Skoog, F. (1962) Physiol. Plant. 15:473-497)

The plants grow at 23° C., 200 μE and with a 16 h/8 h light/dark rhythm.

After about 5-6 weeks of growth, leaves of said plants are cut into approx. 1 $cm^2$ pieces under sterile conditions.

Bacterial Culture

An agrobacterial colony transformed with the construct for expressing an L-450 activity is picked from an agar plate is with the aid of a sterile plastic tip which is then transferred into approx. 20 ml of liquid YEB medium (Sambrook et al., *Molecular Cloning: A laboratory manual*, Cold Spring Harbor 1989, Cold Spring Harbor Laboratory Press) containing the relevant antibiotics. The volume of said YEB medium is chosen as a function of the number of transformants. Normally, 20 ml of bacterial culture are sufficient in order to produce approx. 80 transgenic tobacco plants. The bacterial culture is grown on a shaker at 200 rpm and 28° C. for 1 day.

On the following day, the bacterial culture is removed by centrifugation at 4000 rpm and taken up in liquid Murashige and Skoog medium.

Transformation

The leaf pieces are briefly dipped into the bacterial suspension and cultured on Murashige and Skoog medium (2% sucrose and 0.7% agar-agar) in the dark for 2 days. The explants are transferred to MS medium containing antibiotics and corresponding hormones, as described in the method of Rocha-Sosa (Rocha-Sosa, M., Sonnewald, U., Frommer, W., Stratmann, M., Schell, J. and Willmitzer, L. 1998, EMBO J. 8: 23-29).

Transgenic lines can then be analyzed for expression of the L450 transgene by means of Northern blot analysis. It is then possible to determine the increase in fresh weight and in the yield of seeds of selected lines in comparison with the wild type.

Example 8

Design and Expression of a Synthetic Transcription Factor Binding Close to the Endogenous L450 Homolog and Activating the Transcription thereof The endogenous ORF of L450 or a homologous ORF in other plant species may also be activated by introducing a synthetic specific activator. For this purpose, a gene for a chimeric zinc finger protein which binds to a specific region in the regulatory region of the L450 ORF or of its homologs in other plants is constructed. The artificial zinc finger protein comprises a specific DNA-binding domain and an activation domain such as, for example, the Herpes simplex virus VP16 domain. Expression of this chimeric activator in plants then results in specific expression of the target gene, here, for example, MOB24.15, or of its homologs in other plant species. The experimental details may be carried out as described in WO 01/52620 or Ordiz M I, (Proc. Natl. Acad. Sci. USA, 2002, Vol. 99, Issue 20, 13290) or Guan, (Proc. Natl. Acad. Sci. USA, 2002, Vol. 99, Issue 20, 13296).

Example 9

Identification of a Line in which a Strong Promoter is Integrated Upstream of L450 and Thus Activates Expression It is furthermore possible for strong ectopic expression of the desired ORF to integrate a strong promoter upstream of said ORF. For this purpose, a population of transgenic *Arabidopsis* plants was generated into which a vector containing the bidirectional mas promoter (Velten, 1984, EMBO J, 3, 2723) at the left T-DNA border was integrated. Said promoter enabled, via its 2' promoter, transcription from the T-DNA via the left border into the adjacent genomic DNA. The genomic DNA was then isolated from the individual plants and pooled according to a specific plan. The method of this reverse screening for T-DNA integrations at a particular locus has been described in detail by Krysan et al., (Krysan., 1999, The Plant Cell, Vol 11, 2283) and references therein. A line in which the T-DNA had integrated upstream of the MOB24.15 ORF was identified. Sequencing of the locus revealed that integration had occurred approx. 30 bp upstream of the start codon in such a way that transcription of the ORF of L450, e.g. also MOB24.15, via the 2' mas promoter could be expected. Enhanced expression of the ORF of L450, e.g. also MOB24.15, in this line, compared to the wild type, was detected by means of Northern blot analysis.

Example 10

Identification of Homologous Genes in other Plant Species

Homologous sequences of other plants were identified by means of special database search tools such as, in particular, the BLAST algorithm (Basic Local Alignment Search Tool, Altschul, 1990, J. Mol. Biol., 215, 403 and Altschul, 1997, Nucl. Acid Res., 25, 3389). The blastn and blastp comparisons were carried out in the standard manner using the BLOSUM-62 scoring matrix (Henikoff, 1992, Proc. Natl. Acad. Sci. USA, 89, 10915). The NCBI GenBank database as well as three libraries of expressed sequence tags (ESTs) of *Brassica napus* cv. "AC Excel", "Quantum" and "Cresor" (canola) and *Oryza sativa* cv. Nippon-Barre (Japonica rice) were studied. The search identified sequences from various plant species, which are highly homologous to the amino acid sequence of MOB24.15 at the nucleotide level or in one of the six possible reading frames. Table 7 lists those sequences which have significant identity at the derived amino acid level.

TABLE 7

Homology comparison of MOB24.15 to homologous genes from other species at the amino acid level.

| Plant species | Accession | Seq. ID | % identity | Similarity |
|---|---|---|---|---|
| Human | PIR: S45343 | 13 | 28% | 42% |
| Mouse | PIR: S29031 | 15 | 28% | 40% |
| Yeast | PIR: S59397 | 11 | 28% | 42% |
| Oryza sativa | Q8W0A7, P0452F10.16 | 3 | 54% | 74% |
| Brassica napus | BN_asm: bn1106c9886 | 5 | 83% | 88% |
| Glycine max | GM: c48958528gm021002 | 7 | 60% | 72% |
| Oryza sativa | OS: oz1116c1058 | 9 | 54% | 70% |

Example 12

Determination of Expression of the Mutant Protein

The observations of the activity of a mutated protein in a transformed host cell are based on the fact that the mutant protein is expressed in a manner and amount similar to that of the wild-type protein. A suitable method for determining the amount of transcription of the mutant gene (an indication of the amount of mRNA available for translation of the gene product) is to carry out a Northern blot (see, for example, Ausubel, (1988) Current Protocols in Molecular Biology, Wiley: New York), providing a primer which is designed so as to bind to the gene of interest with a detectable (usually radioactive or chemiluminescent) label so that, when total RNA of a culture of the organism is extracted, fractionated on a gel, transferred to a stable matrix and incubated with this probe, binding and quantity of the binding of said probe indicate the presence and also the amount of mRNA for said gene. This information is evidence for the degree of transcription of the mutant gene. Total cellular RNA can be isolated from *Corynebacterium glutamicum* by various methods which are known in the art, as described in Bormann, E. R. et al., (1992) Mol. Microbiol. 6: 317-326.

The presence or relative amount of protein translated from said mRNA can be determined using standard techniques such as Western blot (see, for example, Ausubel et al. (1988) "Current Protocols in Molecular Biology", Wiley, New York). This method comprises extracting total cell proteins, separating them by gel electrophoresis, transferring them to a matrix such as nitrocellulose and incubating them with a probe such as an antibody which binds specifically to the desired protein. Said probe is usually provided with a chemiluminescent or colorimetric label which can be readily detected. The presence and observed amount of label indicate the presence and amount of the mutant protein of interest in the cell.

Example 13

In-Vitro Analysis of the Function of Mutant Proteins

The determination of the activities and kinetic parameters of enzymes is well known in the art. Experiments for determining the activity of a particular modified enzyme must be adapted to the specific activity of the wild-type enzyme and this is within the abilities of the skilled worker. Overviews over enzymes in general and also specific details concerning structure, kinetics, principles, methods, applications and examples of determining a multiplicity of enzyme activities may be found, for example, in the following references: Dixon, M., and Webb, E. C: (1979) Enzymes, Longmans, London; Fersht (1985) Enzyme Structure and Mechanism, Freeman, New York; Walsh (1979) Enzymatic Reaction Mechanisms. Freeman, San Francisco; Price, N. C., Stevens, L. (1982) Fundamentals of Enzymology. Oxford Univ. Press: Oxford; Boyer, P. D: ed. (1983) The Enzymes, 3rd edition Academic Press, New York; Bisswanger, H. (1994) Enzymkinetik, 2nd edition VCH, Weinheim (ISBN 3527300325); Bergmeyer, H. U., Bergmeyer, J., Graβl, M. eds (1983-1986) Methods of Enzymatic Analysis, 3rd edition vol. I-XII, Verlag Chemie: Weinheim; and Ullmann's Encyclopedia of Industrial Chemistry (1987) vol. A9, "Enzymes", VCH, Weinheim, pp. 352-363.

Example 14

Analysis of the Influence of Mutated Protein on Production of the Desired Product The effect of genetic modification in an organism, for example a plant or a microorganisms, e.g. *C. glutamicum*, on the production of a desired compound (such as an amino acid) can be determined by growing the modified (micro)organisms under suitable conditions (such as those described above for *Arabidopsis thaliana* or below by way of example and for *C. glutamicum*) and studying the medium and/or the cellular components for increased production of the desired product (i.e. an amino acid, for example). Analytic techniques of this kind are well known to the skilled worker and comprise spectroscopy, thin layer chromatography, various types of coloring methods, enzymic and microbiological methods and analytical chromatography such as high performance liquid chromatography (see, for example, Ullman, Encyclopedia of Industrial Chemistry, vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp 469-714, VCH: Weinheim; Belter, P. A. et al. (1988) Bioseparations: downstream processing for Biotechnology, John Wiley and Sons; Kennedy, J. F. and Cabral, J. M. S. (1992) Recovery processes for biological Materials, John Wiley and Sons; Shaeiwitz, J. A. and Henry, J. D. (1988) Biochemical Separations, in Ullmann's Encyclopedia of Industrial Chemistry, vol. B3; chapter 11, pp. 1-27, VCH: Weinheim; and Dechow, F. J. (1989) Separation and purification techniques in biotechnology, Noyes Publications).

In addition to measuring the desired product, it is likewise possible to analyze other components of the metabolic pathways which are used for producing the desired compound, such as intermediate and secondary products, in order to determine the total productivity of the organism, the yield and/or the efficacy of production of the compound. The analytical methods comprise measurements of the amounts of nutrients in the medium (e.g. sugars, carbohydrates, nitrogen sources, phosphate and other ions), measurements of biomass composition and growth, analysis of production of ordinary metabolites of biosynthetic pathways and measurements of gases generated during fermentation. Standard methods for said measurements are described in Applied Microbial Physiology; A Practical Approach, P. M. Rhodes and P. F. Stanbury, eds. IRL Press, pp. 103-129; 131-163 and 165-192 (ISBN: 0199635773) and the references stated therein.

Example 15

Method for Producing Fine Chemicals in Microorganisms

The method of the invention may be used for increased production of fine chemicals in microorganisms according to the abovementioned examples. A method of this kind is described here, by way of example, for *Corynebacterium glutamicum*.

Example 15.1

In-vivo Mutagenesis

In-vivo mutagenesis of *Corynebacterium glutamicum* may be carried out by passing a plasmid (or other vector) DNA through *E. coli* or other microorganisms (e.g. *Bacillus* spp. or yeasts such as *Saccharomyces cerevisiae*) unable to maintain the integrity of their genetic information. Common mutator strains have mutations in the genes for the DNA repair system (e.g. mutHLS, mutD, mutT, etc., for comparison, see Rupp, W. D. (1996) DNA repair mechanisms in *Escherichia coli* and *Salmonella*, pp. 2277-2294, ASM: Washington). These strains are known to the skilled worker. The use of these strains is illustrated, for example, in Greener, A. and Callahan, M. (1994) Strategies 7; 32-34.

Example 15.2

Growth of Genetically Modified *Corynebacterium glutamicum*-Media and Cultivation Conditions Corynebacteria, for example genetically modified corynebacteria, are grown in synthetic or natural growth media. A number of different growth media for corynebacteria are known and easily obtainable (Lieb et al. (1989) Appl. Microbiol. Biotechnol. 32: 205-210; von der Osten et al. (1998) Biotechnology Letters 11: 11-16; Patent DE 4 120 867; Liebl (1992) "The Genus *Corynebacterium*", in: The Procaryotes, vol. II, Balows, A., et al., eds Springer-Verlag). These media consist of one or more carbon sources, nitrogen sources, inorganic salts, vitamins and trace elements. Preferred carbon sources are sugars such as mono-, di- or polysaccharides.

Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses, or other by-products of sugar refining. It may also be advantageous to add mixtures of various carbon sources. Other possible carbon sources are alcohols and organic acids, such as methanol, ethanol, acetic acid or lactic acid. Nitrogen sources are usually organic or inorganic nitrogen compounds or materials containing these compounds. Examples of nitrogen sources include ammonia gas or ammonium salts such as $NH_4Cl$ or $(NH_4)_2SO_4$, $NH_4OH$, nitrates, urea, amino acids or complex nitrogen sources such as corn steep liquor, soybean meal, soybean protein, yeast extracts, meat extracts and others.

Inorganic salt compounds which may be present in the media include the chloride, phosphorus or sulfate salts of calcium, magnesium, sodium, cobalt, molybdenum, potassium, manganese, zinc, copper and iron. Chelating agents may be added to the medium in order to keep the metal ions in solution. Particularly suitable chelating agents include dihydroxyphenols such as catechol or protocatechuate, or organic acids such as citric acid. The media usually also contain other growth factors such as vitamins or growth promoters, which include, for example, biotin, riboflavin, thiamine, folic acid, nicotinic acid, panthothenate and pyridoxine. Growth factors and salt are often derived from complex media components such as yeast extract, molasses, corn steep liquor and the like. The exact composition of the media compounds depends greatly on the particular experiment and is decided for each case individually.

Information about media optimization is obtainable from the textbook "Applied Microbiol. Physiology, A Practical Approach" (eds P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All media components are sterilized either by heat (1.5 bar and 121° C. for 20 min) or by sterile filtration. The components may be sterilized either together or, if necessary, separately. All media components may be present at the start of the cultivation or optionally be added continuously or batchwise.

The cultivation conditions are defined separately for each experiment. The temperature should be between 15° C. and 45° C. and may be kept constant or changed during the experiment. The pH of the medium should be in the range from 5 to 8.5, preferably around 7.0, and can be maintained by adding buffers to the media. One example of a buffer for this purpose is a potassium phosphate buffer. Synthetic buffers such as MOPS, HEPES; ACES, etc. may be used alternatively or simultaneously. The cultivation pH can be kept constant during the cultivation also by adding NaOH or $NH_4OH$, for example. If complex media components such as yeast extract are used, the requirement for additional buffers is reduced, since many complex compounds have a high buffer capacity. If a fermenter is used for cultivating microorganisms, the pH may also be controlled with gaseous ammonia.

The incubation time is usually in a range from several hours up to several days. This time is selected so that the maximum amount of product accumulates in the broth. The disclosed growth experiments may be carried out in a large number of containers such as microtiter plates, glass tubes, glass flasks or glass or metal fermenters of various sizes. For screening a large number of clones, the microorganisms should be grown in microtiter plates, glass tubes or shaker flasks either with or without baffles. Preference is given to using 100-ml shaker flasks charged with 10% (based on volume) of the required growth medium. The flasks should be shaken on an orbital shaker (amplitude 25 mm) with a speed in the range from 100 to 300 U/min. Evaporation losses can be reduced by maintaining a moist atmosphere; alternatively, a mathematical correction should be carried out for said evaporation losses.

If genetically modified clones are studied, an unmodified control clone or a control clone which contains the basic plasmid without insert should also be tested. The medium is inoculated to an $OD_{600}$ of 0.5-1.5, using cells grown on agar plates such as CM plates (10 g/l glucose, 2.5 g/l NaCl, 2 g/l urea, 10 g/l polypeptone, 5 g/l yeast extract, 5 g/l meat extract, 22 g/l agar pH 6.8 with 2 M NaOH) which have been incubated at 30° C. The media are inoculated either by introducing a saline solution of *C. glutamicum* cells from CM plates or by adding a liquid preculture of this bacterium.

Example 15.3

Purification of the Desired Product from *C. glutamicum* Culture

The desired product can be obtained from *C. glutamicum* cells or from the supernatant of the culture described above by various methods known in the art. If the cells do not secrete the desired product, they may be harvested from the culture by slow centrifugation and may be lysed by standard techniques such as mechanical force or sonication. The cell debris is removed by centrifugation, and the supernatant fraction which contains the soluble proteins is obtained for further purification of the desired compound. If the *C. glutamicum* cells do secrete the product, they are removed from the culture by slow centrifugation, and the supernatant fraction is retained for further purification.

The supernatant fraction from both purification methods is subjected to a chromatography using a suitable resin, with the desired molecule either being retained on the chromatography resin, but many impurities in the sample not, or with the impurities remaining on the resin, but the sample not. These chromatography steps may be repeated, if necessary, using the same or different chromatography resins. The skilled worker is familiar with the selection of suitable chromatography resins and the most effective application to a particular molecule to be purified. The purified product may be concentrated by filtration or ultrafiltration and stored at a temperature at which the stability of the product is at a maximum.

Many purification methods are known in the art which are not confined to the foregoing purification method and which are described, for example, in Bailey, J. E. & Ollis, D. F. Biochemical Engineering Fundamentals, McGraw-Hill: New York (1986).

The identity and purity of the isolated compounds may be determined by standard techniques of the art. These include high performance liquid chromatography (HPLC), spectroscopic methods, coloring methods, thin layer chromatography, NIRS, enzyme assay or microbiological assays. These analytical methods are summarized in: Patek et al. (1994) Appl. Environ. Microbiol. 60: 133-140; Malakhova et al. (1996) Biotekhnologiya 11: 27-32; and Schmidt et al. (1998) Bioprocess Engineer. 19: 67-70. Ulmann's Encyclopedia of Industrial Chemistry (1996) vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley

Example 16a

Engineering Ryegrass Plants

Seeds of several different ryegrass varieties can be used as explant sources for transformation, including the commercial variety Gunne available from Svalof Weibull seed company or the variety Affinity. Seeds are surface-sterilized sequentially with 1% Tween-20 for 1 minute, 100% bleach for 60 minutes, 3 rinses with 5 minutes each with de-ionized and distilled $H_2O$, and then germinated for 3-4 days on moist, sterile filter paper in the dark. Seedlings are further sterilized for 1 minute with 1% Tween-20, 5 minutes with 75% bleach, and rinsed 3 times with ddH20, 5 min each.

Surface-sterilized seeds are placed on the callus induction medium containing Murashige and Skoog basal salts and vitamins, 20 g/l sucrose, 150 mg/l asparagine, 500 mg/l casein hydrolysate, 3 g/l Phytagel, 10 mg/l BAP, and 5 mg/l dicamba. Plates are incubated in the dark at 25° C. for 4 weeks for seed germination and embryogenic callus induction.

After 4 weeks on the callus induction medium, the shoots and roots of the seedlings are trimmed away, the callus is transferred to fresh media, is maintained in culture for another 4 weeks, and is then transferred to MSO medium in light for 2 weeks. Several pieces of callus (11-17 weeks old) are either strained through a 10 mesh sieve and put onto callus induction medium, or are cultured in 100 ml of liquid ryegrass callus induction media (same medium as for callus induction with agar) in a 250 ml flask. The flask is wrapped in foil and shaken at 175 rpm in the dark at 23° C. for 1 week. Sieving the liquid culture with a 40-mesh sieve is collected the cells. The fraction collected on the sieve is plated and is cultured on solid ryegrass callus induction medium for 1 week in the dark at 25° C. The callus is then transferred to and is cultured on MS medium containing 1% sucrose for 2 weeks.

Transformation can be accomplished with either *Agrobacterium* or with particle bombardment methods. An expression vector is created containing a constitutive plant promoter and the cDNA of the gene in a pUC vector. The plasmid DNA is prepared from *E. coli* cells using with Qiagen kit according to manufacturer's instruction. Approximately 2 g of embryogenic callus is spread in the center of a sterile filter paper in a Petri dish. An aliquot of liquid MSO with 10 g/l sucrose is added to the filter paper. Gold particles (1.0 µm in size) are coated with plasmid DNA according to method of Sanford et al., 1993 and are delivered to the embryogenic callus with the following parameters: 500 µg particles and 2 µg DNA per shot, 1300 psi and a target distance of 8.5 cm from stopping plate to plate of callus and 1 shot per plate of callus.

After the bombardment, calli are transferred back to the fresh callus development medium and maintained in the dark at room temperature for a 1-week period. The callus is then transferred to growth conditions in the light at 25° C. to initiate embryo differentiation with the appropriate selection agent, e.g. 250 nM Arsenal, 5 mg/l PPT or 50 mg/L Kanamycin. Shoots resistant to the selection agent are appearing and once rooted are transferred to soil.

Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Transgenic T0 ryegrass plants are propagated vegetatively by excising tillers. The transplanted tillers are maintained in the greenhouse for 2 months until well established. The shoots are defoliated and allowed to grow for 2 weeks.

Example 16b

Engineering Soybean Plants

Soybean can be transformed according to the following modification of the method described in the Texas A&M patent U.S. Pat. No. 5,164,310. Several commercial soybean varieties are amenable to transformation by this method. The cultivar Jack (available from the Illinois Seed Foundation) is commonly used for transformation. Seeds are sterilized by immersion in 70% (v/v) ethanol for 6 min and in 25% commercial bleach (NaOCl) supplemented with 0.1% (v/v) Tween for 20 min, followed by rinsing 4 times with sterile double distilled water. Removing the radicle, hypocotyl and one cotyledon from each seedling propagates seven-day seedlings. Then, the epicotyl with one cotyledon is transferred to fresh germination media in petri dishes and incubated at 25° C. under a 16-hr photoperiod (approx. 100 µE-m-2s-1) for three weeks. Axillary nodes (approx. 4 mm in length) are cut from 3-4 week-old plants. Axillary nodes are excised and incubated in *Agrobacterium* LBA4404 culture.

Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used as described above, including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene to provide constitutive, developmental, tissue or environmental regulation of gene transcription as described above. In this example, the 34S promoter (GenBank Accession numbers M59930 and X16673) is used to provide constitutive expression of the trait gene.

After the co-cultivation treatment, the explants are washed and transferred to selection media supplemented with 500 mg/L timentin. Shoots are excised and placed on a shoot elongation medium. Shoots longer than 1 cm are placed on rooting medium for two to four weeks prior to transplanting to soil.

The primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and is used as recommended by the manufacturer.

Example 16c

Engineering Corn Plants

Transformation of maize (*Zea Mays* L.) is performed with a modification of the method described by Ishida et al. (1996. Nature Biotech 14745-50). Transformation is genotype-dependent in corn and only specific genotypes are amenable to transformation and regeneration. The inbred line A188 (University of Minnesota) or hybrids with A188 as a parent are good sources of donor material for transformation (Fromm et al. 1990 Biotech 8:833-839), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system of Japan Tobacco is described in WO patents WO94/00977 and WO95/06722. Vectors can be constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

Excised embryos are grown on callus induction medium, then maize regeneration medium, containing imidazolinone as a selection agent. The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 generation of single locus insertions of the T-DNA can segregate for the transgene in a 3:1 ratio. Those progeny containing one or two copies of the transgene are tolerant of the imidazolinone herbicide. Homozygous T2 plants can exhibited similar phenotypes as the T1 plants. Hybrid plants (F1 progeny) of homozygous transgenic plants and non-transgenic plants can also exhibited increased similar phenotyps.

Example 16d

Engineering Wheat Plants

Transformation of wheat is performed with the method described by Ishida et al. (1996 Nature Biotech. 14745-50). The cultivar Bobwhite (available from CYMMIT, Mexico) is commonly used in transformation. Immature embryos are co-cultivated with *Agrobacterium tumefaciens* that carry "super binary" vectors, and transgenic plants are recovered through organogenesis. The super binary vector system of Japan Tobacco is described in WO patents WO94/00977 and WO95/06722. Vectors were constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) can be used to provide constitutive expression of the trait gene.

After incubation with *Agrobacterium*, the embryos are grown on callus induction medium, then regeneration medium, containing imidazolinone as a selection agent. The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 generation of single locus insertions of the T-DNA can segregate for the transgene in a 3:1 ratio. Those progeny containing one or two copies of the transgene are tolerant of the imidazolinone herbicide. Homozygous T2 plants exhibited similar phenotypes.

Example 16e

Engineering Rapeseed/Canola Plants

Cotyledonary petioles and hypocotyls of 5-6 day-old young seedlings are used as explants for tissue culture and transformed according to Babic et al.(1998, Plant Cell Rep 17: 183-188). The commercial cultivar Westar (Agriculture Canada) is the standard variety used for transformation, but other varieties can be used.

*Agrobacterium tumefaciens* LBA4404 containing a binary vector are used for canola transformation. Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) can be used to provide constitutive expression of the trait gene.

Canola seeds are surface-sterilized in 70% ethanol for 2 min., and then in 30% Clorox with a drop of Tween-20 for 10 min, followed by three rinses with sterilized distilled water. Seeds are then germinated in vitro 5 days on half strength MS medium without hormones, 1% sucrose, 0.7% Phytagar at 23° C., 16 hr. light. The cotyledon petiole explants with the cotyledon attached are excised from the in vitro seedlings, and are inoculated with *Agrobacterium* by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MSO) for root induction.

Samples of the primary transgenic plants (T0) are analyzed by PCR to confirm the presence of T-DNA. These results are confirmed by Southern hybridization in which DNA is electrophoresed on a 1% agarose gel and are transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Example 16f

Engineering Alfalfa Plants

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required.

Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing a binary vector. Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene that provides constitutive, developmental, tissue or environmental regulation of gene transcription. In this example, the 34S promoter (GenBank Accession numbers M59930 and X16673) can be used to provide constitutive expression of the trait gene.

The explants are cocultivated for 3 d in the dark on SH induction medium containing 288 mg/L Pro, 53 mg/L thioproline, 4.35 g/L K2SO4, and 100·m acetosyringinone. The explants are washed in half-strength Murashige-Skoog medium (Murashige and Skoog, 1962) and plated on the same SH induction medium without acetosyringinone but with a suitable selection agent and suitable antibiotic to inhibit Agrobacterium growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings are transplanted into pots and grown in a greenhouse.

The T0 transgenic plants are propagated by node cuttings and rooted in Turface growth medium. The plants are defoliated and grown to a height of about 10 cm (approximately 2 weeks after defoliation).

Equivalents

The skilled worker knows, or can identify by using simply routine methods, a large number of equivalents of the specific embodiments of the invention. These equivalents are intended to be included in the patent claims below.

We claim:

1. A method for increasing plant growth and/or yield comprising:
growing a transgenic plant that comprises a nucleic acid construct which comprises a nucleic acid molecule selected from the group consisting of (a) a nucleotide sequence at least 95% identical to SEQ ID NO: 1 encoding a polypeptide having L450 activity and (b) a nucleotide sequence encoding a polypeptide at least 95% identical to SEQ ID NO: 2 and having L450 activity, wherein expression of said nucleic acid molecule in the plant results in increased plant growth and/or yield as compared to a plant of the same species that lacks said nucleic acid construct.

2. The method of claim 1, wherein the nucleotide sequence comprises the nucleotide sequence of SEQ ID NO: 1.

3. The method of claim 1, wherein the nucleotide sequence encodes a polypeptide comprising the amino acid sequence of SEQ ID NO: 2.

4. The method of claim 1, wherein the yield is increased.

5. A transgenic plant having faster growth and/or increased yield comprising a nucleic acid construct which comprises a nucleic acid molecule selected from the group consisting of (a) a nucleotide sequence at least 95% identical to SEQ ID NO: 1 encoding a polypeptide having L450 activity and (b) a nucleotide sequence encoding a polypeptide at least 95% identical to SEQ ID NO: 2 and having L450 activity, wherein expression of said nucleic acid molecule in the plant results in faster growth and/or increased yield as compared to a plant of the same species that lacks said nucleic acid construct.

6. The transgenic plant of claim 5, wherein the nucleotide sequence comprises the nucleotide sequence of SEQ ID NO: 1.

7. The transgenic plant of claim 5, wherein the nucleotide sequence encodes a polypeptide comprising the amino acid sequence of SEQ ID NO: 2.

8. The transgenic plant of claim 5, wherein the yield is increased.

* * * * *